United States Patent
Tuller et al.

(10) Patent No.: US 11,236,344 B2
(45) Date of Patent: Feb. 1, 2022

(54) METHODS FOR MODIFYING THE GROWTH RATE OF A CELL

(71) Applicant: Ramot at Tel-Aviv University Ltd., Tel Aviv (IL)

(72) Inventors: Tamir Tuller, Herzeliya Pituach (IL); Hadas Zur, Tel Aviv Jaffa (IL); Rachel Cohen-Kupiec, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 376 days.

(21) Appl. No.: 15/985,082

(22) Filed: May 21, 2018

(65) Prior Publication Data

US 2018/0334679 A1 Nov. 22, 2018

Related U.S. Application Data

(60) Provisional application No. 62/509,132, filed on May 21, 2017.

(51) Int. Cl.
*C12N 15/67* (2006.01)
*C12Q 1/6809* (2018.01)
*C12N 15/79* (2006.01)

(52) U.S. Cl.
CPC ............. *C12N 15/67* (2013.01); *C12N 15/79* (2013.01); *C12Q 1/6809* (2013.01); *C12N 2800/22* (2013.01)

(58) Field of Classification Search
CPC ............................................... C12N 2800/22
USPC ......................................................... 435/325
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,837,028 | A | 6/1989 | Allen |
| 5,019,369 | A | 5/1991 | Presant et al. |

OTHER PUBLICATIONS

Agashe (Mol. Biol. Evol. 2012, 30:549-560).*
Hanson (2018, RNA, 24:1377-1388).*
Brule (Trends in Genetics, 2017, 33:283-297).*
Shaham (2018, DNA Res, 25:195-205).*
Dekel, E., et al., "Optimality and evolutionary tuning of the expression level of a protein." Nature, 2005. 436(7050): p. 588-592.
Shachrai, I., et al., "Cost of Unneeded Proteins in E. coli is Reduced after Several Generations in Exponential Growth." Molecular Cell, 2010. 38(5): p. 758-767.
Gorochowski, T.E., et al., "A minimal model of ribosome allocation dynamics captures trade-offs in expression between endogenous and synthetic genes." ACS Synthetic Biology, 2016.
Ceroni, F., et al., "Quantifying cellular capacity identifies gene expression designs with reduced burden." Nature Methods, 2015. 12(5): p. 415-418.
Mahalik, S., et al., "Genome engineering for improved recombinant protein expression in Escherichia coli." Microbial Cell Factories, 2014. 13(1): p. 1.
Raveh, A., et al., "A model for competition for ribosomes in the cell." Journal of The Royal Society Interface, 2016. 13(116).
Brophy, et al. "Principles of genetic circuit design." Nature Methods, 2014. 11(5): p. 508-520.
Carrera, J., et al., "Empirical model and in vivo characterization of the bacterial response to synthetic gene expression show that ribosome allocation limits growth rate." Biotechnology Journal, 2011. 6(7): p. 773-783.
Klumpp, S., et al., "On Ribosome Load, Codon Bias and Protein Abundance." Public Library of Science One, 2012. 7(11): p. e48542.
Tuller, T. and H. Zur, "Multiple roles of the coding sequence 5' end in gene expression regulation." Nucleic Acids Research, 2015. 43(1): p. 13-28.
Tuller, T., et al., "An Evolutionarily Conserved Mechanism for Controlling the Efficiency of Protein Translation." Cell, 2010. 141(2): p. 344-354.
Gustafsson, C., S. et al., "Codon bias and heterologous protein expression." Trends in Biotechnology, 2004. 22(7): p. 346-353.
Tuller, T., et al., "Composite effects of gene determinants on the translation speed and density of ribosomes." Genome Biology, 2011. 12(11): p. R110.
Dana, A., et al., "The effect of tRNA levels on decoding times of mRNA codons." Nucleic Acids Research, 2014. 42(14): p. 9171-9181.
Wolin, S.L., et al., "Ribosome pausing and stacking during translation of a eukaryotic mRNA." The EMBO Journal, 1988. 7(11): p. 3559-3569.
Poker, G., et al., "Maximizing protein translation rate in the non-homogeneous ribosome flow model: a convex optimization approach." Journal of The Royal Society Interface, 2014. 11(100): p. 20140713.

* cited by examiner

*Primary Examiner* — Valarie E Bertoglio
(74) *Attorney, Agent, or Firm* — The Roy Gross Law Firm, LLC; Roy Gross

(57) ABSTRACT

Genetically modified cells with at least one codon substituted to a synonymous codon, and with modified replicative fitness as compared to the unmodified cell, wherein a slower translating synonymous codon increases replicative fitness and a faster translating codon decreased replicative fitness are provided. Further, vaccine composition comprising those cells as well as methods for modifying replicative fitness of a cell are provided.

18 Claims, 52 Drawing Sheets
(16 of 52 Drawing Sheet(s) Filed in Color)
Specification includes a Sequence Listing.

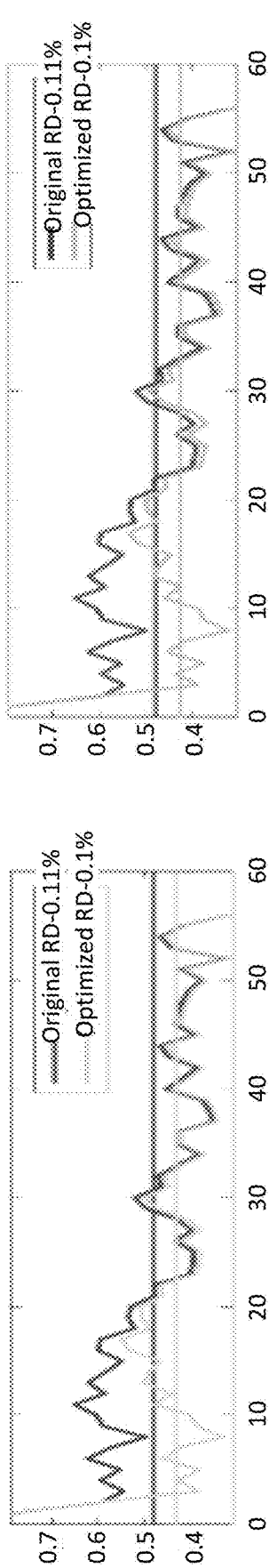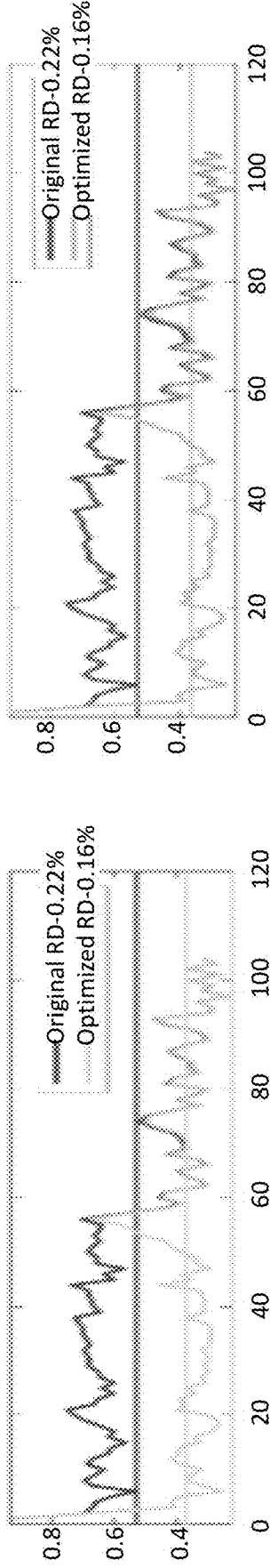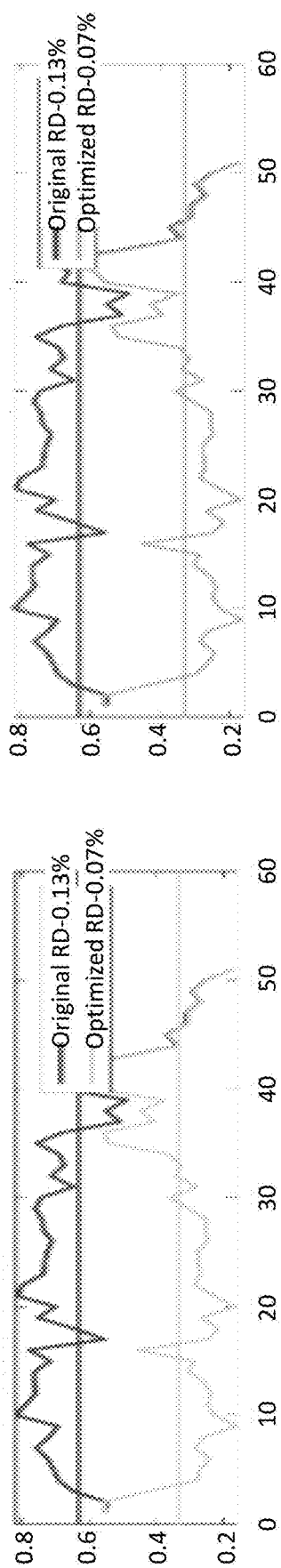
FIGURE 5C
FIGURE 5D

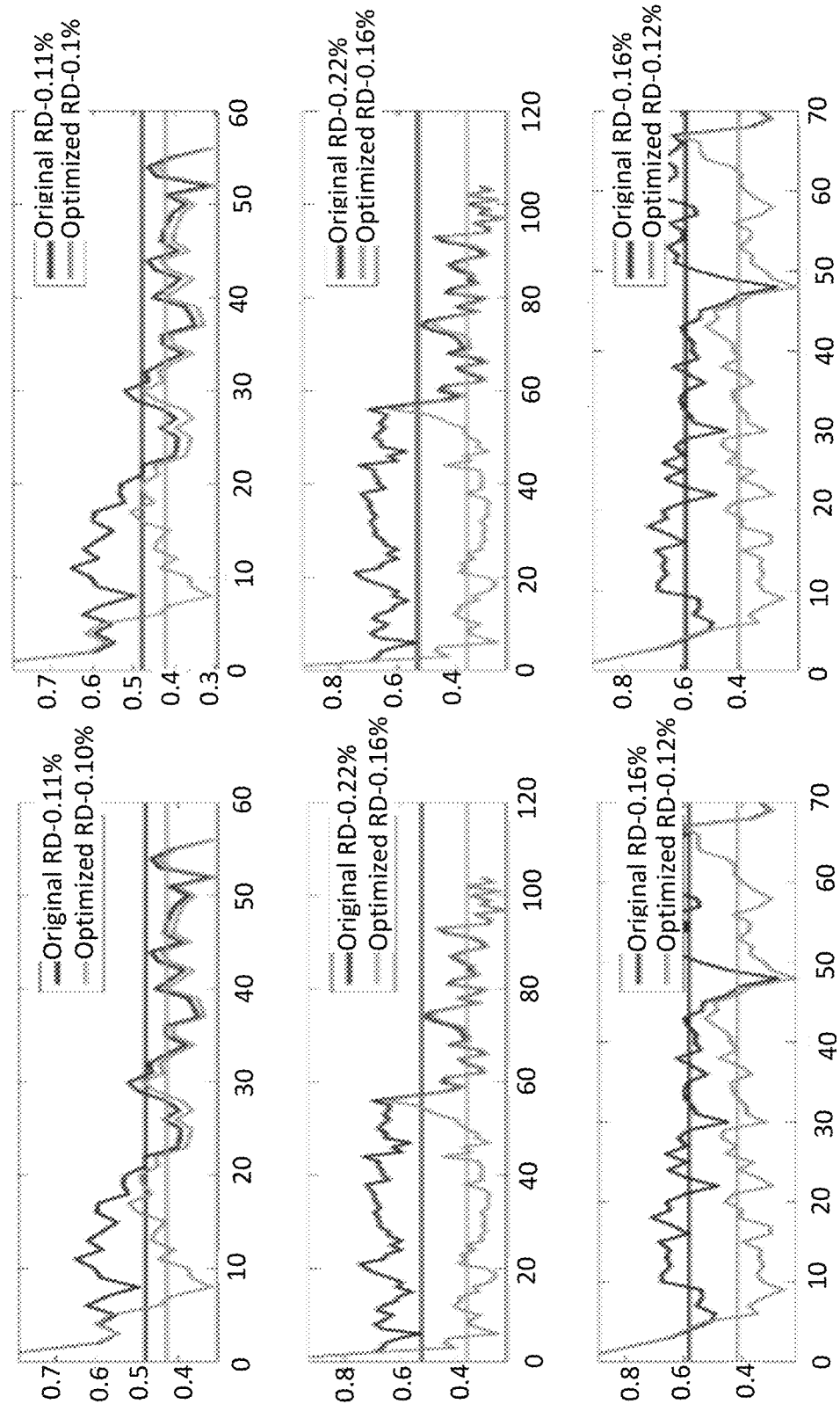

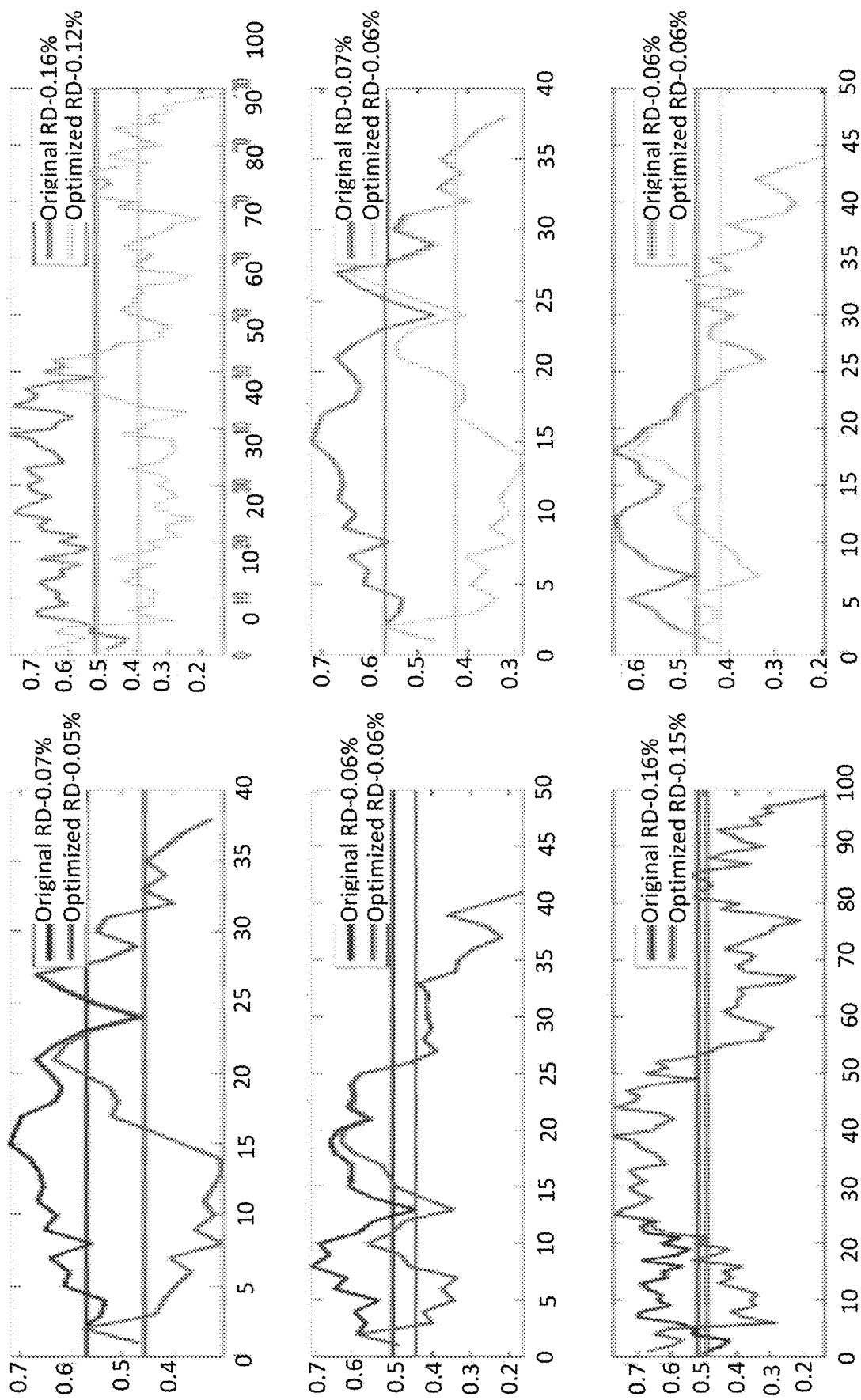

SEQUENCE LISTING

<160> NUMBER OF SEQ ID NOS: 13

<210> SEQ ID NO 1
<211> LENGTH: 1524
<212> TYPE: DNA
<213> ORGANISM: Saccharomyces cerevisiae

<400> SEQUENCE: 1

```
atgactaaat ctgagcagca agccgattca agacataacg ttatcgactt agttggtaac      60
accccattga tcgcactgaa aaaattgcct aaggctttgg gtatcaaacc acaaatttat     120
```

```
gctaagctgg aactatacaa tccaggtggt tccatcaaag acagaattgc caagtctatg      180
gtggaagaag ctgaagcttc cggtagaatt catccttcca gatctactct gatcgaacct      240
acttctggta acaccggtat cggtctagct ttaatcggcg ccatcaaagg ttacagaact      300
atcatcacct tgccggaaaa aatgtctaac gagaaagttt ctgtcctaaa ggctctgggt      360
gctgaaatca tcagaactcc aactgctgct gcctgggatt ctccagaatc acatattggt      420
gttgctaaga agttggaaaa agagattcct ggtgctgtta acttgacca atataacaat       480 atgatgaacc cagaagctca ttactttggt actggtcgcg aaatccaaag acagctagaa      540
gacttgaatt tatttgataa tctacgcgct gttgttgctg gtgctggtac tggtgggact      600
attagcggta tttccaagta cttgaaagaa cagaatgata agatccaaat cgttggtgct      660
gacccattcg gttcaatttt agcccaacct gaaaacttga ataagactga tatcactgac      720
tacaaagttg agggtattgg ttatgatttt gttcctcagg ttttggacag aaaattaatt      780
gatgtttggt ataagacaga cgacaagcct tctttcaaat acgccagaca attgatttct      840
aacgaaggtg tcttggtggg tggttcttcc ggttctgcct tcactgcggt tgtgaaatac      900
tgtgaagacc accctgaact gactgaagat gatgtcattg ttgccatatt cccagattcc      960
atcaggtcgt acctaaccaa attcgtcgat gacgaatggt tgaaaagaa caatttgtgg       1020 gatgatgacg tgttggcccg ttttgactct tcaaagctgg aggcttcgac gacaaaatac      1080
gctgatgtgt ttggtaacgc tactgtaaag gatcttcact gaaaccggt tgtttccgtt       1140 aaggaaaccg ctaaggtcac tgatgttatc aagatattaa agacaatgg ctttgaccaa       1200 ttgcctgtgt tgactgaaga cggcaagttg tctggtttag ttactctctc tgagcttcta      1260
agaaaactat caatcaataa ttcaaacaac gacaacacta taagggtaa atacttggac       1320 ttcaagaaat taaacaattt caatgatgtt tcctcttaca acgaaaataa atccggtaag      1380
aagaagttta ttaaattcga tgaaaactca aagctatctg acttgaatcg tttctttgaa      1440
aaaaactcat ctgccgttat cactgatggc ttgaaaccaa tccatatcgt tactaagatg      1500
gatttactga gctacttagc ataa                                              1524
```

<210> SEQ ID NO 2
<211> LENGTH: 1524
<212> TYPE: DNA
<213> ORGANISM: Artificial
<220> FEATURE:
<223> OTHER INFORMATION: Synthetic

<400> SEQUENCE: 2

```
atgactaaat ctgagcagca agccgattca cggcataacg ttatagactt agttgggaac      60
acgccgttga tcgctctgaa aaaattgcct aaggctttgg gtatcaaacc acaaatttat      120
gctaagctgg agctatacaa tccaggtggt tccatcaaag acagaattgc caagtctatg      180
gtggaagaag ctgaagcttc cggtagaatt catccttcca gatctactct gatcgaacct      240
acttctggta acaccggtat cggtctagct ttaatcggcg ccatcaaagg ttacagaact      300
atcatcacct tgccggaaaa aatgtctaac gagaaagttt ctgtcctaaa ggctctgggt      360
gctgaaatca tcagaactcc aactgctgct gcctgggatt ctccagaatc acatattggt      420
gttgctaaga agttggaaaa agagattcct ggtgctgtta acttgacca atataacaat       480 atgatgaacc cagaagctca ttactttggt actggtcgcg aaatccaaag acagctagaa      540
gacttgaatt tatttgataa tctacgcgct gttgttgctg gtgctggtac tggtgggact      600
```

| | |
|---|---|
| attagcggta tttccaagta cttgaaagaa cagaatgata agatccaaat cgttggtgct | 660 |
| gacccattcg gttcaattt agcccaacct gaaaacttga ataagactga tatcactgac | 720 |
| tacaaagttg agggtattgg ttatgatttt gttcctcagg ttttggacag aaaattaatt | 780 |
| gatgtttggt ataagacaga cgacaagcct tctttcaaat acgccagaca attgatttct | 840 |
| aacgaaggtg tcttggtggg tggttcttcc ggttctgcct tcactgcggt tgtgaaatac | 900 |
| tgtgaagacc accctgaact gactgaagat gatgtcattg ttgccatatt cccagattcc | 960 |
| atcaggtcgt acctaaccaa attcgtcgat gacgaatggt tgaaaaagaa caatttgtgg | 1020 |
| gatgatgacg tgttggcccg ttttgactct tcaaagctgg aggcttcgac gacaaaatac | 1080 |
| gctgatgtgt ttggtaacgc tactgtaaag gatcttcact tgaaaccggt tgtttccgtt | 1140 |
| aaggaaaccg ctaaggtcac tgatgttatc aagatattaa aagacaatgg ctttgaccaa | 1200 |
| ttgcctgtgt tgactgaaga cggcaagttg tctggtttag ttactctctc tgagcttcta | 1260 |
| agaaaactat caatcaataa ttcaaacaac gacaacacta taagggtaa atacttggac | 1320 |
| ttcaagaaat taaacaattt caatgatgtt tcctcttaca acgaaaataa atccggtaag | 1380 |
| aagaagtta ttaaattcga tgaaaactca agctatctg acttgaatcg tttctttgaa | 1440 |
| aaaaactcat ctgccgttat cactgatggc ttgaaaccaa tccatatcgt tactaagatg | 1500 |
| gatttactga gctacttagc ataa | 1524 |

<210> SEQ ID NO 3
<211> LENGTH: 5205
<212> TYPE: DNA
<213> ORGANISM: Saccharomyces cerevisiae

<400> SEQUENCE: 3

| | |
|---|---|
| atggtaggac aacagtattc tagtgctcca ctccgtacag taaaagaggt ccaattcggt | 60 |
| cttttctcac ctgaagaagt tagagcaatc agtgtggccg ccaaaattag atttccagag | 120 |
| acaatggatg aaacccagac gagagcgaaa attggtggtc taaacgaccc taggttaggc | 180 |
| tctattgatc gtaatctgaa gtgtcaaact tgtcaagagg gtatgaacga atgtcctggt | 240 |
| cattttggtc acatagattt agcaaaacct gtatttcatg ttggttttat tgccaaaatt | 300 |
| aagaaagtat gtgagtgtgt ctgtatgcac tgtggtaagc tattactgga tgaacataat | 360 |
| gaattaatga caagctct agcaatcaaa gacagtaaaa aaggtttgc tgcaatttgg | 420 |
| actttatgta aaacaaaaat ggtctgcgaa acagatgtcc cttctgaaga tgatcctact | 480 |
| cagctcgtat caaggggagg ttgtggtaat acacagccta caattcgtaa ggatgggttg | 540 |
| aaattagttg gtagttggaa aaaagataga gccacggggg atgcggatga accagaacta | 600 |
| agagttttaa gtacggagga atcttgaat attttaagc atatctcagt aaaagacttc | 660 |
| actagtttgg gtttcaacga agtttttct cgtccagaat ggatgatttt aacatgcctt | 720 |
| cctgtcccac caccaccggt gcgtccatcc attttccttca atgaatctca agaggtgag | 780 |
| gatgatttaa cctttaaact tgctgatatt ttaaaagcta atattagttt ggaaacacta | 840 |
| gagcataacg gtgctccaca tcatgctatt gaagaagcag agagtttatt acaatttcat | 900 |
| gttgccactt atatggataa tgatattgct ggtcaaccac aagctcttca aaagtccggc | 960 |
| cgtcccgtta atctcattcg tgctcgtttg aagggtaaag agggtcgtat cagaggtaat | 1020 |
| ttaatgggta agcgtgtgga ttttcggca agaactgtta ttctggtga tcctaatttg | 1080 |
| gaattagacc aagtcggtgt tccaaaatct attgccaaga cttaacata cccagaagtg | 1140 |
| gtcacaccat ataacataga tcgtctgacg caacttgtta ggaatggacc aaatgagcac | 1200 |

```
cccggtgcca aatacgtcat tcgtgatagc ggagaccgta tagatttaag atacagtaaa   1260
agggcaggtg atattcaatt acagtatggg tggaaagttg aacgtcatat tatggacaat   1320
gatccagttt tattcaaccg tcaaccttcg ttgcacaaaa tgtccatgat ggcccacaga   1380
gtaaaagtta ttccatattc tacatttaga ttgaatttgt ccgttacatc tccatacaat   1440
gccgatttcg acggtgacga aatgaatctt cacgttcctc agtctgagga acaagggcg   1500 gaactttctc aattatgtgc tgttcctctg caaattgttt caccacaatc taacaaacct   1560
tgtatgggta ttgttcaaga tactttgtgt ggtattcgta aactgacatt aagagataca   1620
tttatagaac ttgatcaagt tttgaatatg ctttattggg ttccagattg ggatggtgtt   1680
attccgacac ctgcaattat caagcccaaa cctttgtggt ccggtaaaca aatcttgtct   1740
gtggctatcc caaacggtat tcatttacaa cgttttgatg agggcactac tctgctttct   1800
ccaaaggata atggtatgct tattattgac ggtcaaatca ttttggtgt agtagagaaa   1860 aaaaccgttg gttcctccaa tggtggttta attcatgttg ttacgagaga aaagggacct   1920
caagtttgtg ctaagttgtt tggtaacata cagaaagttg ttaacttttg gttactacat   1980
aatgggtttt caacaggtat tggtgatacc attgcggacg gcccaacaat gagggaaatt   2040
acagagacaa ttgcagaggc taaaaagaaa gttttggatg ttacgaaaga agcccaggca   2100
aacttattga ctgctaaaca tggtatgact ctccgtgagt cttttgagga taacgttgtt   2160
cggttcctaa atgaagcaag agataaggca ggtcgtttag ctgaagtcaa tttgaaagat   2220
ttgaacaatg tgaaacaaat ggttatggca ggttccaagg gttcatttat taatatcgcg   2280
caaatgtcag cttgtgtagg acagcaatct gttgaaggta aacgtattgc ttttgggttc   2340
gttgatcgta ccttacctca tttctctaaa gatgattact ccccagagtc taaaggtttt   2400
gttgagaact catatttgag aggtttgacc ccacaagaat ttttttttcca tgcaatgggt   2460 ggtcgtgaag gtcttatcga taccgccgtc aaaacagccg aaacaggtta tattcaacgt   2520
cgtttagtga agctctaga agatatcatg gttcattacg ataacaccac aagaaactca   2580
ttgggtaacg ttattcagtt tatttatggt gaagatggta tggatgctgc gcatattgaa   2640
aagcaatcgc tagatactat tggtggctcc gatgcagctt ttgaaaagag atacagagtt   2700
gatttattga atacagacca taccttgat ccctcactat tggaatccgg atctgagata   2760
cttggcgatt tgaaacttca agttctcctg gatgaagaat acaaacaatt agtgaaagat   2820
cgtaaatttt tgagggaagt ttttgttgat ggtgaagcaa actggccatt accagtcaac   2880
ataagacgta ttattcaaaa tgctcaacaa actttccaca tagatcatac gaaaccatct   2940
gatttaacaa tcaaagacat cgttcttggt gtaaaggatt tgcaagaaaa cttattagtg   3000
ttgcgtggta agaatgaaat tatacaaaat gcccagcgag atgcagttac attgttctgc   3060
tgtttattac gttcccgttt ggccacacgt agagttctac aagagtacag actaacaaaa   3120
caggcattcg attgggtatt aagtaatatc gaggcacaat tcctccgttc tgttgttcac   3180
cctggtgaaa tggttggtgt tctagcagcc caatccattg gtgaaccagc cacacaaatg   3240
acccttaaca ccttccattt tgctggtgtt gcttccaaaa aagttacttc tggtgtcccc   3300
cgtttaaagg aaattttgaa tgtggccaaa acatgaaaa ccccttcctt gactgtatac   3360
ttagagcctg gtcatgctgc cgatcaagaa caagcgaagt tgatcagatc tgctatcgag   3420
cataccactt taaagagtgt cactattgct tcagaaattt actatgatcc tgatccacgt   3480
tccacagtta ttccagaaga tgaagaaatt atccaacttc atttctcatt attggatgaa   3540
```

| | |
|---|---|
| gaggctgaac aatcttttga ccaacaatca ccttggttat tacgtctgga actggatcgt | 3600 |
| gcagcaatga atgataaaga cttaacaatg ggtcaggttg gtgaaagaat caagcaaaca | 3660 |
| ttcaaaaatg atttgtttgt tatctggtct gaagacaacg atgagaagtt gatcatccgt | 3720 |
| tgtcgtgttg ttcgtccaaa gtcactagat gctgagactg aagcagaaga agatcatatg | 3780 |
| ttgaagaaaa ttgagaacac aatgttagag aatattacat tacgtggtgt agagaacatc | 3840 |
| gagcgtgttg tcatgatgaa atatgaccgt aaagtaccaa gtccaactgg tgaatacgtt | 3900 |
| aaggaacctg aatgggtgtt ggaaacagat ggtgttaact tatctgaagt tatgactgtt | 3960 |
| cctggtatcg acccaaccag aatctatacc aactccttca ttgatataat ggaagttcta | 4020 |
| ggtattgaag ctggtcgtgc agccttgtat aaagaagttt acaatgttat tgcttctgat | 4080 |
| ggttcgtatg ttaactaccg tcatatggct ttgttagtcg atgttatgac aacccaaggt | 4140 |
| ggcttaactt ctgttactcg tcatggtttc aacagatcaa atacaggtgc cttaatgaga | 4200 |
| tgttcatttg aagaaactgt cgaaattttg tttgaagctg gtgcttcagc cgaattagat | 4260 |
| gattgtcgtg gtgtttcgga aaatgtcatt cttggtcaaa tggctccaat cggtaccggt | 4320 |
| gcatttgatg tgatgatcga tgaggagtca ctggtaaaat acatgccaga acaaaaaata | 4380 |
| actgagattg aagacggaca agatggtggc gtcacaccat acagtaacga aagtggtttg | 4440 |
| gtcaatgcag atcttgacgt taaagatgag ctaatgtttt cacctctggt tgattcgggt | 4500 |
| tcaaatgacg ctatggctgg aggatttaca gcgtacggtg gtgctgatta tggtgaagcc | 4560 |
| acgtctccat ttggtgctta tggtgaagca cctacatctc ccggatttgg agtctcctca | 4620 |
| ccaggctttt ctccaacttc cccaacatac tctcctacct ctccagcgta ctcaccaaca | 4680 |
| tcaccatcgt actcaccaac atcaccatcg tactcgccaa catcaccatc gtactcacct | 4740 |
| acatcaccat cgtattcacc aacgtcacca tcatattcgc caacgtcacc atcatattcg | 4800 |
| ccaacgtcgc catcgtattc tccaacgtca ccatcgtatt cgccaacgtc gccttcctac | 4860 |
| tctcccacgt cgccaagcta cagccctacg tctccttctt attctcctac atctccatca | 4920 |
| tactctccta cgtcaccaag ttacagccca acgtcaccaa gttacagccc aacgtctcca | 4980 |
| gcctattccc caacatcacc aagttatagt cctacatcgc cttcatactc tccaacatca | 5040 |
| ccatcctatt ccccaacatc accttcttac tctcccacct ctccaaacta tagccctact | 5100 |
| tcaccttctt actccccaac atctccaggc tacagcccag atctcctgc atattctcca | 5160 |
| aagcaagacg aacaaaagca taatgaaaat gaaaattcca gatga | 5205 |

<210> SEQ ID NO 4
<211> LENGTH: 5205
<212> TYPE: DNA
<213> ORGANISM: Artificial
<220> FEATURE:
<223> OTHER INFORMATION: Synthetic

<400> SEQUENCE: 4

| | |
|---|---|
| atggtaggac aacagtattc tagtgctcca ctccgaacag taaagaggt tcaattcggg | 60 |
| cttttctcac ctgaggaagt tcgtgcaata agtgtggcag caaaaattag atttccagag | 120 |
| acaatggatg aaacccagac gagagcgaaa attggtggtc taaacgaccc taggttaggc | 180 |
| tctattgatc gtaatctgaa gtgtcaaact tgtcaagagg gtatgaacga atgtcctggt | 240 |
| cattttggtc acatagattt agcaaaacct gtatttcatg ttggttttat tgccaaaatt | 300 |
| aagaaagtat gtgagtgtgt ctgtatgcac tgtggtaagc tattactgga tgaacataat | 360 |
| gaattaatga caagctct agcaatcaaa gacagtaaaa aaaggtttgc tgcaatttgg | 420 |

```
actttatgta aaacaaaaat ggtctgcgaa acagatgtcc cttctgaaga tgatcctact      480
cagctcgtat caaggggagg ttgtggtaat acacagccta caattcgtaa ggatgggttg      540
aaattagttg gtagttggaa aaaagataga gccacggggg atgcggatga accagaacta      600
agagttttaa gtacggagga aatcttgaat attttttaagc atatctcagt aaaagacttc     660
actagtttgg gtttcaacga agttttttct cgtccagaat ggatgatttt aacatgcctt      720
cctgtcccac caccaccggt gcgtccatcc atttccttca atgaatctca aagaggtgag      780
gatgatttaa cctttaaact tgctgatatt ttaaaagcta atattagttt ggaaacacta      840
gagcataacg gtgctccaca tcatgctatt gaagaagcag agagtttatt acaatttcat      900
gttgccactt atatggataa tgatattgct ggtcaaccac aagctcttca aaagtccggc      960
cgtcccgtta aatctattcg tgctcgtttg aagggtaaag agggtcgtat cagaggtaat     1020
ttaatgggta agcgtgtgga ttttttcggca agaactgtta tttctggtga tcctaatttg     1080
gaattagacc aagtcggtgt tccaaaatct attgccaaga ctttaacata cccagaagtg     1140
gtcacaccat ataacataga tcgtctgacg caacttgtta ggaatggacc aaatgagcac     1200
cccggtgcca aatacgtcat tcgtgatagc ggagaccgta tagatttaag atacagtaaa     1260
agggcaggtg atattcaatt acagtatggg tggaaagttg aacgtcatat tatggacaat     1320
gatccagttt tattcaaccg tcaaccttcg ttgcacaaaa tgtccatgat ggcccacaga     1380
gtaaaagtta ttccatattc tacatttaga ttgaatttgt ccgttacatc tccatacaat     1440
gccgatttcg acggtgacga aatgaatctt cacgttcctc agtctgagga acaagggcg     1500 gaactttctc aattatgtgc tgttcctctg caaattgttt caccacaatc taacaaacct     1560
tgtatgggta ttgttcaaga tactttgtgt ggtattcgta aactgacatt aagagataca     1620
tttatagaac ttgatcaagt tttgaatatg ctttattggg ttccagattg ggatggtgtt     1680
attccgacac ctgcaattat caagcccaaa cctttgtggt ccggtaaaca aatcttgtct     1740
gtggctatcc caaacggtat tcatttacaa cgttttgatg agggcactac tctgctttct     1800
ccaaaggata atggtatgct tattattgac ggtcaaatca ttttttggtgt agtagagaaa     1860 aaaaccgttg gttcctccaa tggtggttta attcatgttg ttacgagaga aaagggacct     1920
caagtttgtg ctaagttgtt tggtaacata cagaaagttg ttaacttttg gttactacat     1980
aatgggtttt caacaggtat tggtgatacc attgcgacg gcccaacaat gagggaaatt      2040
acagagacaa ttgcagaggc taaaaagaaa gttttggatg ttacgaaaga agcccaggca     2100
aacttattga ctgctaaaca tggtatgact ctccgtgagt cttttgagga taacgttgtt     2160
cggttcctaa atgaagcaag agataaggca ggtcgtttag ctgaagtcaa tttgaaagat     2220
ttgaacaatg tgaaacaaat ggttatgca ggttccaagg gttcatttat taatatcgcg      2280
caaatgtcag cttgtgtagg acagcaatct gttgaaggta acgtattgc ttttgggttc      2340 gttgatcgta ccttacctca tttctctaaa gatgattact ccccagagtc taaaggtttt     2400
gttgagaact catatttgag aggtttgacc ccacaagaat ttttttttcca tgcaatgggt     2460 ggtcgtgaag gtcttatcga taccgccgtc aaaacagccg aaacaggtta tattcaacgt     2520
cgtttagtga aagctctaga agatatcatg gttcattacg ataacaccac aagaaactca     2580
ttgggtaacg ttattcagtt tatttatggt gaagatggta tggatgctgc gcatattgaa     2640
aagcaatcgc tagatactat tggtggctcc gatgcagctt ttgaaaagag atacagagtt     2700
gatttattga atacagacca tacccttgat ccctcactat tggaatccgg atctgagata     2760
```

```
cttggcgatt tgaaacttca agttctcctg gatgaagaat acaaacaatt agtgaaagat    2820
cgtaaatttt tgagggaagt ttttgttgat ggtgaagcaa actggccatt accagtcaac    2880
ataagacgta ttattcaaaa tgctcaacaa actttccaca tagatcatac gaaaccatct    2940
gatttaacaa tcaaagacat cgttcttggt gtaaaggatt tgcaagaaaa cttattagtg    3000
ttgcgtggta agaatgaaat tatacaaaat gcccagcgag atgcagttac attgttctgc    3060
tgtttattac gttcccgttt ggccacacgt agagttctac aagagtacag actaacaaaa    3120
caggcattcg attgggtatt aagtaatatc gaggcacaat tcctccgttc tgttgttcac    3180
cctggtgaaa tggttggtgt tctagcagcc caatccattg gtgaaccagc cacacaaatg    3240
acccttaaca ccttccattt tgctggtgtt gcttccaaaa aagttacttc tggtgtcccc    3300
cgtttaaagg aaattttgaa tgtggccaaa aacatgaaaa ccccttcctt gactgtatac    3360
ttagagcctg gtcatgctgc cgatcaagaa caagcgaagt tgatcagatc tgctatcgag    3420
cataccactt taaagagtgt cactattgct tcagaaattt actatgatcc tgatccacgt    3480
tccacagtta ttccagaaga tgaagaaatt atccaacttc atttctcatt attggatgaa    3540
gaggctgaac aatcttttga ccaacaatca ccttggttat acgtctggga actggatcgt    3600
gcagcaatga atgataaaga cttaacaatg ggtcaggttg gtgaaagaat caagcaaaca    3660
ttcaaaaatg atttgtttgt tatctggtct gaagacaacg atgagaagtt gatcatccgt    3720
tgtcgtgttg ttcgtccaaa gtcactagat gctgagacta agcagaaga agatcatatg    3780 ttgaagaaaa ttgagaacac aatgttagag aatattacat tacgtggtgt agagaacatc    3840
gagcgtgttg tcatgatgaa atatgaccgt aaagtaccaa gtccaactgg tgaatacgtt    3900
aaggaacctg aatgggtgtt ggaaacagat ggtgttaact tatctgaagt tatgactgtt    3960
cctggtatcg acccaaccag aatctatacc aactccttca ttgatataat ggaagttcta    4020
ggtattgaag ctggtcgtgc agccttgtat aaagaagttt acaatgttat tgcttctgat    4080
ggttcgtatg ttaactaccg tcatatggct ttgttagtcg atgttatgac aacccaaggt    4140
ggcttaactt ctgttactcg tcatggtttc aacagatcaa atacaggtgc cttaatgaga    4200
tgttcatttg aagaaactgt cgaaattttg tttgaagctg gtgcttcagc cgaattagat    4260
gattgtcgtg gtgtttcgga aaatgtcatt cttggtcaaa tggctccaat cggtaccggt    4320
gcatttgatg tgatgatcga tgaggagtca ctggtaaaat acatgccaga acaaaaaata    4380
actgagattg aagacggaca agatggtggc gtcacaccat acagtaacga aagtggtttg    4440
gtcaatgcag atcttgacgt taaagatgag ctaatgtttt cacctctggt tgattcgggt    4500
tcaaatgacg ctatggctgg aggatttaca gcgtacggtg tgctgattta tggtgaagcc    4560
acgtctccat ttggtgctta tggtgaagca cctacatctc ccggatttgg agtctcctca    4620
ccaggctttt ctccaacttc cccaacatac tctcctacct ctccagcgta ctcaccaaca    4680
tcaccatcgt actcaccaac atcaccatcg tactcgccaa catcaccatc gtactcacct    4740
acatcaccat cgtattcacc aacgtcacca tcatattcgc caacgtcacc atcatattcg    4800
ccaacgtcgc catcgtattc tccaacgtca ccatcgtatt cgccaacgtc gccttcctac    4860
tctcccacgt cgccaagcta cagccctacg tctccttctt attctcctac atctccatca    4920
tactctccta cgtcaccaag ttacagccca acgtcaccaa gttacagccc aacgtctcca    4980
gcctattccc caacatcacc aagttatagt cctacatcgc cttcatactc tccaacatca    5040
ccatcctatt cccaacatca accttcttac tctcccacct ctccaaacta tagccctact    5100
tcaccttctt actcccccaac atctccaggc tacagcccag gatctcctgc atattctcca    5160
```

```
aagcaagacg aacaaaagca taatgaaaat gaaaattcca gatga              5205
```

<210> SEQ ID NO 5
<211> LENGTH: 1254
<212> TYPE: DNA
<213> ORGANISM: Saccharomyces cerevisiae

<400> SEQUENCE: 5

```
atgtctttat cttcaaagtt gtctgtccaa gatttggact tgaaggacaa gcgtgtcttc    60
atcagagttg acttcaacgt cgtcccattg gacggtaaga agatcacttc taaccaaaga   120
attgttgctg ctttgccaac catcaagtac gttttggaac accacccaag atacgttgtc   180
ttggcttctc acttgggtag accaaacggt gaaagaaacg aaaaatactc tttggctcca   240
gttgctaagg aattgcaatc attgttgggt aaggatgtca ccttcttgaa cgactgtgtc   300
ggtccagaag ttgaagccgc tgtcaaggct tctgccccag ttccgttat tttgttggaa    360
aacttgcgtt accacatcga agaagaaggt tccagaaagg tcgatggtca aaaggtcaag   420
gcttccaagg aagatgttca aaagttcaga cacgaattga gctctttggc tgatgtttac   480
atcaacgatg ccttcggtac cgctcacaga gctcactctt ctatggtcgg tttcgacttg   540
ccacaacgtg ctgccggttt cttgttggaa aaggaattga agtacttcgg taaggctttg   600
gagaacccaa ccagaccatt cttggccatc ttaggtggtg ccaaggttgc tgacaagatt   660
caattgattg acaacttgtt ggacaaggtc gactctatca tcattggtgg tggtatggct   720
ttcaccttca agaaggtttt ggaaaacact gaaatcggtg actccatctt cgacaaggct   780
ggtgctgaaa tcgttccaaa gttgatggaa aaggccaagg ccagggtgt cgaagtcgtc    840
ttgccagtcg acttcatcat tgctgatgct ttctctgctg atgccaacac caagactgtc   900
actgacaagg aaggtattcc agctggctgg caagggttgg acaatggtcc agaatctaga   960
aagttgtttg ctgctactgt tgcaaaggct aagaccattg tctggaacgg tccaccaggt  1020
gttttcgaat cgaaaagtt cgctgctggt actaaggctt tgttagacga agttgtcaag   1080
agctctgctg ctggtaacac cgtcatcatt ggtggtggtg acactgccac tgtcgctaag  1140
aagtacggtg tcactgacaa gatctcccat gtctctactg tggtggtgc ttcttttggaa   1200
ttattggaag gtaaggaatt gccaggtgtt gctttcttat ccgaaaagaa ataa         1254
```

<210> SEQ ID NO 6
<211> LENGTH: 1254
<212> TYPE: DNA
<213> ORGANISM: Artificial
<220> FEATURE:
<223> OTHER INFORMATION: Synthetic

<400> SEQUENCE: 6

```
atgtctttat cttcaaagtt gtctgtccaa gatttagact tgaaggacaa gcgtgtattc    60
atcagagttg acttcaacgt tgttccattg gacggtaaga agatcacttc taaccaaaga   120
attgttgctg ctttgccaac catcaagtac gttttggaac accacccaag atacgttgtc   180
ttggcttctc acttgggtag accaaacggt gaaagaaacg aaaaatactc tttggctcca   240
gttgctaagg aattgcaatc attgttgggt aaggatgtca ccttcttgaa cgactgtgtc   300
ggtccagaag ttgaagccgc tgtcaaggct tctgccccag ttccgttat tttgttggaa    360
aacttgcgtt accacatcga agaagaaggt tccagaaagg tcgatggtca aaaggtcaag   420
gcttccaagg aagatgttca aaagttcaga cacgaattga gctctttggc tgatgtttac   480
```

| | |
|---|---|
| atcaacgatg ccttcggtac cgctcacaga gctcactctt ctatggtcgg tttcgacttg | 540 |
| ccacaacgtg ctgccggttt cttgttggaa aaggaattga agtacttcgg taaggctttg | 600 |
| gagaacccaa ccagaccatt cttggccatc ttaggtggtg ccaaggttgc tgacaagatt | 660 |
| caattgattg acaacttgtt ggacaaggtc gactctatca tcattggtgg tggtatggct | 720 |
| ttcaccttca agaaggtttt ggaaaacact gaaatcggtg actccatctt cgacaaggct | 780 |
| ggtgctgaaa tcgttccaaa gttgatgaaa aaggccaagg ccaagggtgt cgaagtcgtc | 840 |
| ttgccagtcg acttcatcat tgctgatgct ttctctgctg atgccaacac caagactgtc | 900 |
| actgacaagg aaggtattcc agctggctgg caagggttgg acaatggtcc agaatctaga | 960 |
| aagttgtttg ctgctactgt tgcaaaggct aagaccattg tctggaacgg tccaccaggt | 1020 |
| gttttcgaat cgaaaagtt cgctgctggt actaaggctt tgttagacga agttgtcaag | 1080 |
| agctctgctg ctggtaacac cgtcatcatt ggtggtggtg acactgccac tgtcgctaag | 1140 |
| aagtacggtg tcactgacaa gatctcccat gtctctactg gtggtggtgc ttctttggaa | 1200 |
| ttattggaag gtaaggaatt gccaggtgtt gctttcttat ccgaaaagaa ataa | 1254 |

<210> SEQ ID NO 7
<211> LENGTH: 1554
<212> TYPE: DNA
<213> ORGANISM: Saccharomyces cerevisiae

<400> SEQUENCE: 7

| | |
|---|---|
| atggttttgt ctgataagga gttgtttgcc ataaataaga aagccgtcga acaaggtttc | 60 |
| aatgtgaagc ctagattgaa ctataatacg gtcagtggtg tgaacggtcc attagtcatt | 120 |
| ttggaaaagg tcaagttccc acgttacaac gaaattgtta atttgacatt gccagatgga | 180 |
| accgtgagac aaggtcaagt tttggaaatt agaggagata gagccattgt gcaagtgttt | 240 |
| gaaggtacat ctggtattga tgtcaagaag actaccgtgg aattcactgg tgagagtttg | 300 |
| agaattcctg tgtctgaaga catgttgggt agaattttg acggtctgg tagacccatt | 360 |
| gacaacggtc ctaaagtttt cgcagaggat tacttggaca ttaacggttc tcctatcaac | 420 |
| ccatatgctc gtatttatcc agaagaaatg atttctactg tgtttctgc tattgacaca | 480 |
| atgaactcca ttgccagagg tcaaaagatc ccaattttct ccgcatcagg tttaccacac | 540 |
| aacgaaattg cagcacaaat tgtagacag gctggtttgg tgagacctac caaggatgtt | 600 |
| catgatggtc atgaagaaaa tttctccatc gttttttgctg ccatgggtgt caacttggaa | 660 |
| accgctagat ttttcaaaca ggatttcgaa gaaaatgggt ctttggaaag aacttcatta | 720 |
| tttttgaact tggctaatga ccctaccatt gaaagaatta tcactccaag attggccttg | 780 |
| accaccgctg aataccttgc ttaccaaacg gaacgtcatg tgttgaccat cttgaccgat | 840 |
| atgtcatcgt atgctgatgc tcttagagaa gtttccgctg ctagagaaga agttccaggt | 900 |
| agaagaggtt atcctggtta catgtataca gatttgtcca caattatga agagcaggt | 960 |
| agagtagagg gtcgtaacgg gtccatcact caaataccta tcttgacaat gcctaacgat | 1020 |
| gatattacgc atccaattcc ggatttgacc ggttatatta ccgagggtca atcttcgtt | 1080 |
| gaccgtcaat acataacaa gggtatctac ccaccaatca acgtcttgcc ttcgttgagt | 1140 |
| agattgatga atctgccat cggtgaaggt atgaccagaa aggaccacgg tgacgtttct | 1200 |
| aaccaattgt atgccaagta cgccatcggt aaggacgctg ctgctatgaa ggccgttgtc | 1260 |
| ggtgaagagg cgttatccat cgaagataag ttatctttgg aattttgga aaaattcgaa | 1320 |
| aagacccttta tcacacaagg cgcctacgag gacagaaccg ttttcgaaag tttggaccag | 1380 |

| | | |
|---|---|---|
| gcatggagtt tgctaagaat ctaccctaag gagatgttga atagaatctc cccaaagatt | 1440 | |
| cttgatgaat tttacgatag agccagagac gatgccgacg aagatgaaga agatcccgac | 1500 | |
| acaagaagct ccggtaagaa gaaggacgcc agccaagaag aatctctaat ctaa | 1554 | |

<210> SEQ ID NO 8
<211> LENGTH: 1554
<212> TYPE: DNA
<213> ORGANISM: Artificial
<220> FEATURE:
<223> OTHER INFORMATION: Synthetic

<400> SEQUENCE: 8

| | |
|---|---|
| atggttttgt ctgataagga gttgtttgcc ataaataaaa aagcggtgga acaaggtttc | 60 |
| aatgtgaagc ctagattgaa ctataatacg gtcagtggtg tgaacggtcc attagtcatt | 120 |
| ttggaaaagg ttaagttccc acgttacaac gaaattgtta atttgacatt gccagatgga | 180 |
| accgtgagac aaggtcaagt tttgaaaatt agaggagata gagccattgt gcaagtgttt | 240 |
| gaaggtacat ctggtattga tgtcaagaag actaccgtgg aattcactgg tgagagtttg | 300 |
| agaattcctg tgtctgaaga catgttgggt agaattttg acggttctgg tagacccatt | 360 |
| gacaacggtc ctaaagtttt cgcagaggat tacttggaca ttaacggttc tcctatcaac | 420 |
| ccatatgctc gtatttatcc agaagaaatg atttctactg gtgtttctgc tattgacaca | 480 |
| atgaactcca ttgccagagg tcaaaagatc ccaattttct ccgcatcagg tttaccacac | 540 |
| aacgaaattg cagcacaaat tgtagacag gctggtttgg tgagacctac caaggatgtt | 600 |
| catgatggtc atgaagaaaa tttctccatc gttttgctg ccatgggtgt caacttggaa | 660 |
| accgctagat ttttcaaaca ggatttcgaa gaaaatgggt ctttggaaag aacttcatta | 720 |
| ttttgaact tggctaatga ccctaccatt gaaagaatta tcactccaag attggccttg | 780 |
| accaccgctg aataccttgc ttaccaaacg gaacgtcatg tgttgaccat cttgaccgat | 840 |
| atgtcatcgt atgctgatgc tcttagagaa gtttccgctg ctagagaaga agttccaggt | 900 |
| agaagaggtt atcctggtta catgtataca gatttgtcca caattatga aagagcaggt | 960 |
| agagtagagg gtcgtaacgg gtccatcact caaataccta tcttgacaat gcctaacgat | 1020 |
| gatattacgc atccaattcc ggatttgacc ggttatatta ccgagggtca atcttcgtt | 1080 |
| gaccgtcaat tacataacaa gggtatctac ccaccaatca acgtcttgcc ttcgttgagt | 1140 |
| agattgatga atctgccat cggtgaaggt atgaccagaa aggaccacgg tgacgtttct | 1200 |
| aaccaattgt atgccaagta cgccatcggt aaggacgctg ctgctatgaa ggccgttgtc | 1260 |
| ggtgaagagg cgttatccat cgaagataag ttatctttgg aatttttgga aaaattcgaa | 1320 |
| aagacctta tcacacaagg cgcctacgag gacagaaccg ttttcgaaag tttggaccag | 1380 |
| gcatggagtt tgctaagaat ctaccctaag gagatgttga atagaatctc cccaaagatt | 1440 |
| cttgatgaat tttacgatag agccagagac gatgccgacg aagatgaaga agatcccgac | 1500 |
| acaagaagct ccggtaagaa gaaggacgcc agccaagaag aatctctaat ctaa | 1554 |

<210> SEQ ID NO 9
<211> LENGTH: 4638
<212> TYPE: DNA
<213> ORGANISM: Saccharomyces cerevisiae

<400> SEQUENCE: 9

| | |
|---|---|
| atgactggca tcaaagctca agtccatccc ccacctgata gtaccctatt tcatgaggag | 60 |

```
gagaagaaga aagtaggagg caatttacct caaaaggtca taaatcaaca agaaagtggt    120
tctgatcacg ctccatcggg tcaccatcaa taccaccaac tgattaacca tgacgcaaat    180
gacacaaaga cctcaaattc agtttctgat gtgtctaaag gtcagaaaac tgctgactcc    240
aacccggaag gtaagaaaca gtcatcaaaa gacatatttg ttgcctccag cgctcaaaaa    300
accaatcaat tgcccggtcc caacccacag ggaagcatag gagccgtgcc attggaaggt    360
ttacgtccga aggaattcag atcagcacca tctaggaagc caaataaatt cgacacttcg    420
attactaagc ctggcgtctt agacgactta ggcaaacttg atgaaaagga tattaaggaa    480
aaatttcacc tagattccga cgacaagtta tttccatggc aaaatgttgg tgagttccat    540
gcttcaggaa agggttcgcc aaatacaaag atgtccaggg ttataaaagc ttacattctg    600
gaaaatttt ataacgattg gtactgtaat atagccaccg ttcttggaac ttgtttcttc    660
tcatggttat ttgcttacat tgggttttca tggtggtcta tgatatttat cttcttggga    720
actgcgaccg tttacaacgc agaatataca agattcaaca gaaatatcag agatgacttg    780
aaaagagtta cagtcgaaga aaccttgtcg gatcgcgttg aatccactac gtggttgaat    840
tcatttttat caaaattttg ggtgattgac atgccagttt atctcaaca agtcaaagat    900
aacgttaacc ctcaactggc aggtgttgct ccaggttacg tatcgatgc gttagctatc    960
gatgaattca ctctgggctc taaagctccc accataaaag gtattaaatc gtacaccaag   1020
actggtaaaa acactgttga aatggattgg tcatttgcat tcaccccaag cgatgtctcg   1080
gatatgacag ctactgaagc tagggagaag atcaatccaa aaatatctct gggtgtcacg   1140
ttaggaaaaa gttttgtctc taaaacaatg cctattttgg ttgaagacat taacgttgct   1200
ggtaaaatgc gtattaaagt tgaatttggt aaagctttcc caaatatcaa aattgtttct   1260
ttacaacttt tagaaccacc tttgattgat ttcgcactga aaccaattgg tggtgatact   1320
ttaggtcttg atgttatgtc attcttgcct ggtttgaaga gttttgttaa aaacattatc   1380
aactccaata tagggcctat gctattccct ccgaaccatt tggatattaa tgttgaagac   1440
attatggctg ctcaatcaaa agaagctatt ggtgtccttg ccgtaaccat tgcttctgcc   1500
gactctttga aaggctcaga tttcattacc aatactgtcg atccttatat tgttatgact   1560
accgaagatg ctgtgcctgg tacagatgaa gaagtgcgta catctatcaa atcaaatgtt   1620
aaaaatccac gttggaacga aaccaaatat ctattattaa acaccttaga gcaaaagtta   1680
aacttaaagt gctttgactt caatgatgta agaaaagata ccgtaattgg tgatcttcaa   1740
cttgacttgg cagatttact acaaaaccct gttttggata tcaaactgc tgaattaaga   1800
tccggtacaa aatcaaaagg tattttacat tattccttac actggttccc tgtgaaagaa   1860
gataaatcag aggaaaaagc agttgagcgt gccgaagcta aggccaaggg caagaaagaa   1920
gatgaaaacg aggacactac tgaaaaagaa gaagacgaga tgaagaaag ttctcaaact   1980
gatgtcggga ttgccaagat cactttacaa aaggtcaaat atctggatac aaccagttct   2040
atgaccggta gcttgagccc atgtgctgaa ttattcattg atggacaaaa agtaaagagc   2100
tatagaactt tgagacgtat caatgagcca tcttggaatg agaccatcga gttttggtt   2160
ccatcaaaat ctaactctaa gtttgtccta aaaatattcg atgacagaat gaatggtaag   2220
gcgctgatct gtgagtattc atcttcttta gatgatataa tgactacttt agacactgct   2280
caagagtttg ttaaaggctc accacaaggt gacatttatt tggatgtttc ttggaaatca   2340
attgaaatga ccggagcttt tgccgctgca aactctgtaa gcgaacctat ggttgtatt   2400
aagctagacg ttaaggatgc cattatcaag ggtgactat ccggtgtagg ggatgttgat   2460
```

-continued

```
ccatattaca ccgtatcgtt gaatagacgt gttctttaca agtccatata tcattctgat    2520
acggatcatc ccattttga caacagcacc tacgttccta tcttctctcc aaatcaaatt    2580
ttgactctcg aatttcatga ttatcaaaag atcggcaaag accgtttcat tggctctgta    2640
caaattccta catcaaatgt tttcaaaaaa gatcctaaat caggaaaata tgttgggaat    2700
aatggcaaag aagaaatttc aaaactaaaa ttaaaagacc acgaacacaa agttaccgaa    2760
agcattgtca atgtttcaac aacatttatc ccaatcaatc tggtgtattc ccctgaggag    2820
ttggtgaatg ttgagaaact agaaaaggag ttgaaggaaa agaagaaaaa attcgaagct    2880
acccaagaag aaaacgagca agagatgaaa aaaaatccaa aggaatggga agttgccgag    2940
atcgaagacc catttgacag cgatgaaaaa aaaataaaca ggaaggccaa gttatcttta    3000
aacgagttga tcaagcaaaa atctggtatt ttgtctatgc aaatattgga agggactttg    3060
agcccatcct ctgcttacct agaaatctta gcggatgaca tttcgtaccc tgtattcatt    3120
tgcatgaaac catctcaagg taaactaaac tcggagatgg caaatatttt cattagagat    3180
ttgaattaca gtaaactaca ttttagagta tcgaagaaac atattgccaa agattcagat    3240
gatgtcatat ccgaaacttc ctatagtaca ttgaagctac taaagcaagc ttacgaagag    3300
cccatgtggt taaacttcaa tgggtctaaa atgaaggtaa gattttgta cacgcccact    3360 agcgtgaaac tgcctagcag tgaaagtgtt gaagacactg gttatttgaa tataaagctt    3420
atttccggac acggtctgaa gtccgcagat aggaatggct attcagatcc atttgttcac    3480
atctttgtca atgataaaaa agttttcaaa tcgaacatta aaagaaaac attggatccc    3540 gtatggaacg aagatgctaa ataccaatc ctttcaagaa gtaagaatca agtcatattt    3600
aatgttcttg attgggatcg tgcaggtgat aatgacgact taggccaagc ttcacttgac    3660
gtttcctcat tagaagttgg taaaacttac aactggaatt tgaatttaaa cacacaagga    3720
agtatcaaat tacaaggttc attcaaccca gaatatatca agccaagttt tgatatcgtg    3780
aaaggcggta tcactgataa gccgatgaaa atagccagtg gtgcagccca tgcaactgtt    3840
ggcatagctg gtactggtat aggagcagca acaggagttg ccactggtgg tttaaagaaa    3900
ggtggtcacc ttctaaaatc tctaggtggc aatccaatga aagaagcaa gagcagcaat    3960 ggaaatgagt ccaacggtgc aaaaaaatca tcagagaaaa aatcttttga taggagatcc    4020
ccaagtaatt tgaatagcac tagtgtaaca ccaagagctt cactagacta tgatccatca    4080
gtacctaaca caagttacgc gcccgttcaa agcgcatctc ctgtagtcaa gccaactgac    4140
aacacttcta gctcaagcaa caaaaaagat acccctagta gcaactctag aggacattct    4200
cgtgcaagca gttttgcgcg tactttagct cctcatggca cttacaatgg ttttattacc    4260
gtggttgctg cggaaaacgt tgccaagcat gttcaaatta agatctcttt aactcaaggt    4320
ggtagactaa aacacatata caaaacgaaa agccaaaaag ccaataatga tggtgttgcc    4380
gtatttgatg aagagtgctc gttcaaggct tctcccgaag ccaatttggt actgggtgca    4440
atttcccatc aaagactatc gagggacaaa gatcttggta ttgctcaaat caacttgggt    4500
gaccctcaaa ttcaacaaga tggccaaatt tctgtaaaat taggagacgg tcatctgatt    4560
gtaaagatta ttacggtaa agacaagaat ggtcaggtac ctcccgtgcc agaagttcct    4620
caagaataca cgcagtaa                                                  4638
```

<210> SEQ ID NO 10
<211> LENGTH: 4638
<212> TYPE: DNA

<213> ORGANISM: Artificial
<220> FEATURE:
<223> OTHER INFORMATION: Synthetic

<400> SEQUENCE: 10

```
atgactggca tcaaagctca agtccatccc ccgcctgata gtacactctt tcatgaggag      60
gagaagaaga aagtaggagg caatttacct caaaaggtca taaatcaaca agaaaggggt     120
tctgatcacg ctccatcggg tcaccatcaa taccaccaac tgattaacca tgacgcaaat     180
gacacaaaga cctcaaattc agtttctgat gtgtctaaag gtcagaaaac tgctgactcc     240
aacccggaag gtaagaaaca gtcatcaaaa gacatatttg ttgcctccag cgctcaaaaa     300
accaatcaat tgcccggtcc caacccacag ggaagcatag gagccgtgcc attggaaggt     360
ttacgtccga aggaattcag atcagcacca tctaggaagc caaataaatt cgacacttcg     420
attactaagc ctggcgtctt agacgactta ggcaaacttg atgaaaagga tattaaggaa     480
aaatttcacc tagattccga cgacaagtta tttccatggc aaaatgttgg tgagttccat     540
gcttcaggaa agggttcgcc aaatacaaag atgtccaggg ttataaaagc ttacattctg     600
gaaaatttt ataacgattg gtactgtaat atagccaccg ttcttggaac ttgtttcttc      660
tcatggttat ttgcttacat tgggttttca tggtggtcta tgatatttat cttcttggga     720
actgcgaccg tttacaacgc agaatataca agattcaaca gaaatatcag agatgacttg     780
aaaagagtta cagtcgaaga aaccttgtcg gatcgcgttg aatccactac gtggttgaat     840
tcatttttat caaaattttg ggtgatttac atgccagttt tatctcaaca agtcaaagat     900
aacgttaacc tcaactggc aggtgttgct ccaggttacg gtatcgatgc gttagctatc      960
gatgaattca ctctgggctc taaagctccc accataaaag gtattaaatc gtacaccaag    1020
actggtaaaa acactgttga atggattgg tcatttgcat tcacccccaag cgatgtctcg    1080
gatatgacag ctactgaagc tagggagaag atcaatccaa aaatatctct gggtgtcacg    1140
ttaggaaaaa gttttgtctc taaaacaatg cctattttgg ttgaagacat taacgttgct    1200
ggtaaaatgc gtattaaagt tgaatttggt aaagctttcc caaatatcaa aattgtttct    1260
ttacaacttt tagaaccacc tttgattgat ttcgcactga accaattgg tggtgatact     1320
ttaggtcttg atgttatgtc attcttgcct ggtttgaaga gttttgttaa aacattatc    1380
aactccaata tagggcctat gctattccct ccgaaccatt tggatattaa tgttgaagac    1440
attatggctg ctcaatcaaa agaagctatt ggtgtccttg ccgtaaccat tgcttctgcc    1500
gactctttga aaggctcaga tttcattacc aatactgtcg atccttatat tgttatgact    1560
accgaagatg ctgtgcctgg tacagatgaa gaagtgcgta catctatcaa atcaaatgtt    1620
aaaaatccac gttggaacga aaccaaatat ctattattaa acaccttaga gcaaaagtta    1680
aacttaaagt gctttgactt caatgatgta agaaaagata ccgtaattgg tgatcttcaa    1740
cttgacttgg cagatttact acaaaaccct gttttggata tcaaactgc tgaattaaga    1800
tccggtacaa aatcaaaagg tatttacat tattccttac actggttccc tgtgaaagaa    1860
gataaatcag aggaaaaagc agttgagcgt gccgaagcta aggccaaggg caagaaagaa    1920
gatgaaaacg aggacactac tgaaaaagaa gaagacgaga tgaagaaag ttctcaaact     1980
gatgtcggga ttgccaagat cactttacaa aaggtcaaat atctggatac aaccagttct    2040
atgaccggta gcttgagccc atgtgctgaa ttattcattg atggacaaaa agtaaagagc    2100
tatagaactt tgagacgtat caatgagcca tcttggaatg agaccatcga agttttggtt    2160
ccatcaaaat ctaactctaa gtttgtccta aaaatattcg atgacagaat gaatggtaag    2220
```

```
gcgctgatct gtgagtattc atcttcttta gatgatataa tgactacttt agacactgct   2280
caagagtttg ttaaaggctc accacaaggt gacatttatt tggatgtttc ttggaaatca   2340
attgaaatga ccggagcttt tgccgctgca aactctgtaa gcgaacctat tggttgtatt   2400
aagctagacg ttaaggatgc cattatcaag ggtgacttat ccgtgtagg ggatgttgat    2460 ccatattaca ccgtatcgtt gaatagacgt gttctttaca agtccatata tcattctgat   2520
acggatcatc ccattttga caacagcacc tacgttccta tcttctctcc aaatcaaatt    2580
ttgactctcg aatttcatga ttatcaaaag atcggcaaag accgtttcat tggctctgta   2640
caaattccta catcaaatgt tttcaaaaaa gatcctaaat caggaaaata tgttgggaat   2700
aatggcaaag aagaaatttc aaaactaaaa ttaaaagacc acgaacacaa agttaccgaa   2760
agcattgtca atgtttcaac aacatttatc ccaatcaatc tggtgtattc ccctgaggag   2820
ttggtgaatg ttgagaaact agaaaaggag ttgaaggaaa agaagaaaaa attcgaagct   2880
acccaagaag aaaacgagca agagatgaaa aaaaatccaa aggaatggga agttgccgag   2940
atcgaagacc catttgacag cgatgaaaaa aaaataaaca ggaaggccaa gttatcttta   3000
aacgagttga tcaagcaaaa atctggtatt ttgtctatgc aaatattgga agggactttg   3060
agcccatcct ctgcttacct agaaatctta gcggatgaca tttcgtaccc tgtattcatt   3120
tgcatgaaac catctcaagg taaactaaac tcggagatgg caaatatttt cattagagat   3180
ttgaattaca gtaaactaca ttttagagta tcgaagaaac atattgccaa agattcagat   3240
gatgtcatat ccgaaacttc ctatagtaca ttgaagctac taaagcaagc ttacgaagag   3300
cccatgtggt taaacttcaa tgggtctaaa atgaaggtaa gattttttgta cacgcccact   3360 agcgtgaaac tgcctagcag tgaaagtgtt gaagacactg gttatttgaa tataaagctt   3420
atttccggac acggtctgaa gtccgcagat aggaatggct attcagatcc atttgttcac   3480
atctttgtca atgataaaaa agttttcaaa tcgaacatta aaagaaaac attggatccc   3540 gtatggaacg aagatgctaa ataccaatc cttcaagaa gtaagaatca agtcatattt    3600
aatgttcttg attgggatcg tgcaggtgat aatgacgact taggccaagc ttcacttgac   3660
gtttcctcat tagaagttgg taaaacttac aactggaatt tgaatttaaa cacacaagga   3720
agtatcaaat tacaaggttc attcaaccca gaatatatca agccaagttt tgatatcgtg   3780
aaaggcggta tcactgataa gccgatgaaa atagccagtg gtgcagccca tgcaactgtt   3840
ggcatagctg gtactggtat aggagcagca acaggagttg ccactggtgg tttaaagaaa   3900
ggtggtcacc ttctaaaatc tctaggtggc aatccaatga aaagaagcaa gagcagcaat   3960
ggaaatgagt ccaacggtgc aaaaaaatca tcagagaaaa aatcttttga taggagatcc   4020
ccaagtaatt tgaatagcac tagtgtaaca ccaagagctt cactagacta tgatccatca   4080
gtacctaaca caagttacgc gcccgttcaa agcgcatctc ctgtagtcaa gccaactgac   4140
aacacttcta gctcaagcaa caaaaaagat acccctagta gcaactctag aggacattct   4200
cgtgcaagca gttttgcgcg tactttagct cctcatggca cttacaatgg ttttattacc   4260
gtggttgctg cggaaaacgt tgccaagcat gttcaaatta agatctcttt aactcaaggt   4320
ggtagactaa aacacatata caaaacgaaa agccaaaaag ccaataatga tggtgttgcc   4380
gtatttgatg aagagtgctc gttcaaggct ctcccgaag ccaatttggt actgggtgca    4440
atttcccatc aaagactatc gagggacaaa gatcttggta ttgctcaaat caacttgggt   4500
gaccctcaaa ttcaacaaga tggccaaatt tctgtaaaat taggagacgg tcatctgatt   4560
```

<210> SEQ ID NO 11
<211> LENGTH: 4443
<212> TYPE: DNA
<213> ORGANISM: Saccharomyces cerevisiae

<400> SEQUENCE: 11

```
gtaaagatta attacggtaa agacaagaat ggtcaggtac ctcccgtgcc agaagttcct     4620
caagaataca cgcagtaa                                                    4638 atgtataacc cgtaccagca acagggcatg ggttaccagc agcaacagca gcaacagcag       60
caacaaccaa atggattcta cccgcagcag cagcaaggtc agtcttcaaa ccagccccaa      120
ggccagcctc aaccacaaca gcaaatggcg tttaaccagc ctcaggctac cggaattggt      180
gggatgcctc aaagttttgg taattctttc tcaagtatgc cacagcagcc ccaaacgggt      240
tacaataata atggaaataa tggtagtgta tatggtaatg gtaattttgg ccaacaaccc      300
cagcagcaac aacagcaggc gaaaccgcag catacgggat acgtaccaaa ttccagtatg      360
cctatgatga atactactgg caccatgcct ccacctaatc cggctcaaca gcctcagcta      420
caatccatac aacccaagg aacaggctat taccaagctg ctaatactgc aaatgtacac       480
tcagtacaac ctttgcaatc tcaagggaca ggatatattg tgtctacacc caatttgatc      540
tcttctaatc aaacccagca gcccttcag gcccagggca ctggttatta tcaatctcaa       600
cctcaacagg tgccacctcc tcagcaagca cagtccttgc aacctttgaa gccgcagcaa      660
acaggatttt accttcaacc gcaaaaccaa gctcccttag aaccattaaa gcccaccgca      720
actggctttg tcaactcatt tgccaacaac ggtctaaaca atgatatcaa aatccctgcc      780
attagattgt cgtttattac tgcccaagat caggcaaaat ttgagactct attcagatca      840
attgttacca atggttcgaa tactgttccc ggtgctaatt gtaggaaaat tttgatgaga      900
tccggtttgc caccttctca actcgcaaga atttggacgc tttgtgatac atcaaaagca      960
ggtgagttac tgtttcctga atttgcatta gcaatgcatt tgatcaatga tgtcttacaa     1020
ggtgacacta tcccttacga attggattct aagacaaaaa acgaagtttc aagttttatt     1080
gacgccatta atttaagcat tgcaaaccag gattcttccg caacgatgc cccaaaaact      1140
cccctttgatg aattcattac agcgggcgta caaaatttgc aacctcaacc aacaggatat     1200
atgcctcaaa ctagttttgg tatcccatta cagtctcaaa ttactggagg cggtgttgcc     1260
tcggcgttga atcctcaatc cacaggattt atggcaccaa ccactttcaa catgtcaatg     1320
aataccggaa ctccccggatt gaaccccaa attactggag gagcacctgc ctctatgcaa     1380
cccaacatta ctggcaatgc ttttgcaacct cagacaactg gtatgatgcc acagacaact     1440
ggtatgatgc cacagacaac tggtatgatg ccacagactt catttggcgt taatttagga     1500
cctcagttga ccggcggtgc tttgcaatct cagtataccg gaggatatgg ttccgttatg     1560
cccccagcaaa gcggtcctgc aagtatgccc aatttgtcct ttaatcaaca aggattacaa     1620
tctcagttaa ccggggttgca acccaacca acgggttttc taccaccatc taactttagt     1680
gctaccatgc cgttgactgc ccaaaagaca ggatttggta ataacgaaat ttataccaaa     1740
tccaacttta taataacttt aattgataac tcaagtcaag acaaaatttc cacggaggaa     1800
aaatctttgt tttataaaat ttttgaaact tttgatactc aaaacaaagg tttgttagat     1860
tccccactg ctgtggagat tttagaaaaa tctggcttaa atcgtgcaga tttggagcaa     1920
atttggaacc tttgtgatat aaacaacacc ggccaattga ataacaagaa atttgcacta      1980
ggtatgcact ggtttacgg taaattaaac gggaagccaa tccccaatgt cctaccttca      2040
```

```
agtttaattc cctccagcac aaaacttttta gacaacttaa agaaccaatt aaagacagag    2100
ccaacgacca caaaagaaaa accttcgttt ggtaaaatcg atgccttgag ctacaaaaat    2160
aatgatgatg atgttttgcc gaactataga aatcgtagga aggtttactc tgcgaaaaat    2220
gaagagcaat cttcttttc ttcaccatct gctaaatctg ttaatcattc tagcagcacc    2280
cttcaaaccg atgacatttc ggtagataag actgttgaaa agaagacagc gaaaccaaaa    2340
tatgctgggt tttcaagaga aataaatctg aaaatattg cttcactgga aaatgagatc    2400
aaaaatatca gcaatcctga aaactgttat gacagttcta ttccatcaga tttgacaagc    2460
cgctttgatg ccatcatcgc caaacttcca aacctattca atgaaatttc tacaattgat    2520
aatgagatta ccaatgcaaa aattcagttg tatagaaaaa aaaatccttc ttcgataatt    2580
ggatctggtc caaatggtga aataactgaa atgatagga agaaagctaa gagtagggct    2640
ttgttgagag caaggatgtc tgctctaaca ggaaaatcaa cggaatcgga ggattcactt    2700
tccatggaag atgaacagca aagtgctgaa atcaagagaa tccagcagga aaatggtaag    2760
aaccaagaaa tcattaaaga cataaggtca tctatatcag atatttctgc atccttgaag    2820
tctactatga caggatcgaa tatgatatcc aatcaagaat ttgaaagatg ggaatttggc    2880
ataggggttag aagatggtgt tcgtgaattt ttggatgatc tgaagtcaaa ttcaaataaa    2940
tcagtgactg agtcatctcc ctttgtgcct tcctcaacac caaccctgt agatgaccgt    3000
tcctcgtcgc cttcttattc tcagttcaaa actgctgaag aaagagcagc ttatctgaaa    3060
gaacaggcaa aaaagagaat gaaggaaaaa ttagctaaat ttgataagaa taggcgaaat    3120
gttactcaaa gttccagatc gattagcagt gaaaactctc gagaacagcc acaacagatt    3180
gctggttctt ccaatttagt tgaacctaga gcaactccat tccaagaaga aaaatatgtg    3240
gaagtcgctc aaccaactca acctgttcaa tcaacacaac ctgttcaacc aactcaacct    3300
gttcagccaa ctcaacctgt tcagccaact caacctgttc agccaactca acctgttcaa    3360
ccaactcaac ctgttcagaa tgtatataat gcaaagcaag aatccgatga tgaagatgaa    3420
gatgatgaag aaaagcgttt acaagaggag ctaaaacgat tgaaacttaa aaaaaaggct    3480
gataaagaaa aaagacttgc agctttacgt aagcaaattg aggatgctca aaatgaaagt    3540
gacgaagagg agacaaacgg aaaagacaac tttggcggcc atgtgaacgt tcctcaggcc    3600
gctccagtgg caccatctgc agctttttcg caaaattcta ctaatgctcc tcgctcggta    3660
cacgctgctg ttacccctgc cgcaggtaag aacagtactg gtctgccttc cacgacaatg    3720
ggccataatc catacttcaa ggatgcatca gctagctcta catctacttt cgatgctcgc    3780
gctgcagaaa tgcaaagaag aatccaaaga ggattggatg aggacgagga tgatggatgg    3840
tctgatgaag acgagagtaa taccgcgta gctgtagata ataaggttga agaagcaaag    3900
attggtcatc ctgatcatgc acgtgctcca cctgttactg ctgctccctt gccgtctgtt    3960
accctgttc cacctgctgt ccctgtccct caggcgaata cctctaatga aaagagtagt    4020
cctattccaa tagctccgat accaccttct gttactcagg agccaccgt cccgttggct    4080
cccccttgc ctgctgttga tggctttcaa gaacctccaa ttccctcagc acctgcaata    4140
gctactgccg tgcaaaatc gggttcttcc accccagctt tagctggagg cgttttgcct    4200
ccaccccac ctttaccaac tcaacaagct tccacttcag aacctattat cgctcacgtt    4260
gataactaca atggtgctga aaaaggcacg ggcgcatatg gatccgattc tgatgatgac    4320
gttttatcga ttcctgaatc agttggtaca gatgaagagg aagaagggc acaaccagtt    4380
```

-continued

| tctactgcag gtatcccatc aattccacct gcaggtattc ctccaccccc accccttcca | 4440 |
| tga | 4443 |

<210> SEQ ID NO 12
<211> LENGTH: 4443
<212> TYPE: DNA
<213> ORGANISM: Artificial
<220> FEATURE:
<223> OTHER INFORMATION: Synthetic

<400> SEQUENCE: 12

| atgtataacc cgtaccagca acagggcatg gggtatcagc agcaacagca gcaacagcag | 60 |
| caacaaccaa atggattcta ccgcagcag cagcaaggtc agtcttcaaa ccagccccaa | 120 |
| ggccagcctc aaccacaaca gcaaatggcg tttaaccagc tcaggctac cggaattggt | 180 |
| gggatgcctc aaagttttgg taattctttc tcaagtatgc cacagcagcc ccaaacgggt | 240 |
| tacaataata atggaaataa tggtagtgta tatggtaatg gtaattttgg ccaacaaccc | 300 |
| cagcagcaac aacagcaggc gaaaccgcag catacgggat acgtaccaaa ttccagtatg | 360 |
| cctatgatga atactactgg caccatgcct ccacctaatc cggctcaaca gcctcagcta | 420 |
| caatccatac aaccccaagg aacaggctat taccaagctg ctaatactgc aaatgtacac | 480 |
| tcagtacaac cttttgcaatc tcaagggaca ggatattatg tgtctacacc caatttgatc | 540 |
| tcttctaatc aaacccagca gccccttcag gcccagggca ctggttatta tcaatctcaa | 600 |
| cctcaacagg tgccacctcc tcagcaagca cagtccttgc aacctttgaa gccgcagcaa | 660 |
| acaggatttt accttcaacc gcaaaaccaa gctcccttag aaccattaaa gcccaccgca | 720 |
| actggctttg tcaactcatt tgccaacaac ggtctaaaca atgatatcaa aatccctgcc | 780 |
| attagattgt cgtttattac tgcccaagat caggcaaaat ttgagactct attcagatca | 840 |
| attgttacca atggttcgaa tactgtttcc ggtgctaatt gtaggaaaat tttgatgaga | 900 |
| tccggtttgc caccttctca actcgcaaga atttggacgc tttgtgatac atcaaaagca | 960 |
| ggtgagttac tgtttcctga atttgcatta gcaatgcatt tgatcaatga tgtcttacaa | 1020 |
| ggtgacacta tcccttacga attggattct aagacaaaaa acgaagtttc aagtttttatt | 1080 |
| gacgccatta atttaagcat tgcaaaccag gattcttccg caaacgatgc cccaaaaact | 1140 |
| cccctttgatg aattcattac agcgggcgta caaaatttgc aacctcaacc aacaggatat | 1200 |
| atgcctcaaa ctagttttgg tatcccatta cagtctcaaa ttactggagg cggtgttgcc | 1260 |
| tcggcgttga atcctcaatc cacaggattt atggcaccaa ccacttttcaa catgtcaatg | 1320 |
| aataccggaa ctcccggatt gaaccccaa attactggag gagcacctgc ctctatgcaa | 1380 |
| cccaacatta ctggcaatgc tttgcaacct cagacaactg gtatgatgcc acagacaact | 1440 |
| ggtatgatgc cacagacaac tggtatgatg ccacagactt catttggcgt taatttagga | 1500 |
| cctcagttga ccggcggtgc tttgcaatct cagtataccg gaggatatgg ttccgttatg | 1560 |
| ccccagcaaa gcggtcctgc aagtatgccc aatttgtcct ttaatcaaca aggattacaa | 1620 |
| tctcagttaa ccgggttgca accccaacca acgggttttc taccaccatc taactttagt | 1680 |
| gctaccatgc cgttgactgc ccaaaagaca ggatttggta ataacgaaat ttataccaaa | 1740 |
| tccaacttta ataataactt aattgataac tcaagtcaag acaaaatttc cacggaggaa | 1800 |
| aaatctttgt tttataaaat ttttgaaact tttgatactc aaaacaaagg tttgttagat | 1860 |
| tccccccactg ctgtggagat ttttagaaaa tctggcttaa atcgtgcaga tttggagcaa | 1920 |
| atttggaacc tttgtgatat aaacaacacc ggccaattga ataaacaaga atttgcacta | 1980 |

```
ggtatgcact tggtttacgg taaattaaac gggaagccaa tccccaatgt cctaccttca    2040
agtttaattc cctccagcac aaaactttta gacaacttaa agaaccaatt aaagacagag    2100
ccaacgacca caaagaaaaa accttcgttt ggtaaaatcg atgccttgag ctacaaaaat    2160
aatgatgatg atgttttgcc gaactataga aatcgtagga aggtttactc tgcgaaaaat    2220
gaagagcaat cttctttttc ttcaccatct gctaaatctg ttaatcattc tagcagcacc    2280
cttcaaaccg atgacatttc ggtagataag actgttgaaa agaagacagc gaaaccaaaa    2340
tatgctgggt tttcaagaga aataaatctg aaaaatattg cttcactgga aaatgagatc    2400
aaaaatatca gcaatcctga aaactgttat gacagttcta ttccatcaga tttgacaagc    2460
cgctttgatg ccatcatcgc caaacttcca aacctattca atgaaatttc tacaattgat    2520
aatgagatta ccaatgcaaa aattcagttg tatagaaaaa aaaatccttc ttcgataatt    2580
ggatctggtc caaatggtga ataactgaa aatgatagga agaaagctaa gagtagggct     2640
ttgttgagag caaggatgtc tgctctaaca ggaaaatcaa cggaatcgga ggattcactt    2700
tccatggaag atgaacagca aagtgctgaa atcaagagaa tccagcagga aaatggtaag    2760
aaccaagaaa tcattaaaga cataaggtca tctatatcag atatttctgc atccttgaag    2820
tctactatga caggatcgaa tatgatatcc aatcaagaat ttgaaagatg ggaatttggc    2880
atagggttag aagatggtgt tcgtgaattt ttggatgatc tgaagtcaaa ttcaaataaa    2940
tcagtgactg agtcatctcc ctttgtgcct tcctcaacac caaccctgt agatgaccgt     3000 tcctcgtcgc cttcttattc tcagttcaaa actgctgaag aaagagcagc ttatctgaaa    3060
gaacaggcaa aaagagaat gaaggaaaaa ttagctaaat ttgataagaa taggcgaaat     3120
gttactcaaa gttccagatc gattagcagt gaaaactctc gagaacagcc acaacagatt    3180
gctggttctt ccaatttagt tgaacctaga gcaactccat tccaagaaga aaaatatgtg    3240
gaagtcgctc aaccaactca acctgttcaa tcaacacaac ctgttcaacc aactcaacct    3300
gttcagccaa ctcaacctgt tcagccaact caacctgttc agccaactca acctgttcaa    3360
ccaactcaac tgttcagaa tgtatataat gcaaagcaag aatccgatga tgaagatgaa    3420
gatgatgaag aaaagcgttt acaagaggag ctaaaacgat tgaaacttaa aaaaaaggct    3480
gataaagaaa aaagacttgc agctttacgt aagcaaattg aggatgctca aaatgaaagt    3540
gacgaagagg agacaaacgg aaaagacaac tttggcggcc atgtgaacgt tcctcaggcc    3600
gctccagtgg caccatctgc agcttttcg caaaattcta ctaatgctcc tcgctcggta     3660
cacgctgctg ttaccctgc cgcaggtaag aacagtactg gtctgccttc cacgacaatg     3720
ggccataatc catacttcaa ggatgcatca gctagctcta catctacttt cgatgctcgc    3780
gctgcagaaa tgcaaagaag aatccaaaga ggattggatg aggacgagga tgatggatgg    3840
tctgatgaag acgagagtaa taaccgcgta gctgtagata taaggttga agaagcaaag     3900 attggtcatc ctgatcatgc acgtgctcca cctgttactg ctgctccctt gccgtctgtt    3960 accccctgttc cacctgctgt ccctgtccct caggcgaata cctctaatga aaagagtagt    4020
cctattccaa tagctccgat accaccttct gttactcagg agccaccgt cccgttggct     4080 cccccttttgc ctgctgttga tggctttcaa gaacctccaa ttccctcagc acctgcaata    4140
gctactgccg tgcaaaaatc gggttcttcc accccagctt tagctggagg cgttttgcct    4200 ccaccccac ctttaccaac tcaacaagct tccacttcag aacctattat cgctcacgtt      4260
gataactaca atggtgctga aaaaggcacg ggcgcatatg gatccgattc tgatgatgac    4320
```

```
gttttatcga ttcctgaatc agttggtaca gatgaagagg aagaaggggc acaaccagtt    4380
tctactgcag gtatcccatc aattccacct gcaggtattc ctccaccccc acccttcca    4440 tga                                                                 4443

<210> SEQ ID NO 13
<211> LENGTH: 17
<212> TYPE: DNA
<213> ORGANISM: Artificial
<220> FEATURE:
<223> OTHER INFORMATION: Synthetic

<400> SEQUENCE: 13
ctgtaggcac catcaat                                                    17
```

METHODS FOR MODIFYING THE GROWTH RATE OF A CELL

FIELD OF INVENTION

The present invention is directed to the field of genome and growth rate optimization.

BACKGROUND OF THE INVENTION

Amplifying protein production of a heterologous gene is an important biotechnological objective, which translates into considerable economic consequences. However, the flip side is ensuring the survival and proper function of the host, as the heterologous gene sequesters cellular resources necessary for the cell's fitness (and homeostasis), which have been evolutionarily optimized. When a heterologous gene is introduced, it increases the existing competition for the cell's finite resources, and specifically the gene expression machinery, with translation consuming most (up to 75%) of the cellular energy. This impacts the host's physiology, via a noticeable effect of carrying and replicating the heterologous gene, which may interrupt local replicon structures modifying neighboring genes' expression, obstruct other host biomolecules, and compete for cellular resources. It was shown, for example, that optimizing the coding region of a heterologous gene (which competes for the rate limiting free ribosomes) causes a decrease in the translation rate of other genes, which in turn affects the organism's fitness and may reduce the number of functional ribosomes in the cell. Put more basically, excess translation of one gene can reduce the translation rates of other genes. As the host fitness decreases due to overall decreased protein synthesis, the production rate of the heterologous gene also decreases. This can occur to the point of halting cell growth entirely.

One of the crucial aspects affecting protein production in all organisms is the availability of ribosomes, and the addition of a heterologous gene adds further strain on this resource. It has been experimentally shown that ribosomes have a decisive influence on cell growth, and are the rate limiting resource, as ribosomes participate in many biosynthetic activities during exponential growth. Substantial experimental evidence exists, including the linear relation between growth rate and ribosome concentration, and direct observations indicate that the availability of free ribosomes limits overall protein synthesis.

Current approaches to host modification for improved heterologous protein expression, often include introducing/removing genetic material, such as gene knockouts, or expanding the intracellular tRNA pool of the host by over-expressing genes encoding the rarer tRNAs. However, these methods have several drawbacks, most notably the disruption of the regular interplay between cellular components, for example the metabolic effects of changing the tRNA concentrations of a cell and the potential induction of an immune response in vertebrates as a result of under-acetylated tRNA. A method of improving the available ribosome pool without these drawbacks, and thus improving the fitness of an organism, is thus very much needed.

SUMMARY OF THE INVENTION

The present invention provides genetically modified cells with at least one synonymous mutation that modifies the replicative fitness of the cell, wherein a mutation to a slower translating codon increases replicative fitness and a mutation to a faster translating codon decreases replicative fitness. Pharmaceutical compositions comprising a cell of the invention as well as methods of modifying the replicative fitness of a cell are also provided.

According to a first aspect, there is provided a genetically modified cell, wherein at least one coding sequence of the cell's genome comprises at least one codon substituted to a synonymous codon, the synonymous codon translating at a different rate than the at least one codon, wherein the genetically modified cell comprises a modified replicative fitness as compared to an unmodified form of the cell, and wherein a slower translating synonymous codon increases replicative fitness of the modified cell and a faster translating synonymous codon decreases replicative fitness in the modified cell.

According to another aspect, there is provided a vaccine composition comprising, a modified cell of the invention and a pharmaceutically acceptable carrier, excipient or adjuvant, wherein the modified cell comprises a faster translating synonymous codon and the modified cell comprises decreased replicative fitness According to another aspect, there is provided a method for modifying replicative fitness in a cell, comprising introducing at least one synonymous mutation into at least one sequence of the cell's genome, wherein the mutation modifies a free pool of a cellular resource that limits the rate of a cellular process, and wherein a mutation to a slower translating synonymous codon increases replicative fitness in the cell and a mutation to a faster translating synonymous codon decreases replicative fitness in the cell.

According to another aspect, there is provided a method of modifying replicative fitness in a cell, the method comprising modifying ribosome density upstream of a ribosome backup on at least one translating sequence in the cell, wherein increasing ribosome density decreases replicative fitness and decreasing ribosome density increased replicative fitness.

According to some embodiments, the at least one codon substituted to a synonymous codon is located upstream of a predetermined slowly translating codon. According to some embodiments, the synonymous mutation is introduced into a coding region upstream of a predetermined slowly translating codon. According to some embodiments, the synonymous codon is the slowest or fastest translating synonymous codon of said at least one codon. According to some embodiments, the synonymous mutation is a mutation to the codon's slowest or fastest translating synonymous codon.

According to some embodiments, the at least one codon substituted to a synonymous codon is located within codons 11 to 50 from the translational start site of the coding sequence. According to some embodiments, the mutation is introduced into codons 11 to 50 of a coding region.

According to some embodiments, increased replicative fitness comprises an increased free ribosome pool and decreased replicative fitness comprises a decreased free ribosome pool.

According to some embodiments, the synonymous codon is the slowest or fastest translating synonymous codon of the at least one codon.

According to some embodiments, the at least one codon substituted to a synonymous codon does not decrease the translation efficiency of the coding sequence by more than a predetermined threshold. According to some embodiments, the introducing does not decrease the translation efficiency of the coding sequence by more than a predetermined threshold. According to some embodiments, the threshold is at most a 5% reduction in translation efficiency.

According to some embodiments, the cell is a eukaryotic cell or a prokaryotic cell.

According to some embodiments, the cell further comprises a heterologous transgene, the synonymous codon is a slower translating codon and wherein replicative fitness in the modified cell is equal to or greater than replicative fitness in the cell devoid of the heterologous transgene and the at least one synonymous mutation. According to some embodiments, the the cell further comprises a heterologous transgene, the synonymous mutation is to a slower translating codon and wherein replicative fitness in the modified cell is equal to or greater than replicative fitness in the cell devoid of the heterologous transgene and the at least one mutation.

According to some embodiments, the cellular resource is selected from ribosomes, tRNAs, polymerases, transcription factors, elongation factors, and splicing factors and the cellular process is transcription or translation.

According to some embodiments, the method of the invention further comprises determining whether a synonymous mutation would reduce translation efficiency below the threshold, and wherein the determining comprises any one of a Forward Gene Minimization (FGM), Backward Gene Minimization (BGM) and Greedy Gene Minimization (GGM) algorithm.

According to some embodiments, the free ribosome pool is increased by at least 10%.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Left: The genetic code with per synonymous codons relative speeds (see Materials and Methods for calculation details) based on the real *S. cerevisiae* genome, the darkest red signifies the fastest relative codon while the darkest green the slowest. Right: An illustration of the ramp, depicting the benefit of assisting in ribosomal allocation. (FIG. 1B). An illustration of the translation simulation before optimization (where in the first iteration of the approach the first gene will be selected to be optimized, see 1C.), with l denoting the ribosome length, $m_i$ per gene mRNA levels, $α_i$ transcript specific initiation rates, $γ_{cj}$ codon specific elongation rates. (FIG. 1C). An illustration of the translation simulation after the first iteration where the first gene was optimized, as illustrated all the codons viable for modification were converted to their slowest synonymous codon. As can be seen as a result of the modifications the number of ribosomes on the first gene is reduced and the free ribosome pool increases.

(FIGS. 2A-2B) Line charts showing the free ribosomal pool steadily increases with each newly modified gene, for (FIG. 2A) *S. cerevisiae* and (FIG. 2B) *E. coli* respectively. (FIGS. 2C-2D) Line charts showing the number of mutations for each newly modified gene, for (FIG. 2C) *S. cerevisiae* and (FIG. 2D) *E. coli* respectively. The baseline free ribosomal pool of *S. cerevisiae* is 30000 and of *E. coli* is 5600 ribosomes. The FGM algorithm was performed for 100 genes, with 11 translation efficiency (TE) constraints.

(FIG. 3A-3B) Line charts showing the free ribosomal pool steadily increases with each newly modified gene, for (FIG. 3A) *S. cerevisiae* and (FIG. 3B) *E. coli* respectively. (FIG. 3C-3D) Line charts showing the number of mutations for each newly modified gene, for (FIG. 3C) *S. cerevisiae* and (FIG. 3D) *E. coli* respectively. The baseline free ribosomal pool of *S. cerevisiae* is 30000 ribosomes and of *E. coli* is 5600 ribosomes. The BGM algorithm was performed for 100 genes, with 11 TE constraints.

(FIGS. 4A-4B) Line charts showing the free ribosomal pool steadily increases with each newly modified gene, for (FIG. 4A) *S. cerevisiae* and (FIG. 4B) *E. coli* respectively. (FIGS. 4C-4D) Line charts showing the number of mutations for each newly modified gene, for (FIG. 4C) *S. cerevisiae* and (FIG. 4D) *E. coli* respectively. The baseline free ribosomal pool of *S. cerevisiae* is 30000 ribosomes and of *E. coli* is 5600 ribosomes. The GGM algorithm was performed for 100 genes, with 11 TE constraints.

FIGS. 5A-5K: *S. cerevisiae* FGM algorithm ribosomal density profiles for the first 3 modified gene per translation efficiency (TE) constraint before and after mutations, results incorporate the effect of the first 100 mutated genes, mRNA levels as percentage of all genes is indicated, as well as each genes contribution to the free ribosome pool (FRC). (FIG. 5A). TE reduction of 0.1%. (FIG. 5B). TE reduction of 0.5%. (FIG. 5C). TE reduction of 1%. (FIG. 5D). TE reduction of 1.5%. (FIG. 5E). TE reduction of 2%. (FIG. 5F). TE reduction of 2.5%. (FIG. 5G). TE reduction of 3%. (FIG. 5H). TE reduction of 3.5%. (FIG. 5I). TE reduction of 4%. (FIG. 5J). TE reduction of 4.5%. (FIG. 5K). TE reduction of 5%

(FIG. 6A). TE reduction of 0.1%. (FIG. 6B). TE reduction of 0.5%. (FIG. 6C). TE reduction of 1%. (FIG. 6D). TE reduction of 1.5%. (FIG. 6E). TE reduction of 2%. (FIG. 6F). TE reduction of 2.5%. (FIG. 6G). TE reduction of 3%. (FIG. 6H). TE reduction of 3.5%. (FIG. 6I). TE reduction of 4%. (FIG. 6J). TE reduction of 4.5%. (FIG. 6K). TE reduction of 5%.

FIGS. 7A-7K: *S. cerevisiae* GGM algorithm ribosomal density profiles for the first 3 modified gene per translation efficiency (TE) constraint before and after mutations, results incorporate the effect of the first 100 mutated genes, mRNA levels as percentage of all genes is indicated, as well as each genes contribution to the free ribosome pool (FRC). (FIG. 7A). TE reduction of 0.1%. (FIG. 7B). TE reduction of 0.5%. (FIG. 7C). TE reduction of 1%. (FIG. 7D). TE reduction of 1.5%. (FIG. 7E). TE reduction of 2%. (FIG. 7F). TE reduction of 2.5%. (FIG. 7G). TE reduction of 3%. (FIG. 7H). TE reduction of 3.5%. (FIG. 7I). TE reduction of 4%. (FIG. 7J). TE reduction of 4.5%. (FIG. 7K(. TE reduction of 5%.

8A). TE reduction of 0.1%. (FIG. 8B). TE reduction of 0.5%. (FIG. 8C). TE reduction of 1%. (FIG. 8D). TE reduction of 1.5%. (FIG. 8E). TE reduction of 2%. (FIG. 8F). TE reduction of 2.5%. (FIG. 8G). TE reduction of 3%. (FIG. 8H). TE reduction of 3.5%. (FIG. 8I). TE reduction of 4%. (FIG. 8J). TE reduction of 4.5%. (FIG. 8K). TE reduction of 5%.

(FIG. 9A). TE reduction of 0.1%. (FIG. 9B). TE reduction of 0.5%. (FIG. 9C). TE reduction of 1%. (FIG. 9D). TE reduction of 1.5%. (FIG. 9E). TE reduction of 2%. (FIG. 9F). TE reduction of 2.5%. (FIG. 9G). TE reduction of 3%. (FIG. 9H). TE reduction of 3.5%. (FIG. 9I). TE reduction of 4%. (FIG. 9J). TE reduction of 4.5%. (FIG. 9K). TE reduction of 5%.

FIGS. 10A-10K: *E. coli* GGM algorithm ribosomal density profiles for the first 3 modified gene per translation efficiency (TE) constraint before and after mutations, results incorporate the effect of the first 100 mutated genes, mRNA levels as percentage of all genes is indicated, as well as each genes contribution to the free ribosome pool (FRC). (FIG. 10A). TE reduction of 0.1%. (FIG. 10B). TE reduction of 0.5%. (FIG. 10C). TE reduction of 1%. (FIG. 10D). TE reduction of 1.5%. (FIG. 10E). TE reduction of 2%. (FIG. 10F). TE reduction of 2.5%. (FIG. 10G). TE reduction of 3%. (FIG. 10H). TE reduction of 3.5%. (FIG. 10I). TE reduction of 4%. (FIG. 10J). TE reduction of 4.5%. (FIG. 10K). TE reduction of 5%.

(FIG. 11A) A line graph showing the growth curves of WT and mutated strains of *S. cerevisiae*. (FIG. 11B) A photograph of the results of a competition assay between a strain mutated in the VMA2 gene (left dish) and a WT strain (right dish). The mutant strain showed 4 times the number of cells after competition.

DETAILED DESCRIPTION OF THE INVENTION

Figure 1A:
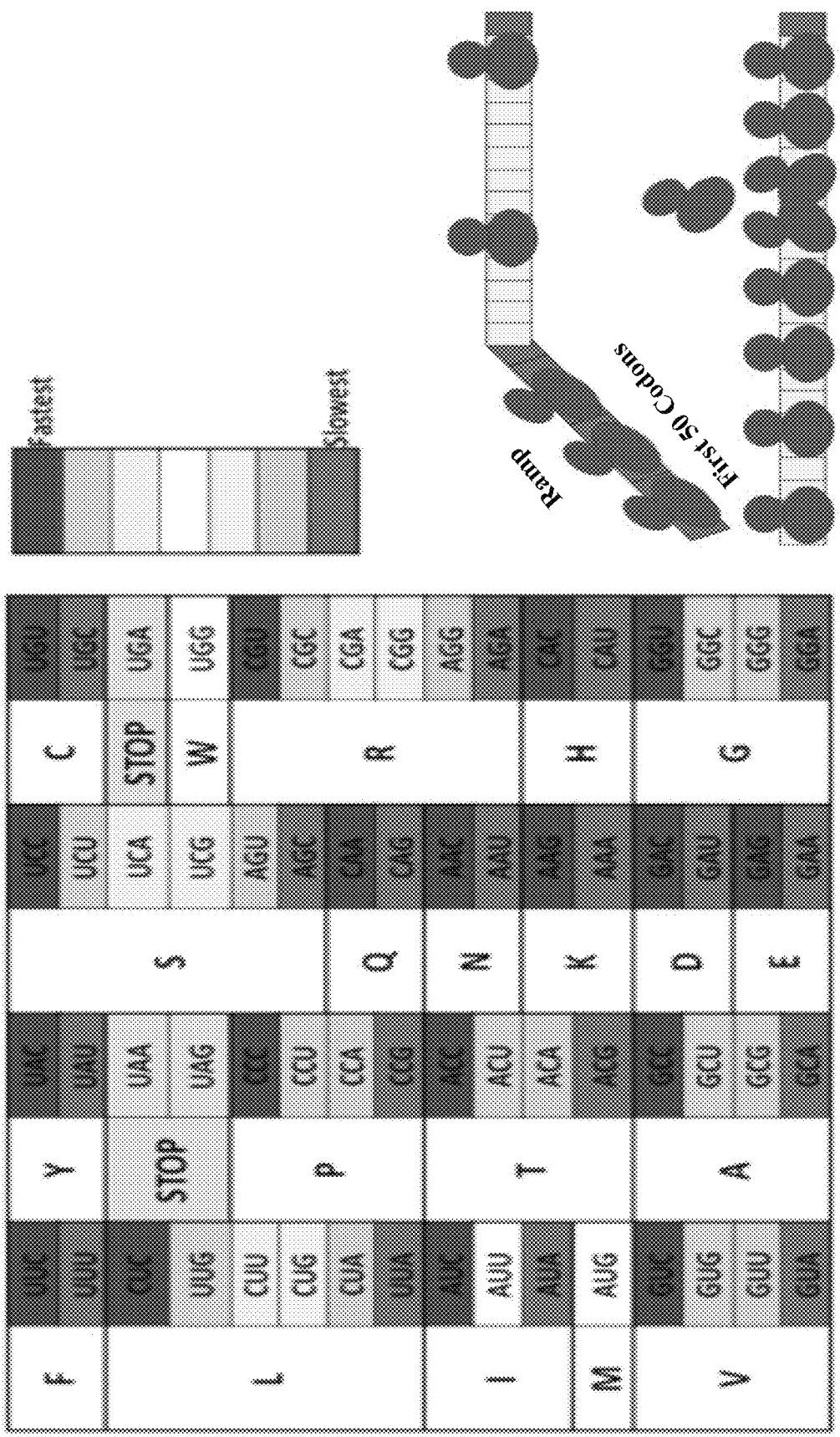
FIGS. 1A-1C.

The present invention provides, in some embodiments, isolated genetically modified cells with at least one codon substituted to a synonymous codon translating at a different rate, and with modified replicative fitness as compared to the unmodified cells, wherein a slower translating synonymous codon increases replicative fitness and a faster translating codon decreased replicative fitness. Vaccine compositions comprising the cells with decreased replicative fitness, as well as methods for modifying replicative fitness of a cell are also provided.

The invention is based on the surprising finding that introduction of synonymous codons with faster and slower translation rates can have an inverse effect on cell fitness from what would be expected. That is introduction of slower translating codons can increase cellular fitness, while introduction of faster translating codons can decrease cellular fitness. This is due to the fact that the free ribosome pool is rate limiting for a cell's global translation. Said differently, when the free ribosome pool is increased the cell can globally translate faster and thus is healthier, whereas when the pool is shrunk the cell's translation is slowed and the cell is less healthy.

One might have assumed that decreasing the translation rate of a codon would decrease translation output and thus would attenuated the cell's health. However, the invention is based, at least in part, on the fact that during translation there are often ribosome backups or traffic jams which create wasted ribosomes that are slowed down by the backup and not translating efficiently. These backups occur when there is a downstream slowly translating codon and upstream codons must stall/wait for this codon to be translated. Decreasing translation rate early in the coding region has the effect of decreasing the traffic headed into the jammed area, and thus decreasing the number of stalled/waiting/wasted ribosomes. The inventors have shown herein, that decreasing the translation rate of early codons can limit the number of wasted ribosomes, while having very limited effects on overall translation output for that protein. With fewer wasted ribosomes sitting and waiting for the ribosomes ahead to translate, the free pool is increased, and the overall fitness is increased, without a significant loss in the translation of the modified sequence. Stated simply, the inventors have found an unexpected inverse correlation between ribosome density upstream of a ribosome backup and replicative fitness.

By one aspect, the present invention concerns a genetically modified cell, wherein at least one coding sequence of the cell's genome comprises, at least one codon substituted to a synonymous codon, the synonymous codon being a slower translating codon than the at least one codon, and wherein the genetically modified cell has an increased replicative fitness as compared to an unmodified form of the same cell.

By another aspect, the present invention concerns a genetically modified cell, wherein at least one coding sequence of the cell's genome comprises, at least one codon substituted to a synonymous codon, the synonymous codon being a faster translating codon than the at least one codon, and wherein the genetically modified cell has a decreased replicative fitness as compared to an unmodified form of the same cell.

By another aspect, the present invention concerns a genetically modified cell, wherein at least one coding sequence of the cell's genome comprises at least one codon substituted to a synonymous codon, the synonymous codon translating at a different rate than the at least one codon, wherein the genetically modified cell comprises a modified replicative fitness as compared to an unmodified form of the cell, and wherein a slower translating synonymous codon increases replicative fitness of the modified cell and a faster translating synonymous codon decreases replicative fitness in the modified cell.

By another aspect, the present invention concerns an isolated genetically modified organism, wherein at least one coding sequence of the organism's genome comprises, at least one codon substituted to a synonymous codon, and wherein the genetically modified organism has a modified replicative fitness as compared to an unmodified form of the same organism.

By another aspect, there is provided a method for increasing replicative fitness in a cell, comprising introducing at least one mutation into at least one sequence of the cell's genome, wherein the mutation increases a free pool of a limited cellular resource in the cell.

By another aspect, there is provided a method for decreasing replicative fitness in a cell, comprising introducing at least one mutation into at least one sequence of the cell's genome, wherein the mutation decreases a free pool of a limited cellular resource in the cell.

By another aspect, there is provided a method for modifying replicative fitness in a cell, the method comprising introducing at least one synonymous mutation into at least one sequence of the cells genome, wherein the mutation modified a free pool of a cellular resource that limits the rate of a cellular process and wherein a mutation to a slower translating synonymous codon increases replicative fitness in the cell and a mutation to a faster translating synonymous codon decreases replicative fitness in the cell.

By another aspect, there is provided a method for modifying replicative fitness in an organism, comprising introducing at least one mutation into at least one sequence of said organism's genome, wherein said mutation modifies a free pool of a limited cellular resource.

By another aspect, there is provided a method for increasing replicative fitness in a cell, comprising introducing at least one synonymous mutation into at least one coding sequence of the cell's genome, wherein the mutation increases a free ribosome pool in the cell.

By another aspect, there is provided a method for decreasing replicative fitness in a cell, comprising introducing at least one synonymous mutation into at least one coding sequence of the cell's genome, wherein the mutation decreases a free ribosome pool in the cell.

By another aspect, there is provided a method for modifying replicative fitness in a cell, the method comprising modifying the free ribosome pool in a cell, wherein increasing the free ribosome pool increases replicative fitness and decreasing the free ribosome pool decreases replicative fitness.

By another aspect, there is provided a method of modifying replicative fitness in a cell, the method comprising increasing or decreasing an amount of ribosomes on at least one translating sequence in the cell, wherein the amount of ribosomes are translating at a rate dependent on downstream ribosomes translating a slowly translating codon.

By another aspect, there is provided a method of modifying replicative fitness in a cell, the method comprising modifying ribosome density upstream of a ribosome backup on at least one translating sequence in the cell, wherein increasing ribosome density decreases replicative fitness in the cell and decreasing ribosome density increases replicative fitness in the cell.

In some embodiments, the cell is prokaryotic cell. In some embodiments, the cell is a fungal cell. In some embodiments, the cell is a bacterial cell. In some embodiments, the cell is an archaeal cell. In some embodiments, the cell is a eukaryotic cell. In some embodiments, the cell is a plant cell. In some embodiments, the cell is a mammalian cell. In some embodiments, the cell is a human cell. In some embodiments, the cell is in culture. In some embodiments, the cell is in vivo. In some embodiments, the cell is a disease cell. In some embodiments, the cell has a reduced replicative fitness. In some embodiments, the cell is a stem cell. In some embodiments, the cell comprises a heterologous transgene or a heterologous gene.

In some embodiments, the cell is an organism. In some embodiments, the organism is a single celled organism, a multi-celled organism or a virus. In some embodiments, the organism is a prokaryote. In some embodiments, the cell is a eukaryote. In some embodiments, the single celled organism is selected from the group consisting of: a bacterium, a fungus, a protozoon, an archaeon and an alga. In some embodiments, the multi-celled organism is a plant. In some embodiments, the multi-celled organism is a mammal. In some embodiments, the virus is a virulent or a non-virulent virus. In some embodiments, the virus is a human virus. In some embodiments, the organism comprises a heterologous transgene, or a heterologous gene. In some embodiments, the cell comprises a heterologous transgene, or a heterologous gene. In some embodiments, the cell or organism expresses a heterologous transgene, or a heterologous gene.

In some embodiments, the mutation it is a silent mutation. In some embodiments of the methods of the invention, the mutation is a synonymous mutation. In some embodiments, the mutation does not alter protein function. In some embodiments, the mutation alters protein function. In some embodiments, the mutation alters protein localization. In some embodiments, the mutation alters transcription rate. In some embodiments, the mutation alters translation rate. In some embodiments, the mutation alters a protein binding site. In some embodiments, the protein binding site is a transcription factor binding site.

In some embodiments of the methods of the invention, the sequence is a coding sequence. In some embodiments, the sequence is a regulatory sequence. In some embodiments, the regulatory sequence is selected from a promoter, a 3' UTR or a 5'UTR. In some embodiments, the sequence is an intronic sequence.

As used herein, the term "coding sequence" refers to a nucleic acid sequence that when translated results in an expressed protein. In some embodiments, the coding sequence is to be used as a basis for making codon alterations. In some embodiments, the coding sequence is a gene. In some embodiments, the coding sequence is a viral gene. In some embodiments, the coding sequence is a bacterial gene. In some embodiments, the coding sequence is a mammalian gene. In some embodiments, the coding sequence is a human gene. In some embodiments, the coding sequence is a portion of one of the above listed genes. In some embodiments, the coding sequence is a heterologous transgene. In some embodiments, the above listed genes are wild type, endogenously expressed genes. In some embodiments, the above listed genes have been genetically modified or in some way altered from their endogenous formulation. These alterations may be changes to the coding region such that the protein the gene codes for is altered.

The term "heterologous transgene" as used herein refers to a gene that originated in one species and is being expressed in another. In some embodiments, the transgene is a part of a gene originating in another organism. In some embodiments, the heterologous transgene is a gene to be overexpressed. In some embodiments, expression of the heterologous transgene in a wild-type cell reduces global translation in the wild-type cell.

In some embodiments, expression of the heterologous transgene in a wild-type cell reduces global translation efficiency in the wild-type cell. In some embodiments, expression of the heterologous transgene in a genetically modified cell of the invention reduces global translation as compared to a wild-type cell. In some embodiments, expression of the heterologous transgene in a genetically modified cell of the invention reduces global translation efficiency less than in a wild-type cell. In some embodiments, expression of the heterologous transgene in a genetically modified cell of the invention does not reduce global translation efficiency in the modified cell. In some embodiments, the replicative fitness of the modified cell comprising a heterologous transgene is equal to or greater than replicative fitness in the cell devoid of the heterologous transgene and the at least one mutation. In some embodiments the reduction in the wild-type cell is at least 5, 10, 15, 20, 25, 30, 35, 40, 45, or 50%. Each possibility represents a separate embodiment of the invention. In some embodiments, the reduction in the modified cell is at most 1, 2, 3, 5, 10, 15, 20, 25 or 30%. Each possibility represents a separate embodiment of the invention. It will be understood by one skilled in the art, that introduction of a heterologous transgene which is actively transcribed puts a greater strain on the cell by using up more of the free resources. Specifically, by using up free ribosomes transgenes have been known to decrease global translation rates. By first introducing a synonymous mutation that increases the free ribosome pool, the modified cell is better equipped to deal with the demands of the transgene.

The term "codon" refers to a sequence of three DNA or RNA nucleotides that correspond to a specific amino acid or stop signal during protein synthesis. The codon code is degenerate, in that more than one codon can code for the same amino acid. Such codons that code for the same amino acid are known as "synonymous" codons. Thus, for example, CUU, CUC, CUA, CUG, UUA, and UUG are synonymous codons that code for Leucine. Synonymous codons are not used with equal frequency. In general, the most frequently used codons in a particular cell are those for which the cognate tRNA is abundant, and the use of these codons enhances the rate of protein translation. Conversely, tRNAs for rarely used codons are found at relatively low levels, and the use of rare codons is thought to reduce translation rate. Thus, codon translation rate can be calculated for a cell or organism based on the abundancy of each cognate tRNA. "Codon bias" as used herein refers generally to the non-equal usage of the various synonymous codons, and specifically to the relative frequency at which a given synonymous codon is used in a defined sequence or set of sequences.

As used herein, the term "silent mutation" refers to a mutation that does not affect or has little effect on protein functionality. A silent mutation can be a synonymous mutation and therefore not change the amino acids at all, or a silent mutation can change an amino acid to another amino acid with the same functionality or structure, thereby having no or a limited effect on protein functionality.

Synonymous codons are provided in FIG. 1A. A heat map of the relative rates of translation of the codons in *S. cerevisiae* is provided, wherein the darker the red coloring the faster the codon is translated and the darker the green coloring the slower the codon is translated. Methods of measuring abundance of tRNAs and other relevant factors and elongation rates in a cell of organism are well known in the art. In some embodiments, the synonymous codon is the slowest translating synonymous codon of said at least one codon.

As used herein the term "replicative fitness" refers to the health of a cell or organism as measured by its capacity to divide and its speed of cellular division. In some embodiments, modifying replicative fitness is increasing or decreasing replicative fitness. In some embodiments, modifying is increasing or decreasing. In some embodiments, greater replicative fitness comprises a shorter doubling time of a dividing cell or single celled organism. In some embodiments, greater replicative fitness comprises a faster rate of cellular division. In some embodiments, greater replicative fitness comprises an increased free pool of a cellular resource. In some embodiments, greater replicative fitness comprises an increased free ribosome pool. In some embodiments, greater replicative fitness comprises an increased free RNA polymerase (RNAP) pool. In some embodiments, the replicative fitness is fitness when competing against another organism or cell. In some embodiments, the replicative fitness is fitness when under a stress. In some embodiments, the replicative fitness is fitness when increased protein production is required for cell survival. In some embodiments, increased or decreased fitness is increased or decreased survival under a stress.

The term "cellular resource" as used herein refers to any substance, nucleic acid, protein, organelle, lipid, metabolite or carbohydrate that a cell requires for optimal function. One skilled in the art will understand that a cellular resource can be abundant or limited. The limited availability of a cellular resource may be a common trait in all biology, such as the limited availability of ribosomes and RNAP in all known cell types and species or may be limited only in certain circumstances or in certain cells. In some embodiments, the cellular resource limits the rate of a cellular process. In some embodiments, the resource is the rate limiting resource. In some embodiments, a cellular resource is selected from the group consisting of: organelles, nucleic acids, proteins, lipids, metabolites, splicing factors and carbohydrates. In some embodiments, the organelle is a ribosome. In some embodiments, a cellular resource is selected from ribosomes, tRNAs, polymerases, transcription factors and elongation factors. In some embodiments, a cellular resource is selected from ribosomes, tRNAs, polymerases, transcription factors and elongation factors and the cellular process is transcription or translation. In some embodiments, the nucleic acid is a tRNA. In some embodiments, the protein is an enzyme. In some embodiments, the enzyme is a polymerase. In some embodiments, the polymerase is RNA polymerase (RNAP). In some embodiments, the protein is a transcription factor or an elongation factor. In some embodiments, the cellular resource is selected from: ribosomes, tRNAs, polymerases, enzymes, transcription factors and elongation factors. In some embodiments, the cellular resource is ribosomes. In some embodiments, the cellular resource is free ribosomes.

As used herein, the term "cellular process" refers to a process that occurs in the cell that the cell requires for optimal function. In some embodiments, a cellular process has a rate limiting step or resource that control the rate of the process. Examples of cellular processes include transcription, translation, metabolism, catabolism, respiration and molecular transport. In some embodiments, the cellular process is transcription, translation or both. In some embodiments, the cellular process is translation. In some embodiments, the cellular process is translational elongation.

In some embodiments, the replicative fitness of the modified cell or organism is at least 5%, 10%, 20%, 30%, 40%, 50%, 60%, 70%, 80%, 90%, 100%, 150%, 200%, 250%, 300%, 350%, 400%, 450% or 500% greater than the replicative fitness of the unmodified form of the same organism. Each possibility represents a separate embodiment of the invention. In some embodiments, the pool of free ribosomes is increased by at least 5%, 10%, 20%, 30%, 40%, 50%, 60%, 70%, 80%, 90%, 100%, 150%, 200%, 250%, 300%, 350%, 400%, 450% or 500% as compared to the pool in the unmodified form of the same organism. Each possibility represents a separate embodiment of the invention.

In some embodiments, the at least one codon substituted to a synonymous codon or the synonymous mutation is located upstream of a predetermined slowly translated codon. Predetermined slowly translated codons can be found by examining a gene body and identifying codons with rare tRNA cognates. Further slowly translated codons can be predetermined based on the ribosome density, as described herein below. In some embodiments, the amount of ribosomes on a translating sequence is ribosome density. In some embodiments, a method of the invention comprises altering ribosome density on at least one translating sequence. In some embodiments, the ribosome density is altered upstream of a slowly translating codon. In some embodiments, the amount of ribosomes to be altered (increased or decreased) are translated at a slowed rate. In some embodiments, the amount of ribosomes to be altered are translating at a decreased rate. In some embodiments, the amount of ribosomes to be altered are translating at a suboptimal rate. In some embodiments, the amount of ribosomes to be altered are translating at a rate below what is possible based on the codons the ribosomes are translating. In some embodiments, the amount of ribosomes to be altered are translating at a rate that is dependent on downstream translation. In some embodiments, the amount of ribosomes to be altered are translating at a rate that is dependent on a downstream ribosome backup. In some embodiments, the amount of ribosomes to be altered are translating at a rate that is dependent on downstream ribosomes translation rates. In some embodiments, the downstream translation rates are slow due to a slowly translating codon.

In some embodiments, the at least one codon substituted to a synonymous codon or the synonymous mutation is located upstream of a ribosome backup or traffic jam. As used herein, a "ribosome traffic jam" or "ribosome backup" refers to a region on a currently translating mRNA in which the ribosome density is greatly increased as compared to the ribosome density after the region. In some embodiments, the density in the traffic jam region is at least 5%, 10%, 20%, 30%, 40%, 50%, 60%, 70%, 80%, 90%, 100%, 150%, 200%, 250%, 300%, 350%, 400%, 450% or 500% more than the density after the region. Each possibility represents a separate embodiment of the invention. Calculating ribosome density is known in the art and can be achieved by assays such as, but not limited to, ribosome profiling and ribosome foot-printing. In some embodiments, the synonymous mutation or modification of ribosome density occurs upstream of a ribosome backup.

In some embodiments, the synonymous mutation substitutes a codon for a slower translating synonymous codon. In some embodiments, the synonymous mutation substitutes a codon for its slowest translating synonymous codon. In some embodiments, the synonymous mutation alleviates a ribosome backup. In some embodiments, the synonymous mutation generates a more uniform translational elongation rate. In some embodiments, the synonymous mutation generates a more uniform ribosome progression rate in the coding sequence.

In some embodiments, the synonymous mutation substitutes a codon for a faster translating synonymous codon. In some embodiments, the synonymous mutation substitutes a codon for its fastest translating synonymous codon. In some embodiments, the synonymous mutation increases a ribosome backup. In some embodiments, the synonymous mutation increases the number of ribosome with a slower than optimal translation rate.

In some embodiments, the at least one codon substituted to a synonymous codon or the synonymous mutation is located within codons 11 to 50 from the translational start site of the coding sequence. One skilled in the art will be familiar with codon numbering in a coding sequence. The first three bases of the open reading frame (generally ATG) will be numbered codon 1, and the next three bases codon 2 and so on, until the stop translation codon. The first about 50 codons in a coding sequence are herein referred to as the ramp region or just the ramp. In some embodiments, the at least one codon substituted to a synonymous codon or the synonymous mutation is located within the ramp of the coding sequence. In some embodiments, the ramp is the first 50, 55, 60, 65, 70, 75, 80, 85, 90, 95 or 100 codons. Each possibility represents a separate embodiment of the invention.

The first about 10 codons of a coding sequence may contain important regulatory information, and thus mutations and substitutions should be avoided in this region. In some embodiments, the at least one codon substituted to a synonymous codon or the synonymous mutation is located within codons 6-100, 11-100, 16-100, 6-95, 11-95, 16-95, 6-90, 11-90, 16-90, 6-85, 11-85, 16-85, 6-80, 11-80, 16-80, 6-75, 11-75, 16-75, 6-70, 11-70, 16-70, 6-65, 11-65, 16-65, 6-60, 11-60, 16-60, 6-55, 11-65, 16-65, 6-50, 11-50, 16-50, 6-45, 11-45, or 16-45 from the translational start site of the coding sequence.

In some embodiments, at least one coding sequences of the cell's genome comprises at least one codon substituted to a synonymous codon. In some embodiments, at least 5, 10, 15, 20, 25, 30, 35, 40, 45, 50, 55, 60, 65, 70, 75, 80, 85, 90, 95, 100, 125, 150, 175, 200, 250, 300, 350, 400, 450, or 500 sequences of the cell's genome comprise at least one codon substituted to a synonymous codon. Each possibility represents a separate embodiment of the invention. In some embodiments, every coding sequence of the cell's genome comprises at least one codon substituted to a synonymous codon. In some embodiments, at least 100 coding sequences of the cell's genome comprise at least one codon substituted to a synonymous codon.

In some embodiments, the mutation is introduced into a coding region. In some embodiments, the mutation is introduced into a coding region that comprises a slowly translating codon. In some embodiments, the mutation is introduced into a coding region upstream of a predetermined slowly translating codon. In some embodiments, the slowly translating codon is not in the first 10, 20, 30, 40, 50, 60, 70, 80, 90 or 100 codons. Each possibility represents a separate embodiment of the invention.

In some embodiments, at least one synonymous mutation is introduced into at least 1, 5, 10, 15, 20, 25, 30, 35, 40, 45, 50, 55, 60, 65, 70, 75, 80, 85, 90, 95, or 100 sequences of the cell's genome. Each possibility represents a separate embodiment of the invention. In some embodiments, at least one synonymous mutation is introduced into at least 100 coding sequences.

In some embodiments, at least one coding sequences of the cell's genome comprises at least 1, 2, 3, 5, 10, 15, 20, 25, 30, 35, 40, 45, or 50 codons substituted to a synonymous codon. Each possibility represents a separate embodiment of the invention. In some embodiments, at least one 1, 2, 3, 5, 10, 15, 20, 25, 30, 35, 40, 45, or 50 synonymous mutations are introduced at least one coding sequence. Each possibility represents a separate embodiment of the invention.

In some embodiments, the at least one codon substituted to a synonymous codon or a synonymous mutation does not decrease the translation efficiency (TE) by more than a predetermined threshold. In some embodiments, the at least one codon substituted to a synonymous codon or a synonymous mutation does not decrease the translation rate by more than a predetermined threshold. In some embodiments, the translational efficiency and/or translational rate is of the coding sequence. In some embodiments, the translational efficiency and/or translational rate is global TE or translational rate. In some embodiments, the expressing of the coding sequence is not decreased by more than a predetermined threshold. A predetermined threshold can be established as described herein. Any threshold wherein the reduction of protein expression does not compromise the fitness of the cell or organism is acceptable. In some embodiments, the threshold is selected from: a 5% reduction, a 4.5% reduction, a 4% reduction, a 3.5% reduction, a 3% reduction, a 2.5% reduction, a 2% reduction, a 1.5% reduction, a 1% reduction, a 0.5% reduction and a 0.1% reduction in translation efficiency. In some embodiments, the threshold is a 5% reduction in translation efficiency. In some embodiments, the threshold is not more than a 5% reduction, a 4.5% reduction, a 4% reduction, a 3.5% reduction, a 3% reduction, a 2.5% reduction, a 2% reduction, a 1.5% reduction, a 1% reduction, a 0.5% reduction and a 0.1% reduction in translation efficiency. In some embodiments, the threshold is not more than a 5% reduction.

In some embodiments, all codons whose substitution to a synonymous codon would not reduce translation efficiency below the threshold, have been substituted to a synonymous codon. In some embodiments, a synonymous mutation is introduced into all codons that would not reduce translation efficiency below said threshold. It will be understood to one of skill in the art that many combinations of substitutions or mutations can be employed to increase replicative fitness that will also result in a reduction in TE that is below the threshold. All combinations that remain below the threshold are contemplated by this invention. Determination of which substitutions or mutations to make can be achieved using any algorithm that picks substitutions that increase replicative fitness while staying below the threshold. Examples of such algorithms can be found herein below and include FGM, BGM and GGM.

In some embodiments, the cell is an *S. cerevisiae* cell and the coding sequence is selected from at least one of the following genes: RPO21, PGK1, CYS4, VMA2, TCB3 and PAN1.

In some embodiments, the coding sequence of CYS4 comprises the following sequence:

(SEQ ID NO: 1)
ATGACTAAATCTGAGCAGCAAGCCGATTCAAGACATAACGTTATCGACTT

AGTTGGTAACACCCCATTGATCGCACTGAAAAAATTGCCTAAGGCTTTGG

GTATCAAACCACAAATTTATGCTAAGCTGGAACTATACAATCCAGGTGGT

TCCATCAAAGACAGAATTGCCAAGTCTATGGTGGAAGAAGCTGAAGCTTC

CGGTAGAATTCATCCTTCCAGATCTACTCTGATCGAACCTACTTCTGGTA

ACACCGGTATCGGTCTAGCTTTAATCGGCGCCATCAAAGGTTACAGAACT

ATCATCACCTTGCCGGAAAAAATGTCTAACGAGAAAGTTTCTGTCCTAAA

GGCTCTGGGTGCTGAAATCATCAGAACTCCAACTGCTGCTGCCTGGGATT

CTCCAGAATCACATATTGGTGTTGCTAAGAAGTTGGAAAAAGAGATTCCT

GGTGCTGTTATACTTGACCAATATAACAATATGATGAACCCAGAAGCTCA

TTACTTTGGTACTGGTCGCGAAATCCAAAGACAGCTAGAAGACTTGAATT

TATTTGATAATCTACGCGCTGTTGTTGCTGGTGCTGGTACTGGTGGGACT

ATTAGCGGTATTTCCAAGTACTTGAAAGAACAGAATGATAAGATCCAAAT

CGTTGGTGCTGACCCATTCGGTTCAATTTTAGCCCAACCTGAAAACTTGA

ATAAGACTGATATCACTGACTACAAAGTTGAGGGTATTGGTTATGATTTT

GTTCCTCAGGTTTTGGACAGAAAATTAATTGATGTTTGGTATAAGACAGA

CGACAAGCCTTCTTTCAAATACGCCAGACAATTGATTTCTAACGAAGGTG

TCTTGGTGGGTGGTTCTTCCGGTTCTGCCTTCACTGCGGTTGTGAAATAC

TGTGAAGACCACCCTGAACTGACTGAAGATGATGTCATTGTTGCCATATT

CCCAGATTCCATCAGGTCGTACCTAACCAAATTCGTCGATGACGAATGGT

TGAAAAAGAACAATTTGTGGGATGATGACGTGTTGGCCCGTTTTGACTCT

TCAAAGCTGGAGGCTTCGACGACAAAATACGCTGATGTGTTTGGTAACGC

TACTGTAAAGGATCTTCACTTGAAACCGGTTGTTTCCGTTAAGGAAACCG

CTAAGGTCACTGATGTTATCAAGATATTAAAAUACAATGGCTTTGACCAA

TTGCCTGTGTTGACTGAAGACGGCAAGTTGTCTGGTTTAGTTACTCTCTC

TGAGCTTCTAAGAAAACTATCAATCAATAATTCAAACAACGACAACACTA

TAAAGGGTAAATACTTGGACTTCAAGAAATTAAACAATTTCAATGATGTT

TCCTCTTACAACGAAAATAAATCCGGTAAGAAGAAGTTTATTAAATTCGA

TGAAAACTCAAAGCTATCTGACTTGAATCGTTTCTTTGAAAAAAACTCAT

CTGCCGTTATCACTGATGGCTTGAAACCAATCCATATCGTTACTAAGATG

GATTTACTGAGCTACTTAGCATAA.

In some embodiments, the mutated coding sequence of CYS4 comprises the following sequence:

(SEQ ID NO: 2)
ATGACTAAATCTGAGCAGCAAGCCGATTCACGGCATAACGTTATAGACTT

AGTTGGGAACACGCCGTTGATCGCTCTGAAAAAATTGCCTAAGGCTTTGG

GTATCAAACCACAAATTTATGCTAAGCTGGAGCTATACAATCCAGGTGGT

TCCATCAAAGACAGAATTGCCAAGTCTATGGTGGAAGAAGCTGAAGCTTC

CGGTAGAATTCATCCTTCCAGATCTACTCTGATCGAACCTACTTCTGGTA

ACACCGGTATCGGTCTAGCTTTAATCGGCGCCATCAAAGGTTACAGAACT

ATCATCACCTTGCCGGAAAAAATGTCTAACGAGAAAGTTTCTGTCCTAAA

GGCTCTGGGTGCTGAAATCATCAGAACTCCAACTGCTGCTGCCTGGGATT

CTCCAGAATCACATATTGGTGTTGCTAAGAAGTTGGAAAAAGAGATTCCT

GGTGCTGTTATACTTGACCAATATAACAATATGATGAACCCAGAAGCTCA

TTACTTTGGTACTGGTCGCGAAATCCAAAGACAGCTAGAAGACTTGAATT

TATTTGATAATCTACGCGCTGTTGTTGCTGGTGCTGGTACTGGTGGGACT

ATTAGCGGTATTTCCAAGTACTTGAAAGAACAGAATGATAAGATCCAAAT

CGTTGGTGCTGACCCATTCGGTTCAATTTTAGCCCAACCTGAAAACTTGA

ATAAGACTGATATCACTGACTACAAAGTTGAGGGTATTGGTTATGATTTT

GTTCCTCAGGTTTTGGACAGAAAATTAATTGATGTTTGGTATAAGACAGA

CGACAAGCCTTCTTTCAAATACGCCAGACAATTGATTTCTAACGAAGGTG

TCTTGGTGGGTGGTTCTTCCGGTTCTGCCTTCACTGCGGTTGTGAAATAC

TGTGAAGACCACCCTGAACTGACTGAAGATGATGTCATTGTTGCCATATT

CCCAGATTCCATCAGGTCGTACCTAACCAAATTCGTCGATGACGAATGGT

TGAAAAAGAACAATTTGTGGGATGATGACGTGTTGGCCCGTTTTGACTCT

TCAAAGCTGGAGGCTTCGACGACAAAATACGCTGATGTGTTTGGTAACGC

TACTGTAAAGGATCTTCACTTGAAACCGGTTGTTTCCGTTAAGGAAACCG

CTAAGGTCACTGATGTTATCAAGATATTAAAAGACAATGGCTTTGACCAA

TTGCCTGTGTTGACTGAAGACGGCAAGTTGTCTGGTTTAGTTACTCTCTC

TGAGCTTCTAAGAAAACTATCAATCAATAATTCAAACAACGACAACACTA

TAAAGGGTAAATACTTGGACTTCAAGAAATTAAACAATTTCAATGATGTT

TCCTCTTACAACGAAAATAAATCCGGTAAGAAGAAGTTTATTAAATTCGA

TGAAAACTCAAAGCTATCTGACTTGAATCGTTTCTTTGAAAAAAACTCAT

CTGCCGTTATCACTGATGGCTTGAAACCAATCCATATCGTTACTAAGATG

GATTTACTGAGCTACT
TAGCATAA.

In some embodiments, the coding sequence of RPO21 comprises the following sequence:

(SEQ ID NO: 3)
ATGGTAGGACAACAGTATTCTAGTGCTCCACTC<u>CGT</u>ACAGTAAAAGAG<u>GT</u>

<u>C</u>CAATTC<u>GGT</u>CTTTTCTCACCT<u>GA</u>AGAAGTT<u>AGA</u>GCA<u>AT</u>CAGTGTG<u>G</u>CCG

<u>CC</u>AAAATTAGATTTCCAGAGACAATGGATGAAACCCAGACGAGAGCGAAA

ATTGGTGGTCTAAACGACCCTAGGTTAGGCTCTATTGATCGTAATCTGAA

GTGTCAAACTTGTCAAGAGGGTATGAACGAATGTCCTGGTCATTTTGGTC

ACATAGATTTAGCAAAACCTGTATTTCATGTTGGTTTTATTGCCAAAATT

AAGAAAGTATGTGAGTGTGTCTGTATGCACTGTGGTAAGCTATTACTGGA

TGAACATAATGAATTAATGAGACAAGCTCTAGCAATCAAAGACAGTAAAA

AAAGGTTTGCTGCAATTTGGACTTTATGTAAAACAAAAATGGTCTGCGAA

ACAGATGTCCCTTCTGAAGATGATCCTACTCAGCTCGTATCAAGGGGAGG

TTGTGGTAATACACAGCCTACAATTCGTAAGGATGGGTTGAAATTAGTTG

GTAGTTGGAAAAAGATAGAGCCACGGGGGATGCGGATGAACCAGAACTA

AGAGTTTTAAGTACGGAGGAAATCTTGAATATTTTTAAGCATATCTCAGT

AAAAGACTTCACTAGTTTGGGTTTCAACGAAGTTTTTTCTCGTCCAGAAT

GGATGATTTTAACATGCCITCCTGTCCCACCACCACCGGTGCGTCCATCC

ATTTCCTTCAATGAATCTCAAAGAGGTGAGGATGATTTAACCTTTAAACT

TGCTGATATTTTAAAAGCTAATATTAGTTTGGAAACACTAGAGCATAACG

GTGCTCCACATCATGCTATTGAAGAAGCAGAGAGTTTATTACAATTTCAT

GTTGCCACTTATATGGATAATGATATTGCTGGTCAACCACAAGCTCTTCA

AAAGTCCGGCCGTCCCGTTAAATCTATTCGTGCTCGTTTGAAGGGTAAAG

AGGGTCGTATCAGAGGTAATTTAATGGGTAAGCGTGTGGATTTTTCGGCA

GAACTGTTATTTCTGGTGATCCTAATTTGGAATTAGACCAAGTCGGTGT

TCCAAAATCTATTGCCAAGACTTTAACATACCCAGAAGTGGTCACACCAT

ATAACATAGATCGTCTGACGCAACTTGTTAGGAATGGACCAAATGAGCAC

CCCGGTGCCAAATACGTCATTCGTGATAGCGGAGACCGTATAGATTTAAG

ATACAGTAAAAGGGCAGGTGATATTCAATTACAGTATGGGTGGAAAGTTG

AACGTCATATTATGGACAATGATCCAGTTIATTCAACCGTCAACCTTCG

TTGCACAAAATGTCCATGATGGCCCACAGAGTAAAAGTTATTCCATATTC

TACATTTAGATTGAATTTGTCCGTTACATCTCCATACAATGCCGATTTCG

ACGGTGACGAAATGAATCTTCACGTTCCTCAGTCTGAGGAAACAAGGGCG

GAACTTTCTCAATTATGTGCTGTTCCTCTGCAAATTGTTTCACCACAATC

TAACAAACCTTGTATGGGTATTGTTCAAGATACTTTGTGTGGTATTCGTA

AACTGACATTAAGAGATACATTTATAGAACTTGATCAAGTTTTGAATATG

CTTTATTGGGTTCCAGATTGGGATGGTGTTATTCCGACACCTGCAATTAT

CAAGCCCAAACCTTTGTGGTCCGGTAAACAAATCTTGTCTGTGGCTATCC

CAAACGGTATTCATTTACAACGTTTTGATGAGGGCACTACTCTGCTTTCT

CCAAAGGATAATGGTATGCTTATTATTGACGGTCAAATCATTTTTGGTGT

AGTAGAGAAAAAAACCGTTGGTTCCTCCAATGGTGGTTTAATTCATGTTG

TTACGAGAGAAAAGGGACCTCAAGTTTGTGCTAAGTTGTTTGGTAACATA

CAGAAAGTTGTTAACTTTTGGTTACTACATAATGGGTTTTCAACAGGTAT

TGGTGATACCATTGCGGACGGCCCAACAATGAGGGAAATTACAGAGACAA

TTGCAGAGGCTAAAAGAAAGTTTTGGATGTTACGAAAGAAGCCCAGGCA

AACTTATTGACTGCTAAACATGGTATGACTCTCCGTGAGTCTTTTGAGGA

TAACGTTGTTCGGTTCCTAAATGAAGCAAGAGATAAGGCAGGTCGTTTAG

CTGAAGTCAATTTGAAAGATTTGAACAATGTGAAACAAATGGTTATGGCA

GGTTCCAAGGGGTTCATTTATTAATATCGCGCAAATGTCAGCTTGTGTAGG

ACAGCAATCTGTTGAAGGTAAACGTATTGCTTTTGGGTTCGTTGATCGTA

CCTTACCTCATTTCTCTAAAGATGATTACTCCCCAGAGTCTAAAGGTTTT

GTTGAGAACTCATATTTGAGAGGTTTGACCCCACAAGAATTTTTTTCCA

TGCAATGGGTGGTCGTGAAGGTCTTATCGATACCGCCGTCAAAACAGCCG

AAACAGGTTATATTCAACGTCGTTTAGTGAAAGCTCTAGAAGATATCATG

GTTCATTACGATAACACCACAAGAAACTCATTGGGTAACGTTATTCAGTT

TATTTATGGTGAAGATGGTATGGATGCTGCGCATATTGAAAAGCAATCGC

TAGATACTATTGGTGGCTCCGATGCAGCTTTTGAAAAGAGATACAGAGTT

GATTTATTGAATACAGACCATACCCTTGATCCCTCACTATTGGAATCCGG

ATCTGAGATACTTGGCGATTTGAAACTTCAAGTTCTCCTGGATGAAGAAT

ACAAACAATTAGTGAAAGATCGTAAATTTTTGAGGGAAGTTTTTGTTGAT

GGTGAAGCAAACTGGCCATTACCAGTCAACATAAGACGTATTATTCAAAA

TGCTCAACAAACTTTCCACATAGATCATACGAAACCATCTGATTTAACAA

TCAAAGACATCGTTCTTGGTGTAAAGGATTTGCAAGAAAACTTATTAGTG

TTGCGTGGTAAGAATGAAATTATACAAAATGCCCAGCGAGATGCAGTTAC

ATTGTTCTGCTGTTTATTACGTTCCCGTTTGGCCACACGTAGAGTTCTAC

AAGAGTACAGACTAACAAAACAGGCATTCGATTGGGTATTAAGTAATATC

GAGGCACAATTCCTCCGTTCTGTTGTTCACCCTGGTGAAATGGTTGGTGT

TCTAGCAGCCCAATCCATTGGTGAACCAGCCACACAAATGACCCTTAACA

CCTTCCATTTTGCTGGTGTTGCTTCCAAAAAAGTTACTTCTGGTGTCCCC

CGTTTAAAGGAAATTTTGAATGTGGCCAAAAACATGAAACCCCTTCCTT

GACTGTATACTTAGAGCCTGGTCATGCTGCCGATCAAGAACAAGCGAAGT

TGATCAGATCTGCTATCGAGCATACCACTTTAAAGAGTGTCACTATTGCT

TCAGAAATTTACTATGATCCTGATCCACGTTCCACAGTTATTCCAGAAGA

TGAAGAAATTATCCAACTTCATTTCTCATTATTGGATGAAGAGGCTGAAC

```
AATCTTTTGACCAACAATCACCTTGGTTATTACGTCTGGAACTGGATCGT
GCAGCAATGAATGATAAAGACTTAACAATGGGTCAGGTTGGTGAAAGAAT
CAAGCAAACATTCAAAAATGATTTGTTTGTTATCTGGTCTGAAGACAACG
ATGAGAAGTTGATCATCCGTTGTCGTGTTGTTCGTCCAAAGTCACTAGAT
GCTGAGACTGAAGCAGAAGAAGATCATATGTTGAAGAAAATTGAGAACAC
AATGTTAGAGAATATTACATTACGTGGTGTAGAGAACATCGAGCGTGTTG
TCATGATGAAATATGACCGTAAAGTACCAAGTCCAACTGGTGAATACGTT
AAGGAACCTGAATGGGTGTTGGAAACAGATGGTGTTAACTTATCTGAAGT
TATGACTGTTCCTGGTATCGACCCAACCAGAATCTATACCAACTCCTTCA
TTGATATAATGGAAGTTCTAGGTATTGAAGCTGGTCGTCAGCCTTGTAT
AAAGAAGTTTACAATGTTATTGCTTCTGATGGTTCGTATGTTAACTACCG
TCATATGGCTTTGTTAGTCGATGTTATGACAACCCAAGGTGGCTTAACTT
CTGTTACTCGTCATGGTTICAACAGATCAAATACAGGTGCCTTAATGAGA
TGTTCATTTGAAGAAACTGTCGAAATTTTGTTTGAAGCTGGTGCTTCAGC
CGAATTAGATGATTGTCGTGGTGTTTCGGAAAATGTCATTCTTGGTCAAA
TGGCTCCAATCGGTACCGGTGCATTTGATGTGATGATCGATGAGGAGTCA
CTGGTAAAATACATGCCAGAACAAAAAATAACTGAGATTGAAGACGGACA
AGATGGTGGCGTCACACCATACAGTAACGAAAGTGGTTTGGTCAATGCAG
ATCTTGACGTTAAAGATGAGCTAATGTTTTCACCTCTGGTTGATTCGGGT
TCAAATGACGCTATGGCTGGAGGATTTACAGCGTACGGTGGTGCTGATTA
TGGTGAAGCCACGTCTCCATTTGGTGCTTATGGTGAAGCACCTACATCTC
CCGGATTTGGAGTCTCCTCACCAGGCTTTTCTCCAACTTCCCCAACATAC
TCTCCTACCTCTCCAGCGTACTCACCAACATCACCATCGTACTCACCAAC
ATCACCATCGTACTCGCCAACATCACCATCGTACTCACCTACATCACCAT
CGTATTCACCAACGTCACCATCATATTCGCCAACGTCACCATCATATTCG
CCAACGTCGCCATCGTATTCTCCAACGTCACCATCGTATTCGCCAACGTC
GCCTTCCTACTCTCCCACGTCGCCAAGCTACAGCCCTACGTCTCCTTCTT
ATTCTCCTACATCTCCATCATACTCTCCTACGTCACCAAGTTACAGCCCA
ACGTCACCAAGTTACAGCCCAACGTCTCCAGCCTATTCCCCAACATCACC
AAGTTATAGTCCTACATCGCCTTCATACTCTCCAACATCACCATCCTATT
CCCCAACATCACCTTCTTACTCTCCCACCTCTCCAAACTATAGCCCTACT
TCACCTTCTTACTCCCCAACATCTCCAGGCTACAGCCCAGGATCTCCTGC
ATATTCTCCAAAGCAAGACGAACAAAAGCATAATGAAAATGAAAATTCCA
GATGA.
```

In some embodiments, the mutated coding sequence of RPO2 1 comprises the following sequence:

```
                                        (SEQ ID NO: 4)
ATGGTAGGACAACAGTATTCTAGTGCTCCACTCCGAACAGTAAAAGAGGT

TCAATTCGGGCTTTTCTCACCTGAGGAAGTTCGTGCAATAAGTGTGGCAG

CAAAAATTAGATTTCCAGAGACAATGGATGAAACCCAGACGAGAGCGAAA

ATTGGTGGTCTAAACGACCCTAGGTTAGGCTCTATTGATCGTAATCTGAA

GTGTCAAACTTGTCAAGAGGGTATGAACGAATGTCCTGGTCATTTGGTC

ACATAGATTTAGCAAAACCTGTATTTCATGTTGGTTTTATTGCCAAAATT

AAGAAAGTATGTGAGTGTGTCTGTATGCACTGTGGTAAGCTATTACTGGA

TGAACATAATGAATTAATGAGACAAGCTCTAGCAATCAAAGACAGTAAAA

AAAGGTTTGCTGCAATTTGGACTTTATGTAAAACAAAAATGGTCTGCGAA

ACAGATGTCCCTTCTGAAGATGATCCTACTCAGCTCGTATCAAGGGGAGG

TTGTGGTAATACACAGCCTACAATTCGTAAGGATGGGTTGAAATTAGTTG

GTAGTTGGAAAAAAGATAGAGCCACGGGGGATGCGGATGAACCAGAACTA

AGAGTTTTAAGTACGGAGGAAATCTTGAATATTTTTAAGCATATCTCAGT

AAAAGACTTCACTAGTTTGGGTTTCAACGAAGTTTTTTCTCGTCCAGAAT

GGATGATTTTAACATGCCTTCCTGTCCCACCACCACCGGTGCGTCCATCC

ATTTCCTTCAATGAATCTCAAAGAGGTGAGGATGATTTAACCTTTAAACT

TGCTGATATTTTAAAAGCTAATATTAGTTTGGAAACACTAGAGCATAACG

GTGCTCCACATCATGCTATTGAAGAAGCAGAGAGTTTATTACAATTTCAT

GTTGCCACTTATATGGATAATGATATTGCTGGTCAACCACAAGCTCTTCA

AAAGTCCGGCCGTCCCGTTAAATCTATTCGTGCTCGTTTGAAGGGTAAAG

AGGGTCGTATCAGAGGTAATTTAATGGGTAAGCGTGTGGATTTTTCGGCA

AGAACTGTTATTTCTGGTGATCCTAATTTGGAATTAGACCAAGTCGGTGT

TCCAAAATCTATTGCCAAGACTTTAACATACCCAGAAGTGGTCACACCAT

ATAACATAGATCGTCTGACGCAACTTGTTAGGAATGGACCAAATGAGCAC

CCCGGTGCCAAATACGTCATTCGTGATAGCGGAGACCGTATAGATTTAAG

ATACAGTAAAAGGGCAGGTGATATTCAATTACAGTATGGGTGGAAAGTTG

AACGTCATATTATGGACAATGATCCAGTTTTATTCAACCGTCAACCTTCG

TTGCACAAAATGTCCATGATGGCCCACAGAGTAAAAGTTATTCCATATTC

TACATTTAGATTGAATTTGTCCGTTACATCTCCATACAATGCCGATTTCG

ACGGTGACGAAATGAATCTTCACGTTCCTCAGTCTGAGGAAACAAGGGCG

GAACTTTCTCAATTATGTGCTGTTCCTCTGCAAATTGTTTCACCACAATC

TAACAAACCTTGTATGGGTATTGTTCAAGATACTTTGTGTGGTATTCGTA

AACTGACATTAAGAGATACATTTATAGAACTTGATCAAGTTTTGAATATG

CTTTATTGGGTTCCAGATTGGGATGGTGTTATTCCGACACCTGCAATTAT

CAAGCCCAAACCTTTGTGGTCCGGTAAACAAATCTTGTCTGTGGCTATCC

CAAACGGTATTCATTTACAACGTTTTGATGAGGGCACTACTCTGCTTTCT

CCAAAGGATAATGGTATGCTTATTATTGACGGTCAAATCATTTTTGGTGT

AGTAGAGAAAAAACCGTTGGTTCCTCCAATGGTGGTTTAATTCATGTTG

TTACGAGAGAAAAGGGACCTCAAGTTTGTGCTAAGTTGTTTGGTAACATA

CAGAAAGTTGTTAACTTTTGGTTACTACATAATGGGTTTTCAACAGGTAT

TGGTGATACCATTGCGGACGGCCCAACAATGAGGGAAATTACAGAGACAA

TTGCAGAGGCTAAAAAGAAAGTTTTGGATGTTACGAAAGAAGCCCAGGCA

AACTTATTGACTGCTAAACATGGTATGACTCTCCGTGAGTCTITTGAGGA

TAACGTTGTTCGGTTCCTAAATGAAGCAAGAGATAAGGCAGGTCGTTTAG
```

```
CTGAAGTCAATTTGAAAGATTTGAACAATGTGAAACAAATGGTTATGGCA
GGTTCCAAGGGTTCATTTATTAATATCGCGCAAATGTCAGCTTGTGTAGG
ACAGCAATCTGTTGAAGGTAAACGTATTGCTTTTGGGTTCGTTGATCGTA
CCTTACCTCATTTCTCTAAAGATGATTACTCCCCAGAGTCTAAAGGTTTT
GTTGAGAACTCATATTTGAGAGGTTTGACCCCACAAGAATTTTTTTTCCA
TGCAATGGGTGGTCGTGAAGGTCTTATCGATACCGCCGTCAAAACAGCCG
AAACAGGTTATATTCAACGTCGTTTAGTGAAAGCTCTAGAAGATATCATG
GTTCATTACGATAACACCACAAGAAACTCATTGGGTAACGTTATTCAGTT
TATTTATGGTGAAGATGGTATGGATGCTGCGCATATTGAAAAGCAATCGC
TAGATACTATTGGTGGCTCCGATGCAGCTTTTGAAAAGAGATACAGAGTT
GATTTATTGAATACAGACCATACCCTTGATCCCTCACTATTGGAATCCGG
ATCTGAGATACTTGGCGATTTGAAACTTCAAGTTCTCCTGGATGAAGAAT
ACAAACAATTAGTGAAAGATCGTAAATTTTTGAGGGAAGTTTTTGTTGAT
GGTGAAGCAAACTGGCCATTACCAGTCAACATAAGACGTATTATTCAAAA
TGCTCAACAAACTTTCCACATAGATCATACGAAACCATCTGATTTAACAA
TCAAAGACATCGTTCTTGGTGTAAAGGATTTGCAAGAAAACTTATTAGTG
TTGCGTGGTAAGAATGAAATTATACAAAATGCCCAGCGAGATGCAGTTAC
ATTGTTCTGCTGTTTATTACGTTCCCGTTTGGCCACACGTAGAGTTCTAC
AAGAGTACAGACTAACAAAACAGGCATTCGATTGGGTATTAAGTAATATC
GAGGCACAATTCCTCCGTTCTGTTGTTCACCCTGGTGAAATGGTTGGTGT
TCTAGCAGCCCAATCCATTGGTGAACCAGCCACACAAATGACCCTTAACA
CCTTCCATTTTGCTGGTGTTGCTTCCAAAAAAGTTACTTCTGGTGTCCCC
CGTTTAAAGGAAATTTTGAATGTGGCCAAAAACATGAAAACCCCTTCCTT
GACTGTATACTTAGAGCCTGGTCATGCTGCCGATCAAGAACAAGCGAAGT
TGATCAGATCTGCTATCGAGCATACCACTTTAAAGAGTGTCACTATTGCT
TCAGAAATTTACTATGATCCTGATCCACGTTCCACAGTTATTCCAGAAGA
TGAAGAAATTATCCAACTTCATTTCTCATTATTGGATGAAGAGGCTGAAC
AATCTTTTGACCAACAATCACCTTGGTTATTACGTCTGGAACTGGATCGT
GCAGCAATGAATGATAAAGACTTAACAATGGGTCAGGTTGGTGAAAGAAT
CAAGCAAACATTCAAAAATGATTTGTTTGTTATCTGGTCTGAAGACAACG
ATGAGAAGTTGATCATCCGTTGTCGTGTTGTTCGTCCAAAGTCACTAGAT
GCTGAGACTGAAGCAGAAGAAGATCATATGTTGAAGAAAATTGAGAACAC
AATGTTAGAGAATATTACATTACGTGGTGTAGAGAACATCGAGCGTGTTG
TCATGATGAAATATGACCGTAAAGTACCAAGTCCAACTGGTGAATACGTT
AAGGAACCTGAATGGGTGTTGGAAACAGATGGTGTTAACTTATCTGAAGT
TATGACTGTTCCTGGTATCGACCCAACCAGAATCTATACCAACTCCTTCA
TTGATATAATGGAAGTTCTAGGTATTGAAGCTGGTCGTGCAGCCTTGTAT
AAAGAAGTTTACAATGTTATTGCTTCTGATGGTTCGTATGTTAACTACCG
TCATATGGCTTTGTTAGTCGATGTTATGACAACCCAAGGTGGCTTAACTT
CTGTTACTCGTCATGGTTTCAACAGATCAAATACAGGTGCCTTAATGAGA
TGTTCATTTGAAGAAACTGTCGAAATTTTGTTTGAAGCTGGTGCTTCAGC
CGAATTAGATGATTGTCGTGGTGTTTCGGAAAATGTCATTCTTGGTCAAA
TGGCTCCAATCGGTACCGGTGCATTTGATGTGATGATCGATGAGGAGTCA
CTGGTAAAATACATGCCAGAACAAAAAATAACTGAGATTGAAGACGGACA
AGATGGTGGCGTCACACCATACAGTAACGAAAGTGGTTTGGTCAATGCAG
ATCTTGACGTTAAAGATGAGCTAATGTTTTCACCTCTGGTTGATTCGGGT
TCAAATGACGCTATGGCTGGAGGATTTACAGCGTACGGTGGTGCTGATTA
TGGTGAAGCCACGTCTCCATTTGGTGCTTATGGTGAAGCACCTACATCTC
CCGGATTTGGAGTCTCCTCACCAGGCTTTTCTCCAACTTCCCCAACATAC
TCTCCTACCTCTCCAGCGTACTCACCAACATCACCATCGTACTCACCAAC
ATCACCATCGTACTCGCCAACATCACCATCGTACTCACCTACATCACCAT
CGTATTCACCAACGTCACCATCATATTCGCCAACGTCACCATCATATTCG
CCAACGTCGCCATCGTATTCTCCAACGTCACCATCGTATTCGCCAACGTC
GCCTTCCTACTCTCCCACGTCGCCAAGCTACAGCCCTACGTCTCCTTCTT
ATTCTCCTACATCTCCATCATACTCTCCTACGTCACCAAGTTACAGCCCA
ACGTCACCAAGTTACAGCCCAACGTCTCCAGCCTATTCCCCAACATCACC
AAGTTATAGTCCTACATCGCCTTCATACTCTCCAACATCACCATCCTATT
CCCCAACATCACCTTCTTACTCTCCCACCTCTCCAAACTATAGCCCTACT
TCACCTTCTTACTCCCCAACATCTCCAGGCTACAGCCCAGGATCTCCTGC
ATATTCTCCAAAGCAAGACGAACAAAAGCATAATGAAAATGAAAATTCCA
GATGA.
```

In some embodiments, the coding sequence of PGK1 comprises the following sequence:

(SEQ ID NO: 5)
```
ATGTCTTTATCTTCAAAGTTGTCTGTCCAAGATTTGGACTTGAAGGACAA
GCGTGTCTTCATCAGAGTTGACTTCAACGTCGTCCCATTGGACGGTAAGA
AGATCACTTCTAACCAAAGAATTGTTGCTGCTTTGCCAACCATCAAGTAC
GTTTTGGAACACCACCCAAGATACGTTGTCTTGGCTTCTCACTTGGGTAG
ACCAAACGGTGAAAGAAACGAAAAATACTCTTTGGCTCCAGTTGCTAAGG
AATTGCAATCATTGTTGGGTAAGGATGTCACCTTCTTGAACGACTGTGTC
GGTCCAGAAGTTGAAGCCGCTGTCAAGGCTTCTGCCCCAGGTTCCGTTAT
TTTGTTGGAAAACTTGCGTTACCACATCGAAGAAGAAGGTTCCAGAAAGG
TCGATGGTCAAAAGGTCAAGGCTTCCAAGGAAGATGTTCAAAAGTTCAGA
CACGAATTGAGCTCTTTGGCTGATGTTTACATCAACGATGCCTTCGGTAC
CGCTCACAGAGCTCACTCTTCTATGGTCGGTTTCGACTTGCCACAACGTG
CTGCCGGTTTCTTGTTGGAAAAGGAATTGAAGTACTTCGGTAAGGCTTTG
GAGAACCCAACCAGACCATTCTTGGCCATCTTAGGTGGTGCCAAGGTTGC
TGACAAGATTCAATTGATTGACAACTTGTTGGACAAGGTCGACTCTATCA
TCATTGGTGGTGGTATGGCTTTCACCTTCAAGAAGGTTTTGGAAAACACT
GAAATCGGTGACTCCATCTTCGACAAGGCTGGTGCTGAAATCGTTCCAAA
GTTGATGGAAAAGGCCAAGGCCAAGGGTGTCGAAGTCGTCTTGCCAGTCG
```

-continued
ACTTCATCATTGCTGATGCTTTCTCTGCTGATGCCAACACCAAGACTGTC

ACTGACAAGGAAGGTATTCCAGCTGGCTGGCAAGGGTTGGACAATGGTCC

AGAATCTAGAAAGTTGTTTGCTGCTACTGTTGCAAAGGCTAAGACCATTG

TCTGGAACGGTCCACCAGGTGTTTTCGAATTCGAAAAGTTCGCTGCTGGT

ACTAAGGCTTTGTTAGACGAAGTTGTCAAGAGCTCTGCTGCTGGTAACAC

CGTCATCATTGGTGGTGGTGACACTGCCACTGTCGCTAAGAAGTACGGTG

TCACTGACAAGATCTCCCATGTCTCTACTGGTGGTGGTGCTTCTTTGGAA

TTATTGGAAGGTAAGGAATTGCCAGGTGTTGCTTTCTTATCCGAAAAGAA

ATAA.

In some embodiments, the mutated coding sequence of PGK1 comprises the following sequence:

(SEQ ID NO: 6)
ATGTCTTTATCTTCAAAGTTGTCTGTCCAAGAT<u>TTA</u>GACTTGAAGGACAA

GCGT<u>GT</u>ATTCATCAGAGTTGACTTCAAC<u>GTTGTT</u>CCATTGGACGGTAAGA

AGATCACTTCTAACCAAAGAATTGTTGCTGCTTTGCCAACCATCAAGTAC

GTTTTGGAACACCACCCAAGATACGTTGTCTTGGCTTCTCACTTGGGTAG

ACCAAACGGTGAAAGAAACGAAAAATACTCTTTGGCTCCAGTTGCTAAGG

AATTGCAATCATTGTTGGGTAAGGATGTCACCTTCTTGAACGACTGTGTC

GGTCCAGAAGTTGAAGCCGCTGTCAAGGCTTCTGCCCCAGGTTCCGTTAT

TTTGTTGGAAAACTTGCGTTACCACATCGAAGAAGAAGGTTCCAGAAAGG

TCGATGGTCAAAAGGTCAAGGCTTCCAAGGAAGATGTTCAAAAGTTCAGA

CACGAATTGAGCTCTTTGGCTGATGTTTACATCAACGATGCCTTCGGTAC

CGCTCACAGAGCTCACTCTTCTATGGTCGGTTTCGACTTGCCACAACGTG

CTGCCGGTTTCTTGTTGGAAAAGGAATTGAAGTACTTCGGTAAGGCTTTG

GAGAACCCAACCAGACCATTCTTGGCCATCTTAGGTGGTGCCAAGGTTGC

TGACAAGATTCAATTGATTGACAACTTGTTGGACAAGGTCGACTCTATCA

TCATTGGTGGTGGTATGGCTTTCACCTTCAAGAAGGTTTTGGAAAACACT

GAAATCGGTGACTCCATCTTCGACAAGGCTGGTGCTGAAATCGTTCCAAA

GTTGATGGAAAAGGCCAAGGCCAAGGGTGTCGAAGTCGTCTTGCCAGTCG

ACTTCATCATTGCTGATGCTTTCTCTGCTGATGCCAACACCAAGACTGTC

ACTGACAAGGAAGGTATTCCAGCTGGCTGGCAAGGGTTGGACAATGGTCC

AGAATCTAGAAAGTTGTTTGCTGCTACTGTTGCAAAGGCTAAGACCATTG

TCTGGAACGGTCCACCAGGTGTTTTCGAATTCGAAAAGTTCGCTGCTGGT

ACTAAGGCTTTGTTAGACGAAGTTGTCAAGAGCTCTGCTGCTGGTAACAC

CGTCATCATTGGTGGTGGTGACACTGCCACTGTCGCTAAGAAGTACGGTG

TCACTGACAAGATCTCCCATGTCTCTACTGGTGGTGGTGCTTCTTTGGAA

TTATTGGAAGGTAAGGAATTGCCAGGTGTTGCTTTCTTATCCGAAAAGAA

ATAA.

In some embodiments, the coding sequence of VMA2 comprises the following sequence:

(SEQ ID NO: 7)
ATGGTTTTGTCTGATAAGGAGTTGTTTGCCATAAAT<u>AAGAAA</u><u>GCCGTC</u>GA

ACAAGGTTTCAATGTGAAGCCTAGATTGAACTATAATACGGTCAGTGGTG

TGAACGGTCCATTAGTCATTTTGGAAAAG<u>GTC</u>AAGTTCCCACGTTACAAC

GAAATTGTTAATTTGACATTGCCAGATGGAACCGTGAGACAAGGTCAAGT

TTTGGAAATTAGAGGAGATAGAGCCATTGTGCAAGTGTTTGAAGGTACAT

CTGGTATTGATGTCAAGAAGACTACCGTGGAATTCACTGGTGAGAGTTTG

AGAATTCCTGTGTCTGAAGACATGTTGGGTAGAATTTTTGACGGTTCTGG

TAGACCCATTGACAACGGTCCTAAAGTTTTCGCAGAGGATTACTTGGACA

TTAACGGTTCTCCTATCAACCCATATGCTCGTATTTATCCAGAAGAAATG

ATTTCTACTGGTGTTTCTGCTATTGACACAATGAACTCCATTGCCAGAGG

TCAAAAGATCCCAATTTTCTCCGCATCAGGTTTACCACACAACGAAATTG

CAGCACAAATTTGTAGACAGGCTGGTTTGGTGAGACCTACCAAGGATGTT

CATGATGGTCATGAAGAAAATTTCTCCATCGTTTTTGCTGCCATGGGTGT

CAACTTGGAAACCGCTAGATTTTTCAAACAGGATTTCGAAGAAAATGGGT

CTTTGGAAAGAACTTCATTATTTTTGAACTTGGCTAATGACCCTACCATT

GAAAGAATTATCACTCCAAGATTGGCCTTGACCACCGCTGAATACCTTGC

TTACCAAACGGAACGTCATGTGTTGACCATCTTGACCGATATGTCATCGT

ATGCTGATGCTCTTAGAGAAGTTTCCGCTGCTAGAGAAGAAGTTCCAGGT

AGAAGAGGTTATCCTGGTTACATGTATACAGATTTGTCCACAATTTATGA

AAGAGCAGGTAGAGTAGAGGGTCGTAACGGGTCCATCACTCAAATACCTA

TCTTGACAATGCCTAACGATGATATTACGCATCCAATTCCGGATTTGACC

GGTTATATTACCGAGGGTCAAATCTTCGTTGACCGTCAATTACATAACAA

GGGTATCTACCCACCAATCAACGTCTTGCCTTCGTTGAGTAGATTGATGA

AATCTGCCATCGGTGAAGGTATGACCAGAAAGGACCACGGTGACGTTTCT

AACCAATTGTATGCCAAGTACGCCATCGGTAAGGACGCTGCTGCTATGAA

GGCCGTTGTCGGTGAAGAGGCGTTATCCATCGAAGATAAGTTATCTTTGG

AATTTTTGGAAAAATTCGAAAAGACCTTTATCACACAAGGCGCCTACGAG

GACAGAACCGTTTTCGAAAGTTTGGACCAGGCATGGAGTTTGCTAAGAAT

CTACCCTAAGGAGATGTTGAATAGAATCTCCCCAAAGATTCTTGATGAAT

TTTACGATAGCCAGAGACGATGCCGACGAAGATGAAGAAGATCCCGAC

ACAAGAAGCTCCGGTAAGAAGAAGGACGCCAGCCAAGAAGAATCTCTAAT

CTAA.

In some embodiments, the mutated coding sequence of VMA2 comprises the following sequence:

(SEQ ID NO: 8)
ATGGTTTTGTCTGATAAGGAGTTGTTTGCCATAAAT<u>AAAAAA</u><u>GCGGTG</u>GA

ACAAGGTTTCAATGTGAAGCCTAGATTGAACTATAATACGGTCAGTGGTG

TGAACGGTCCATTAGTCATTTTGGAAAAG<u>GTT</u>AAGTTCCCACGTTACAAC

GAAATTGTTAATTTGACATTGCCAGATGGAACCGTGAGACAAGGTCAAGT

TTTGGAAATTAGAGGAGATAGAGCCATTGTGCAAGTGTTTGAAGGTACAT

-continued

```
CTGGTATTGATGTCAAGAAGACTACCGTGGAATTCACTGGTGAGAGTTTG
AGAATTCCTGTGTCTGAAGACATGTTGGGTAGAATTTTTGACGGTTCTGG
TAGACCCATTGACAACGGTCCTAAAGTTTTCGCAGAGGATTACTTGGACA
TTAACGGTTCTCCTATCAACCCATATGCTCGTATTTATCCAGAAGAAATG
ATTTCTACTGGTGTTTCTGCTATTGACACAATGAACTCCATTGCCAGAGG
TCAAAAGATCCCAATTTTCTCCGCATCAGGTTTACCACACAACGAAATTG
CAGCACAAATTTGTAGACAGGCTGGTTTGGTGAGACCTACCAAGGATGTT
CATGATGGTCATGAAGAAAATTTCTCCATCGTTTTTGCTGCCATGGGTGT
CAACTTGGAAACCGCTAGATTTTTCAAACAGGATTTCGAAGAAAATGGGT
CTTTGGAAAGAACTTCATTATTTTTGAACTTGGCTAATGACCCTACCATT
GAAAGAATTATCACTCCAAGATTGGCCTTGACCACCGCTGAATACCTTGC
TTACCAAACGGAACGTCATGTGTTGACCATCTTGACCGTATGTCATCGT
ATGCTGATGCTCTTAGAGAAGTTTCCGCTGCTAGAGAAGAAGTTCCAGGT
AGAAGAGGTTATCCTGGTTACATGTATACAGATTTGTCCACAATTTATGA
AAGAGCAGGTAGAGTAGAGGGTCGTAACGGGTCCATCACTCAAATACCTA
TCTTGACAATGCCTAACGATGATATTACGCATCCAATTCCGGATTTGACC
GGTTATATTACCGAGGGTCAAATCTTCGTTGACCGTCAATTACATAACAA
GGGTATCTACCCACCAATCAACGTCTTGCCTTCGTTGAGTAGATTGATGA
AATCTGCCATCGGTGAAGGTATGACCAGAAAGGACCACGGTGACGTTTCT
AACCAATTGTATGCCAAGTACGCCATCGGTAAGGACGCTGCTGCTATGAA
GGCCGTTGTCGGTGAAGAGGCGTTATCCATCGAAGATAAGTTATCTTTGG
AATTTTTGGAAAAATTCGAAAAGACCTTTATCACACAAGGCGCCTACGAG
GACAGAACCGTTTTCGAAAGTTTGGACCAGGCATGGAGTTTGCTAAGAAT
CTACCCTAAGGAGATGTTGAATAGAATCTCCCCAAAGATTCTTGATGAAT
TTTACGATAGACCCAGAGACGATGCCGACGAAGATGAAGAAGATCCCGAC
ACAAGAAGCTCCGGTAAGAAGAAGGACGCCAGCCAAGAAGAATCTCTAAT
CTAA.
```

In some embodiments, the coding sequence of TCB3 comprises the following sequence:

```
                                         (SEQ ID NO: 9)
ATGACTGGCATCAAAGCTCAAGTCCATCCCCCACCTGATAGTACCCTATT
TCATGAGGAGGAGAAGAAGAAAGTAGGAGGCAATTTACCTCAAAAGGTCA
TAAATCAACAAGAAAGGGGTTCTGATCACGCTCCATCGGGTCACCATCAA
TACCACCAACTGATTAACCATGACGCAAATGACACAAAGACCTCAAATTC
AGTTTCTGATGTGTCTAAAGGTCAGAAAACTGCTGACTCCAACCCGGAAG
GTAAGAAACAGTCATCAAAAGACATATTTGTTGCCTCCAGCGCTCAAAAA
ACCAATCAATTGCCCGGTCCCAACCCACAGGGAAGCATAGGAGCCGTGCC
ATTGGAAGGTTTACGTCCGAAGGAATTCAGATCAGCACCATCTAGGAAGC
CAAATAAATTCGACACTTCGATTACTAAGCCTGGCGTCTTAGACGACTTA
GGCAAACTTGATGAAAAGGATATTAAGGAAAAATTTCACCTAGATTCCGA
CGACAAGTTATTTCCATGGCAAAATGTTGGTGAGTTCCATGCTTCAGGAA
AGGGTTCGCCAAATACAAAGATGTCCAGGGTTATAAAAGCTTACATTCTG
GAAAATTTTTATAACGATTGGTACTGTAATATAGCCACCGTTCTTGGAAC
TTGTTTCTTCTCATGGTTATTTGCTTACATTGGGTTTTCATGGTGGTCTA
TGATATTTATCTTCTTGGGAACTGCGACCGTTTACAACGCAGAATATACA
AGATTCAACAGAAATATCAGAGATGACTTGAAAAGAGTTACAGTCGAAGA
AACCTTGTCGGATCGCGTTGAATCCACTACGTGGTTGAATTCATTTTTAT
CAAAATTTTGGGTGATTTACATGCCAGTTTTATCTCAACAAGTCAAAGAT
AACGTTAACCCTCAACTGGCAGGTGTTGCTCCAGGTTACGGTATCGATGC
GTTAGCTATCGATGAATTCACTCTGGGCTCTAAAGCTCCCACCATAAAAG
GTATTAAATCGTACACCAAGACTGGTAAAAACACTGTTGAAATGGATTGG
TCATTTGCATTCACCCCAAGCGATGTCTCGGATATGACAGCTACTGAAGC
TAGGGAGAAGATCAATCCAAAAATATCTCTGGGTGTCACGTTAGGAAAAA
GTTTTGTCTCTAAAACAATGCCTATTTTGGTTGAAGACATTAACGTTGCT
GGTAAAATGCGTATTAAAGTTGAATTTGGTAAAGCTTTCCCAAATATCAA
AATTGTTTCTTTACAACTTTTAGAACCACCTTTGATTGATTTCGCACTGA
AACCAATTGGTGGTGATACTTTAGGTCTTGATGTTATGTCATTCTTGCCT
GGTTTGAAGAGTTTTGTTAAAAACATTATCAACTCCAATATAGGGCCTAT
GCTATTCCCTCCGAACCATTTGGATATTAATGTTGAAGACATTATGGCTG
CTCAATCAAAAGAAGCTATTGGTGTCCTTGCCGTAACCATTGCTTCTGCC
GACTCTTTGAAAGGCTCAGATTTCATTACCAATACTGTCGATCCTTATAT
TGTTATGACTACCGAAGATGCTGTGCCTGGTACAGATGAAGAAGTGCGTA
CATCTATCAAATCAAATGTTAAAAATCCACGTTGGAACGAAACCAAATAT
CTATTATTAAACACCTTAGAGCAAAAGTTAAACTTAAAGTGCTTTGACTT
CAATGATGTAAGAAAAGATACCGTAATTGGTGATCTTCAACTTGACTTGG
CAGATTTACTACAAAACCCTGTTTTGGATAATCAAACTGCTGAATTAAGA
TCCGGTACAAAATCAAAAGGTATTTTACATTATTCCTTACACTGGTTCCC
TGTGAAAGAAGATAAATCAGAGGAAAAAGCAGTTGAGCGTGCCGAAGCTA
AGGCCAAGGGCAAGAAAGAAGATGAAAACGAGGACACTACTGAAAAAGAA
GAAGACGAGAATGAAGAAGTTCTCAAACTGATGTCGGGATTGCCAAGAT
CACTTTACAAAAGGTCAAATATCTGGATACAACCAGTTCTATGACCGGTA
GCTTGAGCCCATGTGCTGAATTATTCATTGATGGACAAAAAGTAAAGAGC
TATAGAACTTTGAGACGTATCAATGAGCCATCTTGGAATGAGACCATCGA
AGTTTTGGTTCCATCAAAATCTAACTCTAAGTTTGTCCTAAAAATATTCG
ATGACAGAATGAATGGTAAGGCGCTGATCTGTGAGTATTCATCTTCTTTA
GATGATATAATGACTACTTTAGACACTGCTCAAGAGTTTGTTAAAGGCTC
ACCACAAGGTGACATTTATTTGGATGTTTCTTGGAAATCAATTGAAATGA
CCGGAGCTTTTGCCGCTGCAAACTCTGTAAGCGAACCTATTGGTTGTATT
AAGCTAGACGTTAAGGATGCCATTATCAAGGGTGACTTATCCGGTGTAGG
GGATGTTGATCCATATTACACCGTATCGTTGAATAGACGTGTTCTTTACA
AGTCCATATATCATTCTGATACGGATCATCCCATTTTTGACAACAGCACC
```

```
TACGTTCCTATCTTCTCTCCAAATCAAATTTTGACTCTCGAATTTCATGA

TTATCAAAAGATCGGCAAAGACCGTTTCATTGGCTCTGTACAAATTCCTA

CATCAAATGTTTTCAAAAAAGATCCTAAATCAGGAAAATATGTTGGGAAT

AATGGCAAAGAAGAAATTTCAAAACTAAAATTAAAAGACCACGAACACAA

AGTTACCGAAAGCATTGTCAATGTTTCAACAACATTTATCCCAATCAATC

TGGTGTATTCCCCTGAGGAGTTGGTGAATGTTGAGAAACTAGAAAAGGAG

TTGAAGGAAAAGAAGAAAAAATTCGAAGCTACCCAAGAAGAAAACGAGCA

AGAGATGGAAAAAAATCCAAAGGAATGGGAAGTTGCCGAGATCGAAGACC

CATTTGACAGCGATGAAAAAAAATAAACAGGAAGGCCAAGTTATCTTTA

AACGAGTTGATCAAGCAAAAATCTGGTATTTTGTCTATGCAAATATTGGA

AGGGACTTTGAGCCCATCCTCTGCTTACCTAGAAATCTTAGCGGATGACA

TTTCGTACCCTGTATTCATTTGCATGAAACCATCTCAAGGTAAACTAAAC

TCGGAGATGGCAAATATTTTCATTAGAGATTTGAATTACAGTAAACTACA

TTTTAGAGTATCGAAGAAACATATTGCCAAAGATTCAGATGATGTCATAT

CCGAAACTTCCTATAGTACATTGAAGCTACTAAAGCAAGCTTACGAAGAG

CCCATGTGGTTAAACTTCAATGGGTCTAAAATGAAGGTAAGATTTTGTA

CACGCCCACTAGCGTGAAACTGCCTAGCAGTGAAAGTGTTGAAGACACTG

GTTATTTGAATATAAAGCTTATTTCCGGACACGGTCTGAAGTCCGCAGAT

AGGAATGGCTATTCAGATCCATTTGTTCACATCTTTGTCAATGATAAAAA

AGTTTTCAAATCGAACATTAAAAGAAAACATTGGATCCCGTATGGAACG

AAGATGCTAAAATACCAATCCTTTCAAGAAGTAAGAATCAAGTCATATTT

AATGTTCTTGATTGGGATCGTGCAGGTGATAATGACGACTTAGGCCAAGC

TTCACTTGACGTTTCCTCATTAGAAGTTGGTAAAACTTACAACTGGAATT

TGAATTTAAACACACAAGGAAGTATCAAATTACAAGGTTCATTCAACCCA

GAATATATCAAGCCAAGTTTTGATATCGTGAAAGGCGGTATCACTGATAA

GCCGATGAAAATAGCCAGTGGTGCAGCCCATGCAACTGTTGGCATAGCTG

GTACTGGTATAGGAGCAGCAACAGGAGTTGCCACTGGTGGTTTAAAGAAA

GGTGGTCACCTTCTAAAATCTCTAGGTGGCAATCCAATGAAAAGAAGCAA

GAGCAGCAATGGAAATGAGTCCAACGGTGCAAAAAAATCATCAGAGAAA

AATCTTTTGATAGGAGATCCCCAAGTAATTTGAATAGCACTAGTGTAACA

CCAAGAGCTTCACTAGACTATGATCCATCAGTACCTAACACAAGTTACGC

GCCCGTTCAAAGCGCATCTCCTGTAGTCAAGCCAACTGACAACACTTCTA

GCTCAAGCAACAAAAAGATACCCCTAGTAGCAACTCTAGAGGACATTCT

CGTCCAAGCAGTTTTGCGCGTACTTTAGCTCCTCATGGCACTTACAATGG

TTTTATTACCGTGGTTGCTGCGGAAAACGTTGCCAAGCATGTTCAAATTA

AGATCTCTTTAACTCAAGGTGGTAGACTAAAACACATATACAAAACGAAA

AGCCAAAAAGCCAATAATGATGGTGTTGCCGTATTTGATGAAGAGTGCTC

GTTCAAGGCTTCTCCCGAAGCCAATTTGGTACTGGGTGCAATTTCCCATC

AAAGACTATCGAGGGACAAAGATCTTGGTATTGCTCAAATCAACTTGGGT

GACCCTCAAATTCAACAAGATGGCCAAATTTCTGTAAAATTAGGAGACGG

TCATCTGATTGTAAAGATTAATTACGGTAAAGCAAGAATGGTCAGGTAC

CTCCCGTGCCAGAAGTTCCTCAAGAATACACGCAGTAA.
```

In some embodiments, the mutated coding sequence of TCB3 comprises the following sequence:

```
                                        (SEQ ID NO: 10)
ATGACTGGCATCAAAGCTCAAGTCCATCCCCCGCCTGATAGTACACTCTT

TCATGAGGAGGAGAAGAAGAAAGTAGGAGGCAATTTACCTCAAAAGGTCA

TAAATCAACAAGAAAGGGGTTCTGATCACGCTCCATCGGGTCACCATCAA

TACCACCAACTGATTAACCATGACGCAAATGACACAAAGACCTCAAATTC

AGTTTCTGATGTGTCTAAAGGTCAGAAAACTGCTGACTCCAACCCGGAAG

GTAAGAAACAGTCATCAAAAGACATATTTGTTGCCTCCAGCGCTCAAAAA

ACCAATCAATTGCCCGGTCCCAACCCACAGGGAAGCATAGGAGCCGTGCC

ATTGGAAGGTTTACGTCCGAAGGAATTCAGATCAGCACCATCTAGGAAGC

CAAATAAATTCGACACTTCGATTACTAAGCCTGGCGTCTTAGACGACTTA

GGCAAACTTGATGAAAAGGATATTAAGGAAAAATTTCACCTAGATTCCGA

CGACAAGTTATTTCCATGGCAAAATGTTGGTGAGTTCCATGCTTCAGGAA

AGGGTTCGCCAAATACAAAGATGTCCAGGGTTATAAAAGCTTACATTCTG

GAAAATTTTTATAACGATTGGTACTGTAATATAGCCACCGTTCTTGGAAC

TTGTTTCTTCTCATGGTTATTTGCTTACATTGGGTTTTCATGGTGGTCTA

TGATATTTATCTTCTTGGGAACTGCGACCGTTTACAACGCAGAATATACA

AGATTCAACAGAAATATCAGAGATGACTTGAAAAGAGTTACAGTCGAAGA

AACCTTGTCGGATCGCGTTGAATCCACTACGTGGTTGAATTCATTTTTAT

CAAAATTTTGGGTGATTTACATGCCAGTTTTATCTCAACAAGTCAAAGAT

AACGTTAACCCTCAACTGGCAGGTGTTGCTCCAGGTTACGGTATCGATGC

GTTAGCTATCGATGAATTCACTCTGGGCTCTAAAGCTCCCACCATAAAAG

GTATTAAATCGTACACCAAGACTGGTAAAAACACTGTTGAAATGGATTGG

TCATTTGCATTCACCCCAAGCGATGTCTCGGATATGACAGCTACTGAAGC

TAGGGAGAAGATCAATCCAAAAATATCTCTGGGTGTCACGTTAGGAAAAA

GTTTTGTCTCTAAAACAATGCCTATTTTGGTTGAAGACATTAACGTTGCT

GGTAAAATGCGTATTAAAGTTGAATTTGGTAAAGCTTTCCCAAATATCAA

AATTGTTTCTTTACAACTTTTAGAACCACCTTTGATTGATTTCGCACTGA

AACCAATTGGTGGTGATACTTTAGGTCTTGATGTTATGTCATTCTTGCCT

GGTTTGAAGAGTTTTGTTAAAAACATTATCAACTCCAATATAGGGCCTAT

GCTATTCCCTCCGAACCATTTGGATATTAATGTTGAAGACATTATGGCTG

CTCAATCAAAAGAAGCTATTGGTGTCCTTGCCGTAACCATTGCTTCTGCC

GACTCTTTGAAAGGCTCAGATTTCATTACCAATACTGTCGATCCTTATAT

TGTTATGACTACCGAAGATGCTGTGCCTGGTACAGATGAAGAAGTGCGTA

CATCTATCAAATCAAATGTTAAAAATCCACGTTGGAACGAAACCAAATAT

CTATTATTAAACACCTTAGAGCAAAAGTTAAACTTAAAGTGCTTTGACTT

CAATGATGTAAGAAAAGATACCGTAATTGGTGATCTTCAACTTGACTTGG
```

-continued

```
CAGATTTACTACAAAACCCTGTTTTGGATAATCAAACTGCTGAATTAAGA

TCCGGTACAAAATCAAAAGGTATTTTACATTATTCCTTACACTGGTTCCC

TGTGAAAGAAGATAAATCAGAGGAAAAAGCAGTTGAGCGTGCCGAAGCTA

AGGCCAAGGGCAAGAAAGAAGATGAAAACGAGGACACTACTGAAAAAGAA

GAAGACGAGAATGAAGAAAGTTCTCAAACTGATGTCGGGATTGCCAAGAT

CACTTTACAAAAGGTCAAATATCTGGATACAACCAGTTCTATGACCGGTA

GCTTGAGCCCATGTGCTGAATTATTCATTGATGGACAAAAAGTAAAGAGC

TATAGAACTTTGAGACGTATCAATGAGCCATCTTGGAATGAGACCATCGA

AGTTTTGGTTCCATCAAAATCTAACTCTAAGTTTGTCCTAAAAATATTCG

ATGACAGAATGAATGGTAAGGCGCTGATCTGTGAGTATTCATCTTCTTTA

GATGATATAATGACTACTTTAGACACTGCTCAAGAGTTTGTTAAAGGCTC

ACCACAAGGTGACATTTATTTGGATGTTTCTTGGAAATCAATTGAAATGA

CCGGAGCTTTTGCCGCTGCAAACTCTGTAAGCGAACCTATTGGTTGTATT

AAGCTAGACGTTAAGGATGCCATTATCAAGGGTGACTTATCCGGTGTAGG

GGATGTTGATCCATATTACACCGTATCGTTGAATAGACGTGTTCTTTACA

AGTCCATATATCATTCTGATACGGATCATCCCATTTTTGACAACAGCACC

TACGTTCCTATCTTCTCTCCAAATCAAATTTTGACTCTCGAATTTCATGA

TTATCAAAGATCGGCAAAGACCGTTTCATTGGCTCTGTACAAATTCCTA

CATCAAATGTTTTCAAAAAAGATCCTAAATCAGGAAAATATGTTGGGAAT

AATGGCAAAGAAGAAATTTCAAAACTAAAATTAAAAGACCACGAACACAA

AGTTACCGAAAGCATTGTCAATGTTTCAACAACATTTATCCCAATCAATC

TGGTGTATTCCCCTGAGGAGTTGGTGAATGTTGAGAAACTAGAAAAGGAG

TTGAAGGAAAGAAGAAAAAATTCGAAGCTACCCAAGAAGAAAACGAGCA

AGAGATGGAAAAAAATCCAAAGGAATGGGAAGTTGCCGAGATCGAAGACC

CATTTGACAGCGATGAAAAAAAAATAAACAGGAAGGCCAAGTTATCTTTA

AACGAGTTGATCAAGCAAAAATCTGGTATTTTGTCTATGCAAATATTGGA

AGGGACTTTGAGCCCATCCTCTGCTTACCTAGAAATCTTAGCGGATGACA

TTTCGTACCCTGTATTCATTTGCATGAAACCATCTCAAGGTAAACTAAAC

TCGGAGATGGCAAATATTTTCATTAGAGATTTGAATTACAGTAAACTACA

TTTTAGAGTATCGAAGAAACATATTGCCAAAGATTCAGATGATGTCATAT

CCGAAACTTCCTATAGTACATTGAAGCTACTAAAGCAAGCTTACGAAGAG

CCCATGTGGTTAAACTTCAATGGGTCTAAAATGAAGGTAAGATTTTGTA

CACGCCCACTAGCGTGAAACTGCCTAGCAGTGAAAGTGTTGAAGACACTG

GTTATTTGAATATAAAGCTTATTTCCGGACACGGTCTGAAGTCCGCAGAT

AGGAATGGCTATTCAGATCCATTTGTTCACATCTTTGTCAATGATAAAAA

AGTTTTCAAATCGAACATTAAAAAGAAACATTGGATCCCGTATGGAACG

AAGATGCTAAAATACCAATCCTTTCAAGAAGTAAGAATCAAGTCATATTT

AATGTTCTTGATTGGGATCGTGCAGGTGATAATGACGACTTAGGCCAAGC

TTCACTTGACGTTTCCTCATTAGAAGTTGGTAAAACTTACAACTGGAATT

TGAATTTAAACACACAAGGAAGTATCAAATTACAAGGTTCATTCAACCCA
```

```
GAATATATCAAGCCAAGTTTTGATATCGTGAAAGGCGGTATCACTGATAA

GCCGATGAAAATAGCCAGTGGTGCAGCCCATGCAACTGTTGGCATAGCTG

GTACTGGTATAGGAGCAGCAACAGGAGTTGCCACTGGTGGTTTAAAGAAA

GGTGGTCACCTTCTAAAATCTCTAGGTGGCAATCCAATGAAAAGAAGCAA

GAGCAGCAATGGAAATGAGTCCAACGGTGCAAAAAAATCATCAGAGAAAA

AATCTTTTGATAGGAGATCCCCAAGTAATTTGAATAGCACTAGTGTAACA

CCAAGAGCTTCACTAGACTATGATCCATCAGTACCTAACACAAGTTACGC

GCCCGTTCAAAGCGCATCTCCTGTAGTCAAGCCAACTGACAACACTTCTA

GCTCAAGCAACAAAAAGATACCCCTAGTAGCAACTCTAGAGGACATTCT

CGTGCAAGCAGTTTTGCGCGTACTTTAGCTCCTCATGGCACTTACAATGG

TTTTATTACCGTGGTTGCTGCGGAAAACGTTGCCAAGCATGTTCAAATTA

AGATCTCTTTAACTCAAGGTGGTAGACTAAAACACATATACAAAACGAAA

AGCCAAAAAGCCAATAATGATGGTGTTGCCGTATTTGATGAAGAGTGCTC

GTTCAAGGCTTCTCCCGAAGCCAATTTGGTACTGGGTGCAATTTCCCATC

AAAGACTATCGAGGGACAAAGATCTTGGTATTGCTCAAATCAACTTGGGT

GACCCTCAAATTCAACAAGATGGCCAAATTTCTGTAAAATTAGGAGACGG

TCATCTGATTGTAAAGATTAATTACGGTAAAGACAAGAATGGTCAGGTAC

CTCCCGTGCCAGAAGTTCCTCAAGAATACACGCAGTAA.
```

In some embodiments, the coding sequence of PAN1 comprises the following sequence:

(SEQ ID NO: 11)
```
ATGTATAACCCGTACCAGCAACAGGGCATGGGTTACCAGCAGCAACAGCA

GCAACAGCAGCAACAACCAAATGGATTCTACCCGCAGCAGCAGCAAGGTC

AGTCTTCAAACCAGCCCCAAGGCCAGCCTCAACCACAACAGCAAATGGCG

TTTAACCAGCCTCAGGCTACCGGAATTGGTGGGATGCCTCAAAGTTTTGG

TAATTCTTTCTCAAGTATGCCACAGCAGCCCCAAACGGGTTACAATAATA

ATGGAAATAATGGTAGTGTATATGGTAATGGTAATTTTGGCCAACAACCC

CAGCAGCAACAACAGCAGGCGAAACCGCAGCATACGGGATACGTACCAAA

TTCCAGTATGCCTATGATGAATACTACTGGCACCATGCCTCCACCTAATC

CGGCTCAACAGCCTCAGCTACAATCCATACAACCCCAAGGAACAGGCTAT

TACCAAGCTGCTAATACTGCAAATGTACACTCAGTACAACCTTTGCAATC

TCAAGGGACAGGATATTATGTGTCTACACCCAATTTGATCTCTTCTAATC

AAACCCAGCAGCCCCTTCAGGCCCAGGGCACTGGTTATTATCAATCTCAA

CCTCAACAGGTGCCACCTCCTCAGCAAGCACAGTCCTTGCAACCTTTGAA

GCCGCAGCAAACAGGATTTTACCTTCAACCGCAAAACCAAGCTCCCTTAG

AACCATTAAAGCCCACCGCAACTGGCTTTGTCAACTCATTTGCCAACAAC

GGTCTAAACAATGATATCAAAATCCCTGCCATTAGATTGTCGTTTATTAC

TGCCCAAGATCAGGCAAATTTGAGACTCTATTCAGATCAATTGTTACCA

ATGGTTCGAATACTGTTTCCGGTGCTAATTGTAGGAAAATTTTGATGAGA

TCCGGTTTGCCACCTTCTCAACTCGCAAGAATTTGGACGCTTTGTGATAC

ATCAAAAGCAGGTGAGTTACTGTTTCCTGAATTTGCATTAGCAATGCATT
```

-continued

TGATCAATGATGTCTTACAAGGTGACACTATCCCTTACGAATTGGATTCT

AAGACAAAAAACGAAGTTTCAAGTTTTATTGACGCCATTAATTTAAGCAT

TGCAAACCAGGATTCTTCCGCAAACGATGCCCCAAAAACTCCCTTTGATG

AATTCATTACAGCGGGCGTACAAAATTTGCAACCTCAACCAACAGGATAT

ATGCCTCAAACTAGTTTTGGTATCCCATTACAGTCTCAAATTACTGGAGG

CGGTGTTGCCTCGGCGTTGAATCCTCAATCCACAGGATTTATGGCACCAA

CCACTTTCAACATGTCAATGAATACCGGAACTCCCGGATTGAACCCCCAA

ATTACTGGAGGAGCACCTGCCTCTATGCAACCCAACATTACTGGCAATGC

TTTGCAACCTCAGACAACTGGTATGATGCCACAGACAACTGGTATGATGC

CACAGACAACTGGTATGATGCCACAGACTTCATTTGGCGTTAATTTAGGA

CCTCAGTTGACCGGCGGTGCTTTGCAATCTCAGTATACCGGAGGATATGG

TTCCGTTATGCCCCAGCAAAGCGGTCCTGCAAGTATGCCCAATTTGTCCT

TTAATCAACAAGGATTACAATCTCAGTTAACCGGGTTGCAACCCCAACCA

ACGGGTTTTCTACCACCATCTAACTTTAGTGCTACCATGCCGTTGACTGC

CCAAAAGACAGGATTTGGTAATAACGAAATTTATACCAAATCCAACTTTA

ATAATAACTTAATTGATAACTCAAGTCAAGACAAAATTTCCACGGAGGAA

AAATCTTTGTTTTATAAAATTTTTGAAACTTTTGATACTCAAAACAAAGG

TTTGTTAGATTCCCCCACTGCTGTGGAGATTTTTAGAAAATCTGGCTTAA

ATCGTGCAGATTTGGAGCAAATTTGGAACCTTTGTGATATAAACAACACC

GGCCAATTGAATAAACAAGAATTTGCACTAGGTATGCACTTGGTTTACGG

TAAATTAAACGGGAAGCCAATCCCCAATGTCCTACCTTCAAGTTTAATTC

CCTCCAGCACAAAACTTTTAGACAACTTAAAGAACCAATTAAAGACAGAG

CCAACGACCACAAAAGAAAAACCTTCGTTTGGTAAAATCGATGCCTTGAG

CTACAAAAATAATGATGATGATGTTTTGCCGAACTATAGAAATCGTAGGA

AGGTTTACTCTGCGAAAAATGAAGAGCAATCTTCTTTTTCTTCACCATCT

GCTAAATCTGTTAATCATTCTAGCAGCACCCTTCAAACCGATGACATTTC

GGTAGATAAGACTGTTGAAAAGAAGACAGCGAAACCAAAATATGCTGGGT

TTTCAAGAGAATAAATCTGAAAAATATTGCTTCACTGGAAAATGAGATC

AAAAATATCAGCAATCCTGAAAACTGTTATGACAGTTCTATTCCATCAGA

TTTGACAAGCCGCTTTGATGCCATCATCGCCAAACTTCCAAACCTATTCA

ATGAAATTTCTACAATTGATAATGAGATTACCAATGCAAAAATTCAGTTG

TATAGAAAAAAAATCCTTCTTCGATAATTGGATCTGGTCCAAATGGTGA

AATAACTGAAAATGATAGGAAGAAAGCTAAGAGTAGGGCTTTGTTGAGAG

CAAGGATGTCTGCTCTAACAGGAAAATCAACGGAATCGGAGGATTCACTT

TCCATGGAAGATAACAGCAAAGTGCTGAAATCAAGAGAATCCAGCAGGA

AAATGGTAAGAACCAAGAAATCATTAAAGACATAAGGTCATCTATATCAG

ATATTTCTGCATCCTTGAAGTCTACTATGACAGGATCGAATATGATATCC

AATCAAGAATTTGAAAGATGGGAATTTGGCATAGGGTTAGAAGATGGTGT

TCGTGAATTTTTGGATGATCTGAAGTCAAATTCAAATAAATCAGTGACTG

AGTCATCTCCCTTTGTGCCTTCCTCAACACCAACCCCTGTAGATGACCGT

TCCTCGTCGCCTTCTTATTCTCAGTTCAAAACTGCTGAAGAAAGAGCAGC

TTATCTGAAAGAACAGGCAAAAAAGAGAATGAAGGAAAAATTAGCTAAAT

TTGATAAGAATAGGCGAAATGTTACTCAAAGTTCCAGATCGATTAGCAGT

GAAAACTCTCGAGAACAGCCACAACAGATTGCTGGTTCTTCCAATTTAGT

TGAACCTAGAGCAACTCCATTCCAAGAAGAAAAATATGTGGAAGTCGCTC

AACCAACTCAACCTGTTCAATCAACACAACCTGTTCAACCAACTCAACCT

GTTCAGCCAACTCAACCTGTTCAGCCAACTCAACCTGTTCAGCCAACTCA

ACCTGTTCAACCAACTCAACCTGTTCAGAATGTATATAATGCAAAGCAAG

AATCCGATGATGAAGATGAAGATGATGAAGAAAAGCGTTTACAAGAGGAG

CTAAAACGATTGAAACTTAAAAAAAAGGCTGATAAAGAAAAAAGACTTGC

AGCTTTACGTAAGCAAATTGAGGATGCTCAAAATGAAAGTGACGAAGAGG

AGACAAACGGAAAAGACAACTTTGGCGGCCATGTGAACGTTCCTCAGGCC

GCTCCAGTGGCACCATCTGCAGCTTTTTCGCAAAATTCTACTAATGCTCC

TCGCTCGGTACACGCTGCTGTTACCCCTGCCGCAGGTAAGAACAGTACTG

GTCTGCCTTCCACGACAATGGGCCATAATCCATACTTCAAGGATGCATCA

GCTAGCTCTACATCTACTTTCGATGCTCGCGCTGCAGAAATGCAAAGAAG

AATCCAAAGAGGATTGGATGAGGACGAGGATGATGGATGGTCTGATGAAG

ACGAGAGTAATAACCGCGTAGCTGTAGATAATAAGGTTGAAGAAGCAAAG

ATTGGTCATCCTGATCATGCACGTGCTCCACCTGTTACTGCTGCTCCCTT

GCCGTCTGTTACCCCTGTTCCACCTGCTGTCCCTGTCCCTCAGGCGAATA

CCTCTAATGAAAGAGTAGTCCTATTCCAATAGCTCCGATACCACCTTCT

GTTACTCAGGAGCCACCCGTCCCGTTGGCTCCCCCTTTGCCTGCTGTTGA

TGGCTTTCAAGAACCTCCAATTCCCTCAGCACCTGCAATAGCTACTGCCG

TGCAAAAATCGGGTTCTTCCACCCCAGCTTTAGCTGGAGGCGTTTTGCCT

CCACCCCCACCTTTACCAACTCAACAAGCTTCCACTTCAGAACCTATTAT

CGCTCACGTTGATAACTACAATGGTGCTGAAAAAGGCACGGGCGCATATG

GATCCGATTCTGATGATGACGTTTTATCGATTCCTGAATCAGTTGGTACA

GATGAAGAGGAAGAAGGGGCACAACCAGTTTCTACTGCAGGTATCCCATC

AATTCCACCTGCAGGTATTCCTCCACCCCCACCCCTTCCATGA.

In some embodiments, the mutated coding sequence of PAN1 comprises the following sequence:

(SEQ ID NO: 12)
ATGTATAACCCGTACCAGCAACAGGGCATG<u>GGGTATC</u>AGCAGCAACAGCA

GCAACAGCAGCAACAACCAAATGGATTC<u>TATC</u>CGCAGCAGCAGCAAGGTC

AGTCTTCAAACCAGCCCCAAGGCCAGCCTCAACCACAACAGCAAATGGCG

TTTAACCAGCCTCAGGCTACCGGAATTGGTGGGATGCCTCAAAGTTTTGG

TAATTCTTTCTCAAGTATGCCACAGCAGCCCCAAACGGGTTACAATAATA

ATGGAAATAATGGTAGTGTATATGGTAATGGTAATTTTGGCCAACAACCC

CAGCAGCAACAACAGCAGGCGAAACCGCAGCATACGGGATACGTACCAAA

TTCCAGTATGCCTATGATGAATACTACTGGCACCATGCCTCCACCTAATC

CGGCTCAACAGCCTCAGCTACAATCCATACAACCCCAAGGAACAGGCTAT

-continued

TACCAAGCTGCTAATACTGCAAATGTACACTCAGTACAACCTTTGCAATC

TCAAGGGACAGGATATTATGTGTCTACACCCAATTTGATCTCTTCTAATC

AAACCCAGCAGCCCCTTCAGGCCCAGGGCACTGGTTATTATCAATCTCAA

CCTCAACAGGTGCCACCTCCTCAGCAAGCACAGTCCTTGCAACCTTTGAA

GCCGCAGCAAACAGGATTTTACCTTCAACCGCAAAACCAAGCTCCCTTAG

AACCATTAAAGCCCACCGCAACTGGCTTTGTCAACTCATTTGCCAACAAC

GGTCTAAACAATGATATCAAAATCCCTGCCATTAGATTGTCGTTTATTAC

TGCCCAAGATCAGGCAAAATTTGAGACTCTATTCAGATCAATTGTTACCA

ATGGTTCGAATACTGTTTCCGGTGCTAATTGTAGGAAAATTTTGATGAGA

TCCGGTTTGCCACCTTCTCAACTCGCAAGAATTTGGACGCTTTGTGATAC

ATCAAAAGCAGGTGAGTTACTGTTTCCTGAATTTGCATTAGCAATGCATT

TGATCAATGATGTCTTACAAGGTGACACTATCCCTTACGAATTGGATTCT

AAGACAAAAAACGAAGTTTCAAGTTTTATTGACGCCATTAATTTAAGCAT

TGCAAACCAGGATTCTTCCGCAAACGATGCCCCAAAAACTCCCTTTGATG

AATTCATTACAGCGGGCGTACAAAATTTGCAACCTCAACCAACAGGATAT

ATGCCTCAAACTAGTTTTGGTATCCCATTACAGTCTCAAATTACTGGAGG

CGGTGTTGCCTCGGCGTTGAATCCTCAATCCACAGGATTTATGGCACCAA

CCACTTTCAACATGTCAATGAATACCGGAACTCCCGGATTGAACCCCCAA

ATTACTGGAGGAGCACCTGCCTCTATGCAACCCAACATTACTGGCAATGC

TTTGCAACCTCAGACAACTGGTATGATGCCACAGACAACTGGTATGATGC

CACAGACAACTGGTATGATGCCACAGACTTCATTTGGCGTTAATTTAGGA

CCTCAGTTGACCGGCGGTGCTTTGCAATCTCAGTATACCGGAGGATATGG

TTCCGTTATGCCCCAGCAAAGCGGTCCTGCAAGTATGCCCAATTTGTCCT

TTAATCAACAAGGATTACAATCTCAGTTAACCGGGTTGCAACCCCAACCA

ACGGGTTTTCTACCACCATCTAACTTTAGTGCTACCATGCCGTTGACTGC

CCAAAAGACAGGATTTGGTAATAACGAAATTTATACCAAATCCAACTTTA

ATAATAACTTAATTGATAACTCAAGTCAAGACAAAATTTCCACGGAGGAA

AAATCTTTGTTTTATAAAATTTTTGAAACTTTTGATACTCAAAACAAAGG

TTTGTTAGATTCCCCACTGCTGTGGAGATTTTTAGAAAATCTGGCTTAA

ATCGTGCAGATTTGGAGCAAATTTGGAACCTTTGTGATATAAACAACACC

GGCCAATTGAATAAACAAGAATTTGCACTAGGTATGCACTTGGTTTACGG

TAAATTAAACGGGAAGCCAATCCCCAATGTCCTACCTTCAAGTTTAATTC

CCTCCAGCACAAAACTTTTAGACAACTTAAAGAACCAATTAAAGACAGAG

CCAACGACCACAAAAGAAAAACCTTCGTTTGGTAAAATCGATGCCTTGAG

CTACAAAAATAATGATGATGATGTTTTGCCGAACTATAGAAATCGTAGGA

AGGTTTACTCTGCGAAAAATGAAGAGCAATCTTCTTTTTCTTCACCATCT

GCTAAATCTGTTAATCATTCTAGCAGCACCCTTCAAACCGATGACATTTC

GGTAGATAAGACTGTTGAAAAGAAGACAGCGAAACCAAAATATGCTGGGT

TTTCAAGAGAAATAAATCTGAAAAATATTGCTTCAGTGGAAAATGAGATC

AAAAATATCAGCAATCCTGAAAACTGTTATGACAGTTCTATTCCATCAGA

TTTGACAAGCCGCTTTGATGCCATCATCGCCAAACTTCCAAACCTATTCA

ATGAAATTTCTACAATTGATAATGAGATTACCAATGCAAAAATTCAGTTG

TATAGAAAAAAAATCCTTCTTCGATAATTGGATCTGGTCCAAATGGTGA

AATAACTGAAAATGATAGGAAGAAAGCTAAGAGTAGGGCTTTGTTGAGAG

CAAGGATGTCTGCTCTAACAGGAAAATCAACGGAATCGGAGGATTCACTT

TCCATGGAAGATGAACAGCAAAGTGCTGAAATCAAGAGAATCCAGCAGGA

AAATGGTAAGAACCAAGAAATCATTAAAGACATAAGGTCATCTATATCAG

ATATTTCTGCATCCTTGAAGTCTACTATGACAGGATCGAATATGATATCC

AATCAAGAATTTGAAAGATGGGAATTTGGCATAGGGTTAGAAGATGGTGT

TCGTGAATTTTTGGATGATCTGAAGTCAAATTCAAATAAATCAGTGACTG

AGTCATCTCCCTTTGTGCCTTCCTCAACACCAACCCCTGTAGATGACCGT

TCCTCGTCGCCTTCTTATTCTCAGTTCAAAACTGCTGAAGAAAGAGCAGC

TTATCTGAAAGAACAGGCAAAAAAGAGAATGAAGGAAAAATTAGCTAAAT

TTGATAAGAATAGGCGAAATGTTACTCAAAGTTCCAGATCGATTAGCAGT

GAAAACTCTCGAGAACAGCCACAACAGATTGCTGGTTCTTCCAATTTAGT

TGAACCTAGAGCAACTCCATTCCAAGAAGAAAAATATGTGGAAGTCGCTC

AACCAACTCAACCTGTTCAATCAACACAACCTGTTCAACCAACTCAACCT

GTTCAGCCAACTCAACCTGTTCAGCCAACTCAACCTGTTCAGCCAACTCA

ACCTGTTCAACCAACTCAACCTGTTCAGAATGTATATAATGCAAAGCAAG

AATCCGATGATGAAGATGAAGATGATGAAGAAAAGCGTTTACAAGAGGAG

CTAAAACGATTGAAACTTAAAAAAAAGGCTGATAAAGAAAAAAGACTTGC

AGCTTTACGTAAGCAAATTGAGGATGCTCAAAATGAAAGTGACGAAGAGG

AGACAAACGGAAAAGACAACTTTGGCGGCCATGTGAACGTTCCTCAGGCC

GCTCCAGTGGCACCATCTGCAGCTTTTTCGCAAAATTCTACTAATGCTCC

TCGCTCGGTACACGCTGCTGTTACCCCTGCCGCAGGTAAGAACAGTACTG

GTCTGCCTTCCACGACAATGGGCCATAATCCATACTTCAAGGATGCATCA

GCTAGCTCTACATCTACTTTCGATGCTCGCGCTGCAGAAATGCAAAGAAG

AATCCAAAGAGGATTGGATGAGGACGAGGATGATGGATGGTCTGATGAAG

ACGAGAGTAATAACCGCGTAGCTGTAGATAATAAGGTTGAAGAAGCAAAG

ATTGGTCATCCTGATCATGCACGTGCTCCACCTGTTACTGCTGCTCCCTT

GCCGTCTGTTACCCCTGTTCCACCTGCTGTCCCTGTCCCTCAGGCGAATA

CCTCTAATGAAAGAGTAGTCCTATTCCAATAGCTCCGATACCACCTTCT

GTTACTCAGGAGCCACCCGTCCCGTTGGCTCCCCTTTGCCTGCTGTTGA

TGGCTTTCAAGAACCTCCAATTCCCTCAGCACCTGCAATAGCTACTGCCG

TGCAAAAATCGGGTTCTTCCACCCCAGCTTTAGCTGGAGGCGTTTTGCCT

CCACCCCCACCTTTACCAACTCAACAAGCTTCCACTTCAGAACCTATTAT

CGCTCACGTTGATAACTACAATGGTGCTGAAAAAGGCACGGGCGCATATG

GATCCGATTCTGATGATGACGTTTTATCGATTCCTGAATCAGTTGGTACA

GATGAAGAGGAAGAAGGGGCACAACCAGTTTCTACTGCAGGTATCCCATC

AATTCCACCTGCAGGTATTCCTCCACCCCACCCCCTTCCATGA.

Introduction of a mutation into the genome of a cell is well known in the art. Any known genome editing method may be employed, so long as the mutation is specific to the location and change that is desired. Non-limiting examples of mutation methods include, site-directed mutagenesis, CRISPR/Cas9 and TALEN.

In some embodiments, the method further comprises determining whether a synonymous mutation would reduce translation efficiency below the threshold. In some embodiments, the method further comprises determining for a given synonymous mutation the reduction in translation efficiency caused. In some embodiments, the method further comprises comparing the reduction caused to the threshold. In some embodiments, determining whether a synonymous mutation or substitution would reduce translation efficiency below the threshold comprises examining each codon sequentially starting at the 5' end of the coding sequence or starting at the 3' end of the coding sequence. In some embodiments, determining whether a synonymous mutation or substitution would reduce translation efficiency below the threshold comprises examining all codon substitutions possible in the coding sequence simultaneously and selecting mutations in descending order of how greatly they increase the free ribosome pool. In some embodiments, determining whether a synonymous mutation or substitution would reduce translation efficiency below the threshold comprises performing any one of the Forward Gene Minimization (FGM), Backward Gene Minimization (BGM) and Greedy Gene Minimization (GGM) algorithms.

The terms "express" or "expression" as used herein refers to the biosynthesis of a product, including the transcription and/or translation of said gene product or a non-coding RNA. Thus, expression of a nucleic acid molecule may refer to transcription of the nucleic acid fragment (e.g., transcription resulting in mRNA or other functional RNA) and/or translation of RNA into a precursor or mature protein (polypeptide).

By another aspect there is provided, a pharmaceutical composition comprising a cell of the invention and a pharmaceutically acceptable carrier, excipient or adjuvant. In some embodiments, the modified cell comprises a faster translating synonymous codon, the modified cell comprises decreased replicative fitness and the composition is a vaccine composition. By attenuating the health of a bacterium or other infectious agent, a live vaccine against the bacterium or infectious agent can be generated. In some embodiments, the composition is an immunogenic composition.

The terms "vaccine composition" and "vaccine" as used herein are interchangeable and refers to a product, the administration of which is intended to elicit an immune response that is capable of preventing and/or lessening the severity of one or more infections.

It should be understood that an attenuated cell of the invention, where used to elicit a protective immune response (i.e. immunize) in a subject or to prevent a subject from becoming afflicted with a disease, is administered to the subject in the form of a composition additionally comprising a pharmaceutically acceptable carrier. As used herein, the terms "carrier" and "adjuvant" refer to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

By another aspect, there is provided a method for vaccinating a subject at risk of infection, the method comprising, administering to said subject the vaccine composition described herein.

The term "subject at risk of infection" includes but is not limited to a subject with a likelihood of future exposure to an infectious agent, future exposure to an individual or animal infected with the infectious agent, or future exposure to biological mater infected with the infectious agent, or is generally at a higher risk than the general population of contracting the infection.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

EXAMPLES

Material and Methods

Reference *S. cerevisiae* and *E. coli* Genome Assemblies

*S. cerevisiae* genomic data (R64-1-1) was downloaded from BioMart. A reference 'genome' was compiled by taking unspliced transcripts (in this case unspliced ORFs) and flanking them with upstream and downstream segments up to 1000 nt, with the constraint they cannot overlap annotated ORFs unless this causes the segment to be under 30 nt (approximate ribosomal footprint). A reference transcriptome was compiled similarly, only with annotated ORFs, annotated UTRs were added to the ORFs when available, otherwise flanking segments were supplemented as described. Since there is no alternative splicing in *S. cerevisiae*, both the genome and transcriptome contain 6664 genes. There were 4415/6664 annotated 5'UTRs, and 5126/6664 3'UTRs. Considerable specific rRNA contamination may remain even after depletion by subtractive hybridization. Thus, a significant fraction of sequencing reads are derived from digested rRNA present in the monosome sample. Therefore, reads mapping to rRNA are first filtered, against a rigorous rRNA database. Aside from rRNA contamination, there are contaminating sequences derived from other abundant ncRNAs, such as tRNAs. The extent of rRNA and ncRNA contamination can vary, particularly when global changes in protein synthesis alter the fraction of active ribosomes, and thus the number of ribosome-protected footprints relative to other RNAs. Thus, reads are also mapped separately to an annotated non-coding RNA database. rRNA (16 genes), tRNA (299 genes), ncRNA (15 genes), snRNA (6 genes) and snoRNA (77 genes) databases were compiled from BioMart (sc_R64-1-1).

E. coli genomic data for strain k-12 MG1655 (ASM584v2.31) was downloaded from Ensembl Bacteria. The genome and transcriptome were compiled similarly to S. cerevisiae. No annotated UTRs were available, and since the E. coli genome is compact flanking segments of 200 nt instead of 1000 nt were substituted and ensured that also these pseudo UTRs were non-overlapping with annotated ORFs, again unless this causes the segment to be under 27 nt (approximate ribosome size). The E. coli genome has 4140 protein coding genes, 22 rRNAs, 86 tRNAS, and 65 ncRNAs.

Mapping Ribosomal Footprints and mRNA Fragments

The following read (ribosomal footprint or mRNA fragment) mapping protocol was devised and implemented, for each of the replicates separately:

1) The 3' end adapter CTGTAGGCACCATCAAT (SEQ ID NO: 13) was removed from the 51 nt long reads using Cutadapt v1.6, retaining only reads with a minimum length of 24 nt and maximal length of 34 for ribosomal footprints, and 24-40 nt for mRNA fragments, for S. cerevisiae. For E. coli read lengths of 20-42 nt were retained.

2) These reads were then initially mapped against the respective non-coding databases, using Bowtie v1.1.2: -a- best-strata-n 2-seedlen 21-tryhard. In-n mode, alignments may have no more than N mismatches in the seed, which was chosen here to be 2, with the seed length being 21 for S. cerevisiae, and 20 for E. coli, as sequencing errors are more likely near the end of the read. Specifying-a instructs bowtie to report all valid alignments, subject to the alignment policy, enabling us to control the mapping selection process, with-best-strata causing bowtie to report only those alignments in the best alignment "stratum". Throughout the analysis, the Bowtie mapping is executed as described. Reads which mapped against the non-coding databases were removed.

3) The remaining reads were first mapped against the assembled 'genome' using Bowtie as described. The read mapped position is at first attributed to the read's 5' end first nucleotide (Bowtie default) and is then determined according to the heuristic below. Uniquely mapped reads are identified accordingly. Many of the multi-aligned reads are attributable to known duplicated genes and segmental duplications. This is expected for paralogs that are very similar to each other and for internally repeated domains within some genes. If all multi-aligned reads are simply discarded, the end result will be to undercount greatly or even entirely fail to report expression for genes that have closely related paralogs, such as those of the ubiquitin family for example. Specifically, in the dataset, the human transcriptome, many of the alternatively spliced transcripts of a gene bear high similarity.

Multiple aligned reads were extended to 30/27 nt for S. cerevisiae and E. coli respectively (the respective approximated ribosome size), with a mismatch score calculated. Reads with a single minimal mismatch score were deemed unique. Multi-aligned reads were handled after the A-site shift was determined for ribosomal footprints (mRNA fragments mapped position is assumed to be the 5' end first nucleotide). The A-site shift was calculated as a function of the read lengths (a range of 24-34 nt and 20-42 nt, for S. cerevisiae and E. coli respectively, as determined by Cutadapt) at the start codon of the uniquely mapped reads, guided by the logic that the offset between the ribosome A-site and the start of the footprint would be of different proportion in the varying read length. Reads mapped in the vicinity ±50 nt of the start codon were looked at, and the ribosomes real A-site was defined to be 15 nt and 12 nt for S. cerevisiae and E. coli respectively, it was then heuristically hypothesized that the read length A-site position adjusted according to the following formula is:

ASShift=realAS−round((riboSize−readLength)/2); if the read length is shorter than the ribosome size ASShift=realAS+round((readLength−riboSize)/2); otherwise.

Where ASShift is the resultant hypothesised A-site shift, realAS as defined is 15/12 nt, riboSize was taken to be 30/27 nt, for S. cerevisiae and E. coli respectively, and readLength is the read length as determined by Cutadapt. The Matlab's find peaks function was used to find local maxima in the profile induced by the respective read length group mapping. The local peaks were sorted according to prominence and then tested the top three, with the one closest to our hypothesized A-site shift being selected.

Multi-aligned reads were first tested to see if they overlap annotated ORFs, if so they were removed from the multi-aligned contenders (in a few instances this resulted in a uniquely mapped read). Equal contender's vicinity read density was calculated 30/27 nt, for S. cerevisiae and E. coli respectively, upstream and downstream of the mapped read's A-site (the read mapped position). Each of the multiple mapped positions is then assigned a fraction of the read, signifying its relative frequency based on its vicinity read density. In some rare instances the vicinity read density of all the multi-aligned reads is zero (possibly reflecting very recent gene duplication), the reads were then distributed evenly among the mapped positions candidates. The inclusion and proportionate distribution of multiple aligned reads will naturally have variable impact on RNA quantification, with smaller effects on paralogs that are more divergent and larger effects on those that are more similar to each other.

4) Unmapped reads were then mapped to the transcriptome to account for splice junctions.

5) Reads mapped to the transcriptome are integrated into the genome mapping according to the exon positions. Total read count per gene is then calculated according to exon mappings only, with the respective ribosome footprint size taken from the UTRs.

Whole Cell Simulation to Infer RFMNP Parameters

The RFMNP (RFM (Ribosome Flow Model) network was used with a pool) to model translation, which is a general dynamical model for large-scale simultaneous mRNA translation and competition for ribosomes based on combining several ribosome flow models (RFMs), each representing a single copy of a gene, interconnected via a pool of free ribosomes.

According to the RFM a ribosome that occupies the i-th site moves, with rate $\lambda_i$, to the consecutive site provided the latter is not occupied by another ribosome. Transition rates are determined by the codon composition of each site and the tRNA pool of the organism. Briefly, the elongation rate associated with a codon is proportional to the abundance of the tRNA species that recognize it, taking into account the affinity of the interactions between the tRNA species and the codons. Denoting the probability that the i-th site is occupied at time t by $p_i(t)$, it follows that the rate of ribosome flow into/out of the system is given by: $\lambda[1-p_1(t)]$ and $\Lambda_n p_n(t)$ respectively. Hence, the rate of ribosome flow from site i to site i+1 is given by: $\lambda_i p_i(t) [1-p_{i+1}(t)]$. Thus, one gets the following set of differential equations that describe the prOCC33 of translation elongation:

$$\begin{cases} \dfrac{dp_1(t)}{dt} = \lambda[1-p_1(t)] - \lambda_1 p_1(t)[1-p_2(t)] \\ \dfrac{dp_i(t)}{dt} = \lambda_{i-1} p_{i-1}(t)[1-p_i(t)] - \lambda_i p_i(t)[1-p_{i+1}(t)] \ \ 1 < i < n \\ \dfrac{dp_n(t)}{dt} = \lambda_{n-1} p_{n-1}(t)[1-p_1(t)] - \lambda_n p_n(t) \end{cases}$$

The interconnection between the RFMs is performed via the initiation rate of each RFM (gene), modeled as: $G_j = \lambda_{0j}$ tan h (Z/c), where $\lambda_{0j}$ denotes the initiation rate of gene j (local component), Z denotes the free pool of ribosomes (global component), and c is a parameter of the model. The use of tan h is appropriate for modelling a saturating function and is a standard function in ASEP models with a pool, because it is 0 when Z is 0, uniformly bounded and strictly increasing for Z≥0. Furthermore, for Z≤0 the function tan h(Z) takes values in [0,1) so it can also be interpreted as a probability function.

The RFMNP has three parameters which need to be estimated, initiation rates, codon elongation rates, and c (the parameter of the model). A novel iterative algorithm was developed for this purpose:

Initial initiation rates were estimated to be the measured ribosomal read count divided by the mRNA levels (Ribo-Seq measurements described above), and then normalized to have the median of the estimated median initiation rate which is 0.8 per second for *S. cerevisiae*, and 0.6 for *E. coli*.

Initial codon elongation rates were calculated based on the tRNA Adaptation Index (tAI) with a minor adjustment.

Let ni be the number of tRNA isoacceptors recognizing codon i. Let tCGNij be the copy number of the j-th tRNA that recognizes the i-th codon and let Sij be the selective constraint on the efficiency of the codon-anticodon coupling. The absolute adaptiveness was defined, Wi, for each codon i as:

$$W_i = \sum_{j=1}^{n_i} (1 - S_{ij}) tCGN_{ij}$$

The Sij-values can be organized in a vector (S-vector) as described in; each component in this vector is related to one wobble nucleoside-nucleoside paring: I:U, G:U, G:C, I:C, U:A, I:A, etc. Eukaryotic and prokaryotic S values were taken from.

From Wi one obtains pi, which is the probability that a tRNA will be coupled to the codon:

$$p_i = \dfrac{W_i}{\sum_{j=1}^{n_i} tCGN_j}$$

$p_i$ was normalized to have the median of the estimated codon rate which is 6.4 aa/s (growth rate range 2.8-10.0) in *S. cerevisiae*, and 13.5 aa/s (growth rate range 5-22) in *E. coli*. Also, in *S. cerevisiae*, the CGA codon according to tAI is disproportionally slow, and thus it was set to be 10 times the slowest codon. The expected time on codon i $t_i = 1/p_i$. Each gene is coarse grained into sites/chunks of C codons, thus for each chunk the codon times are summed, and the chunk rate is:

$$1 / \sum_{i=1}^{C} t_i.$$

A chunk size of 10 codons (the approximate size of the ribosome) was used. If the last chunk is 5 codons or less, it is incorporated in the chunk before it, in-order to avoid extremely fast chunks which would distort the simulation.

The following iterative steps are then performed:

1) The initiation rates are optimized for each gene separately utilizing the RFM, hill-climbing by increasing or decreasing the current initiation rate by 5% until abs($rd_j - rcm_j$)<ϵ, where $rd_j$ is the estimated RFMNP ribosomal density for gene j, $rcm_j$ is measured ribosomal read count divided by the mRNA levels of gene j, and ϵ is $10^{-3}$. Instead of having the initiation rate as a separate parameter/chunk in the RFMNP calculation, it is incorporated into the first chunk so that a more balanced estimation of the initiation rates is possible, as when simulated as a standalone chunk the initiation rate is estimated to be disproportionally high. In order for the ribosomal read count divided by the mRNA levels (rcm) to be on the same scale of the predicted RFM ribosomal density, it was normalized to have the median of the median ribosomal coverage of an *S. cerevisiae* mRNA molecule and for *E. coli*.

2) Utilizing the optimized initiation rates, and the initial elongation rates, an iterative implementation of RFMNP was performed in order to estimate c, and instead of solving an ODE system as originally suggested per gene, a novel, linear-algebraic approach linking the protein translation rate is used to the maximum eigenvalue of a symmetric, non-negative tridiagonal matrix whose components are functions of the initiation and elongation rates, which provides a substantial speedup, the translation rate which is what used as a proxy of translation efficiency (TE) is the square root of the maximal eigenvalue.

H denotes the number of ribosomes in the system, Z the number of free ribosomes, (H and Z are determined according to the literature, see below), $M_j$ the number of mRNA copies of gene j, and $x_i^j$ the number of ribosomes on segment/chunk i in gene j. In steady-state: H=Z+ ($\Sigma_j \Sigma_i x_i^j \cdot M_j$).

First iteration: Begin by guessing $c_0$, since the logical range for c is between the smallest positive floating-point number s and H, $c_0$=median([s, H]) was chosen, which determines the initiation rate: for each gene j, the initiation rate $G_{0j} = \lambda_{0j}$ tan h (Z/$c_0$), where $\lambda_{0j}$ is the estimated local initiation rate, and tan h (Z/$c_0$) the global initiation rate of gene j, and the RFM model for every gene separately until convergence: $Z_1$=H-($\Sigma_j \Sigma_i x_i^j(0) \cdot M_j$)

Kth iteration: $Z_k$=H-($\Sigma_j \Sigma_i x_i^j(k-1) \cdot M_j$), with k-1 being the resultant density of the previous iteration as input to the current. A binary search is performed on the c range and $G_{kj} = \lambda_{0j}$ tanh (Z/$c_k$).

Termination condition: abs(Z-$Z_k$)<ϵ, with ϵ being $10^2$.

3) The codon elongation rates were greedily optimized to maximize the correlation between measured (Ribo-Seq) ribosomal density (RD) and predicted RFMNP RD (by concatenating the measured and RFMNP RD profile of each gene into one vector respectively). In each iteration, the 61 codons are iterated according to four order schemes: i. From slowest to fastest. ii. From fastest to slowest. iii. From most frequent to least frequent. iv. For 100 random permutations of the order (which are predefined and the same 100 random permutations are utilized throughout the algorithm iterations). First, calculate the initial correlation between Ribo-Seq and RFMNP RD (which is 0.7, $p<10^{-308}$). Then, for each of the order schemes the codons were iterated, and for each codon it was tested if reducing/increasing its translation time by a specified percentage epsilon improves the correlation, while constraining the new codon times to have at least a 0.5 Pearson and Spearman correlation with the original tAI estimated codon rates. Finally, the most successful scheme is selected from the 103 orders, and this determines the optimized codon elongation rates for the next iteration. This was tried with epsilon being 1%, 5%, 10%, 15%, 20%, 25%, 30%, 35%, 40%, 45%, 50%, 55%, 60%, 65%, 70%, 75%, 80%. The correlation with Ribo-Seq were robust across the percentage groups ranging from 0.74-0.85, and 0.82-0.85, in *S. cerevisiae* and *E. coli* respectively. The estimated codon elongation rates resulting from epsilon being 50% and 35% were selected for *S. cerevisiae* and *E. coli* respectively, though results are robust across the percentage groups.

The 3 algorithm steps are performed iteratively (with the initiation rates recalculated with the new optimized codon elongation rates, and c estimated utilizing the newly optimized initiation rates and codon elongation rates) until no improvement larger than $10^{-4}$ on the 3rd step's correlation can be made.

The number of *S. cerevisiae* ribosomes used in the simulation was 200000, with 60000 mRNAs, scaled according to the mRNA levels calculated. The number of free ribosomes in the pool is ~15%, thus 30000. The median ribosomal coverage is 0.1322.

The number of *E. coli* ribosomes used in the simulation was 40000 (growth rate range of 6800-72000), with 4400 mRNAs (growth rate range of 1000-7800). The average length of the transcript portion encoding a gene is 1000 nt, was used to calculate the number of mRNAs in the cell from, and the median ribosomal coverage which is 0.3105 (based on a 60 nt average distance between ribosomes, 27 nt ribosome size, and average mRNA length).

Results are robust to variations in the selected parameters.
Parameter Estimation Randomization Tests To show that the correlation achieved between Ribo-Seq and RFMNP RD in the previous section is indeed related to the elongation rates (i.e. the initial tAI estimation values and the subsequent optimization), the following 100 randomizations were performed. The tAI predicted codon times were randomly permuted and the codon elongation rates calculated according to those randomized times, and then step 1 and step 2 of the estimation algorithm was performed once. RFMNP RD was then predicted for each of the randomizations and correlated it with the Ribo-Seq RD as described above. For *S. cerevisiae* the real correlation achieved for the first iteration was $r^2=0.49$ ($r=0.70$, $p<10^{-308}$), while all 100 randomizations achieved a lower correlation with a mean value of $r^2=0.26$ ($r=0.51$), giving an empirical p-value of 0. Similar results were achieved for *E. coli*, where the real correlation achieved for the first iteration was $r^2=0.67$ ($r=0.82$, $p<10^{-308}$), while all 100 randomizations achieved a lower correlation with a mean value of $r^2=0.59$ ($r=0.77$), giving an empirical p-value of 0. This result is strong as the initiation rates were optimized according to the randomized elongation rates and real Ribo-Seq measurements, thus coupling the initiation and elongation in a synergistic manner.

Another test was performed, where the first iteration optimized initiation rates and c were used, and the size of the free ribosomal pool was predicted while permuting the codon elongation rates based on the initial codon rate tAI estimation values (i.e. unoptimized codon rates) 100 times (in the same manner as the test above). In all cases the free ribosomal pool was lower than the real *S. cerevisiae* free ribosomal pool of 30000 ribosomes, giving an empirical p-value of 0, with the mean predicted free ribosomal pool being 9421. Similar results were achieved for *E. coli* where in all cases the randomized free ribosomal pool prediction was lower than the *E. coli* free ribosomal pool of 5600 ribosomes, giving an empirical p-value of 0, with the mean predicted free ribosomal pool being 2630.

Whole Cell Simulation of Ramp Engineering

The inferred initiation rates, codon elongation rates, and c were used, in order to determine the optimal ramp mutations across the host genome, according to the following RE (Ramp Engineering) greedy algorithm. A mutation is defined as a gene location, a location is defined as the first nucleotide (nt) of a codon, for example, if the second codon is mutated, its location within a gene would be the fourth nt. An RE step is defined as:

Iterate all the host genes, for each gene the first 50 codons are looked at (disregarding the first 10 codons due to important initiation regulatory signals), and mutate a codon to its slowest synonymous codon, as long as it does not reduce the gene's translation rate or efficiency (as calculated by the RFMNP) beyond some threshold τ; 0.1%, 0.5%, 1%, 1.5%, 2%, 2.5%, 3%, 3.5%, 4%, 4.5%, and 5% were chosen as thresholds. The best mutation is the one that most increases the free ribosome pool, and it is selected.

Iterating one mutation at a time across the entire genome is overly time consuming, and also counterproductive, as ultimately, one would like to minimize the number of genes mutated, due to experimental constraints. Thus, 3 variants of the above approach which operate at the gene level were developed:

1) Forward Gene Minimization (FGM): Per gene start at the beginning of the ORF and incorporate all mutations that improve the free ribosomal pool while not reducing the gene's translation rate beyond some threshold τ. In each iteration, the gene which most increases the free ribosomal pool is selected.

2) Backward Gene Minimization (BGM): Similar to FGM, only now it starts at the end of the gene's ORF and traverses backwards. The logic for this variation is that since many important signals are encoded at the beginning of the ORF it may be advantageous to maintain them.

3) Greedy Gene Minimization (GGM): Per gene iterate over all possible mutations and choose the one which most increases the free ribosomal pool. Repeat this procedure until no more mutations can be selected without violating the translation rate threshold τ. Select the gene which most increases the free ribosomal pool.

One could continue until there is no improvement, however it was decided that it terminate after the best 100 genes were selected, as practically/currently it is not feasible to introduce more mutations to generate novel engineered genomes.

Example 1

Fitting a Whole Cell Simulation Model to Experimental Data

Figure 1B:
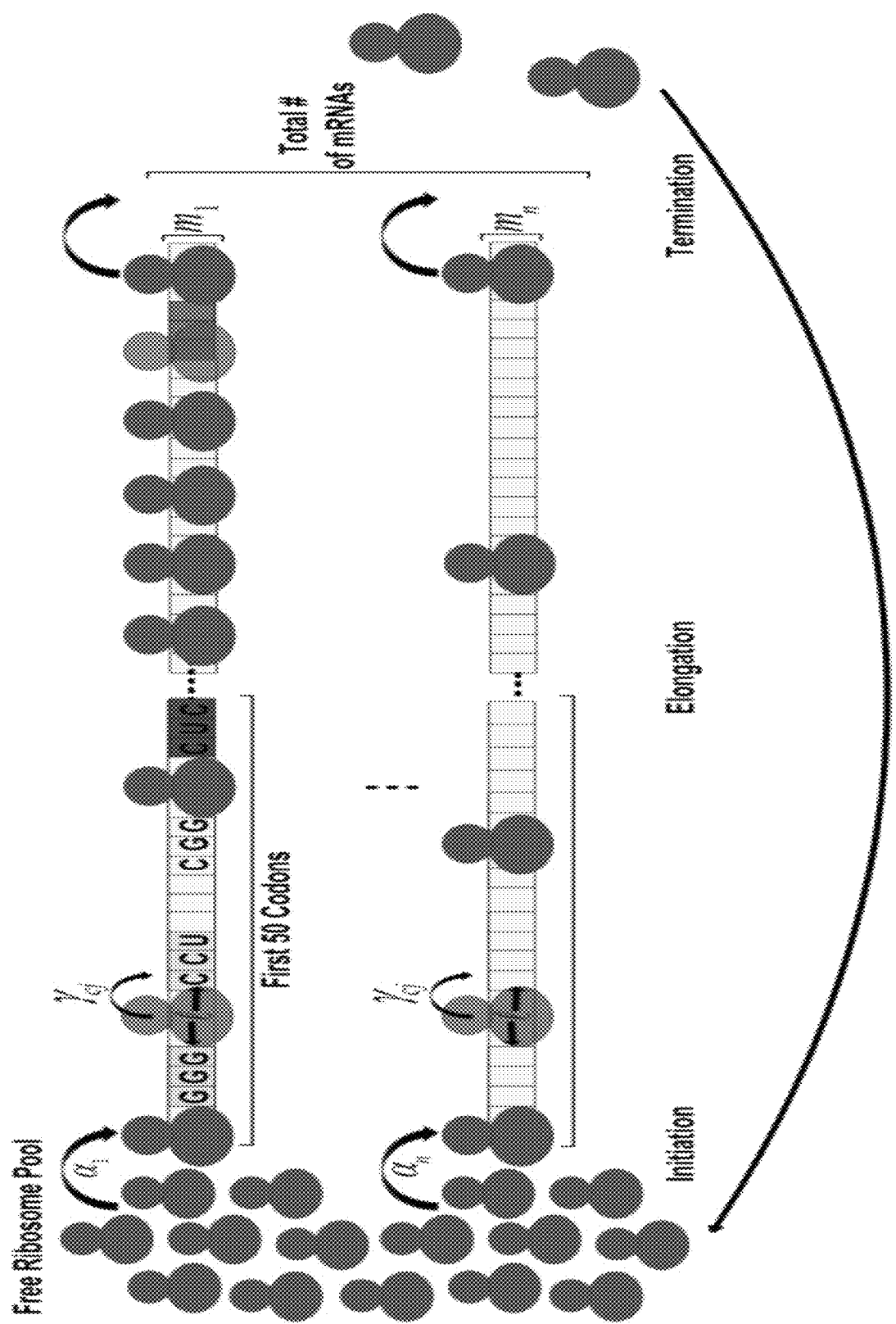
Figure 1C:
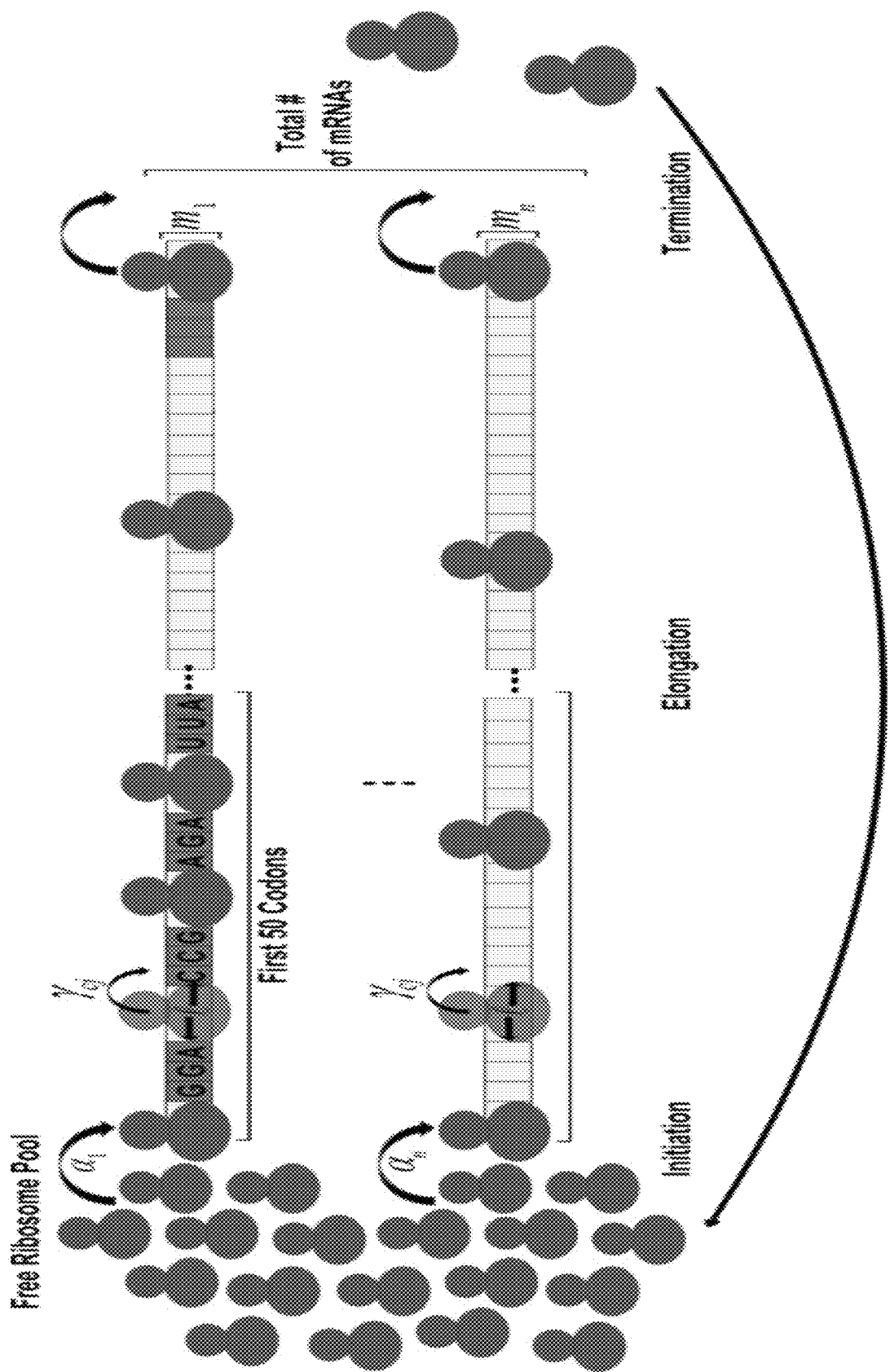
Figure 2A:
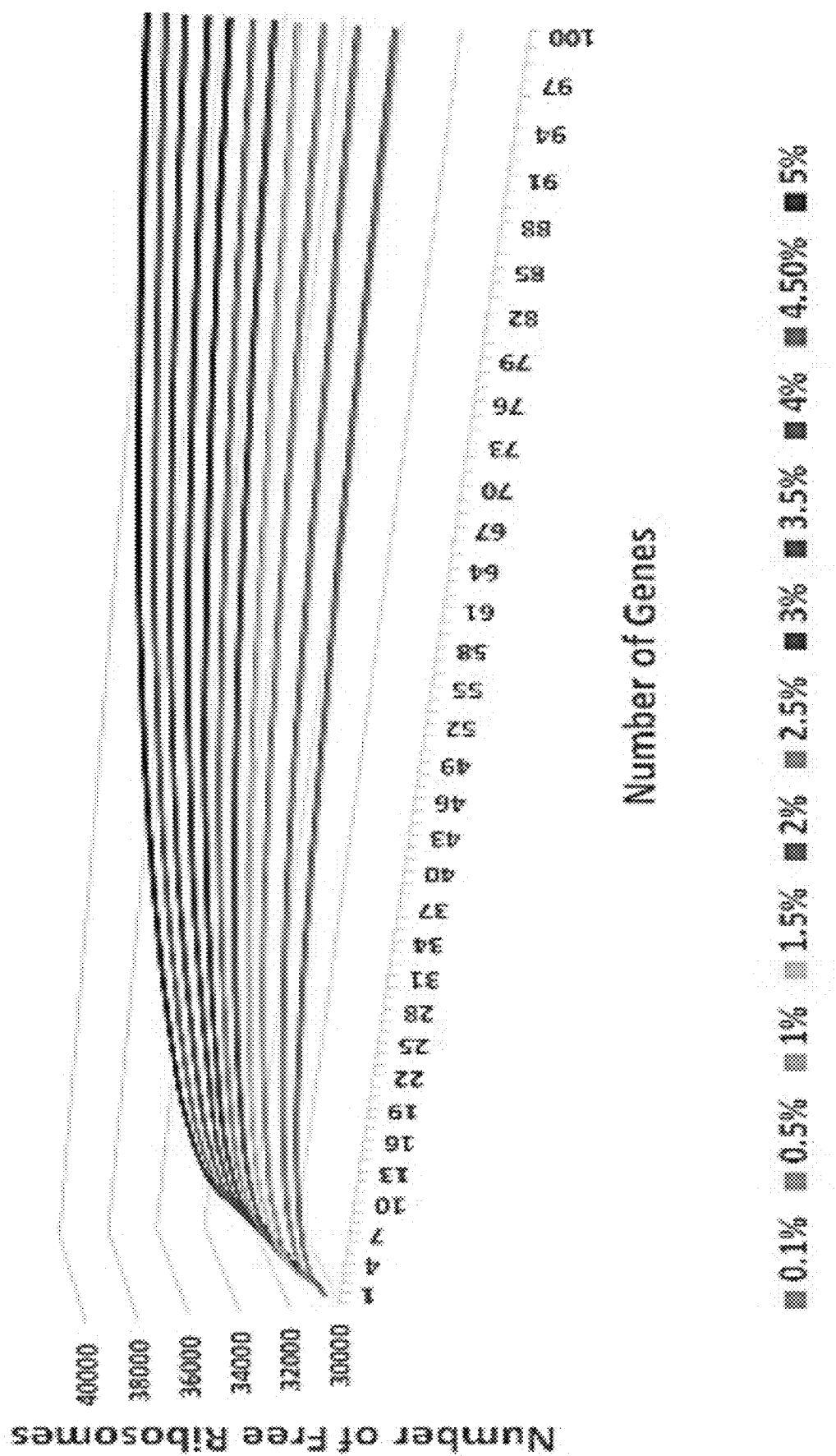
FIGS. 2A-2D.
Figure 2B:
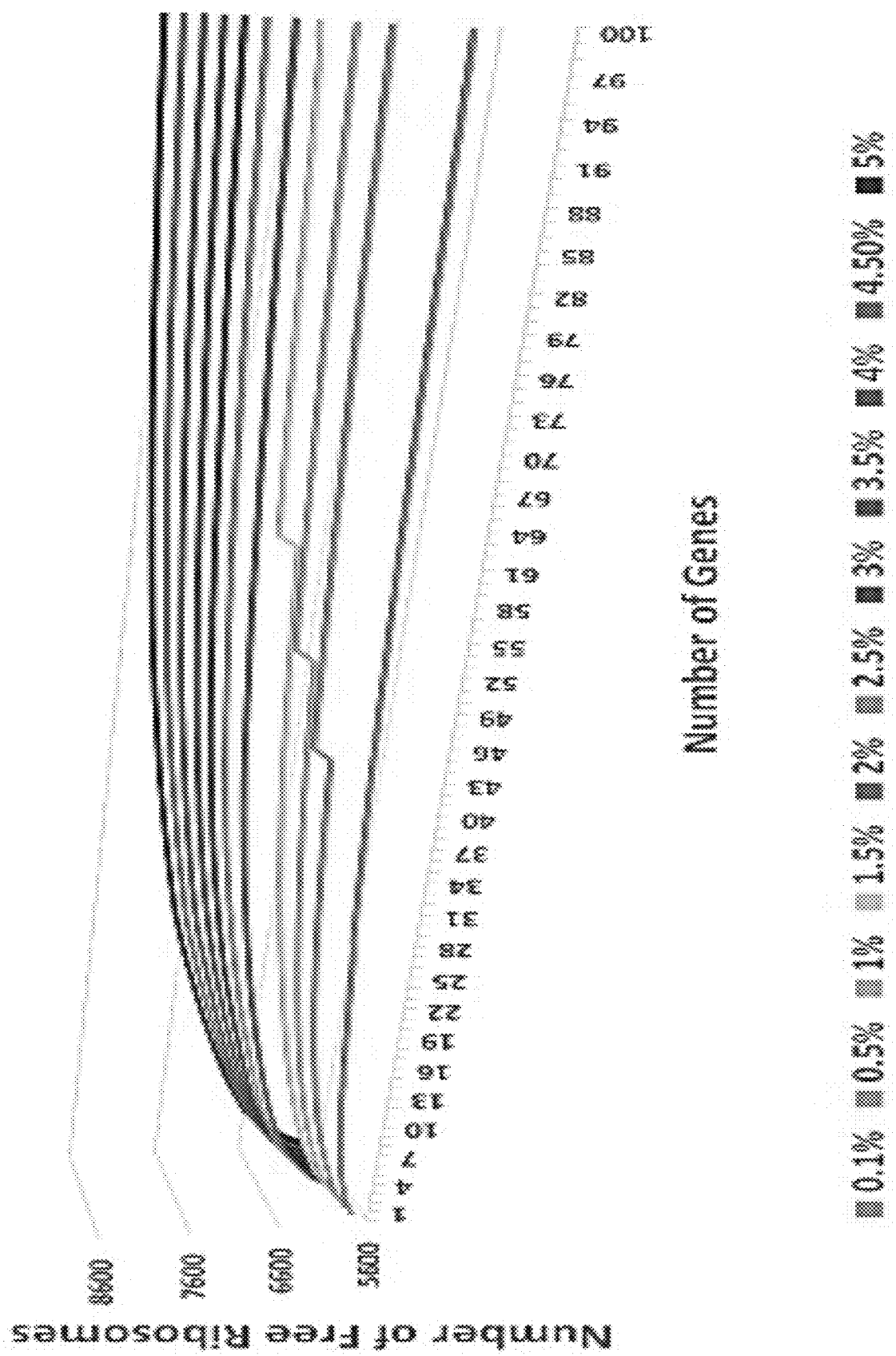
Figure 2C:
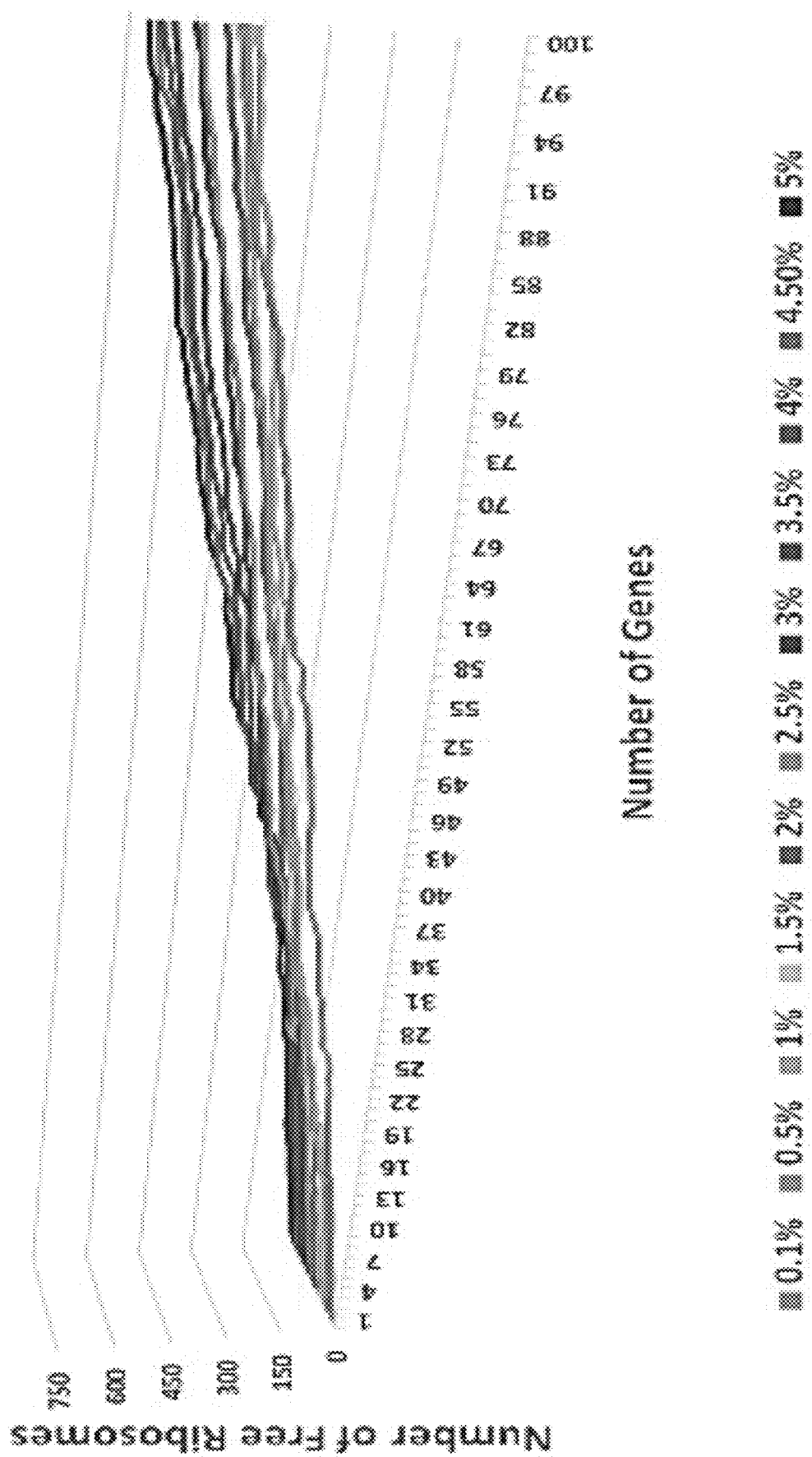
Figure 2D:
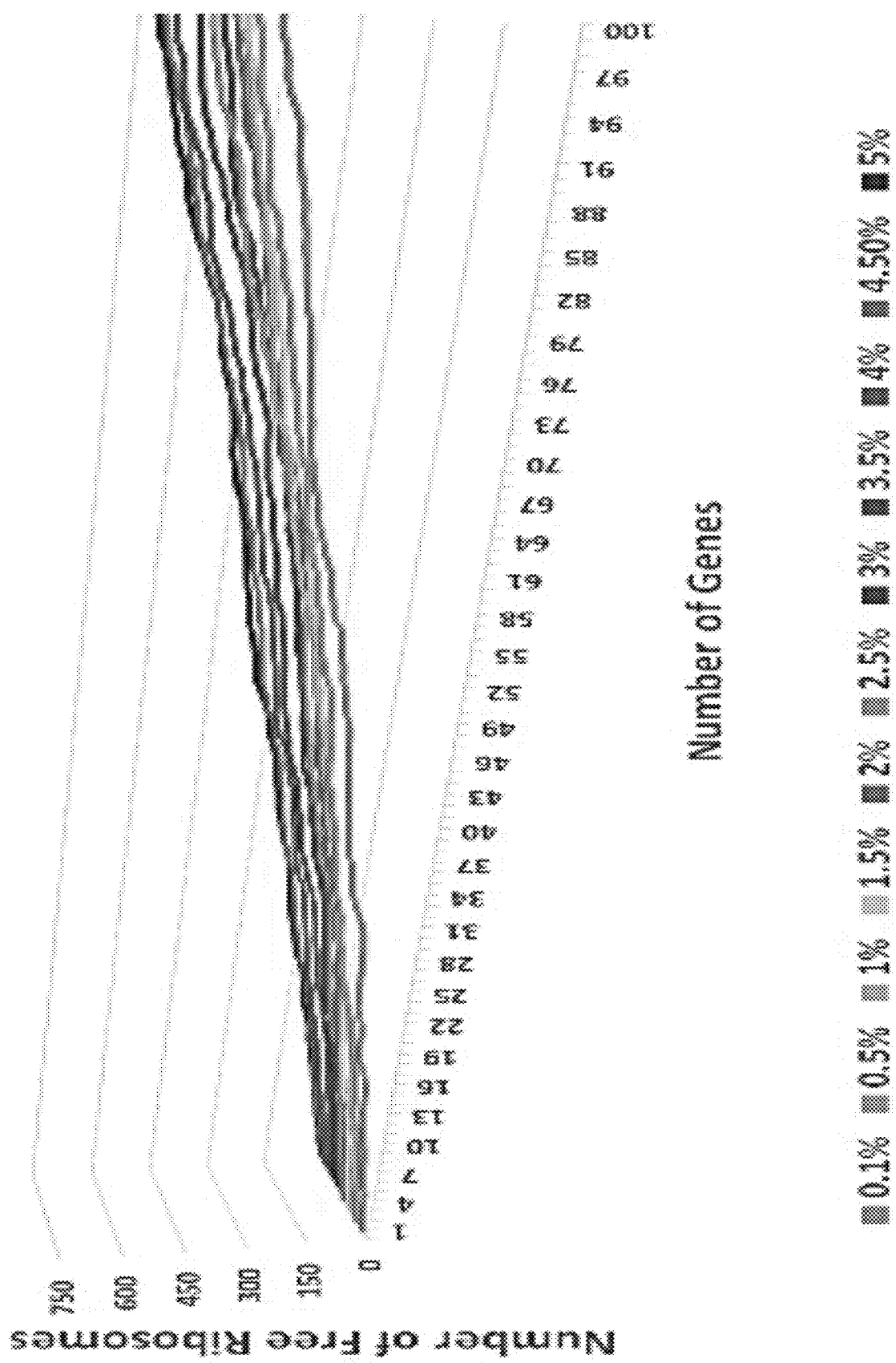
Figure 3A:
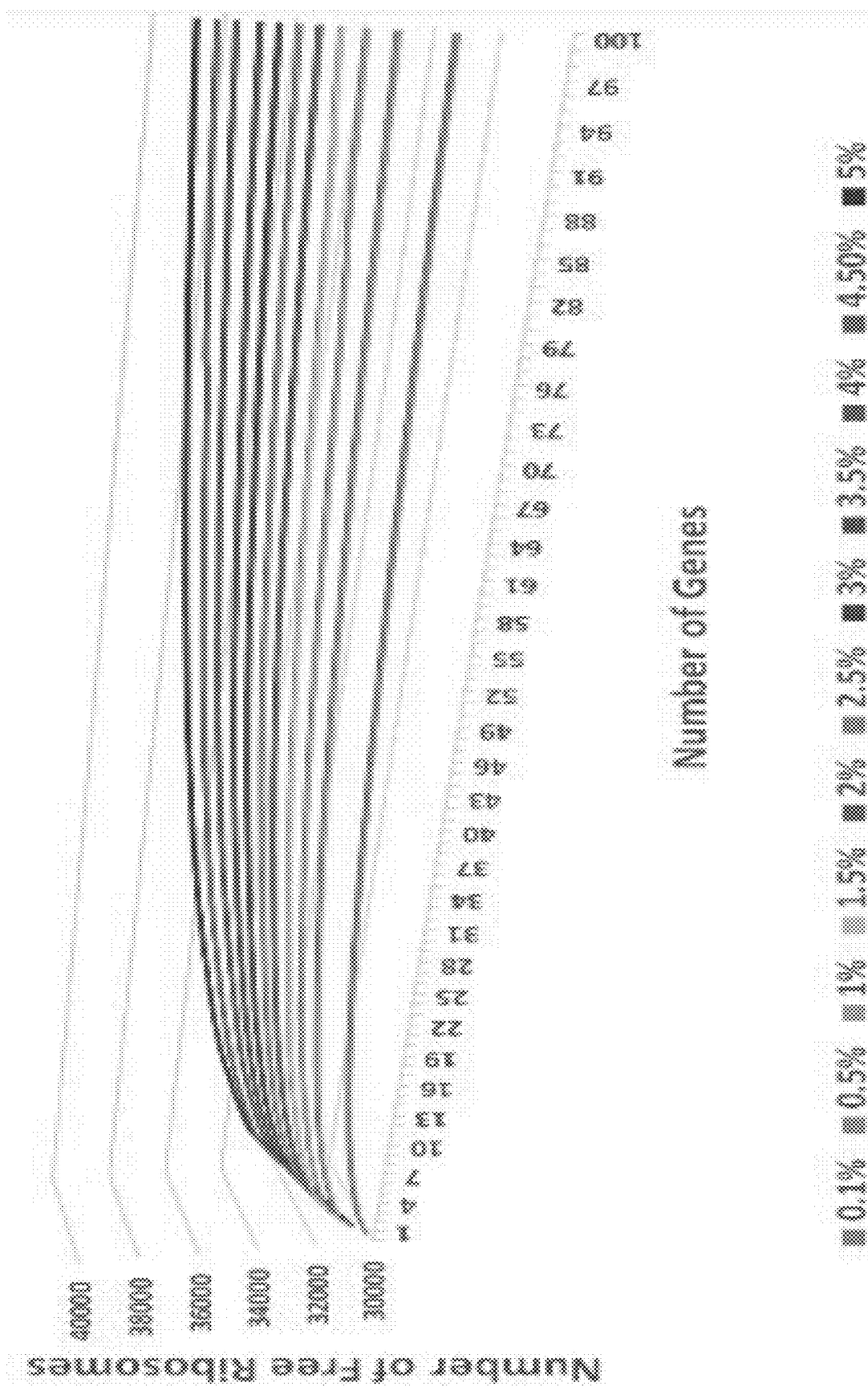
FIGS. 3A-3D.
Figure 3B:
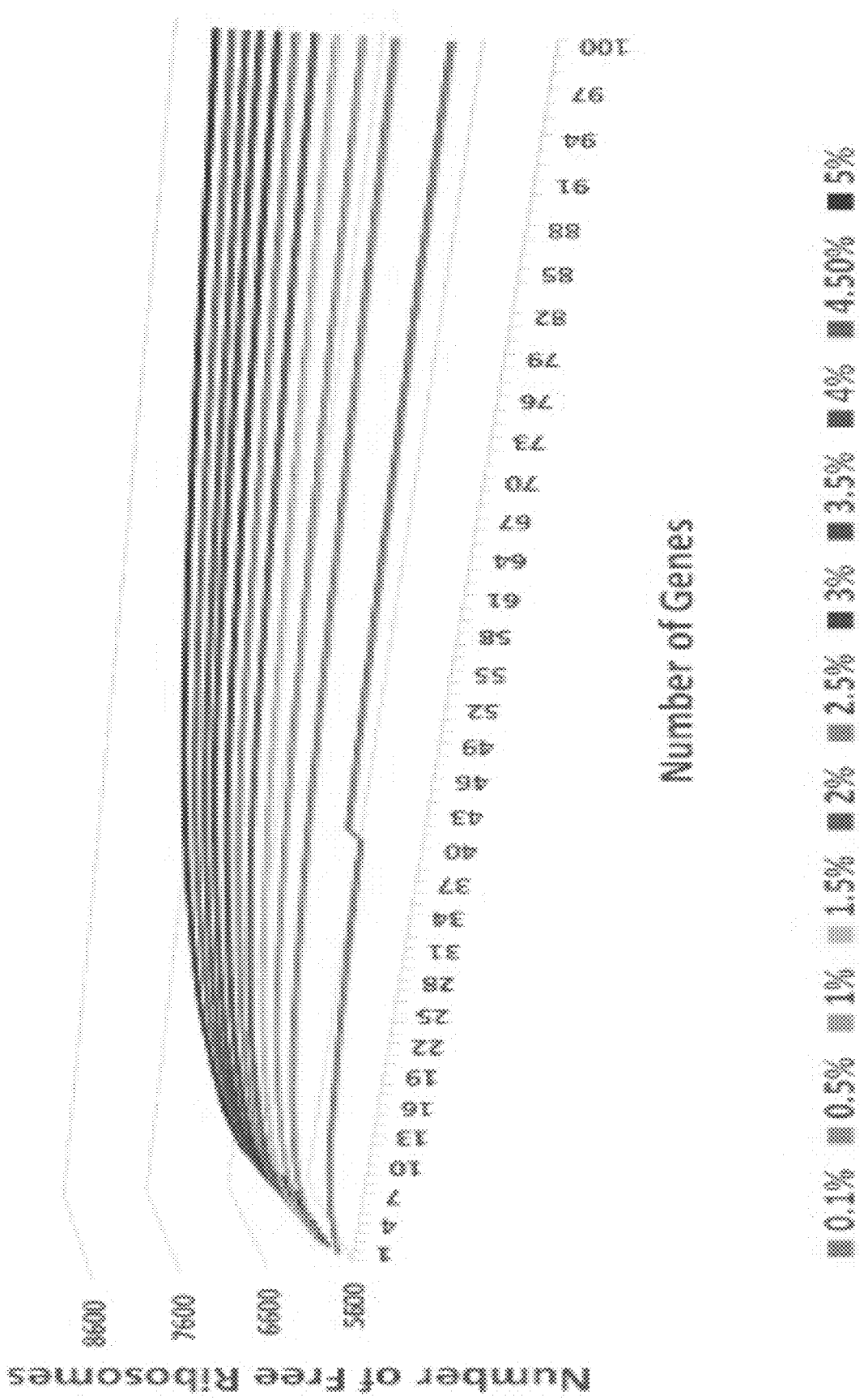
Figure 3C:
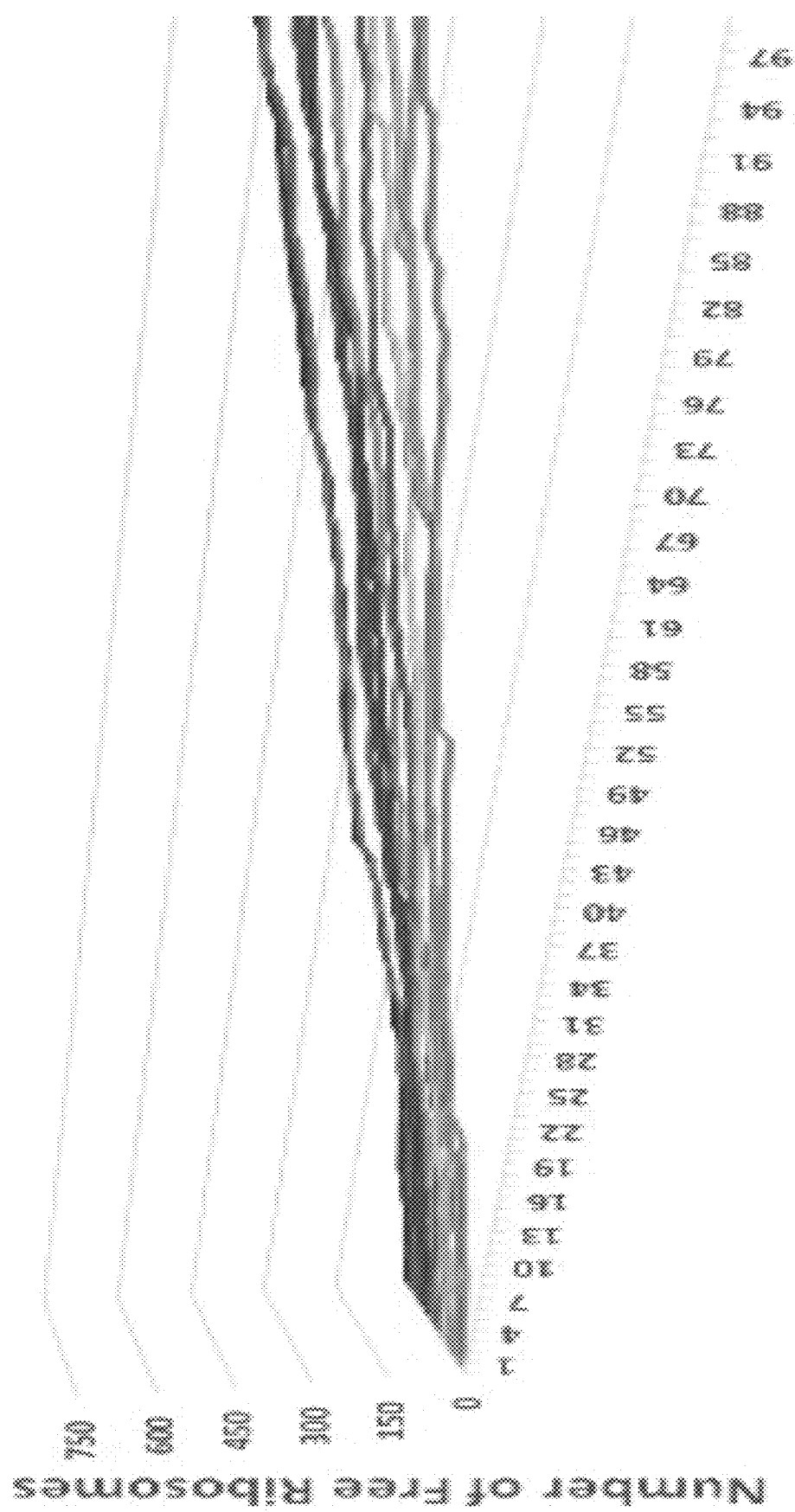
Figure 3D:
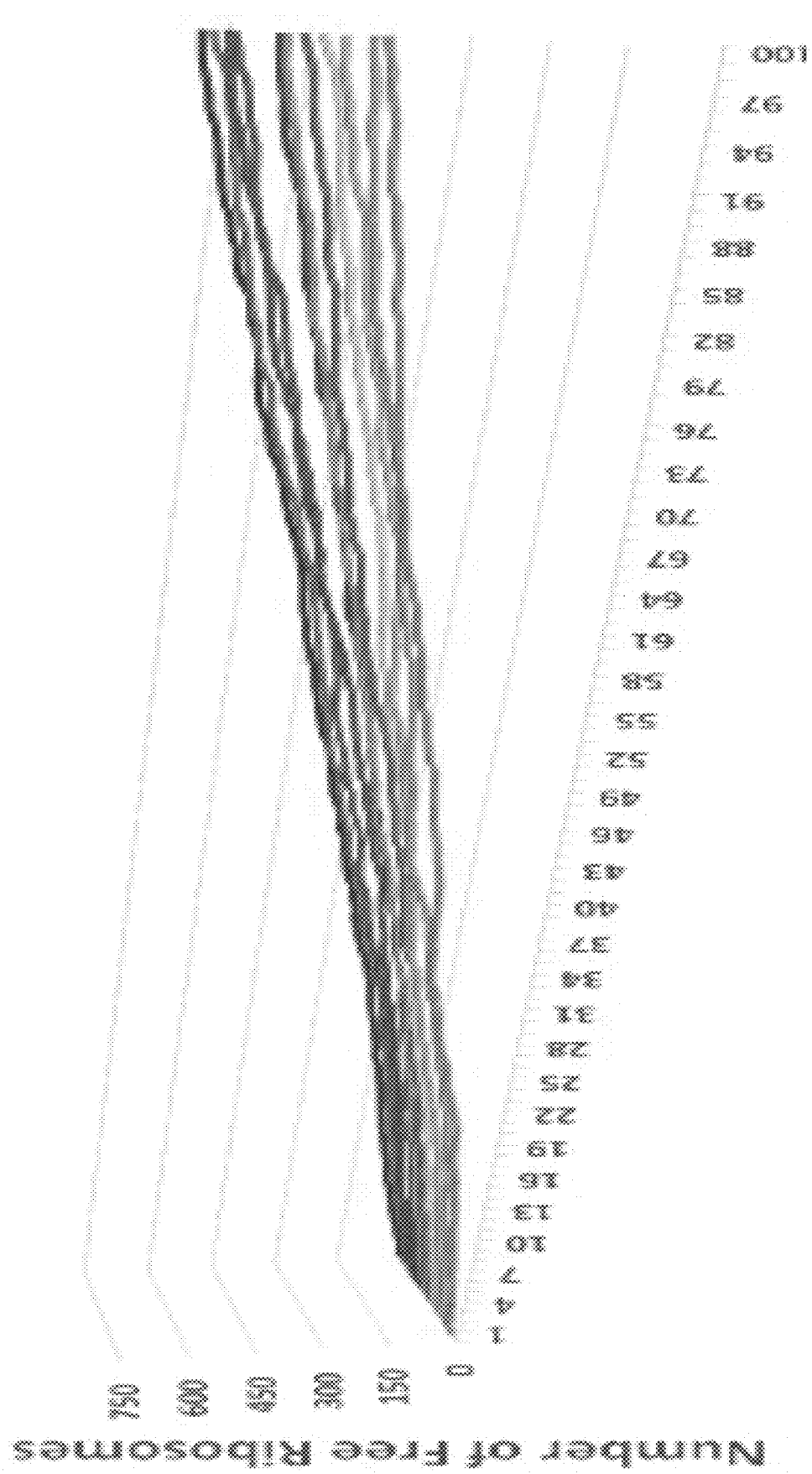
Figure 4A:
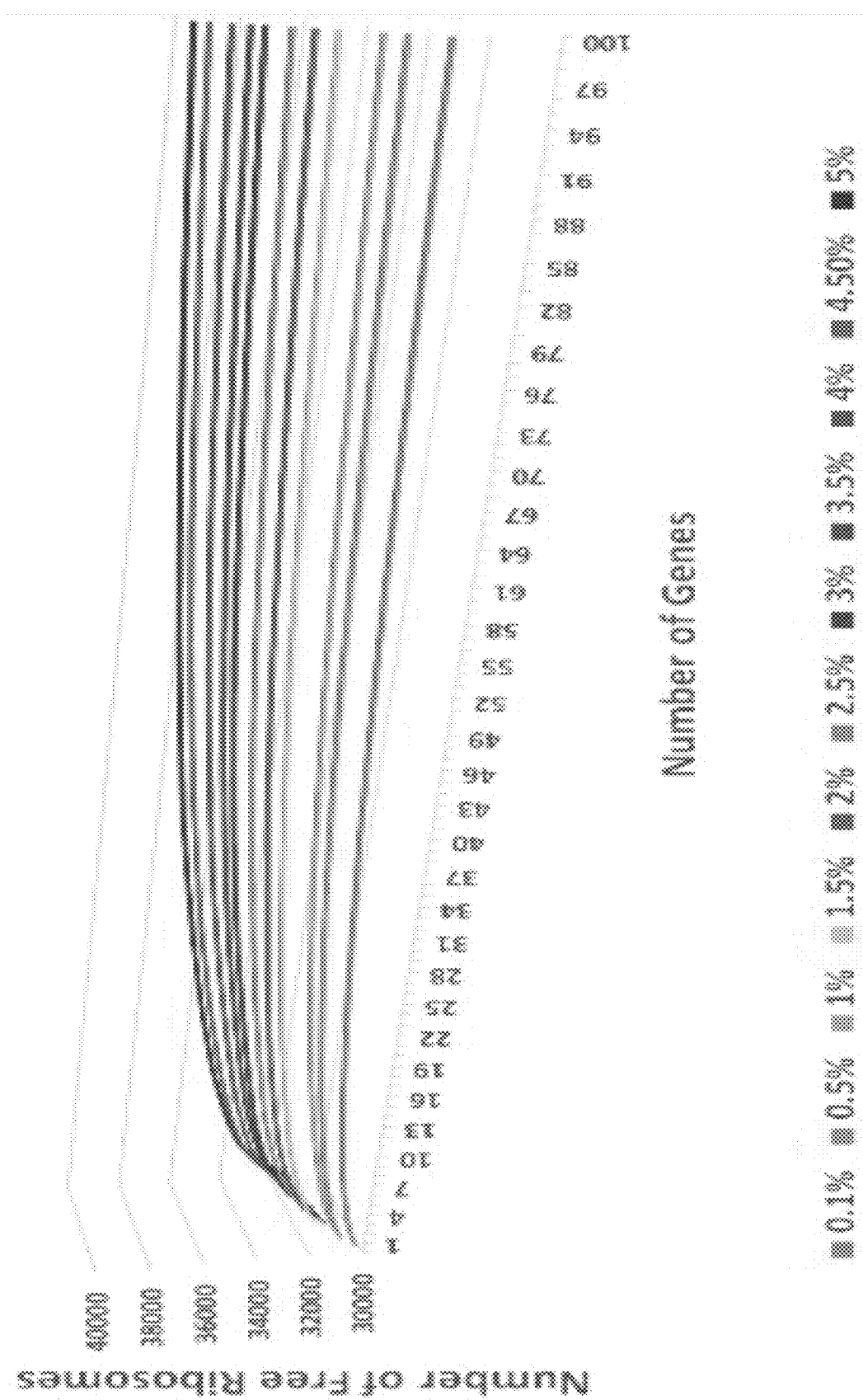
FIGS. 4A-4D.
Figure 4B:
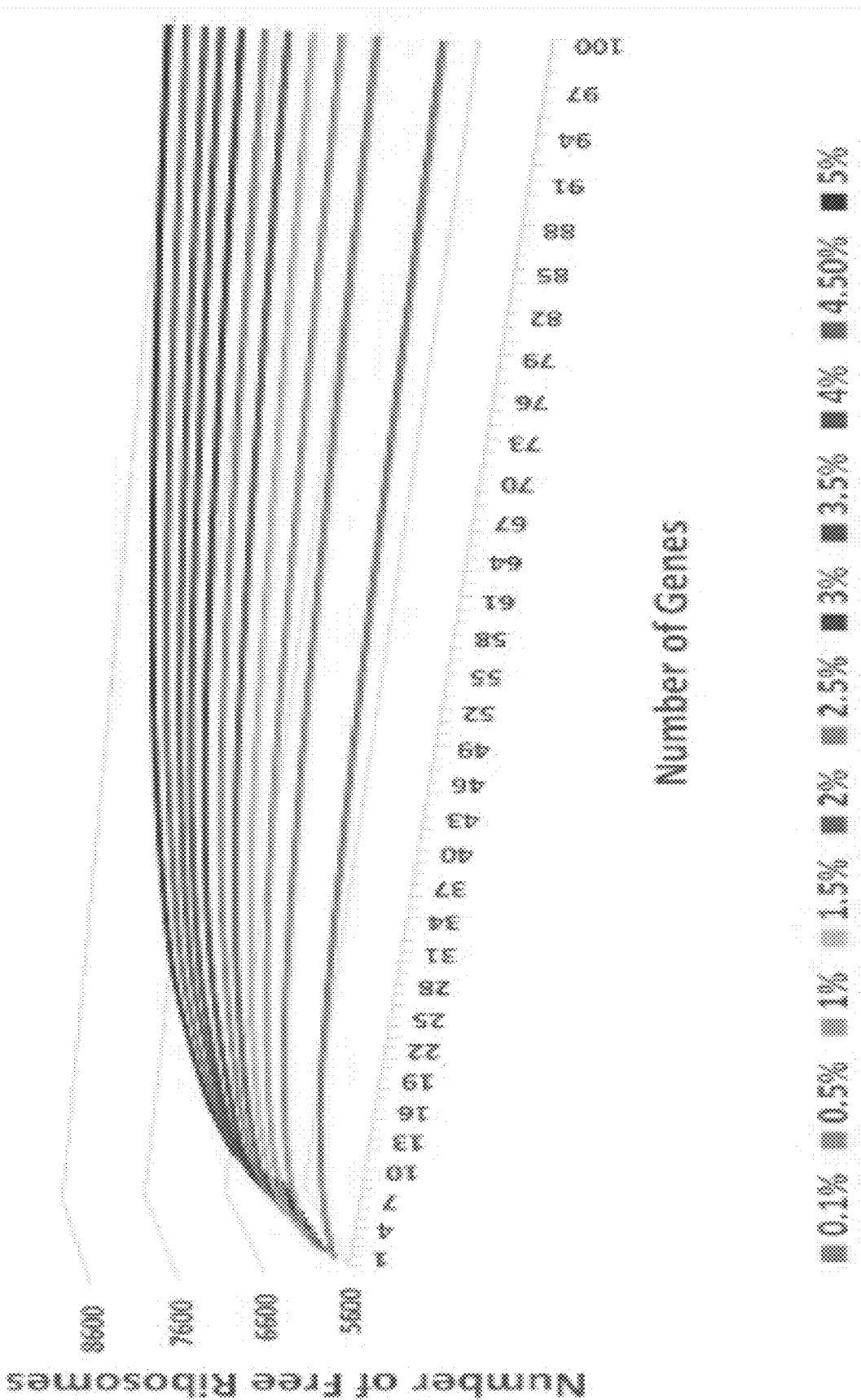
Figure 4C:
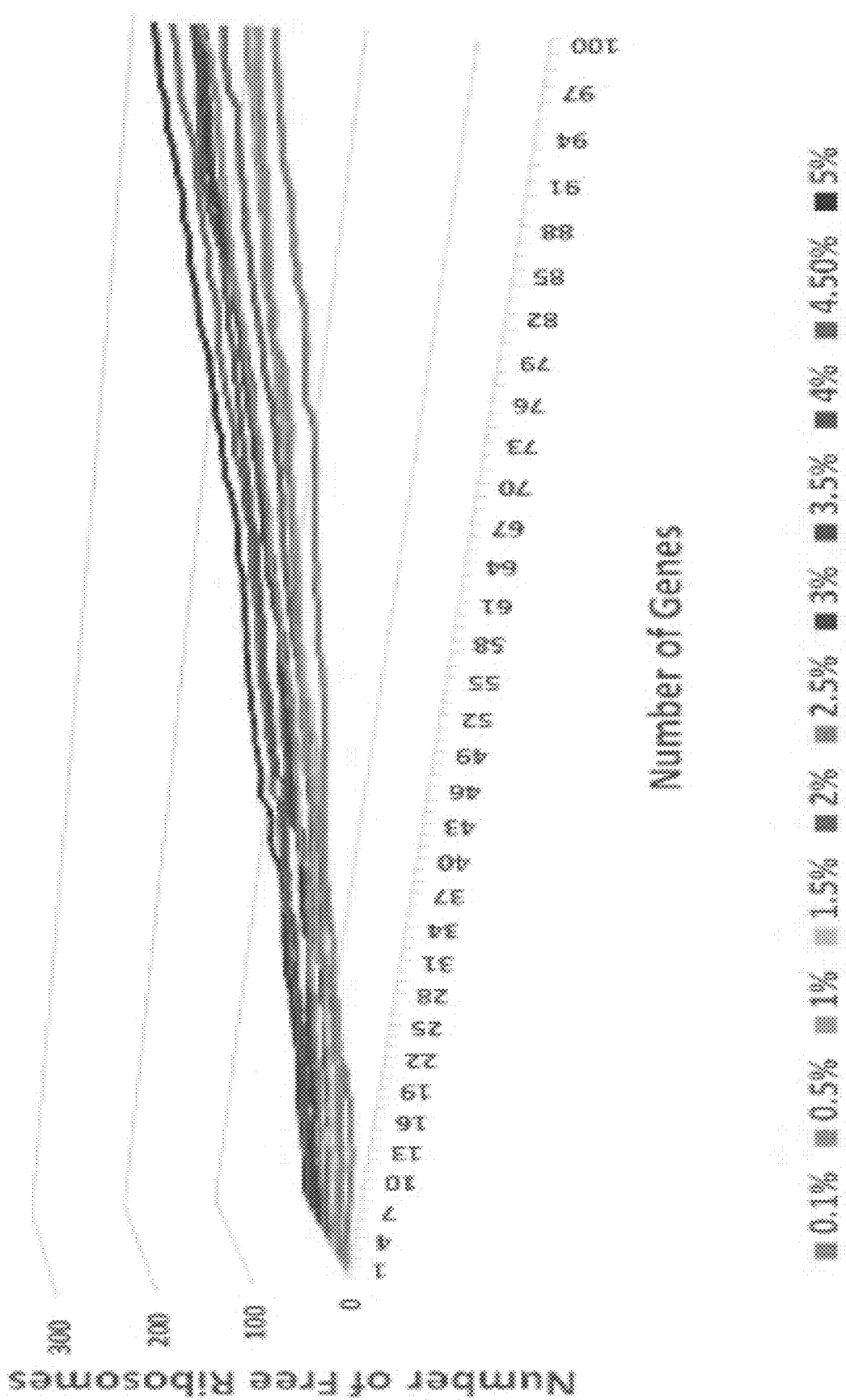
Figure 4D:
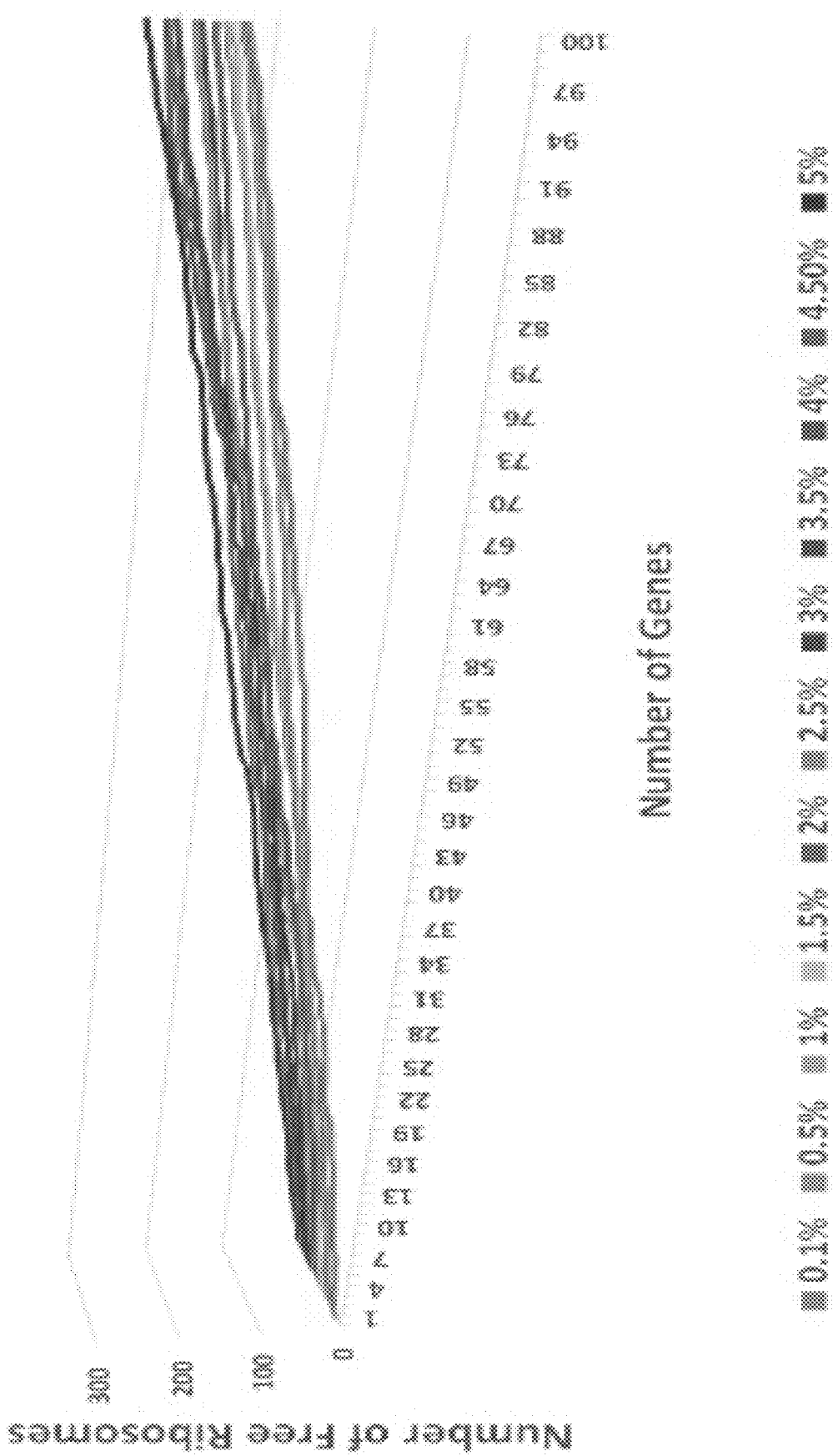
Figures 5A, 5B:
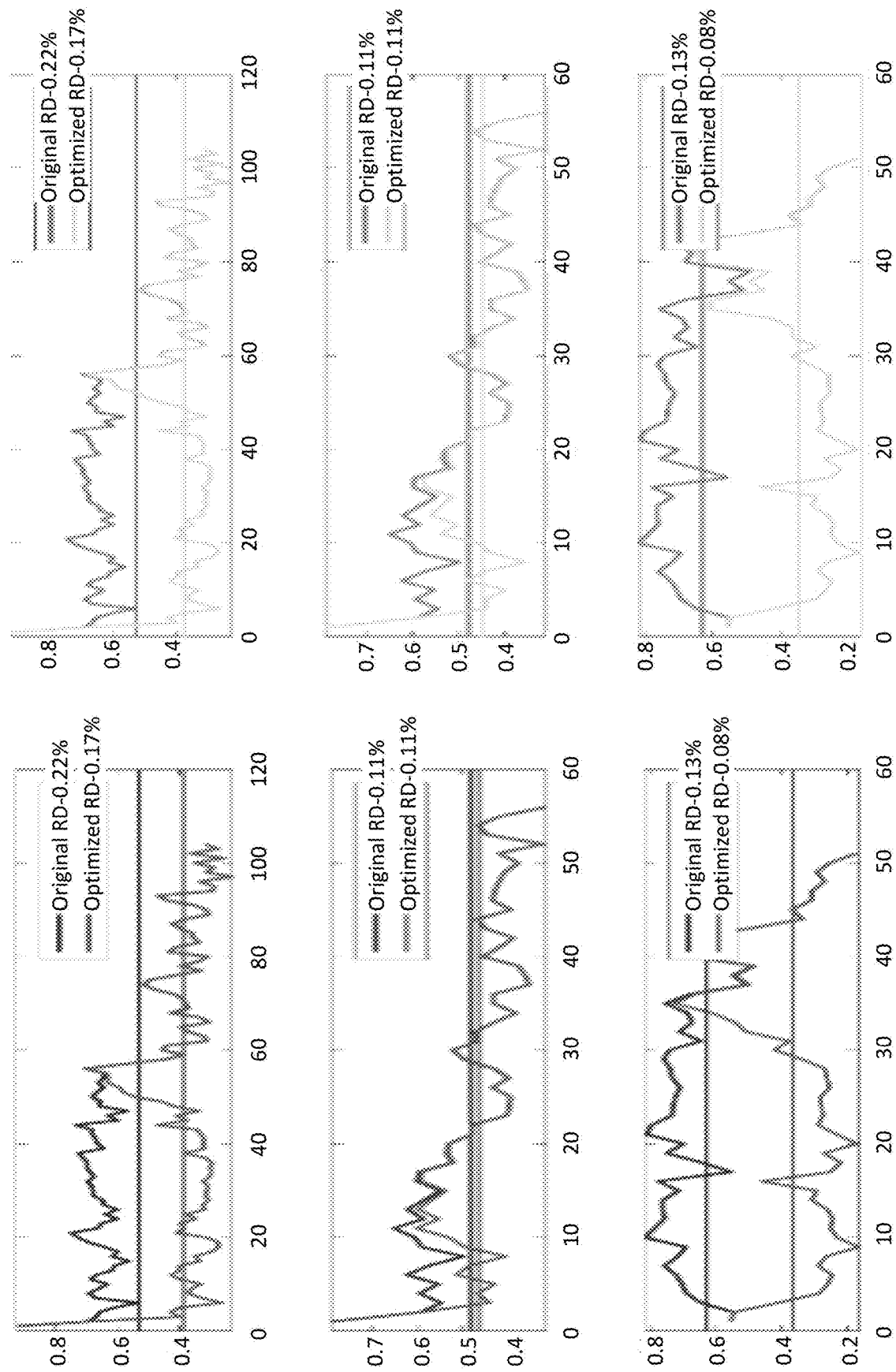
Figures 5E, 5F:
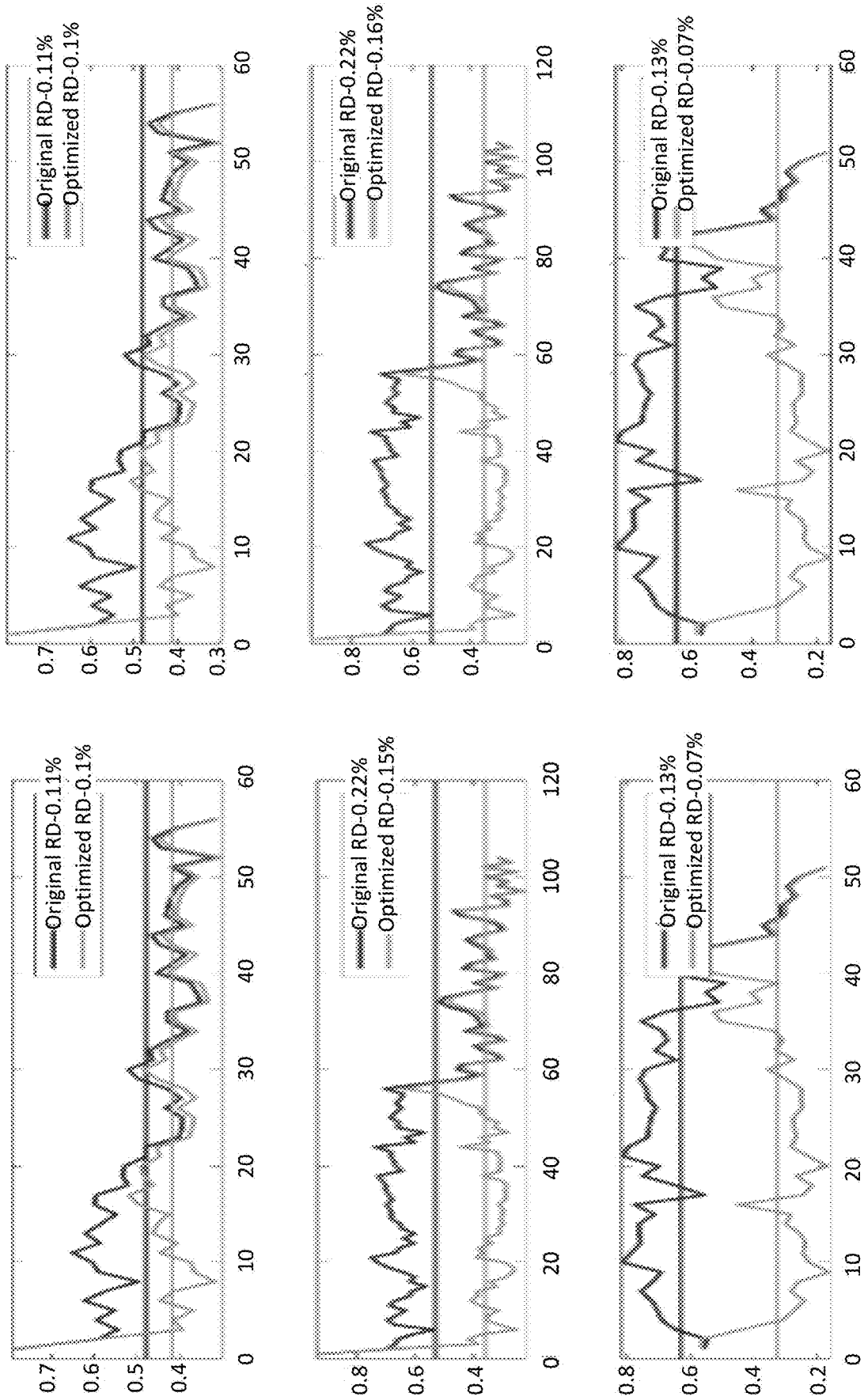
Figures 5G, 5H:
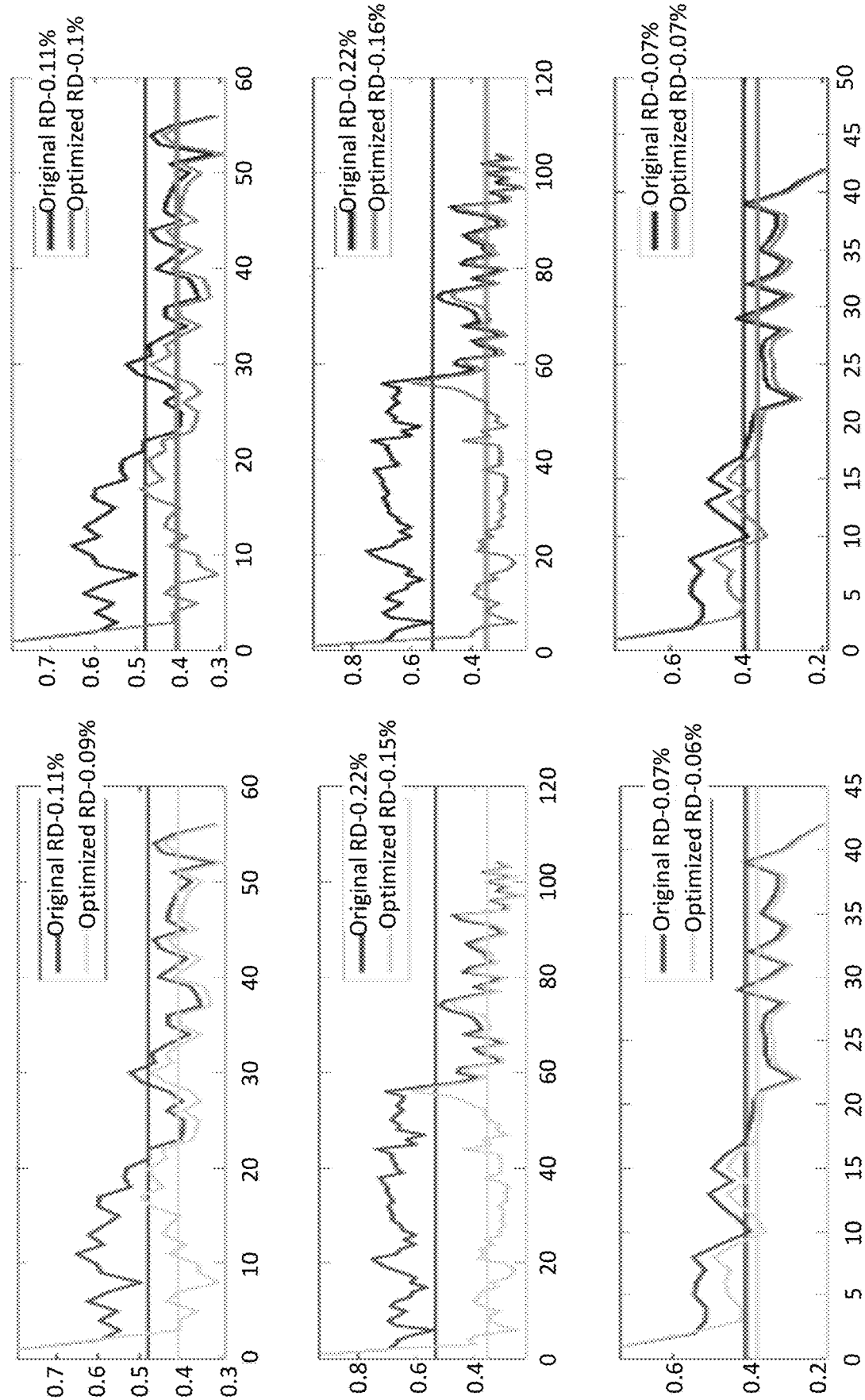
Figures 5I, 5J:
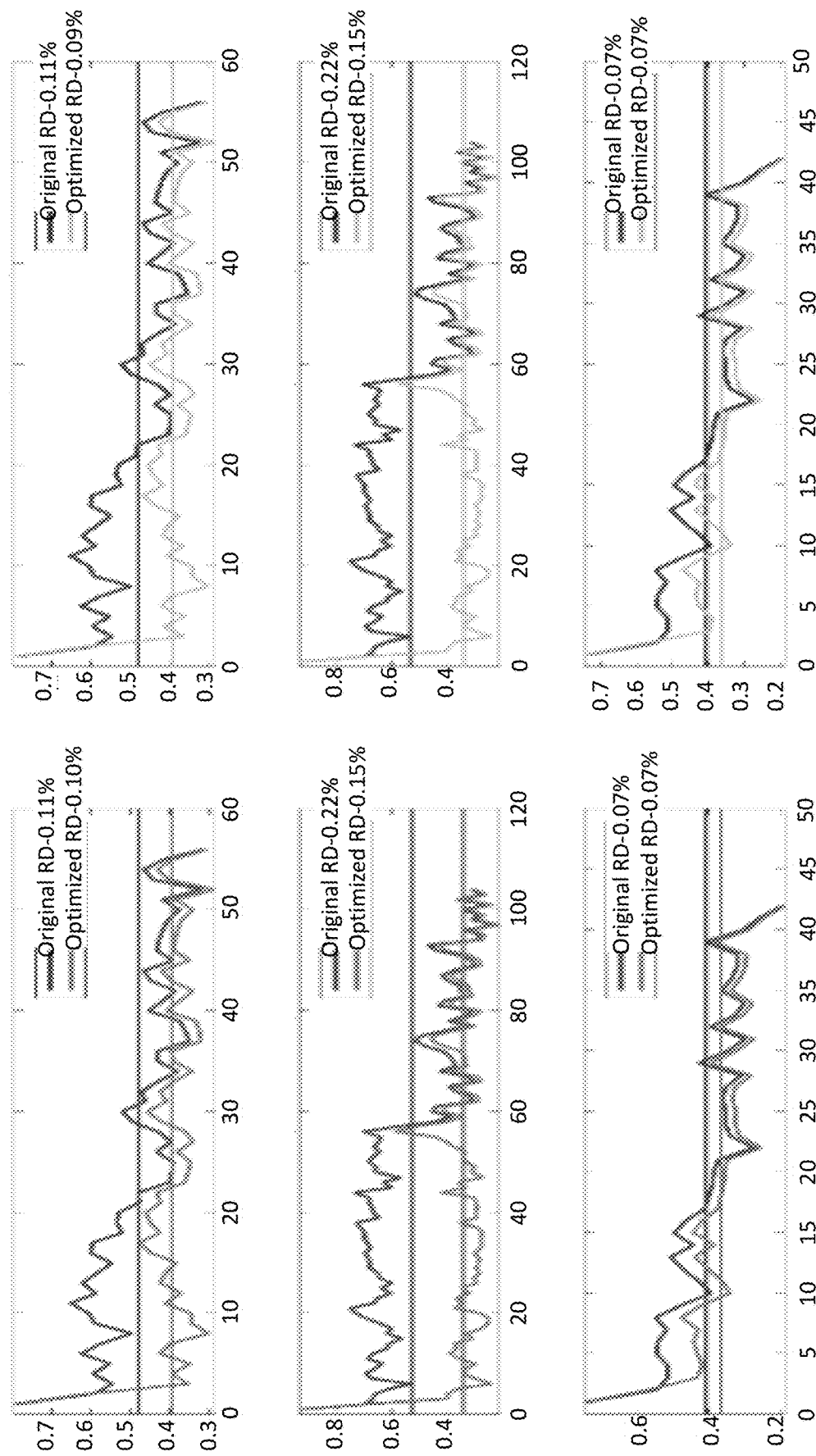
Figure 5K:
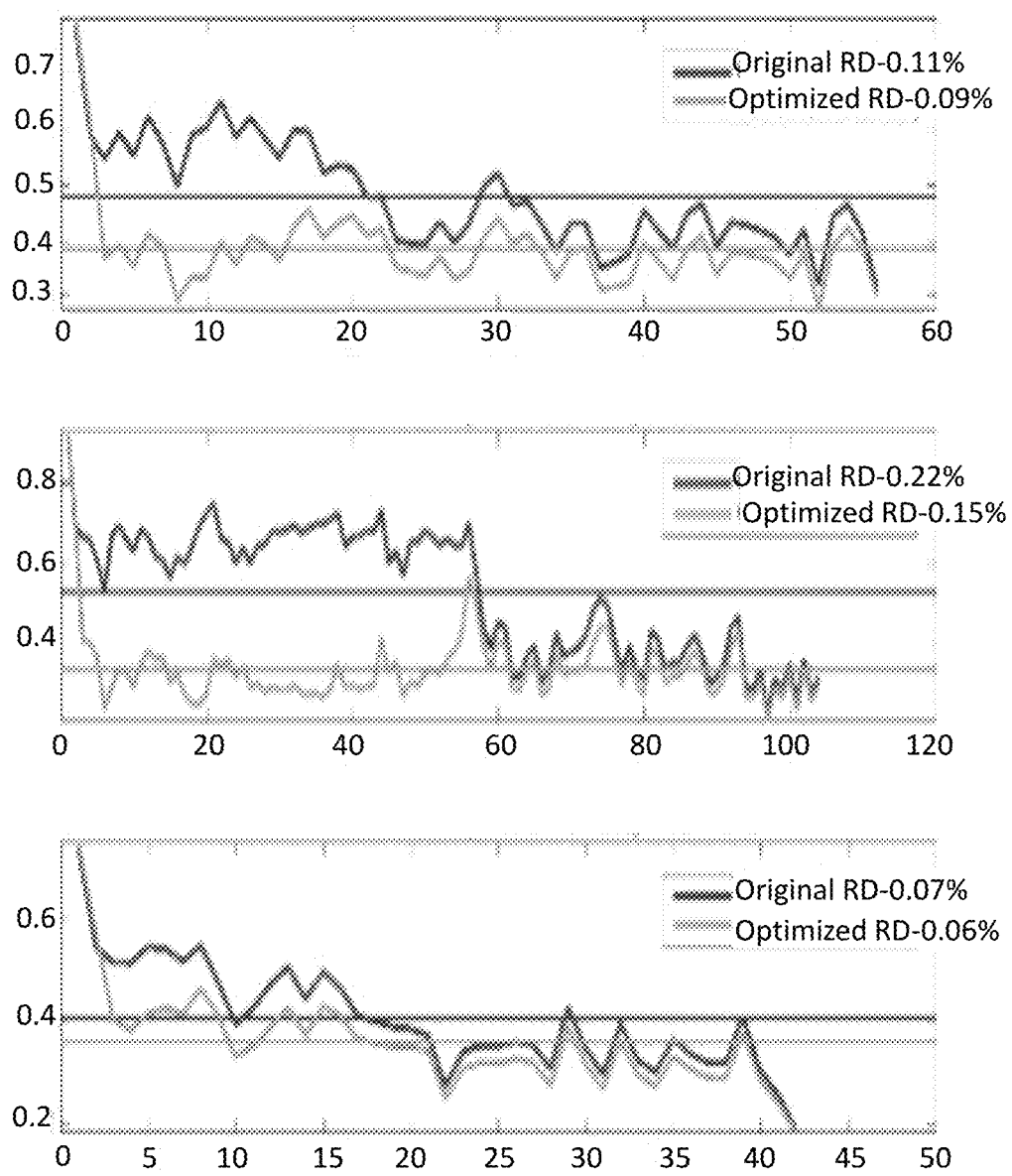
Figures 6A, 6B:
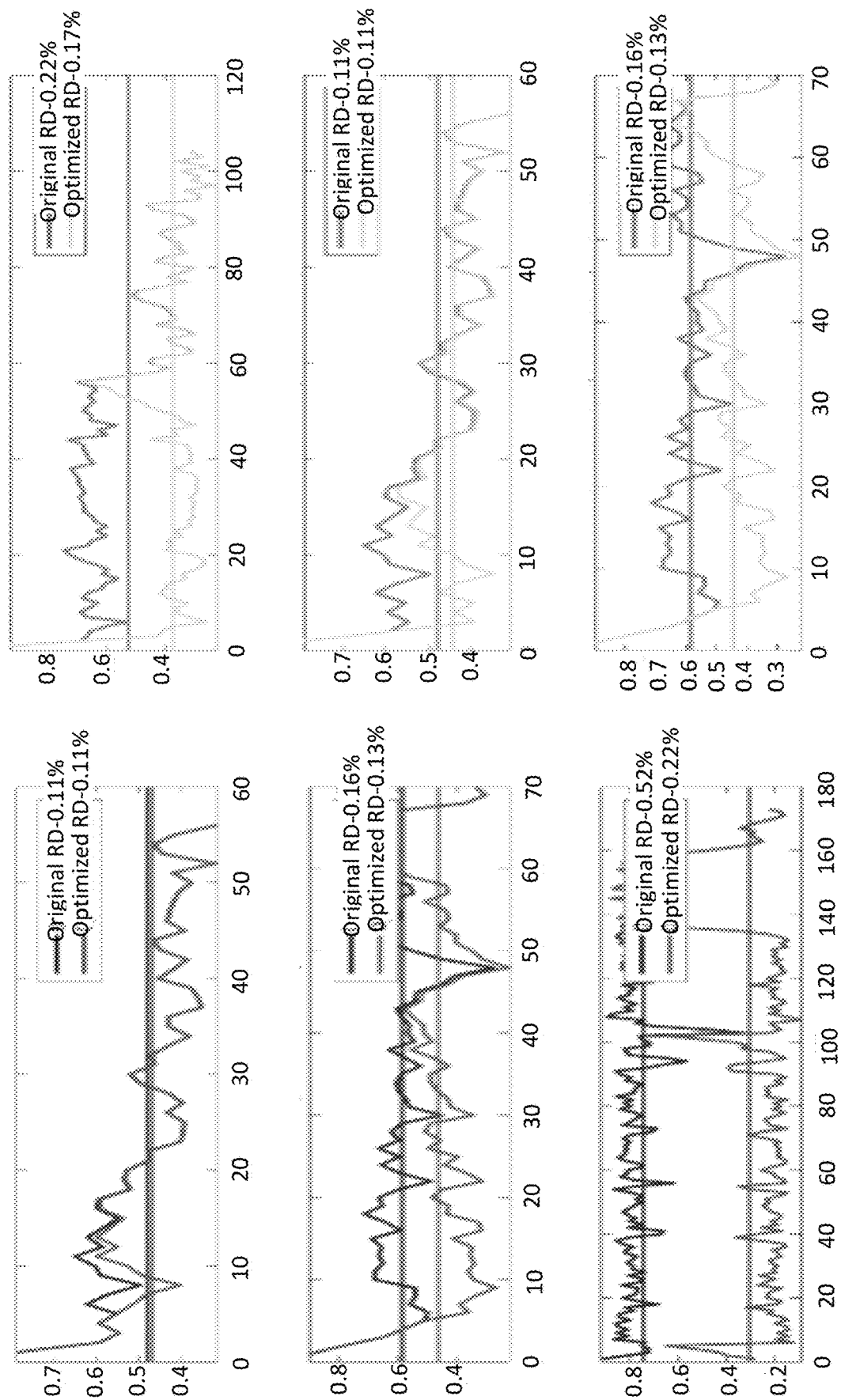
FIGS. 6A-6K: *S. cerevisiae* BGM algorithm ribosomal density profiles for the first 3 modified gene per translation efficiency (TE) constraint before and after mutations, results incorporate the effect of the first 100 mutated genes, mRNA levels as percentage of all genes is indicated, as well as each genes contribution to the free ribosome pool (FRC).
Figures 6C, 6D:
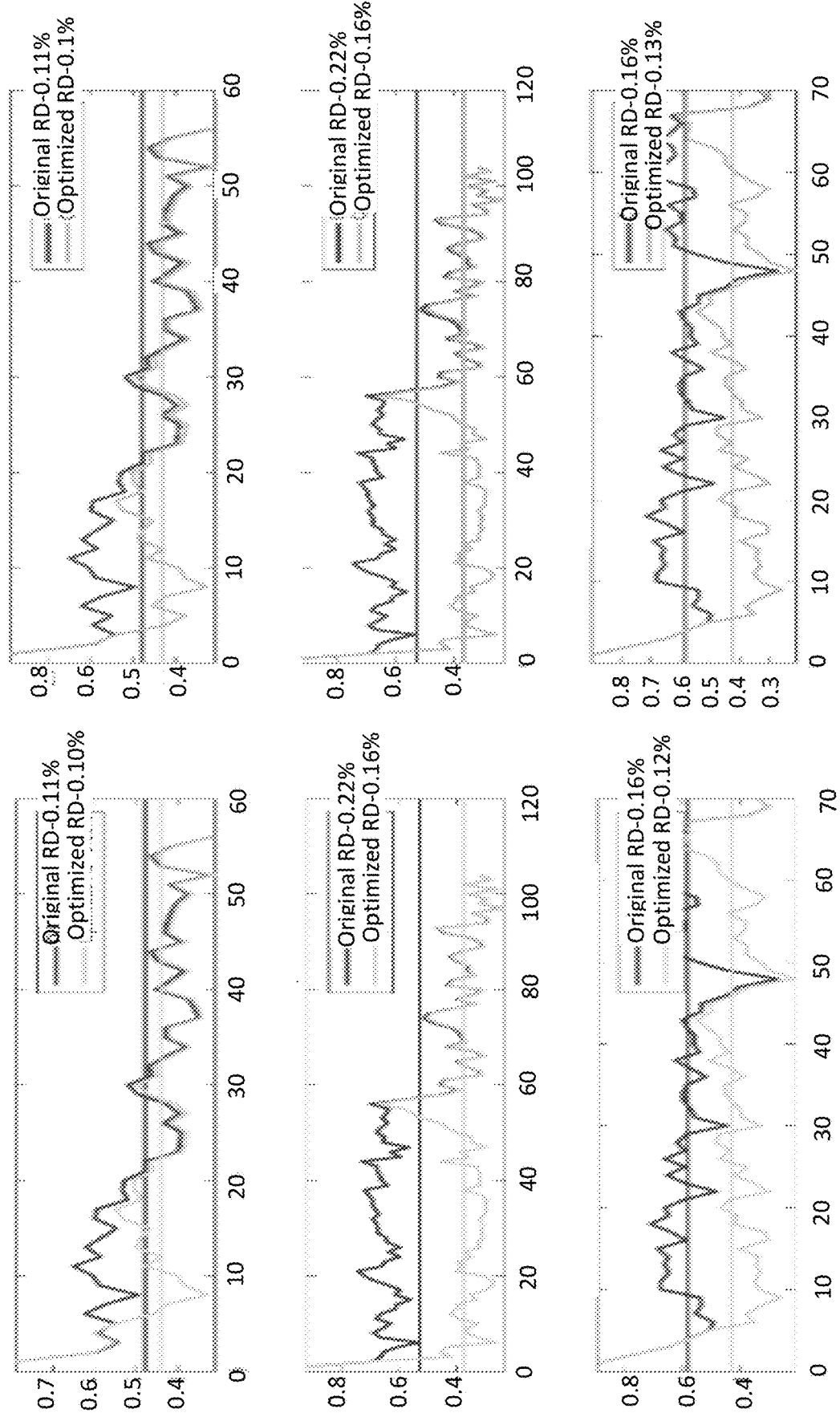
Figures 6E, 6F:
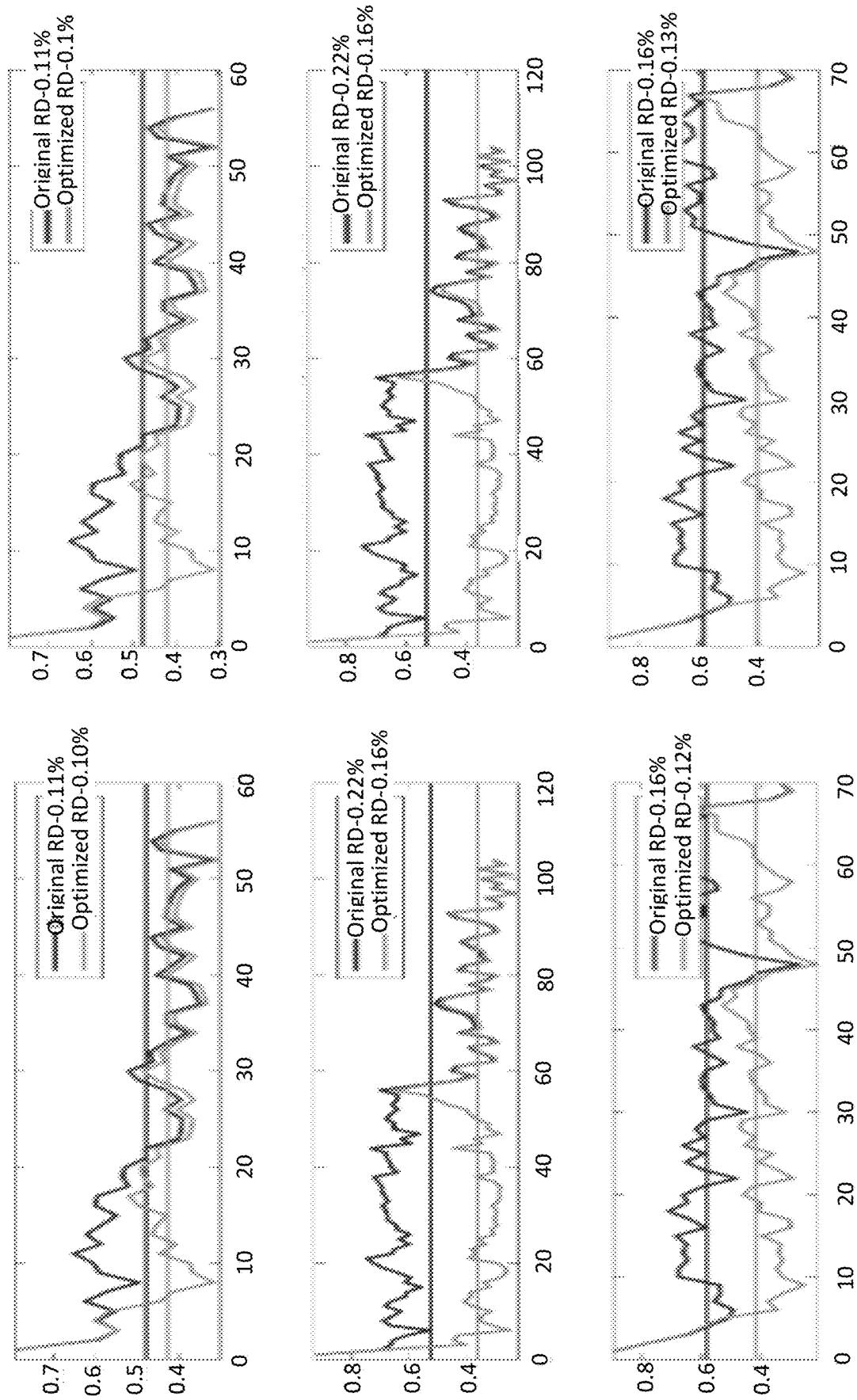
Figures 6G, 6H:
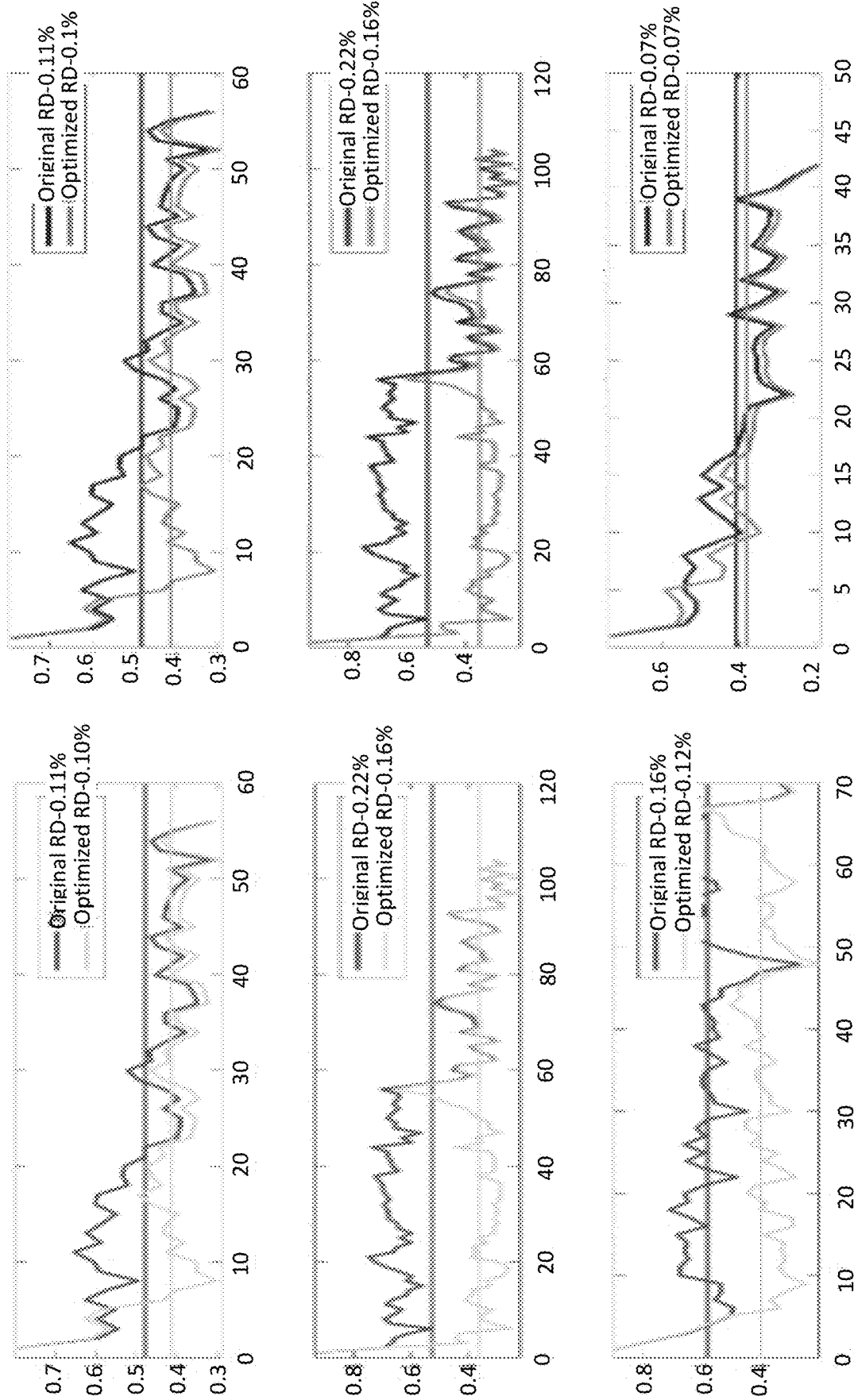
Figures 6I, 6J:
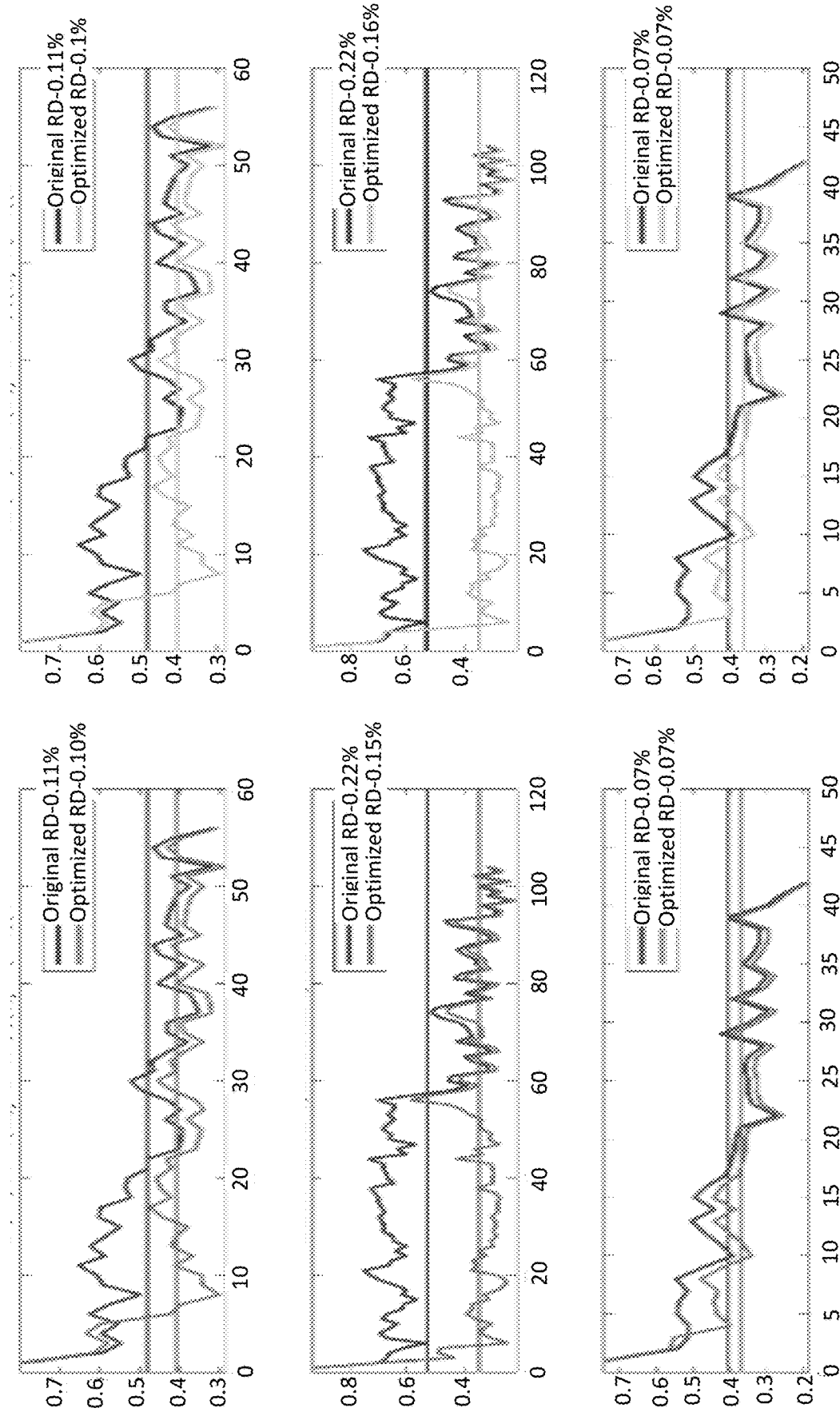
Figure 6K:
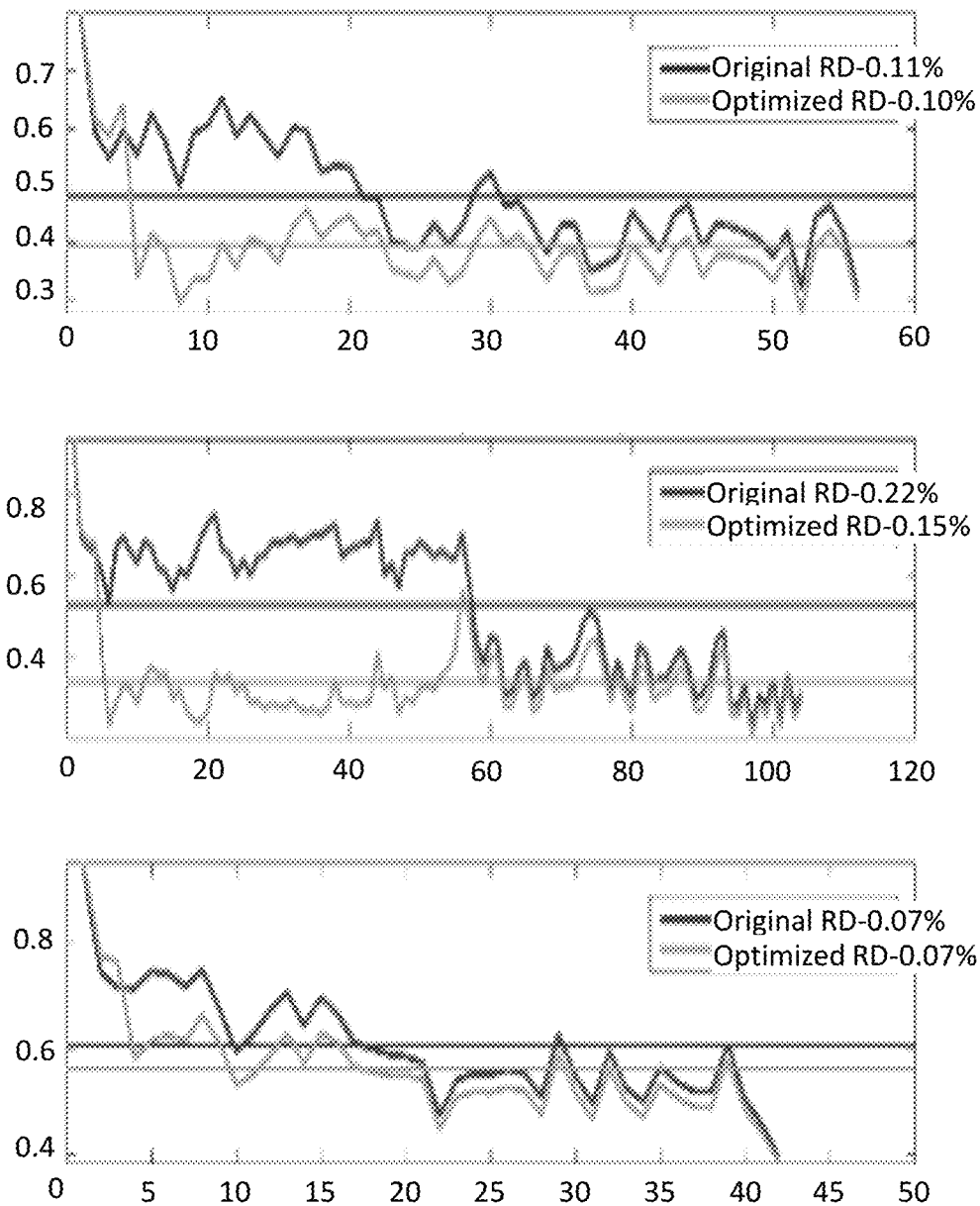
Figures 7A, 7B:
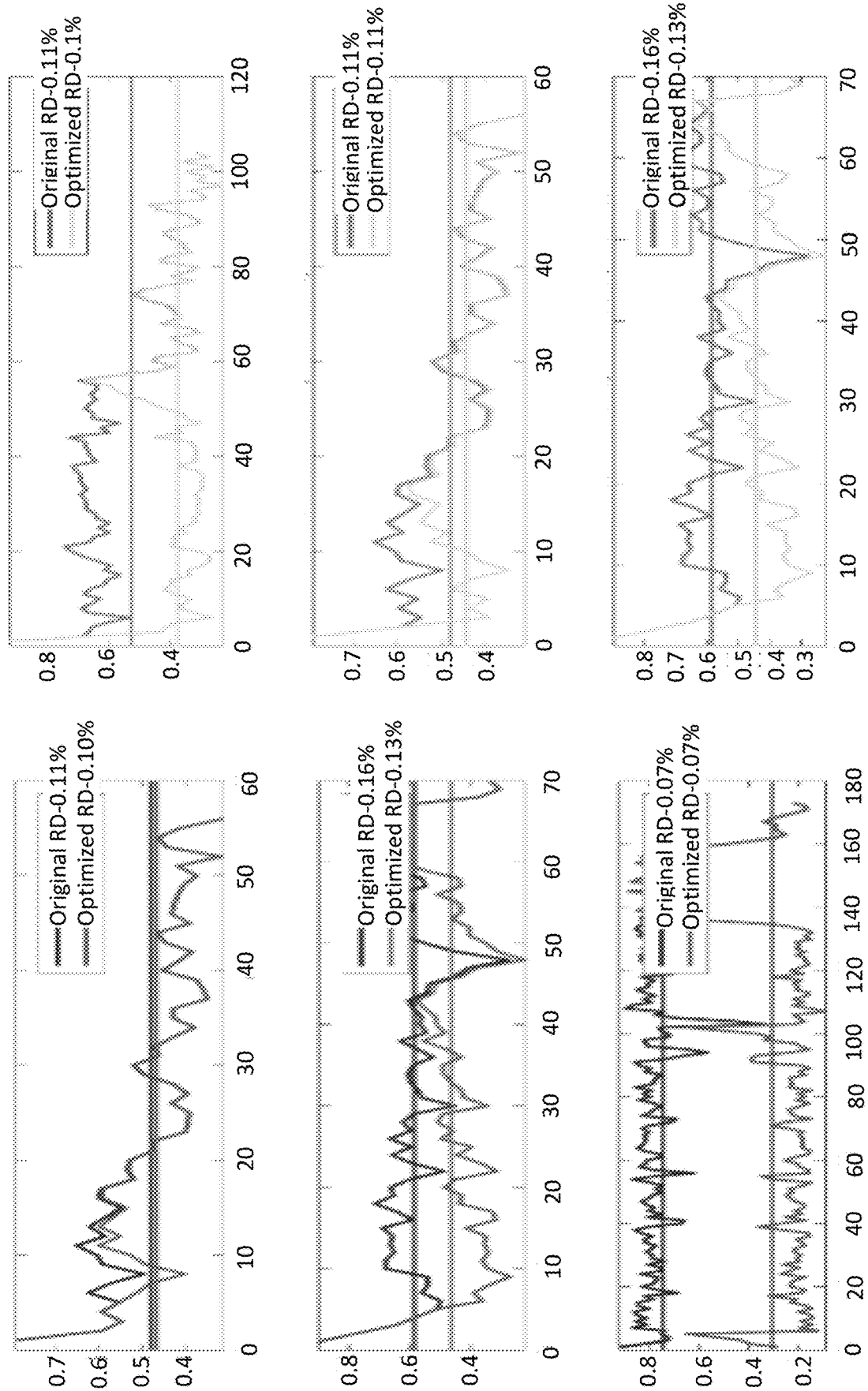
Figures 7C, 7D:
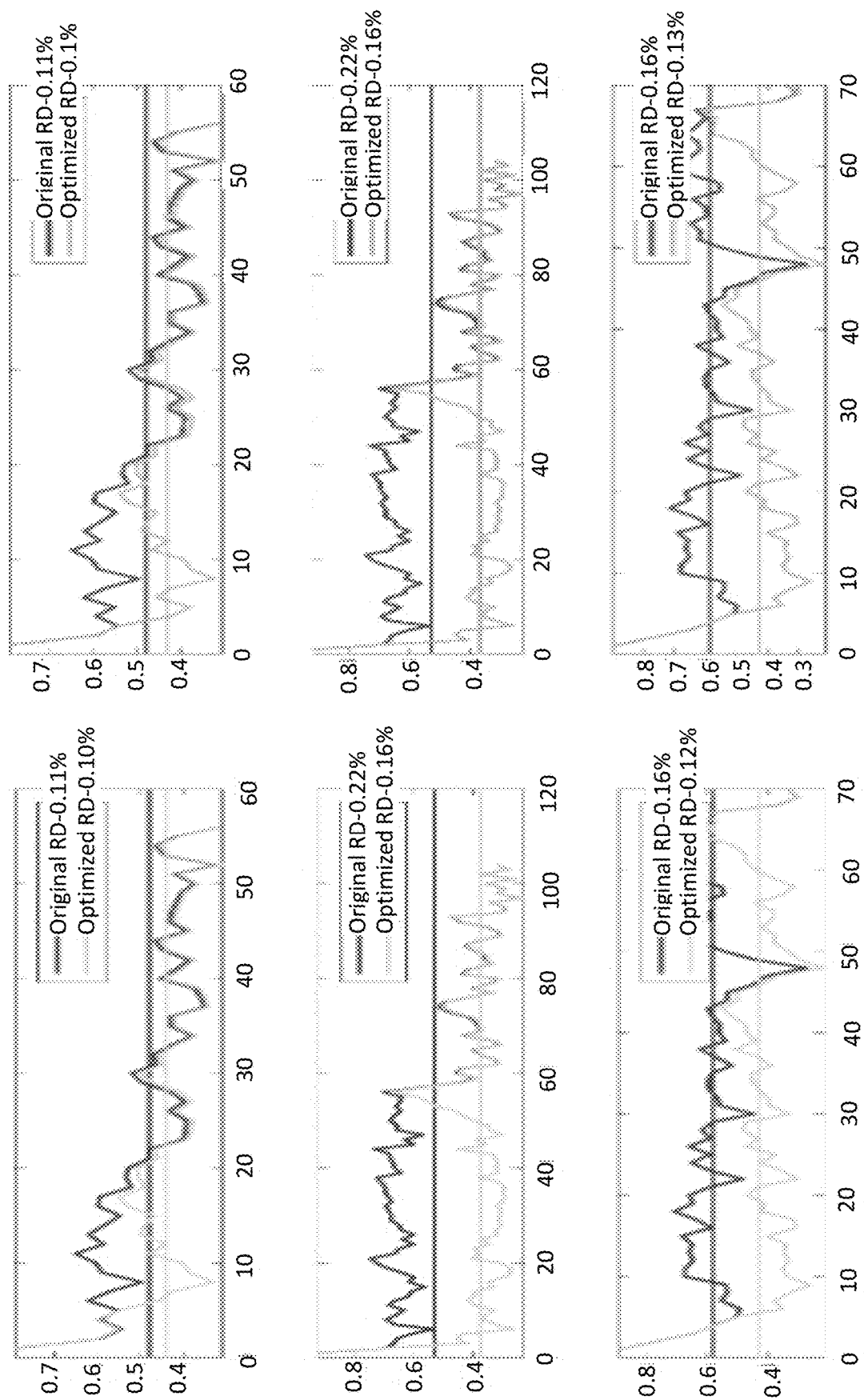
Figures 7G, 7H:
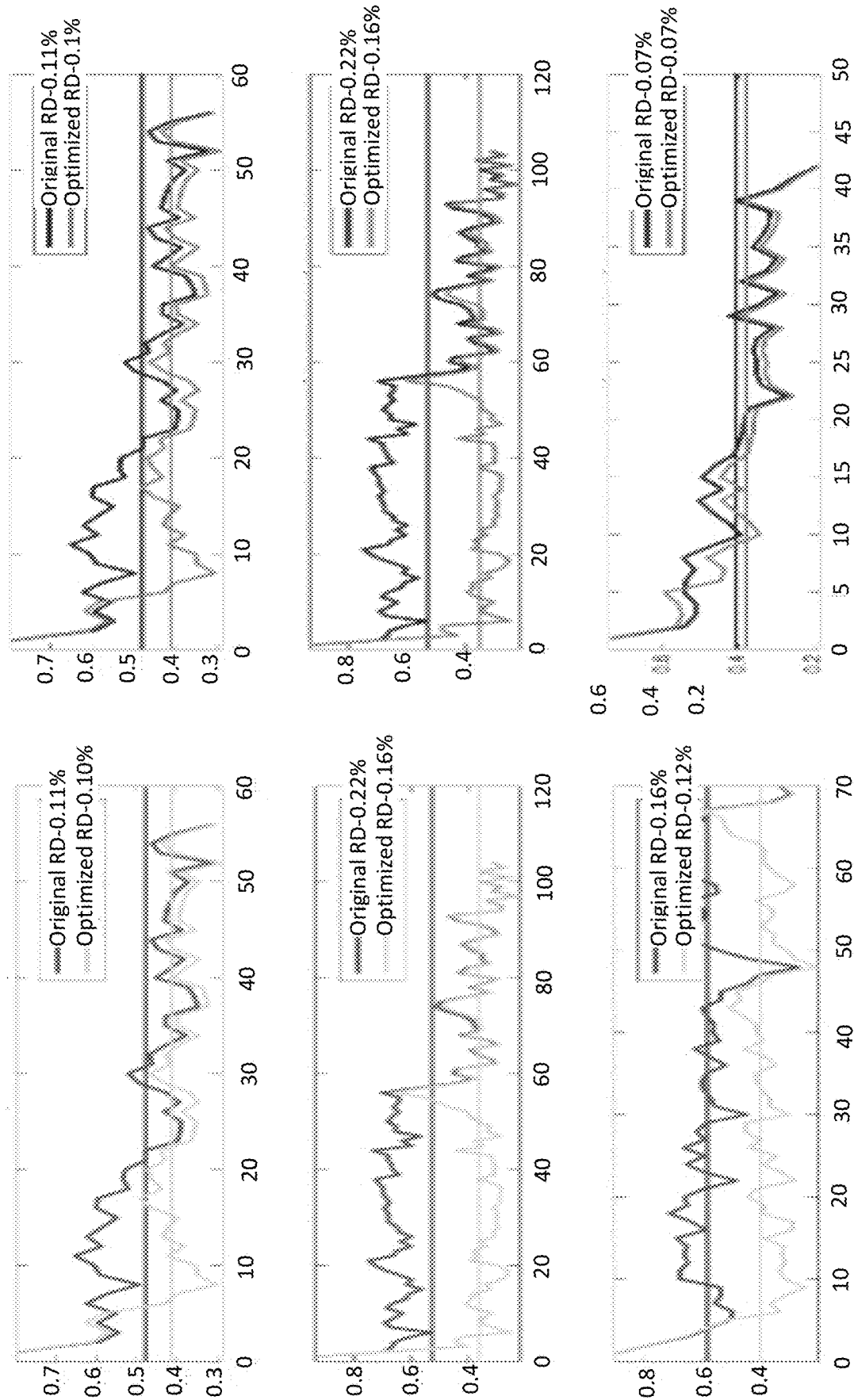
Figures 7I, 7J:
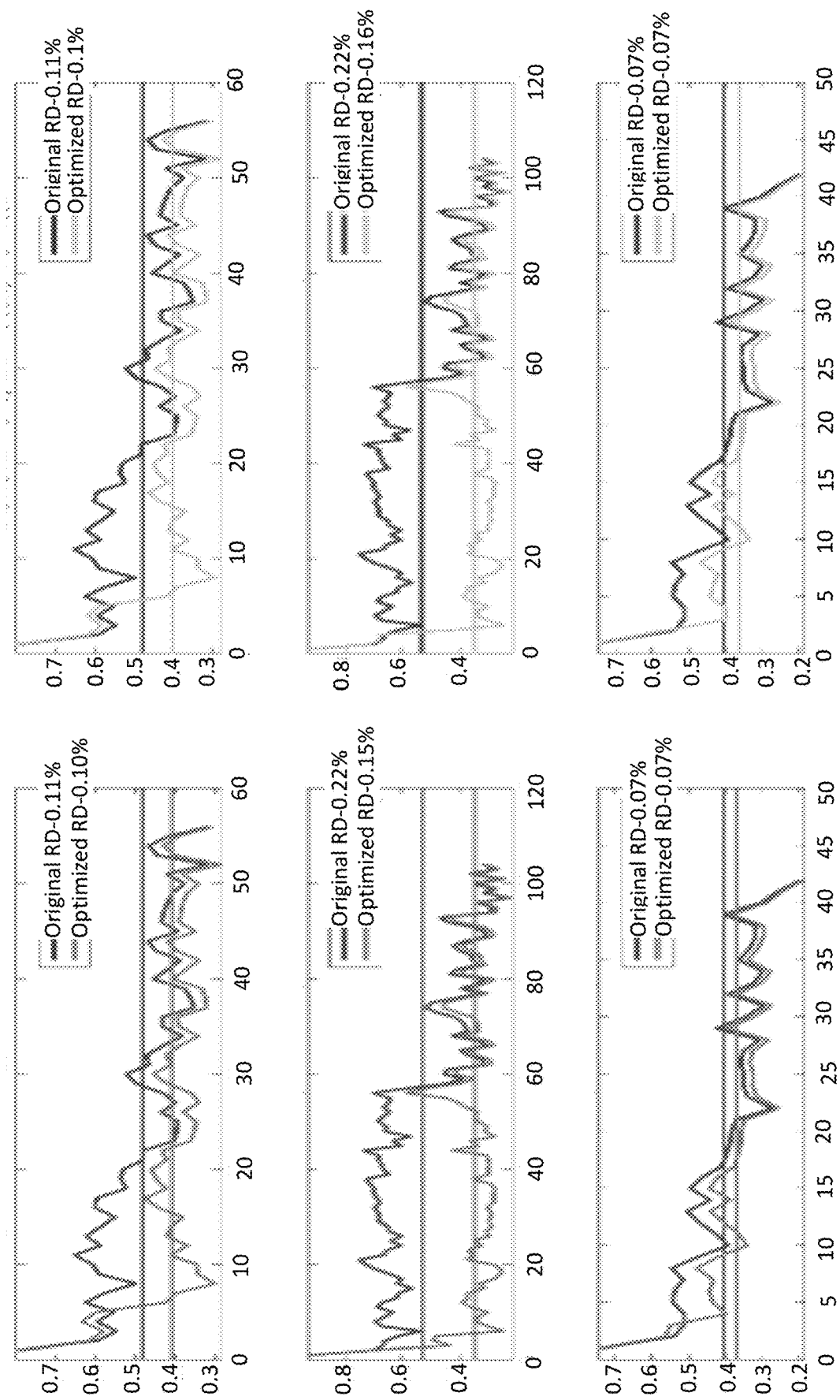
Figure 7K:
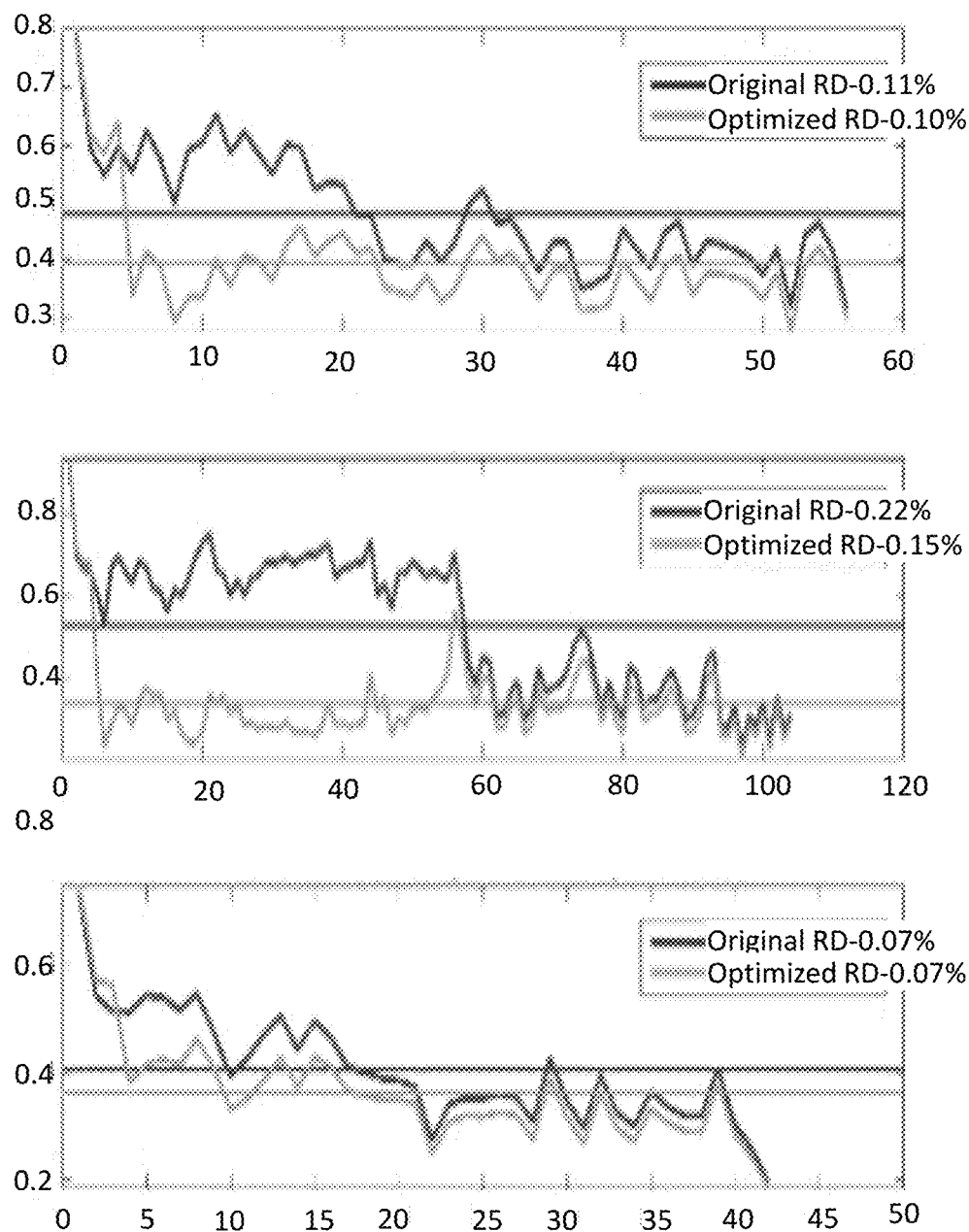
Figures 8A, 8B:
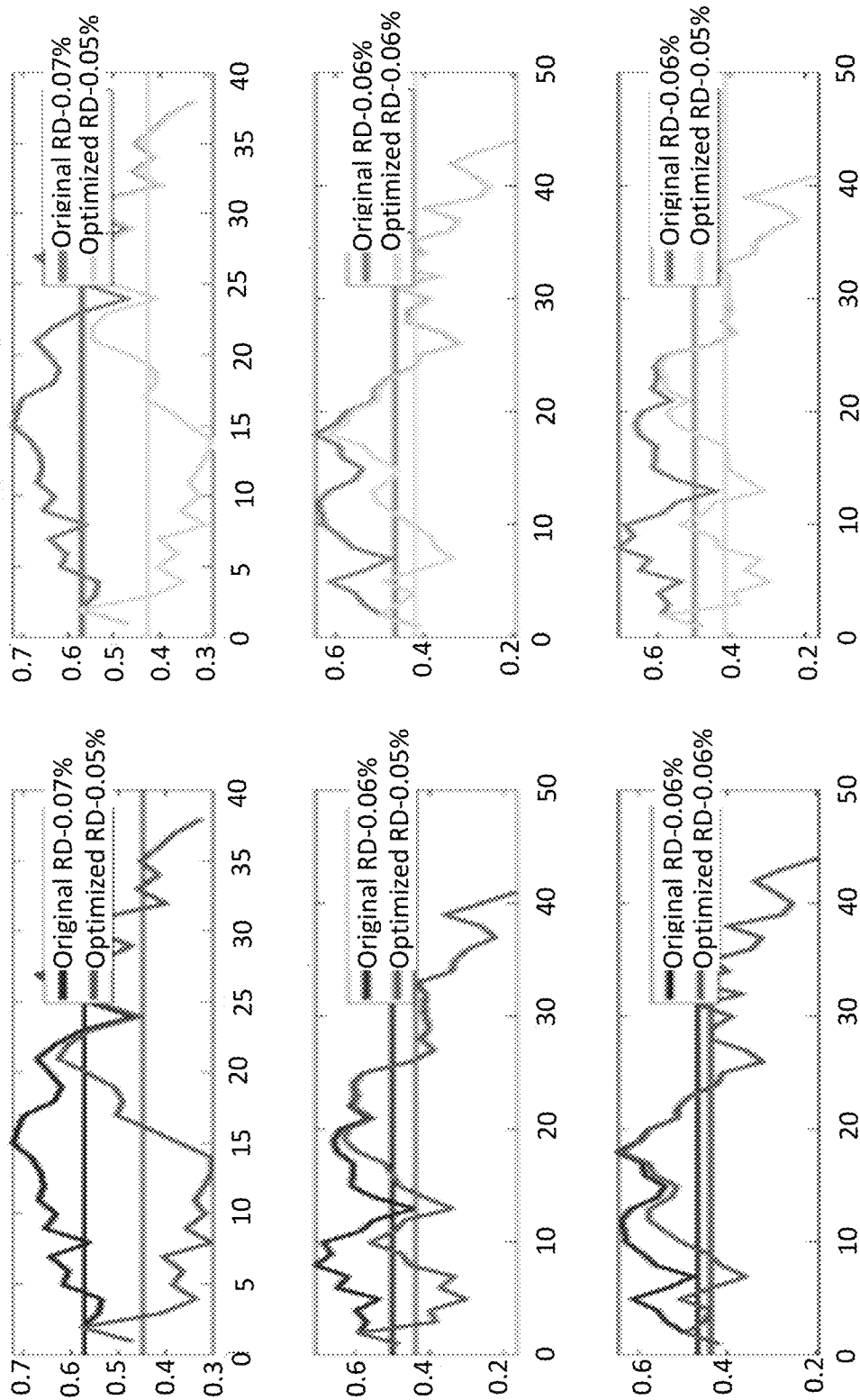
FIGS. 8A-8K: *E. coli* FGM algorithm ribosomal density profiles for the first 3 modified gene per translation efficiency (TE) constraint before and after mutations, results incorporate the effect of the first 100 mutated genes, mRNA levels as percentage of all genes is indicated, as well as each genes contribution to the free ribosome pool (FRC). (FIG.
Figures 8C, 8D:
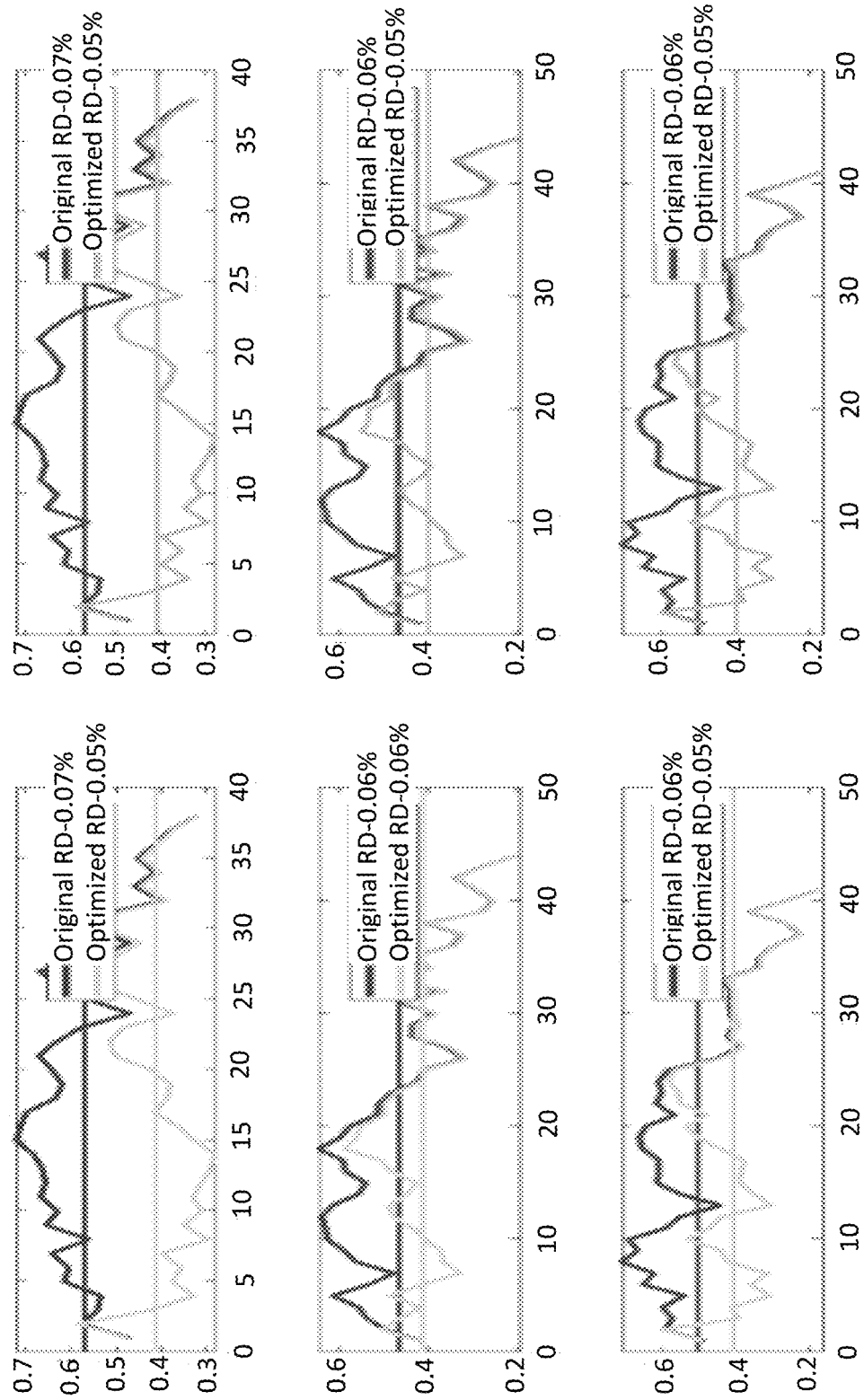
Figures 8E, 8F:
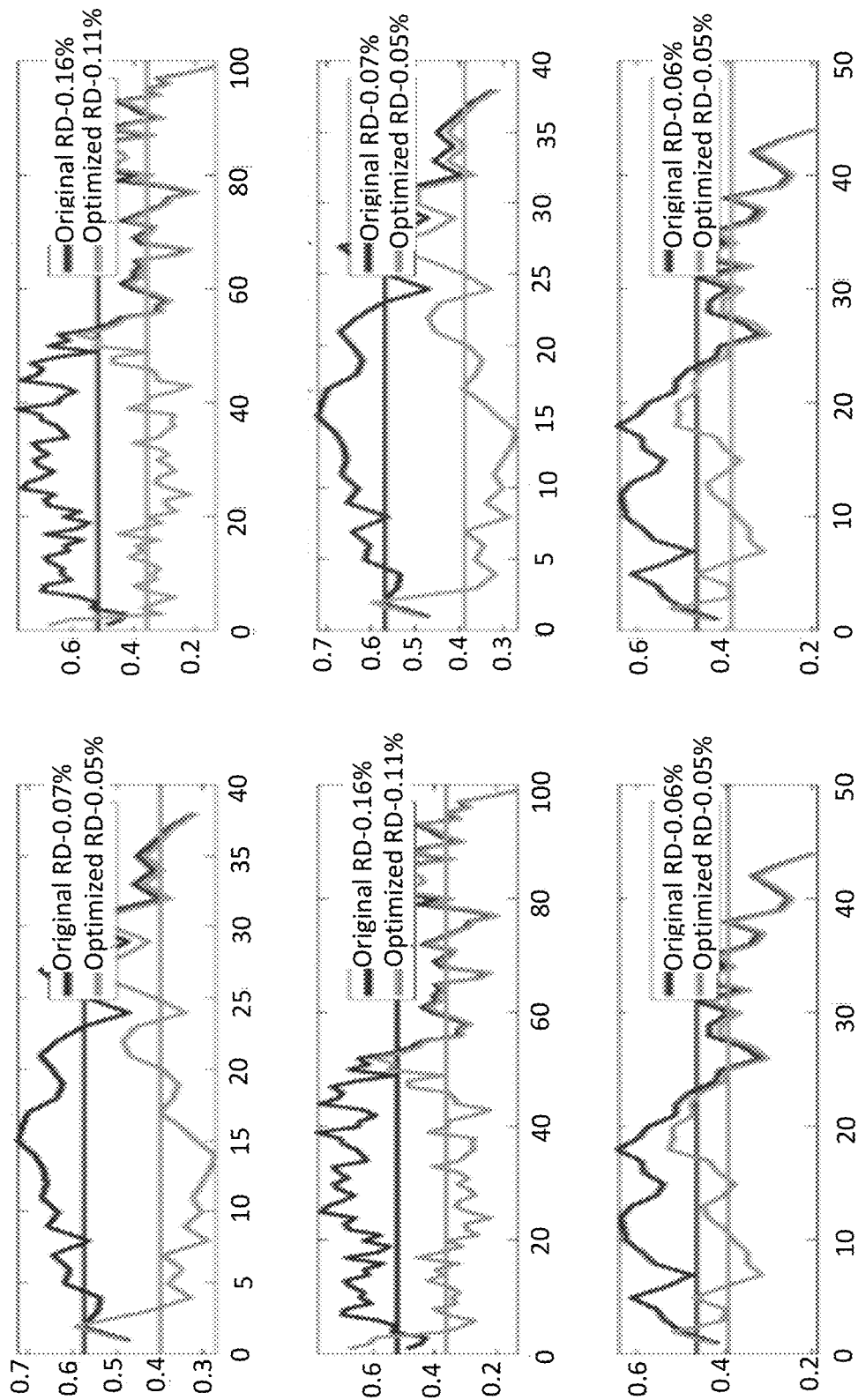
Figures 8G, 8H:
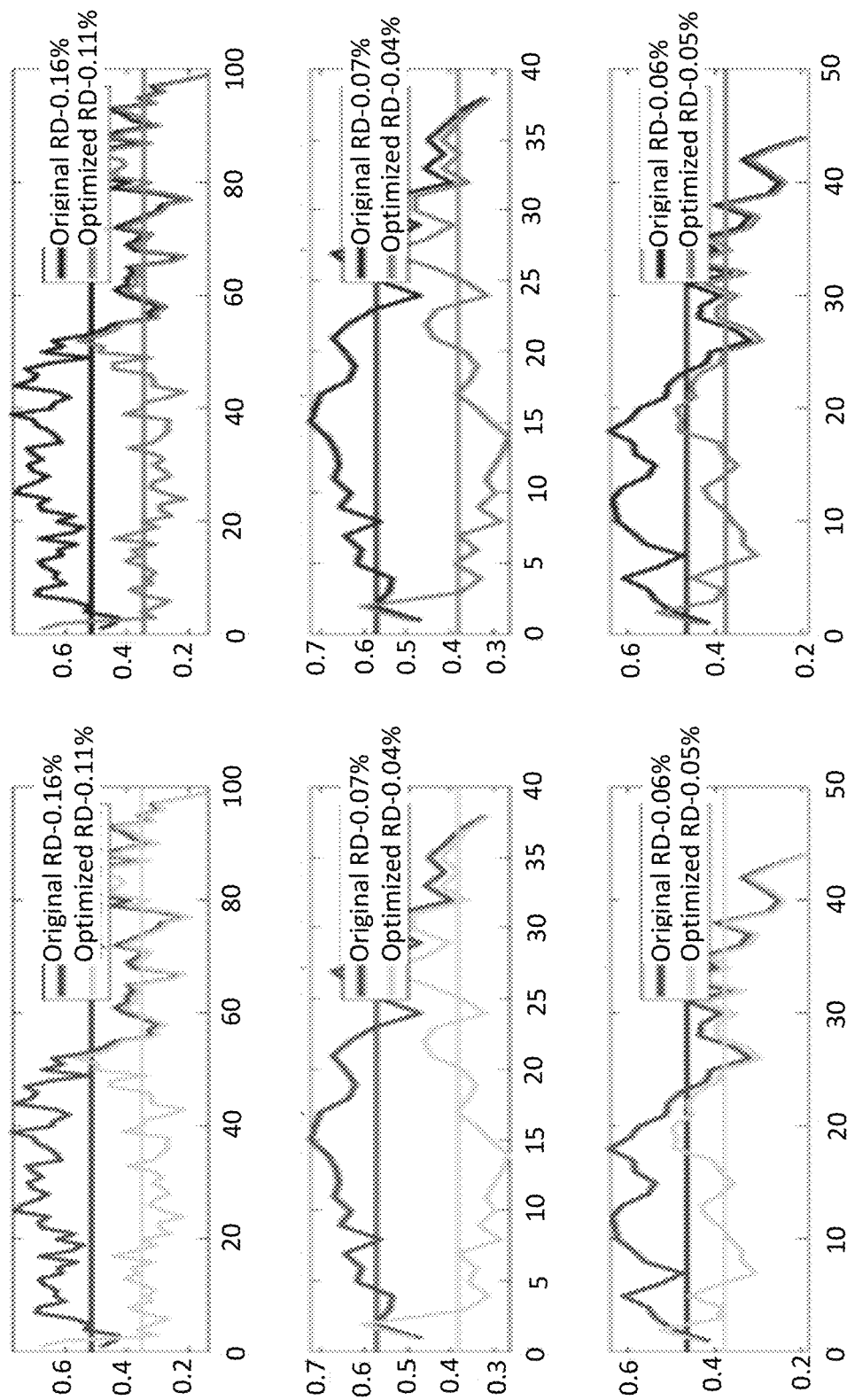
Figures 8I, 8J:
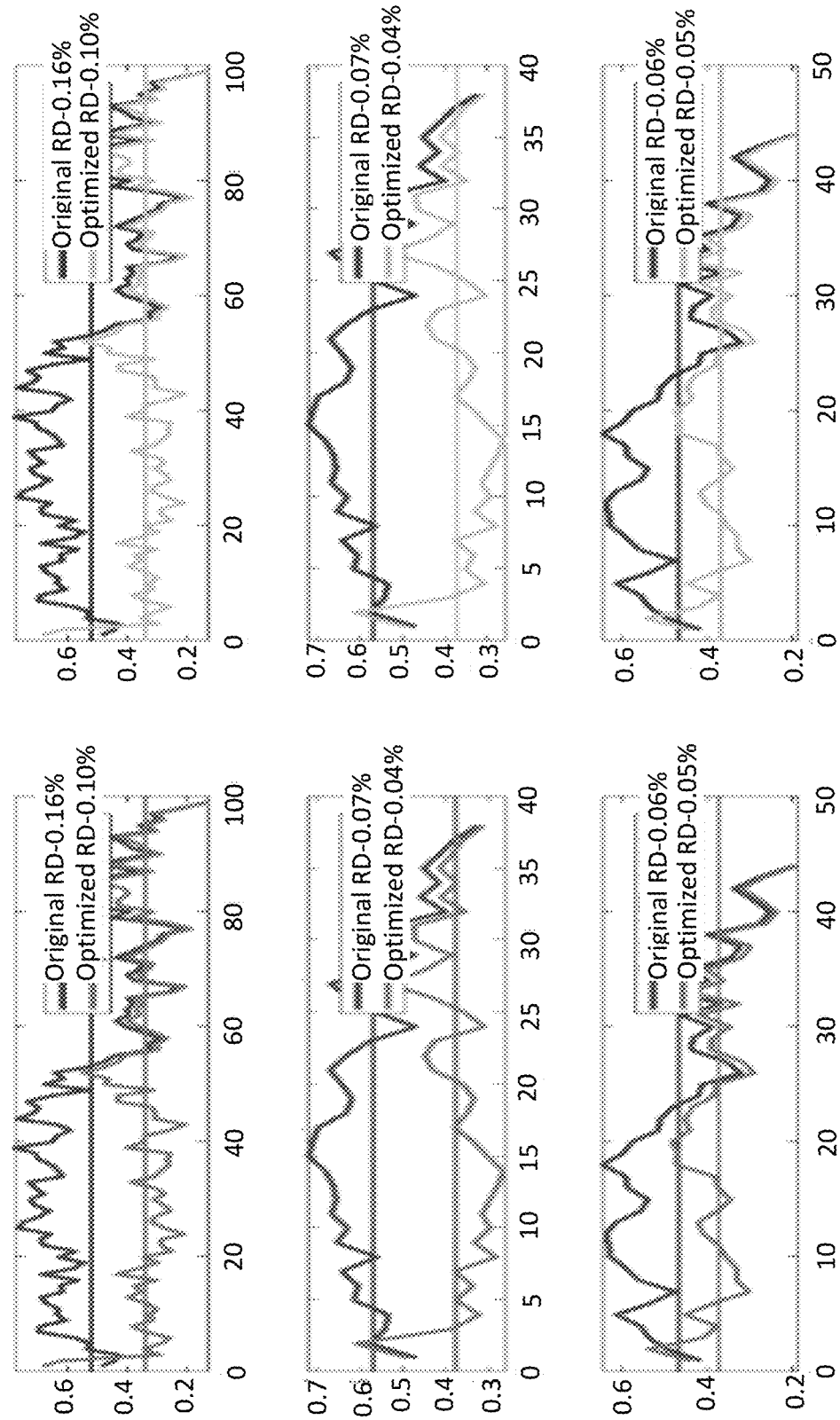
Figure 8K:
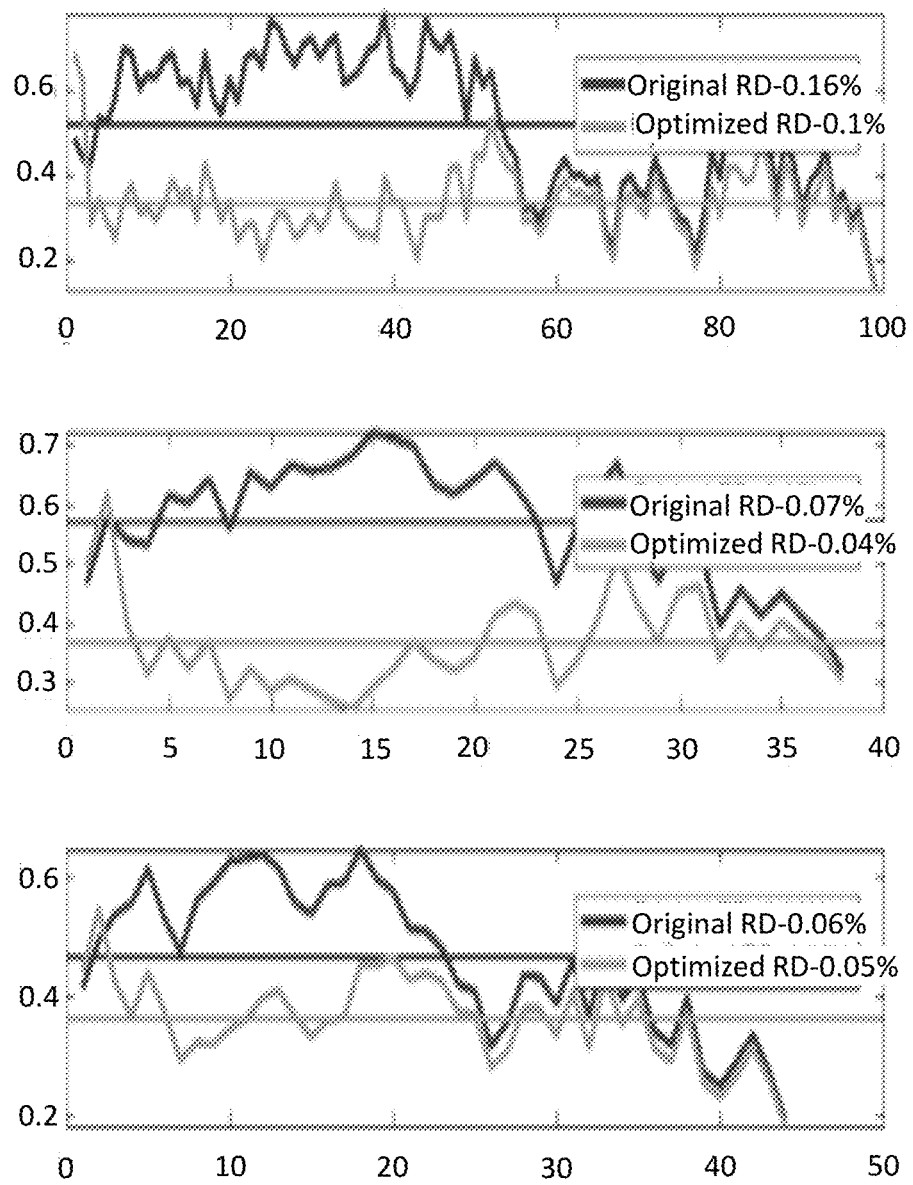
Figures 9A, 9B:
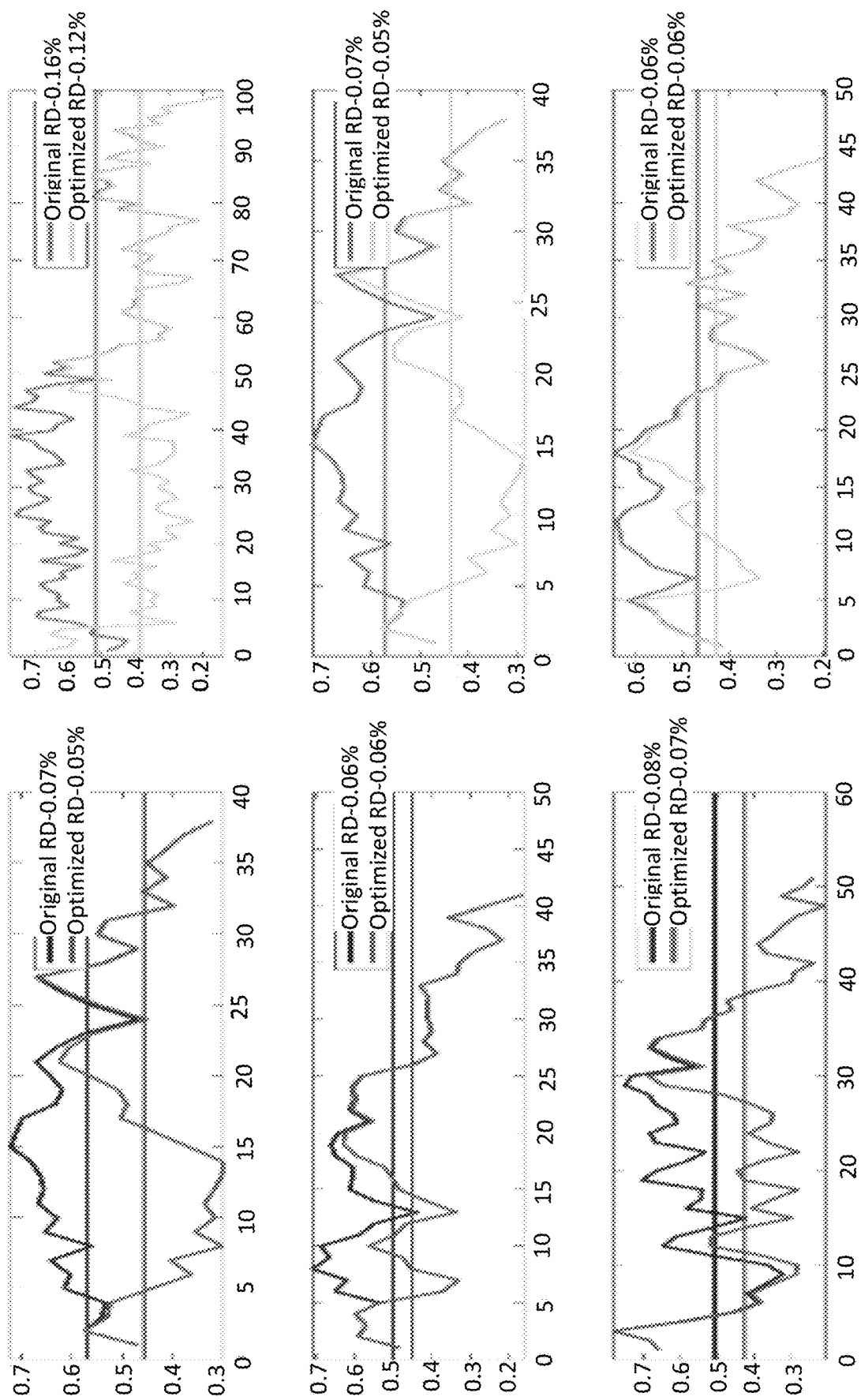
FIGS. 9A-9K: *E. coli* BGM algorithm ribosomal density profiles for the first 3 modified gene per translation efficiency (TE) constraint before and after mutations, results incorporate the effect of the first 100 mutated genes, mRNA levels as percentage of all genes is indicated, as well as each genes contribution to the free ribosome pool (FRC).
Figures 9C, 9D:
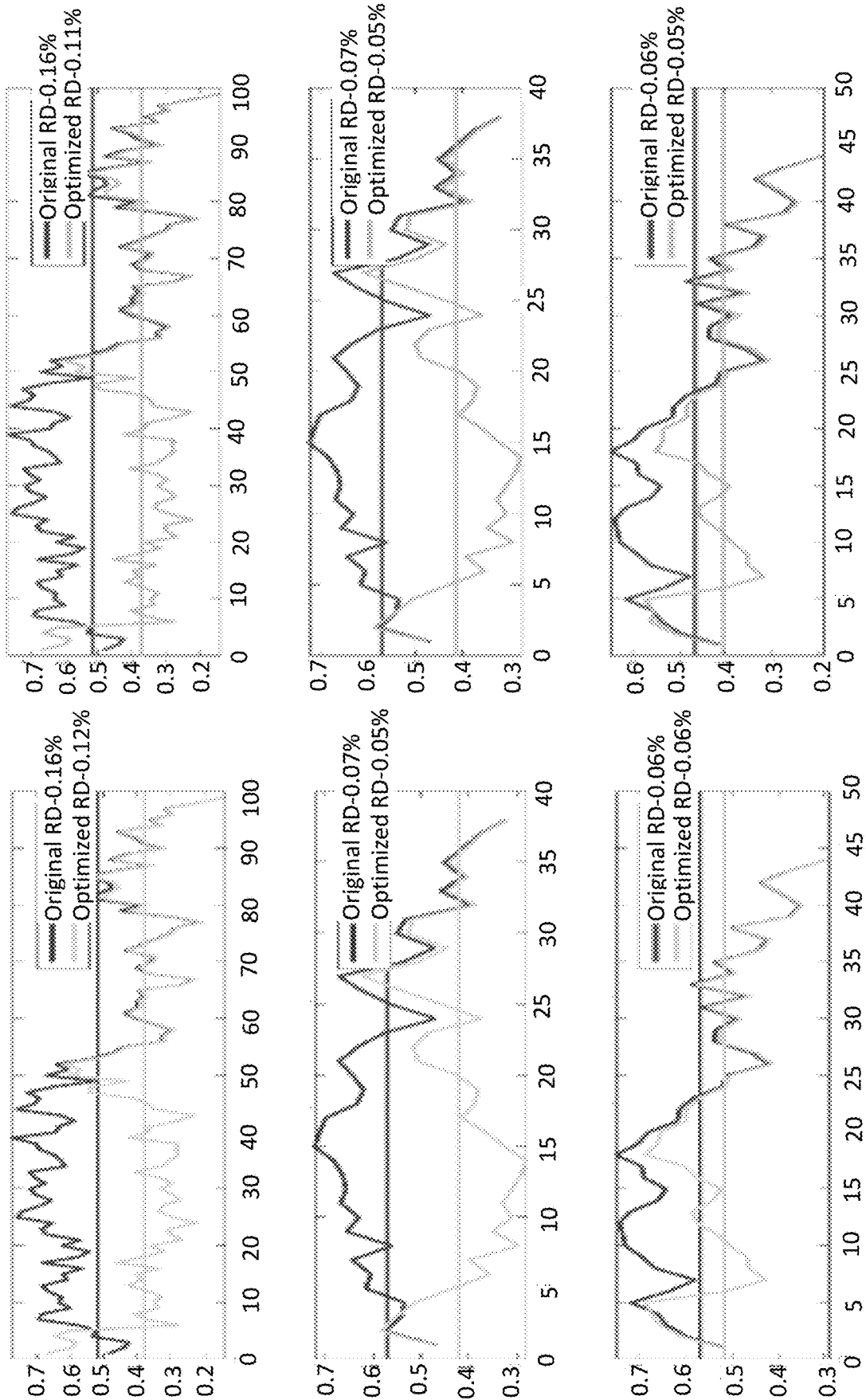
Figures 9E, 9F:
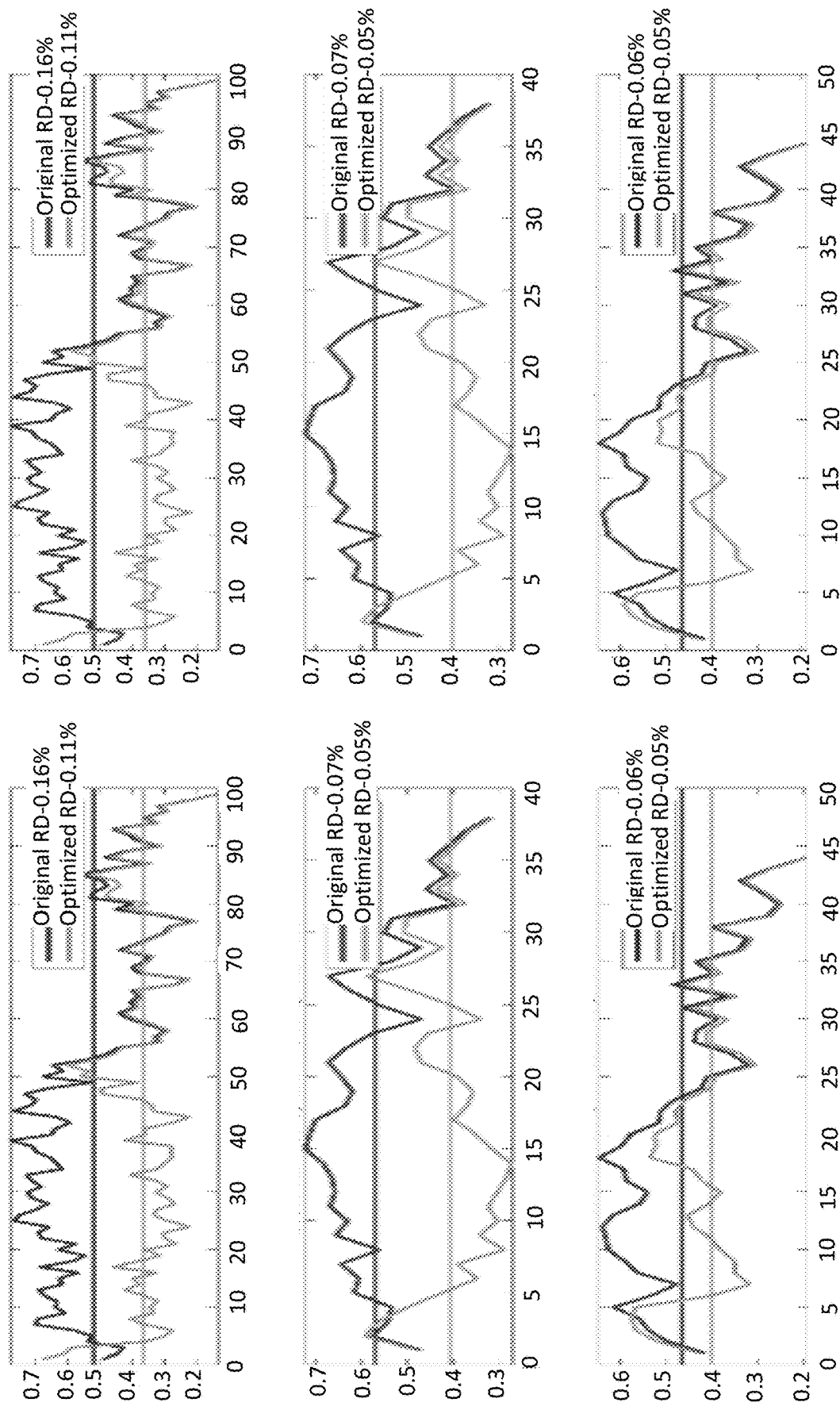
Figures 9G, 9H:
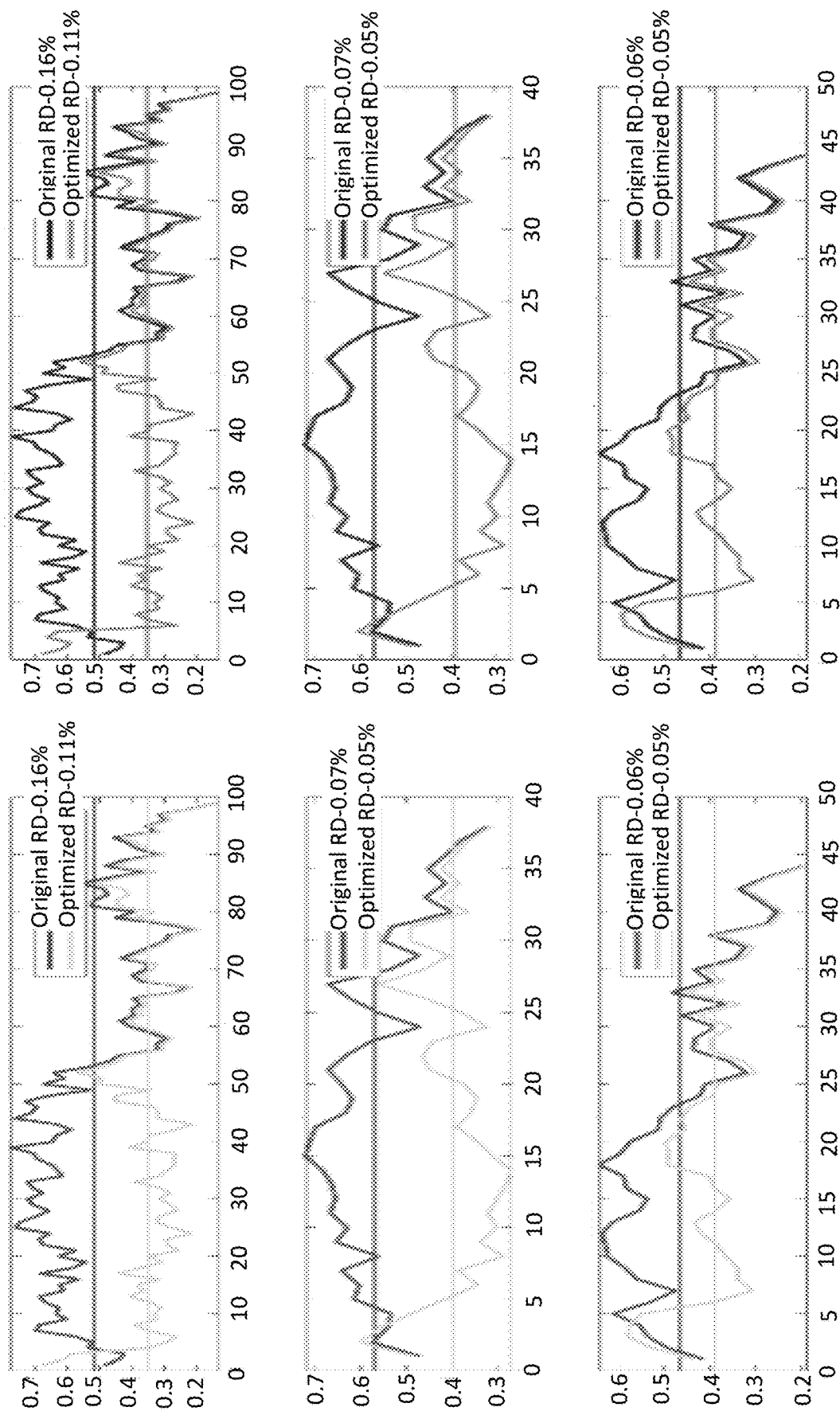
Figures 9I, 9J:
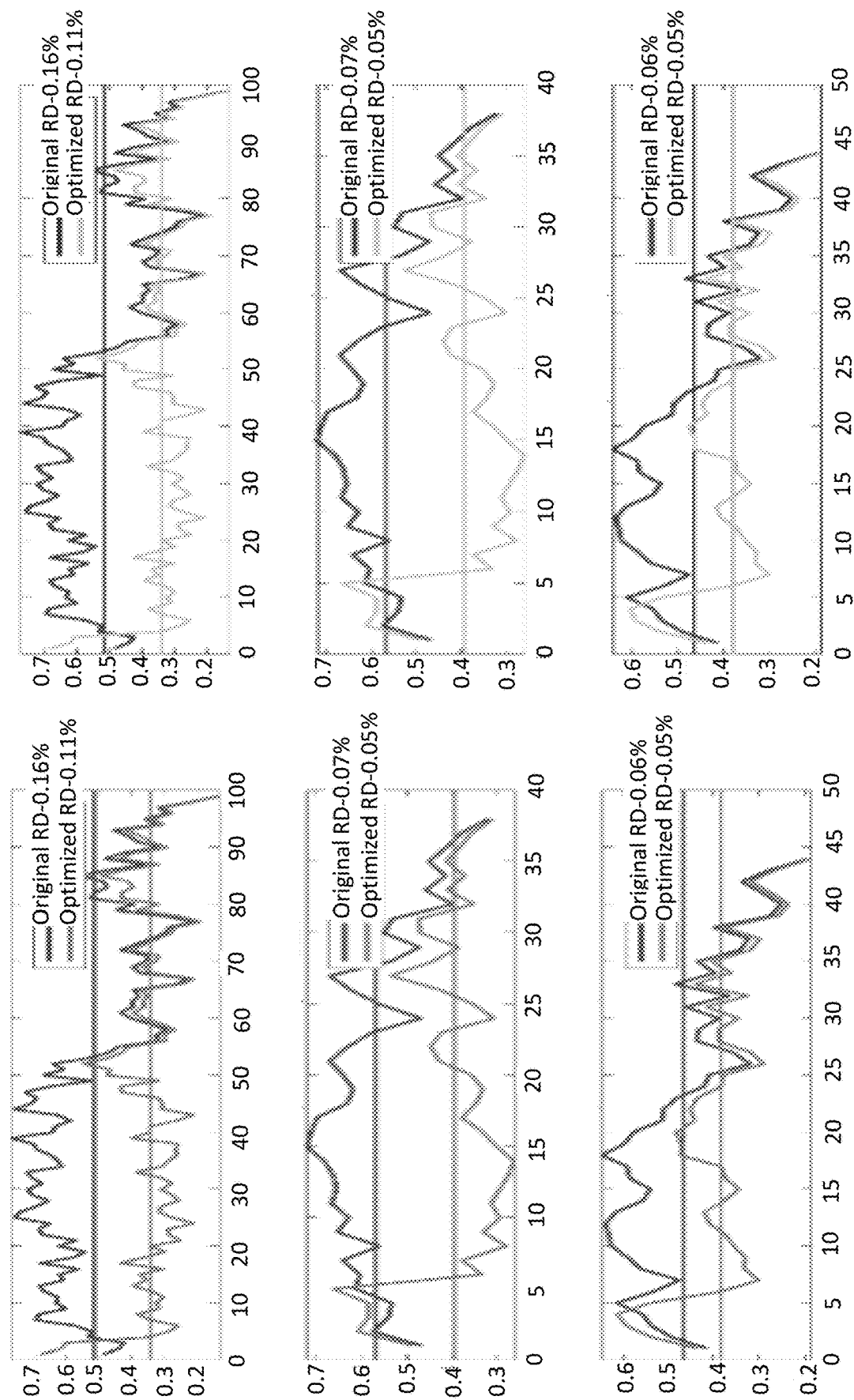
Figure 9K:
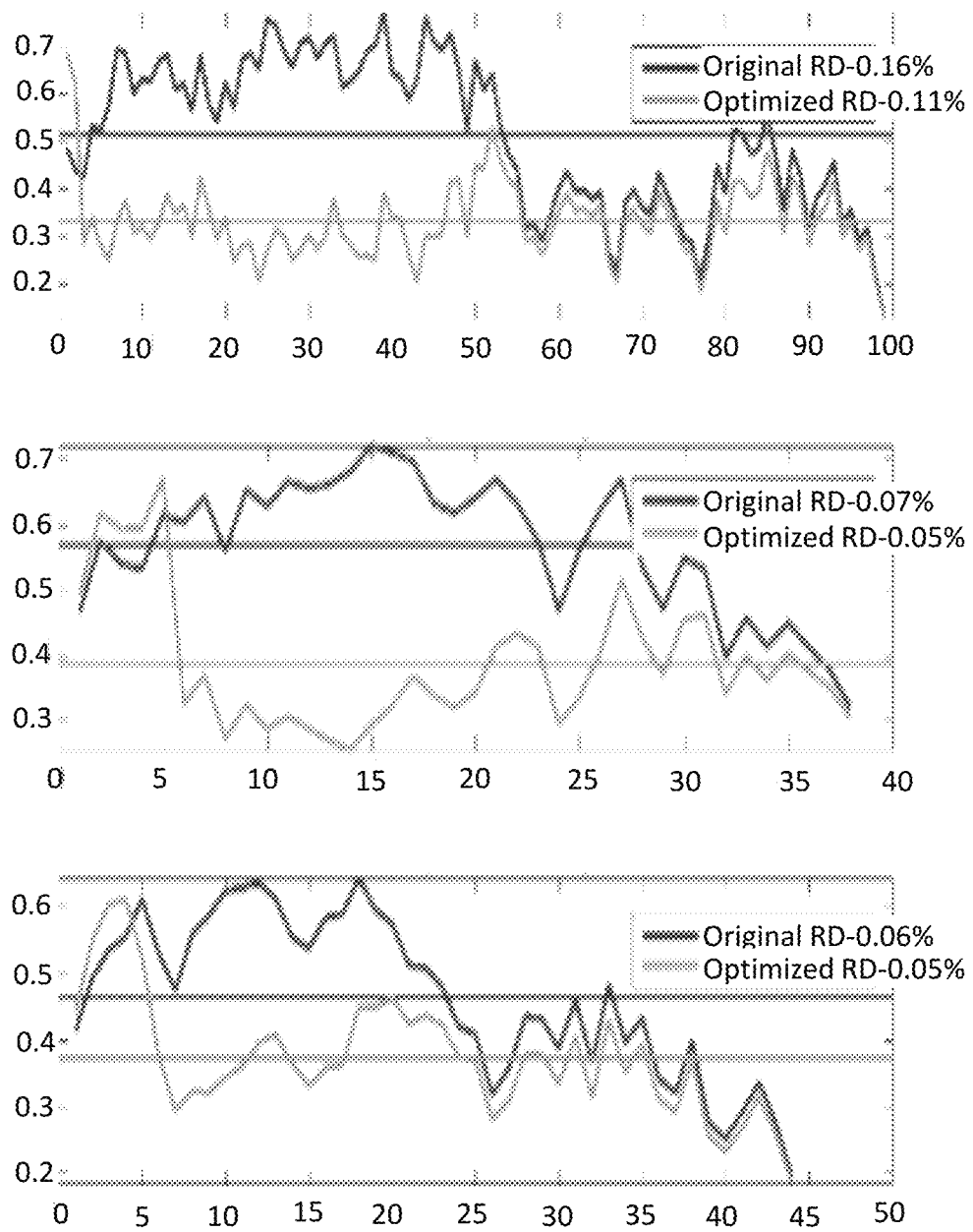
Figures 10C, 10D:
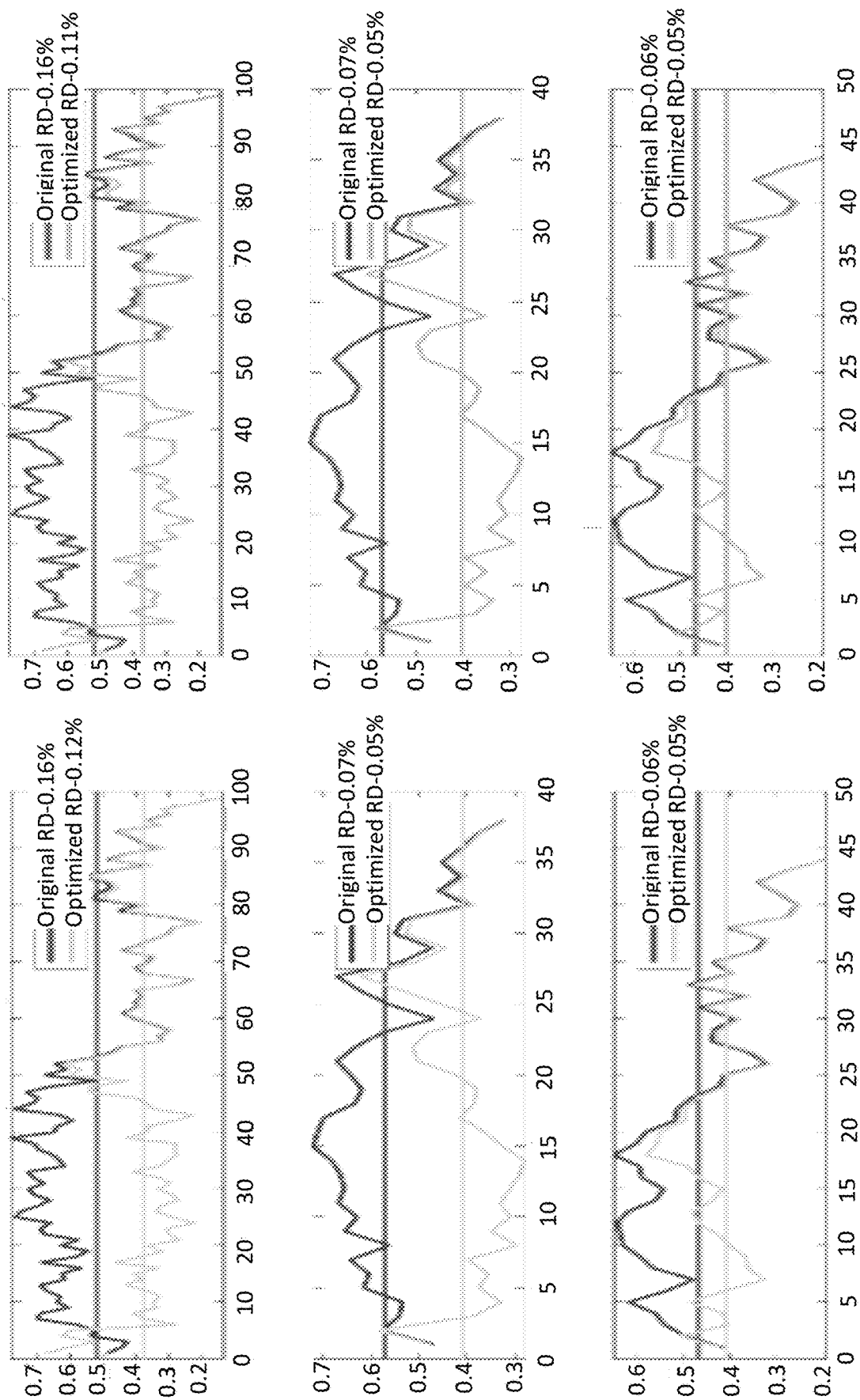
Figures 10E, 10F:
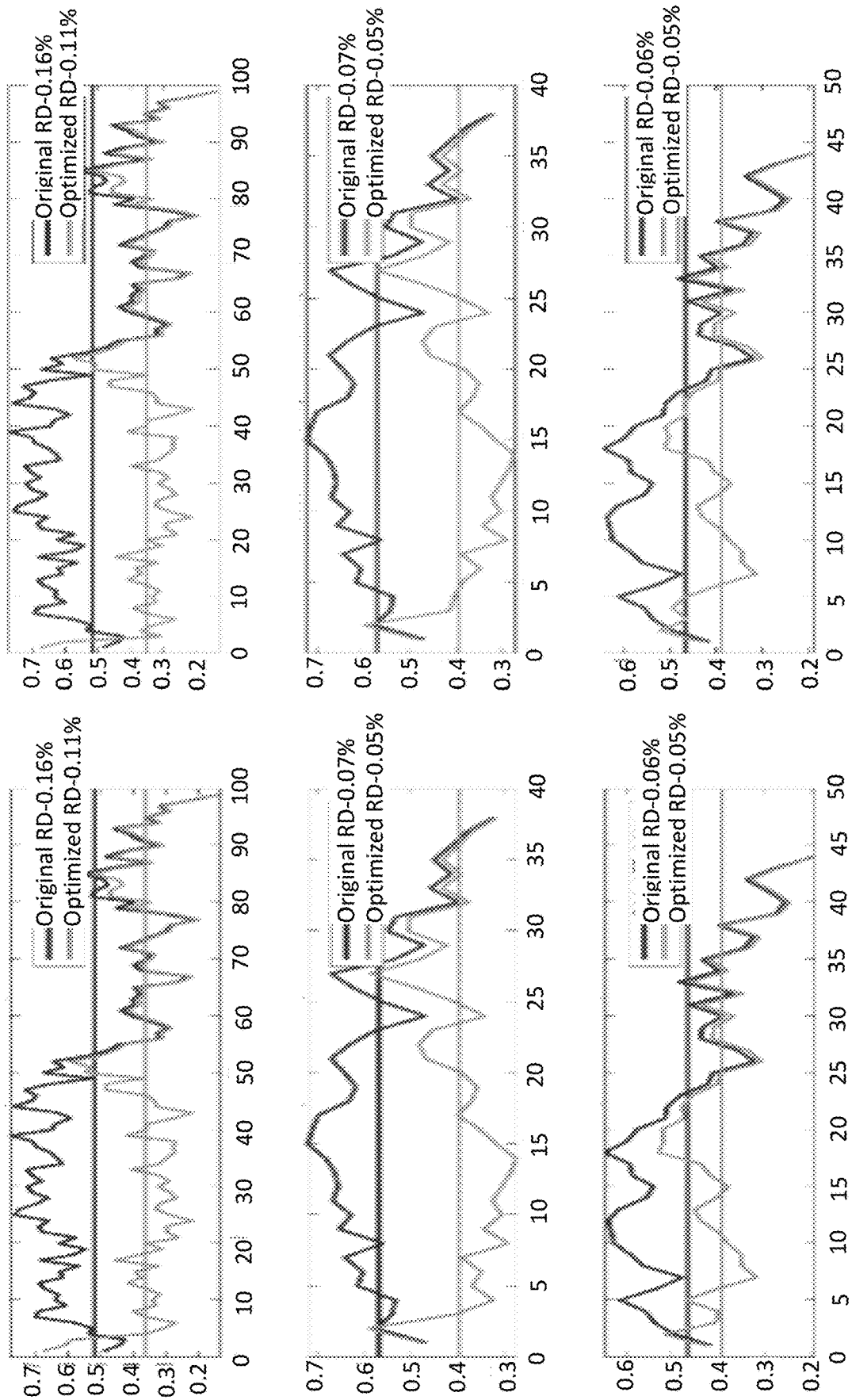
Figures 10G, 10H:
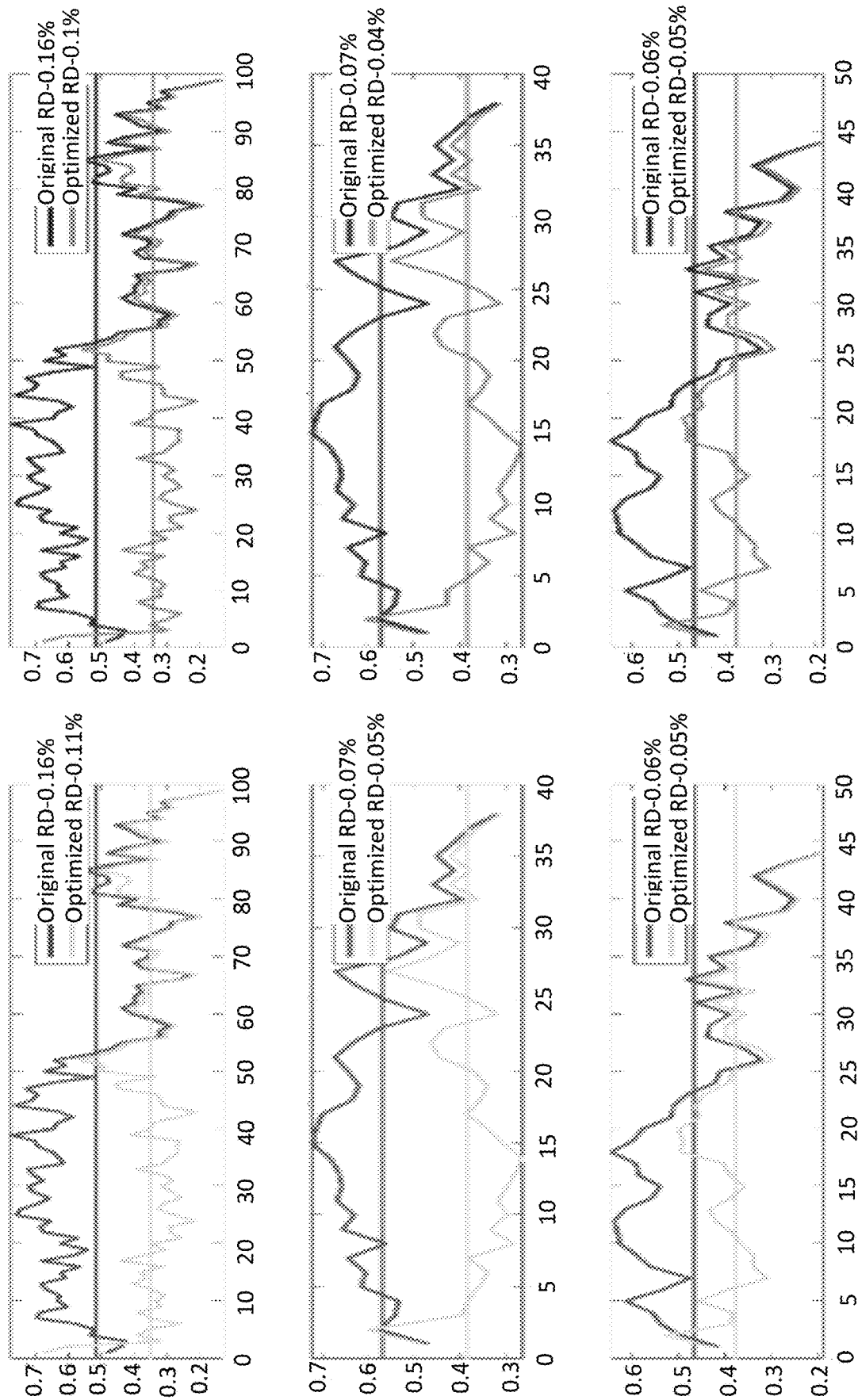
Figures 10I, 10J:
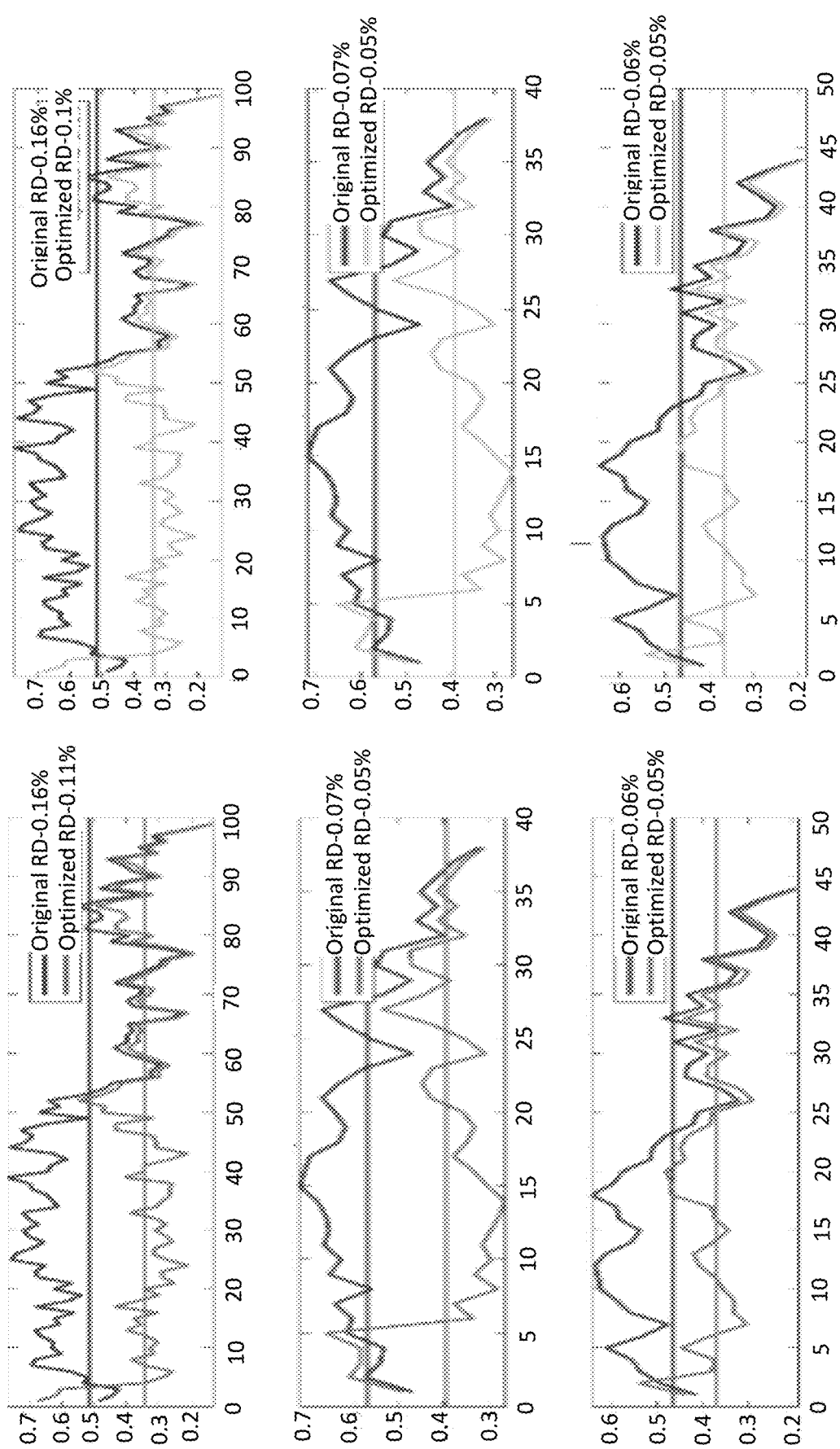
Figure 10K:
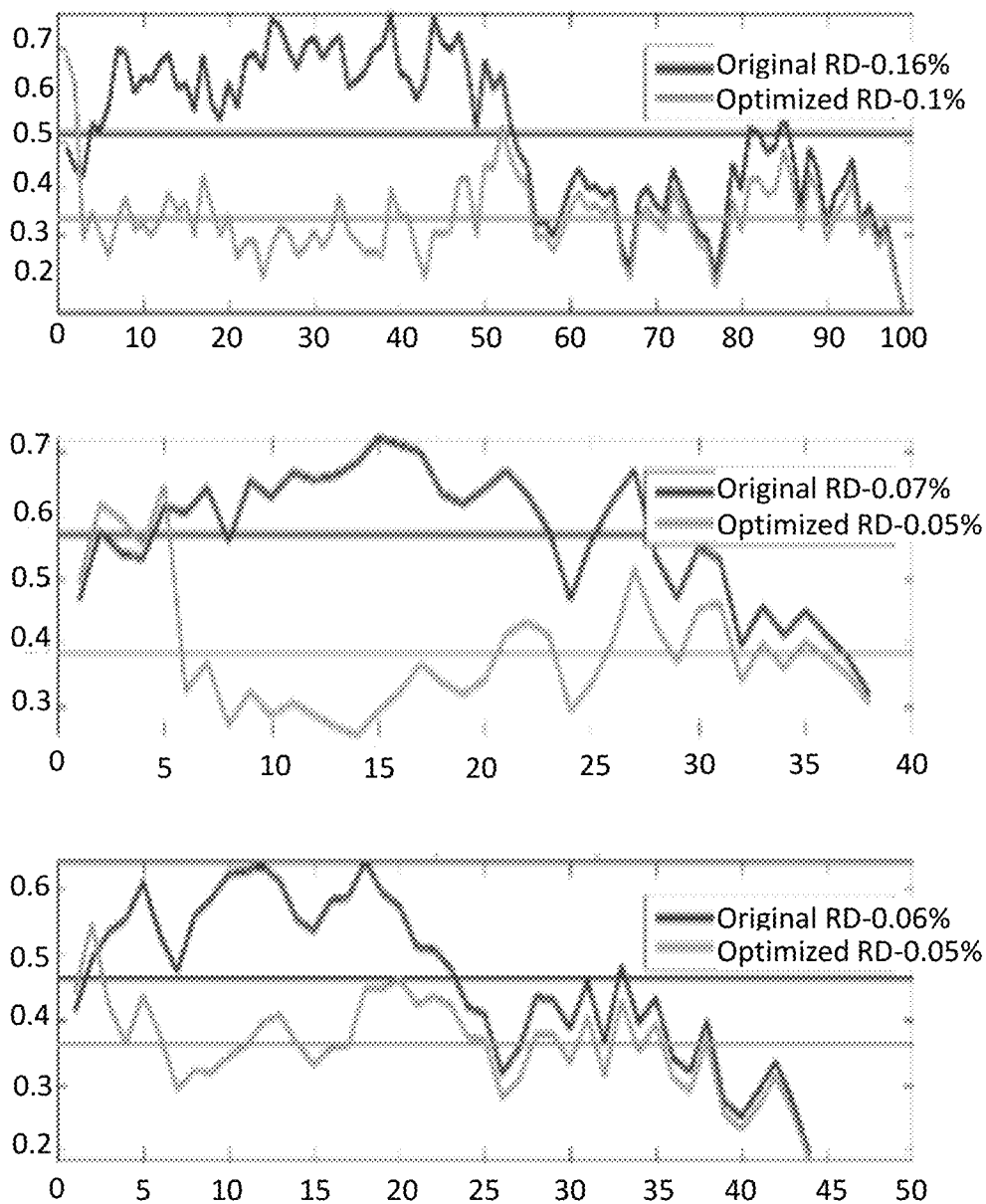

It was shown in both prokaryotes (bacteria and archaea) and eukaryotes that the first ~30-50 codons of the ORF tend to be recognized by tRNA species with lower intracellular abundance, resulting in slower ribosomal elongation speed in this region, which has been termed ramp. The ramp provides several physiological benefits, such as assisting in ribosomal allocation, co-translational folding, and protein maturation. However, when an even slower codon appears later in the gene a backup of ribosomes can form on the gene body (FIG. 1B). This backup, or traffic-jam, is essentially wasted ribosomes as they are not free to translate other proteins and are also not moving along the gene at the maximum speed enabled by the translation machinery. Nevertheless, due to the inherent redundancy of the genetic code, where 61 codons encode only 20 amino acids, the ramp can be further slowed down to eliminate these backups, while maintaining the production of the encoded protein. This is done by engineering silent mutations in the first 50 codons of an endogenous or heterologous gene that increase the free ribosome pool, while at the same time constraining the limits of reduction of translational efficiency that will be allowed (FIG. 1C).

To achieve this, the RFMNP (RFM (Ribosome Flow Model) network with a pool) was used to model translation, which is a general dynamical model for large-scale simultaneous mRNA translation and competition for ribosomes based on combining several ribosome flow models (RFMs), each representing a single copy of a gene, interconnected via a pool of free ribosomes. A novel method to estimate the RFMNP parameters was devised and correlations of 0.85 ($p<10^{-308}$) with the respective Ribo-Seq measurements (see Methods) were achieved. Briefly:

1. Optimize each gene's initiation rate separately via RFM such that the RFM predicted RD will fit the measured RD.
2. Estimate the RFMNP interconnection between RFM's parameter.
3. Greedily optimize the codon elongation rates to maximize the correlation between measured RD and predicted RFMNP RD.

Example 2

Engineering Organism Fitness Based on Whole Cell Simulation

This was followed by the Ramp Engineering (RE) approach, where the ramp region codons (first 50 codons of the ORF, omitting the first ~10 codons due to important regulatory signals related to initiation in that region) of endogenous genes are mutated to their slowest synonymous codons, resulting in an increase in the ribosomal pool, aiding host fitness generally, and upon heterologous gene introduction. Briefly (full details in the Materials and Methods section), the optimal ramp mutations across the host genome were determined according to the following RE greedy algorithm:

Iterate all the host genes, for each gene the first 50 codons (disregarding the first 10) are examined, and a codon is mutated to its slowest synonymous codon, as long as it does not reduce the gene's translation rate (translation efficiency (TE), see Materials and Methods) beyond some threshold r. The thresholds were chosen to be 0.1%, 0.5%, 1%, 1.5%, 2%, 2.5%, 3%, 3.5%, 4%, 4.5%, and 5%. The best mutation is the one that most increases the free ribosome pool, and it is selected.

Iterating one mutation at a time across the entire genome is overly time consuming, and also counterproductive, as ultimately, the number of genes mutated will need to be minimized, due to experimental constraints. Thus, 3 variants of the above approach which operate at the gene level were developed:

1. Forward Gene Minimization (FGM): For each gene start at codon 11 of the ORF and incorporate all mutations that improve the free ribosomal pool while not reducing the gene's translation rate beyond some threshold τ. In each iteration, the gene which most increases the free ribosomal pool is selected.
2. Backward Gene Minimization (BGM): Similar to FGM only now it is started at the 3' end of the first 50 codons (codon 50) and traverses backwards (until and including codon 11). The logic for this variation is that since many important regulatory signals (some related to initiation regulation) are encoded at the beginning of the ORF, they should be maintained as much as possible.
3. Greedy Gene Minimization (GGM): Per gene iterate over all possible mutations and choose the one which most increases the free ribosomal pool. Repeat this procedure until no more mutations can be selected without violating the translation rate threshold τ. Select the gene which most increases the free ribosomal pool.

One could continue mutating genes until there is no improvement in the free ribosome pool, however it was decided to terminate after the best 100 genes were selected, as practically/currently more mutations will not be introduced to generate novel engineered genomes.

Example 3

Engineering in 100 Genes Enables Up to 57% Improvement in Ribosome Allocation in E. coli and 35% Improvement in S. cerevisiae As can be seen in FIGS. 2A-4D for S. cerevisiae and E. coli, utilizing the 3 variants of the RE approach, namely FGM (FIGS. 2A-2D), BGM (FIGS. 3A-3D), and GGM (FIGS. 4A-4D), the free ribosomal pool steadily increases with each newly modified gene. The baseline free ribosomal pool of S. cerevisiae is 30000 ribosomes, and of E. coli is 5600 ribosomes. All algorithms were performed for 100 genes, with 11 TE constraints.

For FGM in S. cerevisiae, for 0.1% reduction in TE the free ribosomal pool after modifying 100 genes is 34111 with 598 mutations, for 0.5% 35118 free ribosomes and 575 mutations, for 1% 36012 free ribosomes and 545 mutations, for 1.5% 36662 free ribosomes and 581 mutations, for 2% 37261 free ribosomes and 593 mutations, for 2.5% 37783 free ribosomes and 633 mutations, for 3% 38380 free ribosomes and 642 mutations, for 3.5% 38946 free ribosomes and 678 mutations, for 4% 39529 free ribosomes and 696 mutations, for 4.5% 40024 free ribosomes and 699 mutations, for 5% 40517 free ribosomes and 710 mutations. At a threshold of 5% the increase in free ribosomes is over 35%.

For FGM in E. coli, for 0.1% reduction in TE the free ribosomal pool after modifying 100 genes is 6490 with 565 mutations, for 0.5% 7154 free ribosomes and 605 mutations, for 1% 7415 free ribosomes and 629 mutations, for 1.5% 7691 free ribosomes and 601 mutations, for 2% 7861 free ribosomes and 616 mutations, for 2.5% 8071 free ribosomes and 650 mutations, for 3% 8231 free ribosomes and 622 mutations, for 3.5% 8375 free ribosomes and 660 mutations, for 4% 8516 free ribosomes and 697 mutations, for 4.5% 8661 free ribosomes and 715 mutations, for 5% 8799 free ribosomes and 720 mutations. At a threshold of 5% the increase in free ribosomes is over 57%.

For BGM in S. cerevisiae, for 0.1% reduction in TE the free ribosomal pool after modifying 100 genes is 33088 with 465 mutations, for 0.5% 34508 34283 free ribosomes and 461 mutations, for 1% 35206 free ribosomes and 497 mutations, for 1.5% 35743 free ribosomes and 513 mutations, for 2% 36196 free ribosomes and 544 mutations, for 2.5% 36608 free ribosomes and 569 mutations, for 3% 37035 free ribosomes and 583 mutations, for 3.5% 37431 free ribosomes and 588 mutations, for 4% 37964 free ribosomes and 590 mutations, for 4.5% 38383 free ribosomes and 631 mutations, for 5% 38851 free ribosomes and 641 mutations. At a threshold of 5% the increase in free ribosomes is over 29%.

For BGM in E. coli, for 0.1% reduction in TE the free ribosomal pool after modifying 100 genes is 6535 with 580 mutations, for 0.5% 6988 free ribosomes and 591 mutations, for 1% 7233 free ribosomes and 629 mutations, for 1.5% 7425 free ribosomes and 659 mutations, for 2% 7574 free ribosomes and 681 mutations, for 2.5% 7705 free ribosomes and 700 mutations, for 3% 7826 free ribosomes and 701 mutations, for 3.5% 7942 free ribosomes and 784 mutations, for 4% 8030 free ribosomes and 764 mutations, for 4.5% 8120 free ribosomes and 793 mutations, for 5% 8236 free ribosomes and 804 mutations. At a threshold of 5% the increase in free ribosomes is over 47%.

For GGM in S. cerevisiae, for 0.1% reduction in TE the free ribosomal pool after modifying 100 genes is 33183 and 220 mutations, for 0.5% 34333 free ribosomes and 230 mutations, for 1% 34890 free ribosomes and 234 mutations, for 1.5% 36063 free ribosomes and 231 mutations, for 2% 36616 free ribosomes and 247 mutations, for 2.5% 37154 free ribosomes and 263 mutations, for 3% 37823 free ribosomes and 257 mutations, for 3.5% 38135 free ribosomes and 259 mutations, for 4% 38575 free ribosomes and 257 mutations, for 4.5% 39131 free ribosomes and 272 mutations, for 5% 39490 free ribosomes and 284 mutations. At a threshold of 5% the increase in free ribosomes is over 31%

For GGM in E. coli, for 0.1% reduction in TE the free ribosomal pool after modifying 100 genes is 6572 and 278 mutations, for 0.5% 7125 free ribosomes and 278 mutations, for 1% 7394 free ribosomes and 289 mutations, for 1.5% 7608 free ribosomes and 280 mutations, for 2% 7795 free ribosomes and 290 mutations, for 2.5% 7962 free ribosomes and 306 mutations, for 3% 8135 free ribosomes and 296 mutations, for 3.5% 8285 free ribosomes and 316 mutations, for 4% 8394 free ribosomes and 322 mutations, for 4.5% 8527 free ribosomes and 316 mutations, for 5% 8667 free ribosomes and 335 mutations. At a threshold of 5% the increase in free ribosomes is over 54%.

FIGS. 5A-10K depict the FGM (FIGS. 5A-5K and FIGS. 8A-8K), BGM (FIGS. 6A-6K and FIGS. 9A-9K), and GGM (FIGS. 7A-7K and FIGS. 10A-10K) algorithm ribosomal density (RD) profiles respectively, for S. cerevisiae and E. coli, for the first 3 modified genes per representative translation efficiency (TE) constraint (expressly 0.1% (FIGS. 5A, 6A, 7A, 8A, 9A, 10A), 0.5% (FIGS. 5B, 6B, 7B, 8B, 9B, 10B), 1% (FIGS. 5C, 6C, 7C, 8C, 9C, 10C), 1.5% (FIGS. 5D, 6D, 7D, 8D, 9D, 10D), 2% (FIGS. 5E, 6E, 7E, 8E, 9E, 10E), 2.5% (FIGS. 5F, 6F, 7F, 8F, 9F, 10F), 3% (FIGS. 5G, 6G, 7G, 8G, 9G, 10G), 3.5% (FIGS. 5H, 6H, 7H, 8H, 9H, 10H), 4% (FIGS. 5I, 6I, 7I, 8I, 9I, 10I), 4.5% (FIGS. 5J, 6J, 7J, 8J, 9J, 10J), 5% (FIGS. 5K, 6K, 7K, 8K, 9K, 10K) before and after mutation, results incorporate the effect of all 100 mutated genes.

Table 1 summarizes the number of additional free ribosomes each of the 3 algorithms enables according to the TE reduction constraint in S. cerevisiae, and Table 2 in E. coli. The free ribosomal pool percentage increase (in parenthesis), and mean number of mutations (in square brackets) performed across the 100 selected genes is also presented.

TABLE 1

| Reduction in TE | FGM Free Ribosomes | BGM Free Ribosomes | GGM Free Ribosomes |
| --- | --- | --- | --- |
| 0.1% | 4111 (13.7%) [5.98] | 3088 (10.29%) [4.65] | 3183 (10.61%) [2.2] |
| 0.5% | 5118 (17.06%) [5.75] | 4508 (15.03%) [4.61] | 4333 (14.44%) [2.3] |
| 1% | 6012 (20.04%) [5.45] | 5206 (17.35%) [4.97] | 4890 (16.3%) [2.34] |
| 1.5% | 6662 (22.21%) [5.81] | 5743 (19.14%) [5.13] | 6063 (20.21%) [2.31] |
| 2% | 7261 (24.2%) [5.93] | 6196 (20.65%) [5.44] | 6616 (22.05%) [2.47] |
| 2.5% | 7783 (25.94%) [6.33] | 6608 (22.03%) [5.69] | 7154 (23.85%) [2.63] |
| 3% | 8380 (27.93%) [6.42] | 7035 (23.45%) [5.83] | 7823 (26.08%) [2.57] |
| 3.5% | 8946 (29.82%) [6.78] | 7431 (24.77%) [5.88] | 8135 (27.12%) [2.59] |
| 4% | 9529 (31.76%) [6.96] | 7964 (26.55%) [5.9] | 8575 (28.58%) [2.57] |
| 4.5% | 10024 (33.41%) [6.99] | 8383 (27.94%) [6.31] | 9131 (30.44%) [2.72] |
| 5% | 10517 (35.06%) [7.1] | 8851 (29.5%) [6.41] | 9490 (31.63%) [2.84] |

TABLE 2

| Reduction in TE | FGM Free Ribosomes | BGM Free Ribosomes | GGM Free Ribosomes |
| --- | --- | --- | --- |
| 0.1% | 890 (15.9%) [5.65] | 935 (16.7%) [5.8] | 972 (17.36%) [2.78] |
| 0.5% | 1554 (27.75%) [6.05] | 1388 (24.79%) [5.91] | 1525 (27.23%) [2.78] |
| 1% | 1815 (32.41%) [6.29] | 1633 (29.16%) [6.29] | 1794 (32.04%) [2.89] |
| 1.5% | 2091 (37.34%) [6.01] | 1825 (32.59%) [6.59] | 2008 (35.86%) [2.8] |
| 2% | 2261 (40.38%) [6.16] | 1974 (35.25%) [6.81] | 2195 (39.2%) [2.9] |
| 2.5% | 2471 (44.13%) [6.5] | 2105 (37.59%) [7] | 2362 (42.18%) [3.06] |
| 3% | 2631 (47%) [6.22] | 2226 (39.75%) [7.01] | 2536 (45.29%) [2.96] |
| 3.5% | 2775 (49.55%) [6.6] | 2342 (41.82%) [7.84] | 2685 (47.95%) [3.16] |
| 4% | 2916 (52.07%) [6.97] | 2430 (43.39%) [7.64] | 2794 (49.89%) [3.22] |
| 4.5% | 3061 (54.66%) [7.15] | 2520 (45%) [7.93] | 2927 (52.27%) [3.16] |
| 5% | 3199 (57.13%) [7.2] | 2636 (47.07%) [8.04] | 3067 (54.77%) [3.35] |

All three algorithms were successful in increasing the free ribosome pool and thereby improving the fitness of *S. cerevisiae* and *E. coli*, though such an approach will theoretically work in any organism or cell. Further, the approach has been demonstrated for engineering of translation, but is of course relevant to other gene expression steps and intracellular processes that involve traffic jams (processes with non-optimal allocation of resources), such as RNAP traffic jams during transcription.

Example 4

Proof of Principle in *S. cerevisiae*

Based on our whole cell simulation for translation in *S. cerevisiae* (60,000 mRNA molecules and 200,000 ribosomes), which was fitted based on experimental data, a list of candidate genes was created. These candidate genes were ones in which specific synonymous mutations are expected to improve the cell's global ribosome allocation, which in turn is expected to directly improve the fitness of the yeast. The six genes selected for testing were RPO21, PGK1, CYS4, VMA2, TCB3 and PAN1.

The CRISPR/Cas9 system was used to mutate these six genes in haploid strains of *S. cerevisiae*. Seven codons of CYS4 were mutated, namely codons 11, 15, 19, 21, 22, 25 and 44 (See SEQ IDs NO: 1-2). Eight codons of RPO21 were mutated, namely codons 12, 17, 20, 25, 28, 30, 33 and 34 (See SEQ IDs NO: 3-4). Four codons of PGK1 were mutated, namely codons 12, 19, 27 and 28 (See SEQ IDs NO: 5-6). Four codons of VMA2 were mutated, namely codons 13, 15, 16 and 44 (See SEQ 1Ds NO: 7-8). Three codons of TCB3 were mutated, namely codons 11, 15 and 16 (See SEQ IDs NO: 9-10). Three codons of PAN1 were mutated, namely codons 11, 12 and 27 (See SEQ IDs NO: 11-12).

First, gRNA and donor DNA sequences were designed, and the relevant sequences were generated. To generate the gene-specific gRNA, plasmid pNA0525 with Leu marker was used, which was linearized with NotI. The Gibson assembly protocol was employed to clone the genes-specific gRNAs into pNA0525.

WT, haploid yeast cells were grown to mid-log and transformed first with plasmid pNA0519 which contains the cas9 gene and His marker. Transformants were selected on —HIS plates. Cas9 expressing cells were grown to mid-log and transformed with the relevant gRNA plasmid and gene-specific Donor DNA (which contains the synonymous mutations that we would like to introduce to the specific gene, using homologous recombination). Transformants were selected on-His-Leu SD plates. Candidates were grown and checked by PCR with primers that span the mutation region, followed by sequencing. Synonymous positive clones were isolated and kept for analysis.

Figure 11A:
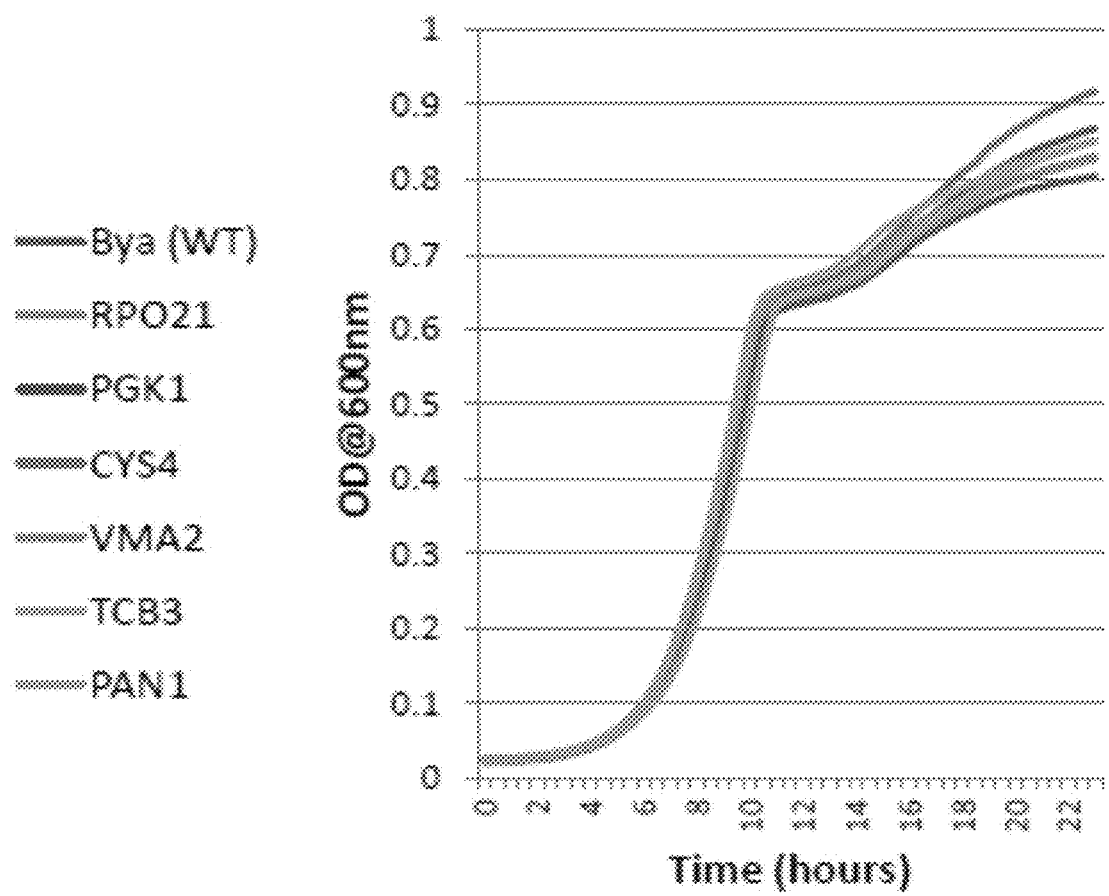
FIGS. 11A-11B.

To analyze the growth rate of the individual mutants was compared to the growth of the WT haploid single cells of synonymous mutants along with WT cells were inoculated into YPD and grown overnight at 30 degrees, shaking at 220 rpm. The next day, the cells are diluted 1:1000 and grown shaking in a 96 or 24 well plates in a Tecan spectrophotometer which runs a growth kinetics of the cells. The differences in growth rate and provided in Table 3. All six mutated strains did indeed show improved robustness and increased growth as compared to the WT strain (FIG. 11A).

TABLE 3

| Strain | % growth of WT |
| --- | --- |
| WT | 100% |
| RPO21 | 120.80% |
| PGK1 | 107.90% |
| CYS4 | 114.10% |
| VMA2 | 103.40% |
| TCB3 | 105.90% |
| PAN1 | 105.90% |

In order to enhance the differences in growth between mutants and WT cells, and to make them visible to the naked eye, a competition experiment was run. In the assay, equal numbers of mutant and WT cells are mixed and allowed to grow for 50 generations (~3 days), in the assumption that the growth advantage will culminate in large difference over time.

Figure 11B:
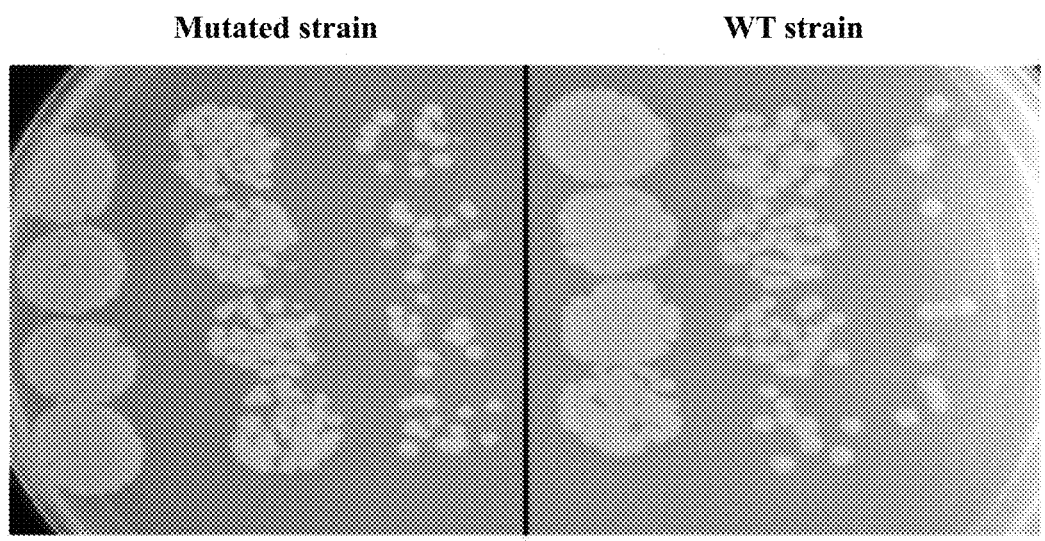

In order to distinguish the mutant from the WT cells after the mixing, each strain was given an antibiotic marker to distinguish them. The WT cells had a hygromycin resistance gene, and a mutant (non-functional) kanamycin resistance gene. Reciprocally, the mutated cells had a kanamycin resistance gene, and a mutant hygromycin resistance gene. After the mixed growing the cells were serially diluted and equal amounts were plated on a Kan plate and a Hygro plate. The colonies that form on Kan represent the portion of the mixed population that had been mutated and he colonies that form of the Hygro represent the portion of the mixed population that was WT. The results for the VMA2 mutant strain (only a 3.3% growth increase) is shown in FIG. 11B. After 3 days there were about 4 times as many mutant cells as WT cells, even with only the minor growth increase conveyed by the mutation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A genetically modified cell, comprising at least one endogenous coding sequence comprising a first codon substituted with a synonymous codon, said synonymous codon(s) translating at a different rate than said first codon, wherein said coding sequence comprises a second codon downstream of said synonymous codon(s), wherein said downstream codon translates at a slower rate than the average translational rate of codons 11 to 50 of said coding sequence, and said genetically modified cell comprises a modified free pool of ribosomes that modulates the rate of translation and replicative fitness as compared to a non-genetically modified control cell, and wherein a slower translating synonymous codon increases both said free pool of ribosomes and said replicative fitness of said modified cell and a faster translating synonymous codon decreases both said free pool of ribosomes and said replicative fitness in said genetically modified cell.

2. The genetically modified cell of claim 1, where said slowly translating codon comprises a ribosome density at least 5% higher than a ribosome density downstream said slowly translating codon.

3. The genetically modified cell of claim 1, where said first codon substituted with a synonymous codon is located within codons 11 to 50 from the translational start site of said coding sequence.

4. The genetically modified cell of claim 1, wherein increased replicative fitness comprises an increased free ribosome pool and decreased replicative fitness comprises a decreased free ribosome pool.

5. The genetically modified cell of claim 1, wherein said synonymous codon is the slowest or fastest translating synonymous codon of said at least one codon.

6. The genetically modified cell of claim 1, wherein said first codon substituted with a synonymous codon does not decrease the translation efficiency of said coding sequence by more than 5%.

7. The genetically modified cell of claim 1, wherein said genetically modified cell further comprises a heterologous transgene, said synonymous codon is a slower translating codon and wherein replicative fitness in the genetically modified cell comprising said heterologous transgene is equal to or greater than replicative fitness in said cell devoid of said heterologous transgene and said at least one synonymous mutation.

8. A method for modifying replicative fitness in a cell, comprising substituting first codon with a synonymous codon in at least one endogenous coding sequence of said cell, wherein said coding sequence comprises a second codon downstream of said synonymous codon(s), wherein said downstream codon is downstream of codon 50 of said endogenous coding sequence and translates at a slower rate than the average translational rate of codons 11 to 50 of said endogenous coding sequence, and said substituting modifies a free pool of ribosomes that modulate the rate of translation and replicative fitness as compared to a unmodified control cell, and wherein substitution to a slower translating synonymous codon increases both said free pool of ribosomes and said replicative fitness in said modified cell and a substitution to a faster translating synonymous codon decreases both said free pool of ribosomes and said replicative fitness in said modified cell.

9. The method of claim 8, wherein said codon is downstream of codon 50 from a translational start site of said coding sequence.

10. The method of claim 8, wherein said synonymous codon is the slowest or fastest translating synonymous codon.

11. The method of claim 8, wherein said substituting does not decrease the translation or expression of said coding sequence by more than 5%.

12. The method of claim 11, further comprising determining whether a synonymous codon would reduce translation efficiency below said threshold, and wherein said determining comprises any one of a Forward Gene Minimization (FGM), Backward Gene Minimization (BGM) and Greedy Gene Minimization (GGM) algorithm.

13. The method of claim 8, wherein said free ribosome pool is increased or decreased by at least 5% as compared to an unmodified form of said cell.

14. The method of claim 8, wherein said cell further comprises a heterologous transgene, said synonymous codon is a slower translating codon and wherein replicative fitness in the modified cell is equal to or greater than replicative fitness in said cell devoid of said heterologous transgene and said at least one substitution.

15. The genetically modified cell of claim 1, wherein said coding region is devoid of a mutation in the first 10 codons.

16. The genetically modified cell of claim 1, wherein said free ribosome pool is increased or decreased by at least 5% as compared to said non-genetically modified control cell.

17. The method of claim 8, wherein said synonymous codon is substituted into a region from codon 11 to 50 from a translational start site of said coding sequence.

18. The genetically modified cell of claim 1, wherein said downstream codon is downstream of codon 50 of said coding sequence.

* * * * *